US006861448B2

(12) United States Patent
Brouillette et al.

(10) Patent No.: US 6,861,448 B2
(45) Date of Patent: Mar. 1, 2005

(54) NAD SYNTHETASE INHIBITORS AND USES THEREOF

(75) Inventors: Wayne J. Brouillette, Pelham, AL (US); Lawrence DeLucas, Birmingham, AL (US); Christie Brouillette, Pelham, AL (US); Sadanandan E. Velu, Birmingham, AL (US); Yong-Chul Kim, Gwangsan-gu (KR); Liyuan Mou, Birmingham, AL (US); R. Stephen Porter, Brentwood, TN (US)

(73) Assignees: Virtual Drug Development, Inc., Brentwood, TN (US); The UAB Research Foundation, Birmingham, AL (US)

( * ) Notice: Subject to any disclaimer, the term of this patent is extended or adjusted under 35 U.S.C. 154(b) by 0 days.

(21) Appl. No.: 10/080,279

(22) Filed: Feb. 22, 2002

(65) Prior Publication Data

US 2003/0083269 A1 May 1, 2003

Related U.S. Application Data

(63) Continuation-in-part of application No. 09/617,258, filed on Jul. 14, 2000, now Pat. No. 6,500,852, which is a continuation of application No. PCT/US99/14839, filed on Jun. 30, 1999, and a continuation-in-part of application No. PCT/US99/00810, filed on Jan. 14, 1999, said application No. 10/080,279, is a continuation-in-part of application No. 09/606,256, filed on Jun. 29, 2000, now Pat. No. 6,673,827, said application No. 10/080,279, is a continuation-in-part of application No. PCT/US00/18029, filed on Jun. 29, 2000, and a continuation-in-part of application No. PCT/US01/22203, filed on Jul. 13, 2001.

(60) Provisional application No. 60/097,880, filed on Aug. 25, 1998, provisional application No. 60/071,399, filed on Jan. 14, 1998, provisional application No. 60/141,436, filed on Jun. 29, 1999, and provisional application No. 60/218,405, filed on Jul. 14, 2000.

(51) Int. Cl.$^7$ .................... A61K 31/275; A61K 31/16; C07C 253/00; C07C 69/76; C07C 211/00

(52) U.S. Cl. .................... 514/512; 514/521; 514/522; 514/615; 558/343; 558/415; 560/8; 560/103; 564/123; 564/282

(58) Field of Search .................... 514/520, 521, 514/522, 615; 558/343, 415; 560/8, 103; 564/123, 282; 568/584

(56) References Cited

U.S. PATENT DOCUMENTS 4,275,068 A 6/1981 Thiele et al.

(List continued on next page.)

FOREIGN PATENT DOCUMENTS

EP 0 090 405 10/1983

(List continued on next page.)

OTHER PUBLICATIONS

CAPLUS DN 123:285534, also cited as EP 646569.*

(List continued on next page.)

*Primary Examiner*—Richard L. Raymond
*Assistant Examiner*—Sudhaker B. Patel
(74) *Attorney, Agent, or Firm*—Womble, Carlyle, Sandridge & Rice, PLLC

(57) ABSTRACT

Disclosed are compounds that inhibit the microbial NAD synthetase enzyme. For example, disclosed are compounds of the formula $Ar_1$—X—$Ar_2$—Y—L—Z—Q, wherein Q is $Q_1Ar_3$ or $Ar_3Q_1$; $Ar_1$, $Ar_2$, and $Ar_3$ are independently aryl or heteroaryl, optionally substituted with one or more substituents; X, Y, and Z are independently selected from the group consisting of a covalent bond or groups containing one or more of C, H, N, O, S atoms; L is a linker and $Q_1$ is an alkylenyl, alkylenyl carbonyloxy alkyl, or alkylenyl carbonylamino alkyl group, optionally having a substituent; a covalent bond; a group containing amidine or guanidine function wherein the amidine or guanidine may be optionally N-substituted with an alkyl; or a zwitterion; or a pharmaceutically acceptable salt thereof. Also disclosed are methods which involve the use of the compounds of the present invention, for example, in treating or preventing a microbial infection in a mammal or plant, killing a prokaryote or decreasing prokaryotic growth, disinfecting a material or environment contaminated by a microbe, increasing food animal production, controlling harm to plants by a pest or insect, and combating agroterrorism. Examples of microbes affected by the compounds of the present invention are bacteria and fungi.

74 Claims, 3 Drawing Sheets

U.S. PATENT DOCUMENTS

| | | |
|---|---|---|
| 4,289,777 A | 9/1981 | Albrecht et al. |
| 4,767,712 A | 8/1988 | Motal et al. |
| 4,797,358 A | 1/1989 | Misaki et al. |
| 4,859,692 A | 8/1989 | Bernstein et al. |
| 4,921,786 A | 5/1990 | Takahashi et al. |
| 5,013,743 A | 5/1991 | Iwahi et al. |
| 5,093,342 A | 3/1992 | Tomoi et al. |
| 5,206,146 A | 4/1993 | Misaki et al. |
| 5,468,768 A | 11/1995 | Cipollina et al. |
| 5,521,197 A | 5/1996 | Audia |
| 5,583,149 A | 12/1996 | Cipollina et al. |
| 5,589,349 A | 12/1996 | Shinzaki et al. |
| 5,622,953 A | 4/1997 | Janssen et al. |
| 5,639,752 A | 6/1997 | Maco |
| 5,659,040 A | 8/1997 | Blatcher et al. |
| 5,708,008 A | 1/1998 | Audia et al. |
| 5,744,488 A | 4/1998 | Cross et al. |
| 5,786,473 A | 7/1998 | Blatcher et al. |
| 5,834,493 A | 11/1998 | Gil Quintero et al. |
| 5,849,764 A | 12/1998 | Goulet et al. |
| 5,932,743 A | 8/1999 | Collini et al. |
| 5,936,098 A | 8/1999 | Yasuda et al. |
| 5,962,474 A | 10/1999 | Audia et al. |
| 5,965,582 A | 10/1999 | Lebaut et al. |
| 5,977,154 A | 11/1999 | Bell et al. |
| 5,981,525 A | 11/1999 | Farina et al. |
| 5,981,550 A | 11/1999 | Goulet et al. |
| 5,981,776 A | 11/1999 | Diaz et al. |
| 5,990,150 A | 11/1999 | Matsui et al. |
| 5,998,438 A | 12/1999 | Slassi et al. |
| 6,022,880 A | 2/2000 | Effland et al. |
| 6,037,123 A | 3/2000 | Benton et al. |
| 6,046,136 A | 4/2000 | James et al. |
| 6,174,873 B1 | 1/2001 | Wrenn, Jr. |
| 6,185,541 B1 | 2/2001 | Benton et al. |
| 6,228,588 B1 | 5/2001 | Benton et al. |
| 6,339,073 B1 | 1/2002 | Pero |

FOREIGN PATENT DOCUMENTS

| | | |
|---|---|---|
| EP | 0 196 530 | 3/1985 |
| EP | 0 196 530 A | 10/1986 |
| EP | A-0268956 | 1/1988 |
| EP | 0 585722 | 3/1994 |
| EP | 646569 * | 4/1995 |
| WO | WO 99 36422 A | 7/1999 |
| WO | WO 00 10996 A | 3/2000 |

OTHER PUBLICATIONS

PubMed Abstract 11959549, also cited as Antimicrob. Agents Chemother. 46/5, 1226–30(2002).*

PubMed Abstract 12380742, also cited as J. Food Prot. 65/10, 1580–5(2002).*

PubMed Abstract 14612543, also cited ac Cancer Res.,63/21,7436–42(2003).*

PubMed 10681987,also cited as Ann.NY Acad. Sci. 894, 168–80(1999).*

PubMed Abstract 11876121, also cited as Indian J. Pediatr. 69/1,49–56(2002).*

Shridhar et al, J. Pharm. Sci.,65/7,1074–78(1976).*

Brouillette et al., "Synthesis of Inhibitors of Prokaryotic NAD Synthase" American Chemical Society. Abstracts of paper. At the National Meeting, American Chemical Society, Washington, DC, US, vol. 218, No. Part 1, Aug. 22, 1999, pp. 295–MEDI, XP000981304 ISSN: 0065–7727 the whole document.

Brouillette et al., "Synthesis of Inhibitors of Prokaryotic NAD Synthetase", Abstract ™295, Divisional of Medicinal Chemistry, 218th National American Chemical Society Meeting, New Orleans, LA, Aug. 22–26, 1999 (Abstract only).

Brouillette et al., Synthesis of NAD Synthetase Inhibitors as Potential Antibacterial Agents, Abstract ™298, Division of Medicinal Chemical, 218th National American Chemical Society Meeting, New Orleans, LA, Aug. 22–26, 1999 (Abstract only).

Cristofoli et al., "The Synthesis of Tethered Heterocyclic Dimers as Inhibitors of NAD Synthetase", Gordon Research Conference on Heterocyclic Chemistry, New Port, Rhode Island, Jun. 28–Jul. 3, 1998 ("Title only").

Cristofoli et al., "The Synthesis of Tethered Heterocyclic Dimers as Inhibitors of NAD Synthetase", Poster presentation, Gordon Research Conference on Heterocyclic Compounds, 1998, Newport, RI (Abstract only).

Fostel et al., "Comparison of responses of DNA topoisomerase I from *Candida albicans* and human cells to four new agents which stimulate topoisomerase–dependent DNA nicking", FEMS Microbiology Letters vol. 138, 1996, pp. 105–111.

Fostel et al., "Identification of the Aminocatechol A–3253 as an in Vitro Poison of DNA Topoisomerase I from *Candida albicans*", Antimicrobial Agents and Chemotherapy, vol. 39, No. 3, Mar. 1995, pp. 586–592.

Garcia et al., "Combinatorial Synthesis of NAD Synthetase Inhibitors", Abstract ™297, division of Medicinal Chemistry, 218th National American Chemical Society Meeting, New Orleans, Louisiana, Aug. 22–26, 1999 ("Title only").

Garcia et al., "Synthesis of Potential NAD Synthetase Inhibitors as Antibacterial Agents", Division of Medicinal Chemistry, American Chemical Society National Meeting, Boston, Massachusetts, Aug. 23–27, 1998 ("Title only").

Garcia et al., "Synthesis of Potential NAD Synthetase Inhibitors as Antibacterial Agents" American Chemical Society (Abstracts). National Meeting, American Chemical Society, Washington, DC, US, vol. 216, No. Part 2, Aug. 23, 1998, pp. 248–MEDI, XP000979956 ISSN:0065–7727.

Groll et al., "Potential new antifungal agents", Current Opinion in Infectious Diseases, vol. 10, 1997, pp. 449–458.

Kauffman et al., "Antifungal Agents in the 1990s", Drugs, 53(4), Apr. 1997, pp. 539–549.

Merck Index 1954, p. 1030, compound No. 6434: Nicotine.

Monk et al. "Fungal Plasma Membrane Proton Pumps as Promising New Antifungal Targets", Critical Reviews in Microbiology, 20(3), 1994, pp. 209–223.

Monk et al., Targeting the fungal plasma membrane proton pump:, Acta Biochimica Polonica, vol. 42, No. 4, 1995, pp. 481–496.

Nafsika H. Georgopapadakou, "Antifungals: mechanism of action and resistance, established and novel drugs", Current Oponion in Microbiology, vol. 1., 1998, pp. 547–557.

Richardson, "Fluconazole, An Orally Active Antifungal Agent", Medicinal Chemistry, 2nd Edition, Academic Press, San Diego, CA 1993.

Rizzi et al., "A novel deamido–NAD+–binding site revealed by the trapped NAD–adenylate intermediate in the NAD+ synthetase structure", Structure, vol. 6, No. 9, 1998, pp. 1129–1140.

Rizzi et al., "Crystal structure of $NC_3$–dependent NAD+ synthetase from *Bacillus subtillis*", The EMBO Journal, vol. 15, No. 19, 1996, pp. 5125–5134.

Schmitt et al., "The Synthesis of Tethered Heterocyclic Dimers as Inhibitors of NAD Synthetase", Division of Medicinal Chemistry, American Chemical Society National Meeting, Boston, Massachusetts, Aug. 23–27, 1998 ("Title only").

Schmitt et al., "The Synthesis of Tethered Heterocyclic Dimers as Inhibitors of NAD Synthetase", Abstracts of Papers of the American Chemical Society, vol. 216, part 2, pp. 247–MEDI, Aug. 23, 1998.

Shibata et al.: "Effect of dietary orotic acid on the levels of liver and blood NAD in rats" Journal of Nutritional Science and Vitaminology., vol. 31, No. 3, 1985, pp. 265–278, XP001064472 XX, XX p. 265, Summary p. 276, paragraph 1.

Shibata et al.: "Effect of dietary paraquat on the enzyme activities involved in tryptophan–niacin metabolism in rats" Agricultural and Biological Chemistry., vol. 52, No. 7, 1988, pp. 1857–1858 XP002193914 Japan Soc. For Bioscience Biotechnology and Agrochem. Tokyo., JP ISSN: 0002–1369 p. 1857, col. 2, line 20—line 23 p. 1858; table 1.

Shridhar et al., "Antimicrobial Agents—Part III+: Synthesis and Antimicrobial Activity of Some New Aryloxyalkyl Esters of 3–Ally/methyl/chloro–4–Hydroxybenzoic Acids", J. Indian Chem. Soc., vol. LVI, Jan. 1979, pp. 74–76.

Shridhar et al., "Antimicrobial Agents: Synthesis and Antimicrobial Activity of New Aryloxyalkyl Esters of p–Hydroxybenzoic Acid", Journal of Pharmaceutical Sciences, vol. 65, No. 7, Jul. 1976, pp. 1074–1078.

Turner et al.: "Production of slaughter steers from forages in the arid west" Journal of Animal Science, vol. 44, No. 5, 1977, pp. 901–907, XP001064470 New York, NY, US ISSN: 0021–8812 p. 905, col. 2, last paragraph– p. 906, col. 1, paragraph 2.

Weinberg, "Antifungal Agents", Principles of Medicinal Chemistry, $4^{th}$ Edition, Williams & Wilkins, Media, PA, Chapter 35, 1995, pp. 803.

Yu et al., "Purification and Properties of Yeast Nicotinamide Adenine Dinucleotide Synthetase", The Journal of Biological Chemistry, vol. 247, Issue of Aug. 10, 1972, pp. 4794–4802.

* cited by examiner

NAD SYNTHETASE INHIBITORS AND USES THEREOF

CROSS-REFERENCE TO RELATED APPLICATIONS

The present application is a continuation-in-part of U.S. patent application Ser. No. 09/617,258, filed Jul. 14, 2000, now U.S. Pat. No. 6,500,852, which is a continuation of International Application No. PCT/US99/14839, filed Jun. 30, 1999, which in turn is a continuation-in-part of International Application No. PCT/US99/00810, filed Jan. 14, 1999, and claims the benefit of U.S. provisional patent application Nos. 60/097,880, filed Aug. 25, 1998 and 60/071,399, filed Jan. 14, 1998. The present application is also a continuation-in-part of U.S. patent application Ser. No. 09/606,256, filed Jun. 29, 2000, now U.S. Pat. No. 6,673,827 which claims the benefit of U.S. provisional patent application No. 60/141,436, filed Jun. 29, 1999, and a continuation-in-part of PCT/US00/18029, filed Jun. 29, 2000. The present application is also a continuation-in-part of International Application No. PCT/US01/22203, filed Jul. 13, 2001, which claims the benefit of U.S. provisional patent application No. 60/218,405, filed Jul. 14, 2000. The disclosures of all of the related applications mentioned herein are incorporated by reference.

STATEMENT REGARDING FEDERALLY SPONSORED RESEARCH AND DEVELOPMENT

Some research that contributed to the invention herein was supported, in part, by a grant from the Government of the United States of America, Defense Advanced Research Projects Agency. The Government may have certain rights in this invention.

FIELD OF THE INVENTION

The present invention in general relates to antimicrobial agents, and in particular, to inhibitors of the nicotinamide adenine dinucleotide (NAD) synthetase enzyme of microbes such as bacteria and fungi. The present invention also relates to the various uses of these antimicrobial agents, including in a method of treating or preventing a microbial infection in a mammal, in a method of treating the environment against microbial contamination, in agriculture, e.g., in raising foodcrops and food animals, in medicine, e.g., to disinfect, sterilize, or decontaminate equipment, devices, rooms, and/or people, and in combating bioterrorism, e.g., agroterrorism.

BACKGROUND OF THE INVENTION

Drug-resistant infectious bacteria, that is, bacteria that are not killed or inhibited by existing antibacterial and antimicrobial compounds, have become an alarmingly serious worldwide health problem. Rubenstein, *Science*, 264, 360 (1994). It is believed that a number of bacterial infections may soon be untreatable unless alternative drug treatments are identified.

Antimicrobial or antibacterial resistance has been recognized since the introduction of penicillin nearly 50 years ago. At that time, penicillin-resistant infections caused by *Staphylococcus aureus* rapidly appeared. Today, hospitals worldwide are facing challenges from the rapid emergence and dissemination of microbes resistant to one or more antimicrobial and antibacterial agents commonly in use today. Several strains of antibiotic-resistant bacteria are now emerging and are becoming a threat to human and animal populations, including those summarized below:

Strains of *Staphylococcus aureus* resistant to methicillin and other antibiotics are endemic in hospitals. Infection with methicillin-resistant *S. aureus* (MRSA) strains may also be increasing in non-hospital settings. Vancomycin is the only effective treatment for MRSA infections. A particularly troubling observation is that *S. aureus* strains with reduced susceptibility to vancomycin have emerged recently in Japan and the United States. The emergence of vancomycin-resistant strains would present a serious problem for physicians and patients.

Increasing reliance on vancomycin has led to the emergence of vancomycin-resistant *enterococci* (VRE), bacteria that infect wounds, the urinary tract and other sites. Until 1989, such resistance had not been reported in U.S. hospitals. By 1993, however, more than 10 percent of hospital-acquired *enterococci* infections reported to the Centers for Disease Control ("CDC") were resistant.

*Streptococcus pneumoniae* causes thousands of cases of meningitis and pneumonia, as well as 7 million cases of ear infection in the United States each year. Currently, about 30 percent of *S. pneumoniae* isolates are resistant to penicillin, the primary drug used to treat this infection. Many penicillin-resistant strains are also resistant to other antimicrobial or antibacterial drugs.

Strains of multi-drug resistant tuberculosis (MDR-TB) have emerged over the last decade and pose a particular threat to people infected with HIV. Drug-resistant strains are as contagious as those that are susceptible to drugs. MDR-TB is more difficult and vastly more expensive to treat, and patients may remain infectious longer due to inadequate treatment. Multi-drug resistant strains of *Mycobacterium tuberculosis* have also emerged in several countries, including the U.S.

Diarrheal diseases cause almost 3 million deaths a year, mostly in developing countries, where resistant strains of highly pathogenic bacteria such as *Shigella dysenteriae, Campylobacter, Vibrio cholerae, Escherichia coli* and *Salmonella* are emerging. Furthermore, recent outbreaks of *Salmonella* food poisoning have occurred in the United States. A potentially dangerous "superbug" known as *Salmonella typhimurium*, resistant to ampicillin, sulfa, streptomycin, tetracycline and chloramphenicol, has caused illness in Europe, Canada and the United States.

In addition to its adverse effect on public health, antimicrobial resistance contributes to higher health care costs. Treating antibiotic resistant infections often requires the use of more expensive or more toxic drugs and can result in longer hospital stays for infected patients. The Institute of Medicine, a part of the National Academy of Sciences, has estimated that the annual cost of treating antibiotic resistant infections in the United States may be as high as $30 billion.

In addition, the use of antibiotics in food animal feeds and the extent to which such use contributes to the development of drug resistance have been under recent discussion, see, e.g., C. Marwick, "Animal Feed Antibiotic Use Raises Drug Resistance Fear," *Journal of the American Medical Association,* 282(2):120–2, Jul. 14, 1999, and T. R. Shryock, "Relationship between usage of antibiotics in food-producing animals and the appearance of antibiotic resistant bacteria," *International Journal of Antimicrobial Agents,* 12(4):275–8, August 1999. The use of antibiotics as well as biocides can lead to antibiotic or drug-resistant organisms, see, e.g., A. D. Russel, "Mechanisms of bacterial resistance to antibiotics and biocides," *Progress in Medicinal Chemistry,* 35:133–97, 1998.

Further, spore-forming bacteria can be lethal. For example, *Bacillus anthracis* causes the deadly disease, anthrax. There exists an uncertainty relating to the efficacy of currently available vaccines against *B. anthracis*. Further, there is a likelihood that terrorists could employ antibiotic-resistant strains, e.g., engineered strains that are not recognized by *B. anthracis* antibodies or common bacteria engineered to carry the virulence gene (see, e.g., T. C. Dixon et al., "Anthrax," *New England Journal of Medicine*, 341 (11), 815–826, September 1999). The foregoing shows that there exists a need for a novel treatment against spore-forming bacteria, particularly *B. anthracis* or bacteria carrying the virulence gene of *B. anthracis*.

Further, the incidence of serious fungal infections, either systemic or topical, continues to increase for plants, animals, and humans. Fungi are plant-like eukaryotes that grow in colonies of single cells, called yeasts, or in filamentous multicellular aggregates, called molds. While many fungi are common in the environment and not harmful to plants or mammals, some are parasites of terrestrial plants and others can produce disease in humans and animals. When present in humans, mycotic (fungal) diseases can include contagious skin and hair infections, noncontagious systemic infections, and noncontagious foodborne toxemias. The incidence of such infections is not insignificant; in the U.S. approximately 10% of the population suffers from contagious skin and hair infections. While few healthy persons develop life-threatening systemic fungal infections, immunocompromised individuals, such as found in pregnancy, congenital thymic defects, or acquired immune deficiency syndrome (AIDS), can become seriously ill. This is further illustrated by the fact that fungal infections have become a major cause of death in organ transplant recipients and cancer patients.

Numerous antifungal agents have been developed for topical use against nonsystemic fungal infections. However, the treatment of systemic fungal infections, particularly in immunocrompromised hosts, continues to be a major objective in infectious disease chemotherapy. The organisms most commonly implicated in systemic infections include *Candida* spp., *Cryptococcus neoformans*, and *Aspergillus* spp., although there are a number of emerging pathogens. The major classes of systemic drugs in use currently are the polyenes (e.g., amphotericin B) and the azoles (e.g., fluconazole). While somewhat effective in otherwise healthy patients, these agents are inadequate in severely immunocompromised individuals. Furthermore, drug resistance has become a serious problem, rendering these antifungal agents ineffective in some individuals.

One reason for the limited number of systemic antifungal agents relates to the fact that, unlike bacteria, which are prokaryotes, yeast and molds are eukaryotes. Thus the biochemical make-up of yeast and molds more closely resembles eukaryotic human and animal cells. In general, this has made it difficult to develop antifungal drugs which selectively target in yeast or mold an essential enzyme or biochemical pathway that has a close analog in humans and animals.

In addition, in view of the risks such as toxicity or carcinogenicity associated with many common pesticides, fungicides, or bactericides, new approaches are needed to control pests, or insects in the environment, as well as microbial diseases in plants and food crops, see, e.g., D. W. Wong and G. H. Robertson, "Combinatorial chemistry and its applications in agriculture and food," *Advances in Experimental Medicine & Biology*, 464:91–105, 1999, and S. H. Zahm and M. H. Ward, "Pesticides and childhood cancer," *Environmental Health Perspectives*, 106, Suppl. 3:893–908, June 1998.

Bioterrorism, especially agricultural bioterrorism (or agroterrorism), is presently of great concern in this country as well as in many countries throughout the world. See, e.g., Joseph W. Foxell, Jr., "Current Trends in Agroterrorism (Antilivestock, Anticrop, and Antisoil Bioagricultural Terrorism) and Their Potential Impact on Food Security", in *Studies in Conflict & Terrorism*, 24, 107–129 (2001); Mark Wheelis, "Agricultural Biowarfare and Bioterrorism—An Analytical Framework and Recommendations for the Fifth BTWC Review Conference", $14^{th}$ *Workshop of the Pugwash Study Group on the Implementation of the Chemical Biological Weapons Conventions*, Geneva, Switzerland, November 2000; Radford G. David, "Agricultural Bioterrorism—New Frontiers" in *Biowarfare*, October 2001; Robert P. Kadlec, Chapter 10, Biological Weapons for Waging Economic Warfare, Battle of the Future, $21^{st}$ *Century Warfare Issues, Aerospace* Power Chronicles; Senator Kay Bailey Hutchison, S. 1563, The Agricultural Bioterrorism Countermeasures Act of 2001, Senate Floor Speech, Oct. 17, 2001, page S. 10796.

Given the above, there exists a need to develop novel antimicrobial agents, especially those which act by different mechanisms than those agents in use currently. There exists a need to develop antibacterial agents that preferentially attack microorganisms and kill or deactivate the harmful organism without causing any attendant undesirable side effects in a human or animal patient.

There also exists a need for methods of treating or preventing microbial infection, methods for treating an environment, methods for treating food crops and animals, methods for decontaminating objects, and/or developing countermeasures against bioterrorism, particularly agrobioterrorism.

The advantages of the present invention as well as inventive features will be apparent from the description below.

BRIEF SUMMARY OF THE INVENTION

The present invention ameliorates some of the disadvantages of previously known antimicrobial agents. The present invention provides antimicrobial agents comprising two aryl moieties linked by a suitable linker, and the antimicrobial agents inhibit the NAD synthetase enzyme of a microbe.

In accordance with an embodiment, the present invention provides a compound of the formula (I):

$$Ar_1-X-Ar_2-Y-L-Z-Q \qquad (I)$$

wherein

Q is $Q_1Ar_3$ or $Ar_3Q_1$;

$Ar_1$, $Ar_2$, and $Ar_3$ are independently aryl or heteroaryl, optionally substituted with one or more substituents; X, Y, and Z are independently selected from the group consisting of a covalent bond or groups containing one or more of C, H, N, O, S atoms; L is a linker and $Q_1$ is an alkylenyl, alkylenyl carbonyloxy alkyl, or alkylenyl carbonylamino alkyl group, optionally having a substituent; a covalent bond; a group containing amidine or guanidine function wherein the amidine or guanidine may be optionally N-substituted with an alkyl; or a zwitterion; or a pharmaceutically acceptable salt thereof.

The present invention further provides a compound of the formula A—B—$(CH_2)_n$—O—CO—$CH_2$—Ph $(NMe_3)^+I^-$, wherein A is a phenyl or indole, optionally substituted with a benzyloxy group; B is a covalent bond or oxygen atom; n is 1–15; and $I^-$ is a pharmaceutically acceptable anion.

Further, the invention provides a method of treating or preventing a microbial infection in a mammal comprising administering to the mammal a treatment effective or treatment preventive amount of a microbial NAD synthetase enzyme inhibitor compound. Still further, a method is provided of killing a prokaryote with an amount of prokaryotic NAD synthetase enzyme inhibitor to reduce or eliminate the production of NAD whereby the prokaryote is killed. Moreover, a method is provided of decreasing prokaryotic growth, comprising contacting the prokaryote with an amount of prokaryotic NAD synthetase enzyme inhibitor effective to reduce or eliminate the production of NAD whereby prokaryotic growth is decreased. Further provided is a disinfecting composition comprising a microbial NAD synthetase enzyme inhibitor. Still further, the invention provides a method of disinfecting a material contaminated by a microbe, comprising contacting a contaminated material with a microbial NAD synthetase enzyme inhibitor compound in an amount sufficient to kill or deactivate the microbe. The present invention provides a method for treating or preventing a microbial infection in a mammal comprising administering to the mammal an effective amount of a compound that inhibits the enzymatic activity of the microbial NAD synthetase.

The present invention, in an embodiment, is based in part on the discovery that NAD synthetase inhibitors are highly effective in inhibiting the growth of a fungus such as yeast, yet exhibit only moderate toxicity in animals. Thus, the present invention includes the use of NAD synthetase inhibitors as antifungal agents for preventing or controlling fungal infections such as parasitic yeast and mold infections in plants, and for the prophylactic or therapeutic treatment, topically and systemically, of fungal infections in humans and animals. The present invention provides a method of killing a fungus with an amount of NAD synthetase enzyme inhibitor to reduce or eliminate the production of NAD whereby the fungus is killed. The present invention also provides a method of decreasing fungus growth, comprising contacting the yeast with an amount of a NAD synthetase enzyme inhibitor effective to reduce or eliminate the production of NAD whereby fungus growth is decreased.

The present invention also provides a method for increasing production of food animals comprising administering to the food animal an effective amount of at least one inhibitor of NAD synthetase of a microbe capable of infecting the food animal. The present invention further provides a method for the treatment or prevention of infection by a spore-forming bacterium in an animal comprising treating an environment of the animal with an effective amount of at least one inhibitor of NAD synthetase of the spore-forming bacterium.

The present invention further provides a method for killing the vegetative cell of a spore-forming bacterium in an environment comprising treating the environment with an effective amount of at least one inhibitor of NAD synthetase of the bacterium.

The present invention also provides a method for treating a fungal or bacterial disease in a plant comprising treating the plant or the environment of the plant with an effective amount of at least one inhibitor of NAD synthetase of the fungus or bacterium. The present invention further provides a method for treating or preventing harm to a plant due to a pest comprising contacting the plant, or an environment thereof, with a pesticidal effective amount of a NAD synthetase enzyme inhibitor of the pest.

The present invention further provides a pharmaceutical composition comprising a compound as described above and a pharmaceutically acceptable carrier. The present invention further provides a method for treating or preventing a microbial infection in a mammal comprising administering to said mammal an effective amount of a compound that binds to the interface of the NAD synthetase enzyme dimer of the microbe.

The present invention further provides a method for combating agroterrorism involving an infective agent on an object comprising treating the object with an amount of a compound effective to inhibit the NAD synthetase of the infective agent.

SPECIFIC DESCRIPTION OF THE INVENTION

Figure 1:
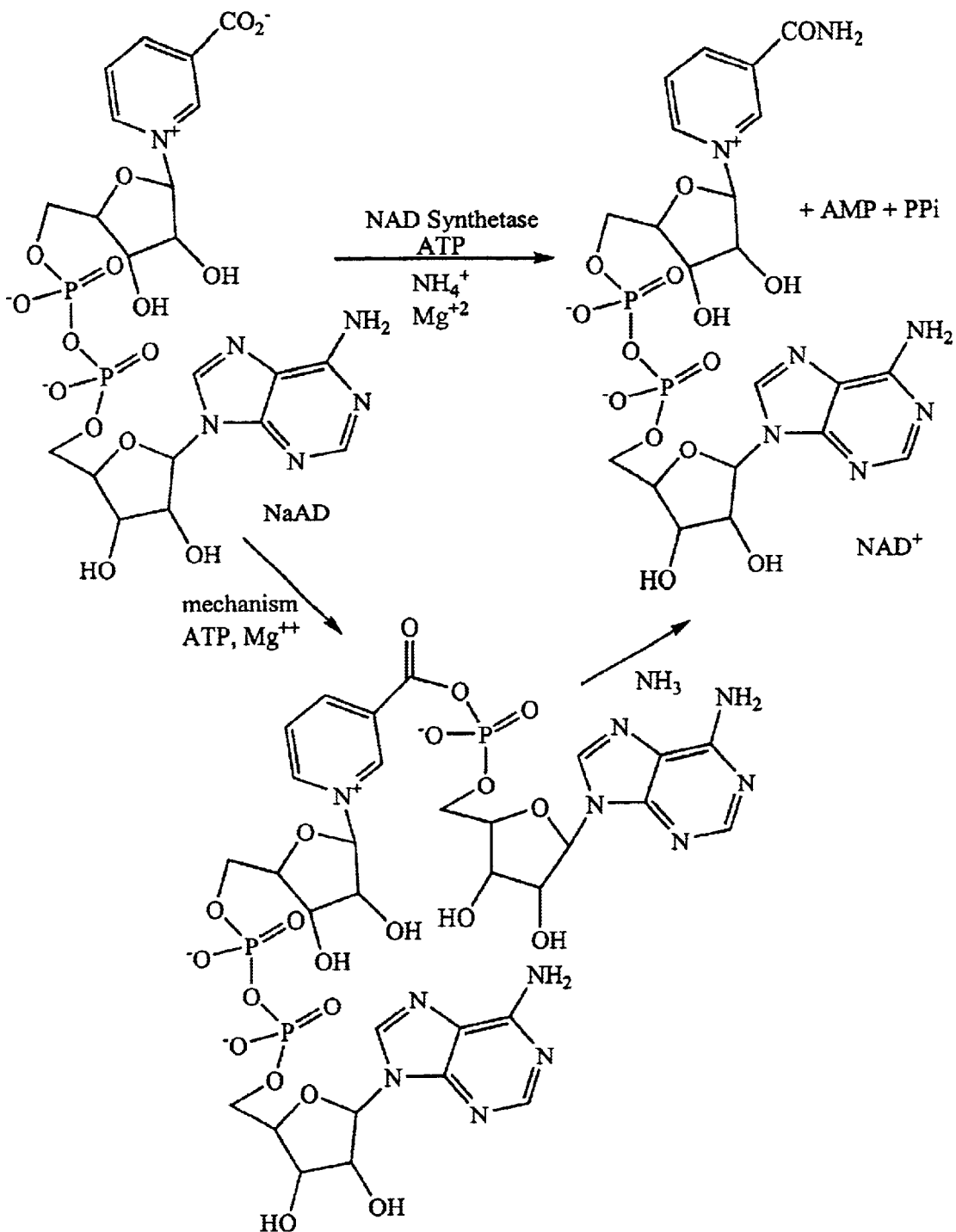
FIG. 1 depicts a reaction scheme wherein the NAD synthetase enzyme catalyzes the final step in the biosynthesis of NAD.

The present invention provides a microbial NAD synthetase enzyme inhibitor, having the formula 1:

(formula 1)
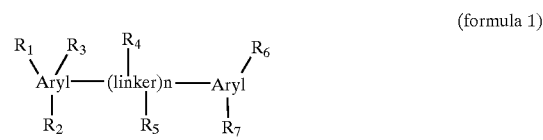

wherein n is an integer of from 1 to 12, $R_1$–$R_7$ each, independently, is H, an unsubstituted or a substituted cyclic or aliphatic group, a branched or unbranched group, wherein the linker is a cyclic or aliphatic, branched or an unbranched alkyl, alkenyl, or an alkynyl group and wherein the linker may also contain heteroatoms.

$R_1$–$R_7$ may also be one of the following groups: H, alkyl, alkenyl, alkynyl, or an aryl. $R_1$–$R_7$, may further be a hydroxyl, ketone, nitro, amino, amidino, guanidino, carboxylate, amide, sulfonate, or halogen or a common derivatives of these groups. Note that n may also be an integer of from 3 to 10, more preferably 5 to 9 and, still more preferably 6 to 9. The "aryl," moieties may be the same or different.

As an example, the present invention provides a microbial NAD synthetase enzyme inhibitor, having formula 2:

(formula 2)
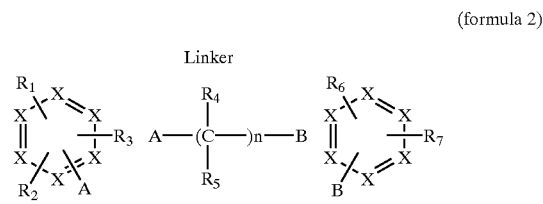

wherein X is a C, N, O or S within a monocyclic or bicyclic moiety, A and B represent the respective sites of attachment for the linker, n is an integer of from 1 to 12, $R_1$–$R_7$ each, independently, is an H, an unsubstituted or a substituted cyclic group, or an aliphatic group, or a branched or an unbranched group, wherein the linker is a saturated or unsaturated cyclic group or an aliphatic branched or unbranched alkyl, alkenyl or alkynyl group, and wherein the linker may also contain heteroatoms.

$R_1$–$R_7$ may also be one of the following groups: H, alkyl, alkenyl, alkynyl, or an aryl group. $R_1$–$R_7$ may also be a hydroxyl, ketone, nitro, amino, amidino, guanidino, carboxylate, amide, sulfonate, or halogen or the common derivatives of these groups. One of skill in the art would know what moieties are considered to constitute derivatives of these groups. In further embodiments, n may also be an integer of from 3 to 10, more preferable 5 to 9 and, still more preferably 6 to 9.

In an embodiments, the linker has the formula A—(C, Heteroatom)n-B. For example, the linker may be an amide, ester, ether, or combinations thereof.

The present invention, in an embodiment, provides a compound of formula (I):

$$Ar_1—X—Ar_2—Y—L—Z—Q \qquad (I)$$

wherein

Q is $Q_1Ar_3$ or $Ar_3Q_1$;

$Ar_1$, $Ar_2$, and $Ar_3$ are independently aryl or heteroaryl, optionally substituted with one or more substituents selected from the group consisting of $C_1$–$C_6$ alkyl, $C_1$–$C_6$ alkoxy, $C_1$–$C_6$ haloalkyl, $C_1$–$C_6$ hydroxyalkyl, $C_1$–$C_6$ alkoxy $C_1$–$C_6$ alkyl, halo, amino, $C_1$–$C_6$ alkylamino, $C_1$–$C_6$ dialkylamino, $C_1$–$C_6$ trialkylamino, $C_1$–$C_6$ alkylamino $C_1$–$C_6$ alkyl, $C_1$–$C_6$ dialkylamino $C_1$–$C_6$ alkyl, $C_1$–$C_6$ trialkylamino $C_1$–$C_6$ alkyl, azido, amine oxide, hydroxy, carboxyl, $C_1$–$C_6$ alkylcarbonyl, $C_1$–$C_6$ alkylcarbonyl $C_1$–$C_6$ alkyl, $C_1$–$C_6$ alkylcarbonyloxy, $C_1$–$C_6$ alkylcarbonyloxy $C_1$–$C_6$ alkyl, $C_1$–$C_6$ alkyloxycarbonyl $C_1$–$C_6$ alkyl, $C_1$–$C_6$ alkyloxycarbonyl, $C_1$–$C_6$ alkylthio, nitro, nitrosyl, cyano, hydroxylamino, sulfonamido, $C_1$–$C_6$ dialkyl sulfonamido, $C_1$–$C_6$ alkylcarbonylamino, formyl, formylamino, mercaptyl, and heterocyclyl; optionally, a ring nitrogen atom of heteroaryl $Ar_1$, $Ar_2$, or $Ar_3$ may be quaternized;

X, Y, and Z are independently selected from the group consisting of a covalent bond, $(CH_2)_mO$, $O(CH_2)_m$, $(CH_2O)_m$, $(OCH_2)_m$, $(CH_2CH_2O)_m$, $(OCH_2CH_2)_m$, $C(=O)O$, $OC(=O)$, $OC(=O)O$, $(CH_2)_mS$, $S(CH_2)_m$, $(CH_2S)_m$, $(SCH_2)_m$, NH, NR, $^{+NR}{}_2$, $C(=O)NH$, $C(=O)NR$, NHC(=O), NRC(=O), CH(OH), and CH(OR), wherein R is $C_1$–$C_6$ alkyl and m is 0–5;

L is $\{(CR_1R_2)_q—(W)_r—(CR_3R_4)_t\}_p$, wherein $R_1$–$R_4$ are independently H, $C_1$–$C_6$ alkyl, $C_1$–$C_6$ alkoxy, $C_1$–$C_6$ haloalkyl, $C_1$–$C_6$ hydroxyalkyl, $C_1$–$C_6$ alkoxy $C_1$–$C_6$ alkyl, halo, amino $C_1$–$C_6$ alkylamino, $C_1$–$C_6$ dialkylamino, azido, hydroxy, aldehyde, $C_1$–$C_6$ acetal, $C_1$–$C_6$ ketal, $C_1$–$C_6$ alkylcarbonyl, $C_1$–$C_6$ alkylcarbonyl $C_1$–$C_6$ alkyl, $C_1$–$C_6$ alkylcarbonyloxy, $C_1$–$C_6$ alkylcarbonyloxy $C_1$–$C_6$ alkyl, $C_1$–$C_6$ alkylthio, nitro, nitrosyl, cyano, sulfonamido, $C_1$–$C_6$ alkylcarbonylamino, or heterocyclyl; W is a moiety selected from the group consisting of alicyclic ring, aromatic ring, heterocyclic ring, combinations of alicyclic, heterocyclic, and/or aromatic rings, $C_2$–$C_6$ alkenyl, dienyl, $C_2$–$C_6$ alkynyl, $C_1$–$C_6$ alkoxy, $C_2$–$C_6$ alkenyloxy, $C_2$–$C_6$ alkynyloxy, anhydrido, enol, ketene, amino, imino, hydrazinyl, epoxy, episulfide, amido, amine oxide, urea, urethane, ester, thioester, carbonate, carbonyl, thiocarbonyl, sulfonyl, diazo, sulfonamido, ether oxygen, ether sulfur, thionyl, silyl, peroxide, lactam, lactone, phenylene, monosaccharide, dri-, tri-, and higher polysaccharides, nucleic acid, amino acid, phosphonyl, phosphoryl, and combinations thereof; q, r, and t are independently 0–20; q, r, and t are not simultaneously 0; and p is 1–6; L, optionally, further including O, N, or S; and $Q_1$ is (i) a $C_1$–$C_6$ alkylenyl, $C_1$–$C_6$ alkylenyl carbonyloxy $C_1$–$C_6$ alkyl, or $C_1$–$C_6$ alkylenyl carbonylamino $C_1$–$C_6$ alkyl group, optionally having a substituent selected from the group consisting of amino, $C_1$–$C_6$ alkylamino, $C_1$–$C_6$ haloalkylamino, $C_1$–$C_6$ haloalkyl $C_1$–$C_6$ alkyl amino, $C_1$–$C_6$ hydroxyalkylamino, $C_1$–$C_6$ hydroxyalkyl $C_1$–$C_6$ alkylamino, $C_1$–$C_6$ dialkylamino, $C_1$–$C_6$ trialkylamino, and heterocyclic containing a nitrogen atom which may be optionally quaternized, (ii) a $C_2$–$C_6$ alkylenyl; (iii) methylenyl with the proviso that Z is other than covalent bond or $O(C=O)$ when Q is $Q_1Ar_3$ wherein $Ar_3$ is a phenyl para substituted with amino, methylamino, dimethylamino, or trimethylamino or $Ar_3$ is a pyridyl or N-methylpyridyl; (iv) a covalent bond with the proviso that when $Ar_3$ is pyridyl, N-methyl pyridyl, or phenyl para substituted with trimethylaminomethyl group, Z is other than a covalent bond or $O(C=O)$; (v) a group containing amidine or guanidine function wherein the amidine or guanidine may be optionally N-substituted with a $C_1$–$C_6$ alkyl; or (vi) a zwitterion; or a pharmaceutically acceptable salt thereof.

The aryl of $Ar_1$, $Ar_2$, and $Ar_3$ includes 1–3 aromatic rings, for example, phenyl, naphthyl, or anthracenyl, preferably phenyl. The heteroaryl of $Ar_1$, $Ar_2$, and $Ar_3$ include 1–3 rings, one or more of which include O, N, or S, preferably N. Examples of heteroaryls include indole, benzopyranone, benzoxazole, benzothiazole, In embodiments of the compound of the present invention, $Ar_1$ is phenyl or phenyl substituted with one or more substituents selected from the group consisting of $C_1$–$C_6$ alkyl, $C_1$–$C_6$ alkoxy, $C_1$–$C_6$ haloalkyl, $C_1$–$C_6$ hydroxyalkyl, $C_1$–$C_6$ alkoxy $C_1$–$C_6$ alkyl, halo, amino, $C_1$–$C_6$ alkylamino, $C_1$–$C_6$ dialkylamino, $C_1$–$C_6$ trialkylamino, $C_1$–$C_6$ alkylamino $C_1$–$C_6$ alkyl, $C_1$–$C_6$ dialkylamino $C_1$–$C_6$ alkyl, $C_1$–$C_6$ trialkylamino $C_1$–$C_6$ alkyl, azido, amine oxide, hydroxy, carboxyl, $C_1$–$C_6$ alkylcarbonyl, $C_1$–$C_6$ alkylcarbonyl $C_1$–$C_6$ alkyl, $C_1$–$C_6$ alkylcarbonyloxy, $C_1$–$C_6$ alkylcarbonyloxy $C_1$–$C_6$ alkyl, $C_1$–$C_6$ alkyloxycarbonyl $C_1$–$C_6$ alkyl, $C_1$–$C_6$ alkyloxycarbonyl, $C_1$–$C_6$ alkylthio, nitro, nitrosyl, cyano, hydroxylamino, sulfonamido, $C_1$–$C_6$ dialkyl sulfonamido, $C_1$–$C_6$ alkylcarbonylamino, formyl, formylamino, mercaptyl, and heterocyclyl.

In preferred embodiments of the compounds of the present invention, $Ar_1$ is phenyl or phenyl substituted with one or more substituents selected from the group consisting of $C_1$–$C_6$ alkoxy, halo, amino, $C_1$–$C_6$ alkylamino, $C_1$–$C_6$ dialkylamino, azido, $C_1$–$C_6$ alkylcarbonyloxy, $C_1$–$C_6$ alkylthio, nitro, cyano, sulfonamido, $C_1$–$C_6$ dialkyl sulfonamido, $C_1$–$C_6$ alkylcarbonylamino, and heterocyclyl.

Embodiments of the compounds of the present invention include compounds wherein $Ar_1$ is phenyl, phenyl substituted with one or more $C_1$–$C_6$ alkoxy, particularly phenyl substituted with one or more methoxy or propoxy. Embodiments of the compounds of the present invention also include compounds wherein $Ar_1$ is phenyl substituted with one or more halo, particularly, one, two, or three chloro or fluoro. Embodiments of the compounds of the present invention also include compounds wherein $Ar_1$ is phenyl substituted with one or more $C_1$–$C_6$ dialkylamino, particularly N,N-dimethylamino. Embodiments of the compounds of the present invention further include compounds wherein $Ar_1$ is phenyl substituted with one or more azido, nitro, and cyano. Embodiments of the compounds of the present invention also include compounds wherein $Ar_1$ is phenyl substituted with one or more $C_1$–$C_6$ dialkyl sulfonamido, particularly N,N-dimethyl sulfonamido. Embodiments of the compounds of the present invention also include compounds wherein $Ar_1$ is phenyl substituted with one or more $C_1$–$C_6$ alkylcarbonyloxy, particularly acetoxy. Embodiments of the compounds of the present invention also include compounds wherein $Ar_1$ is phenyl substituted with one or more $C_1$–$C_6$ alkylcarbonylamino, particularly acetylamino. Embodiments of the compounds of the present invention also include compounds wherein $Ar_1$ is phenyl substituted with one or more $C_1$–$C_6$ alkylthio, particularly methylthio. Embodiments of the compounds of the present invention also include compounds wherein $Ar_1$ is phenyl substituted with one or more heterocyclyl, particularly diazolyl.

In accordance with the present invention, embodiments include compounds wherein $Ar_2$ is phenyl, optionally substituted with one or more substituents selected from the group consisting of $C_1$–$C_6$ alkyl, $C_1$–$C_6$ alkoxy, and $C_1$–$C_6$ alkyloxycarbonyl. In a preferred embodiment, $Ar_2$ is phenyl.

In accordance with the present invention, embodiments also include compounds wherein $Ar_2$ is indolyl or indolyl substituted with one or more substituents selected from the group consisting of $C_1$–$C_6$ alkyl, $C_1$–$C_6$ alkoxy, and $C_1$–$C_6$ alkyloxycarbonyl. In a preferred embodiment, $Ar_2$ is indolyl, particularly indolyl substituted with one or more $C_1$–$C_6$ alkylcarbonyloxy. In another preferred embodiment, $Ar_2$ is benzopyranonyl.

In accordance with the present invention, embodiments include compounds wherein $Ar_3$ is phenyl, indolyl, or pyridyl, optionally substituted with one or more substituents selected from the group consisting of $C_1$–$C_6$ alkyl, $C_1$–$C_6$ alkoxy, amino, $C_1$–$C_6$ alkylamino, $C_1$–$C_6$ dialkylamino, $C_1$–$C_6$ trialkylamino, and nitro. In a particular embodiment, $Ar_3$ is phenyl, optionally substituted with one or more $C_1$–$C_6$ trialkylamino, preferably N,N,N-trimethylamino. In another embodiment, $Ar_3$ is indolyl.

In accordance with an embodiment of the present invention, Q is $Ar_3Q_1$ and $Q_1$ is $C_1$–$C_6$ alkylenyl carbonyloxy $C_1$–$C_6$ alkyl, optionally having a $C_1$–$C_6$ trialkylamino, for example, $Q_1$ is trimethylamino ethylenyl carbonyloxy t-butyl.

In accordance with another embodiment, Q is $Q_1Ar_3$, wherein $Q_1$ is $C_1$–$C_6$ alkylenyl, optionally having a $C_1$–$C_6$ trialkylamino or a heterocyclic containing a quaternized nitrogen atom. Examples of $Q_1$ include methylenyl and trimethylamino ethylenyl, and ethylenyl having a N-alkyl pyrrolidinyl, N-alkyl piperidinyl, or N,N-dialkyl-N-tetrahydropyranyl substituent. In certain embodiments, $Q_1$ is a covalent bond, preferably a single bond, e.g., when $Ar_3$ is N-methyl pyridinyl and Z is NH(C=O) or NR(C=O).

In a preferred embodiment of the compound of the present invention, Z is NH(C=O) or NR(C=O), more preferably NH(C=O).

In an embodiment of the present invention, $Q_1$ is a zwitterion, for example, an internal salt of a natural or synthetic amino acid. In another embodiment of the present invention, $Q_1$ is a group containing amidine or guanidine function wherein the amidine or guanidine may be optionally N-substituted with a $C_1$–$C_6$ alkyl.

In a preferred embodiment of the compounds of the present invention, t is 0. In a particularly preferred embodiment, $R_1$–$R_4$ are H. In another preferred embodiment, q and r are independently 1–7. In yet another preferred embodiment, p is 1–4. Still further preferred embodiments include compounds wherein q and r are 1, q and r are 2, and one of q and r is 1 and the other of q and r is 2.

In an embodiment of the compound of the present invention, X is selected from the group consisting of $CH_2O$, (C=O)O, and covalent bond. In another embodiment of the compound of the present invention, Y is selected from the group consisting of covalent bond and O. An example of a covalent bond is a single bond. In yet another embodiment of the present invention Z is selected from the group consisting of O(C=O), covalent bond, NH(C=O), NR(C=O), O, NR, and $^+NR_2$.

Specific compounds of the present invention include compounds wherein $Ar_1$ is phenyl or a phenyl substituted with chloro, fluoro, methylthio, methoxy, isopropoxy, N,N-dimethylamino, azido, nitro, acetoxy, cyano, acetylamino, sulfonamido, or diazolyl; X is $CH_2O$, (C=O)O, or single bond; $Ar_2$ is phenyl, indolyl, or benzopyranonyl, each of the $Ar_2$ may be substituted with methoxycarbonyl; Y is O, (C=O)O, or single bond; L is $(CH_2)_n$ wherein n is 7–11; Z is O(C=O), NH(C=O), O, single bond, $OCH_2$, $NCH_3$, or $N^+$; $Q_1$ is single bond, $CH_2$—CH(GU)—$CH_2$, (GU)CH—$CH_2$, $CH_2CH(N^+R_5R_6R_7)CH_2$, wherein GU is guanidine, $R_5$, $R_6$, and $R_7$ are alkyl or heterocyclic or together with the $N^+$ forms a heterocyclic; and $Ar_3$ is phenyl, N-methyl pyridinyl, N,N,N-trimethylaminophenyl, or nitrophenyl.

Specific embodiments include compounds wherein $Ar_1$ is phenyl, X is $CH_2O$, $Ar_2$ is phenyl or indolyl; Y is single bond or O; L is $(CH_2)_7$ or $(CH_2)_8$; Z is O, NH(C=O), O(C=O); $Q_1$ is single bond, n-propyl, $CH_2$, $CH(NMe_3)CH_2$, $CH_2$—CH(GU)—$CH_2$, (GU)CH—$CH_2$; and $Ar_3$ is phenyl, indolyl, hydroxyphenyl, nitrophenyl, and N,N,N-trimethylaminophenyl, wherein the hydroxy, nitro and N,N,N-trimethylamino groups may be present in the o-, m-, or p-position. Other embodiments include compounds wherein $Ar_1$ is o-, m-, or p-chlorophenyl; X is $CH_2O$; $Ar_2$ is phenyl; Y is O; L is $(CH_2)_8$; Z is NH(C=O) or O(C=O); $Q_1$ is $CH_2$, single bond, $CH(NMe_3)CH_2$, or CH(N-methylpyrrolidinyl) $CH_2$, and $Ar_3$ is phenyl, N-methyl pyridinyl, or N,N,N-trimethylaminophenyl. Further embodiments include compounds wherein $Ar_1$ is dichlorophenyl wherein the chlorine atoms may be in the 2,3; 2,4; 2,5; 2,6; 3,4; 3,5; or 3,6-position; X is (C=O)O or $CH_2O$; $Ar_2$ is phenyl; Y is O; L is $(CH_2)_8$; Z is NH(C=O); $Q_1$ is single bond, $CH_2$, $CH(NMe_3)CH_2$; and $Ar_3$ is phenyl, N-methyl pyridinyl, or N,N,N-trimethylaminophenyl. Additional embodiments include compounds wherein $Ar_1$ is trichlorophenyl wherein the chlorine atoms may be present in the 2,3,4; 2,4,5; 2,5,6; 3,4,5; or 3,5,6 position; X is (C=O)O; $Ar_2$ is phenyl; Y is O; L is $(CH_2)_8$; Z is NH(C=O); $Q_1$ is $CH_2$, $CH(NMe_3)CH_2$; and $Ar_3$ is phenyl or N,N,N-trimethylaminophenyl. Other embodiments include compounds wherein $Ar_1$ is o-, m-, or p-fluorophenyl; X is (C=O)O; $Ar_2$ is phenyl; Y is O; L is $(CH_2)_8$; Z is NH(C=O); $Q_1$ is $CH(NMe_3)CH_2$; and $Ar_3$ is phenyl. Further embodiments include compounds wherein $Ar_1$ is difluorophenyl wherein the fluorine atoms may be in the 2,3; 2,4; 2,5; 2,6; 3,4; 3,5; or 3,6-position; X is (C=O)O; $Ar_2$ is phenyl; Y is O; L is $(CH_2)_8$; Z is NH(C=O); $Q_1$ is $CH(NMe_3)CH_2$; and $Ar_3$ is phenyl. Additional embodiments include compounds wherein $Ar_1$ is trifluorophenyl wherein the fluorine atoms may be present in the 2,3,4; 2,4,5; 2,5,6; 3,4,5; or 3,5,6 position; X is (C=O)O; $Ar_2$ is phenyl; Y is O; L is $(CH_2)_8$; Z is NH(C=O); $Q_1$ is single bond, $CH_2$, or $CH(NMe_3)CH_2$; and $Ar_3$ is phenyl or N-methyl pyridinyl, or N,N,N-trimethylaminophenyl. Additional embodiments include compounds wherein $Ar_1$ is methoxy phenyl or isopropoxy phenyl, wherein the methoxy or isopropoxy group may be present in the o-, m-, or p-position; X is (C=O)O or $CH_2O$; $Ar_2$ is phenyl; Y is O; L is $(CH_2)_8$; Z is NH(C=O) or O(C=O); $Q_1$ is single bond, $CH_2$, or $CH(NMe_3)CH_2$; and $Ar_3$ is phenyl or N-methyl pyridinyl, or N,N,N-trimethylaminophenyl. In the embodiments above Q is preferably $Q_1Ar_3$.

Particular examples of compounds of the present invention include:
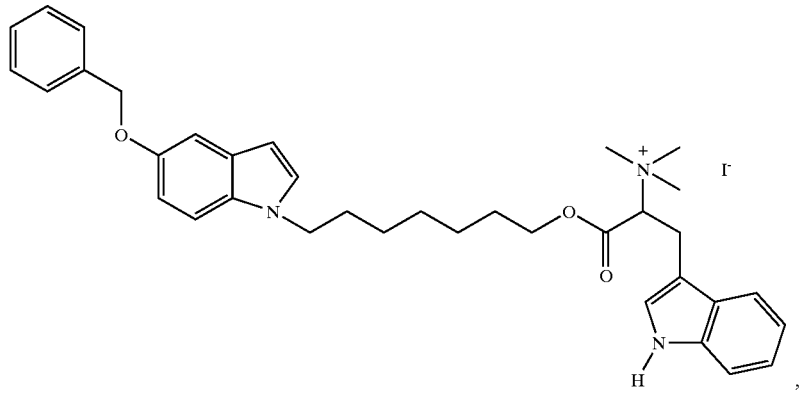
1505
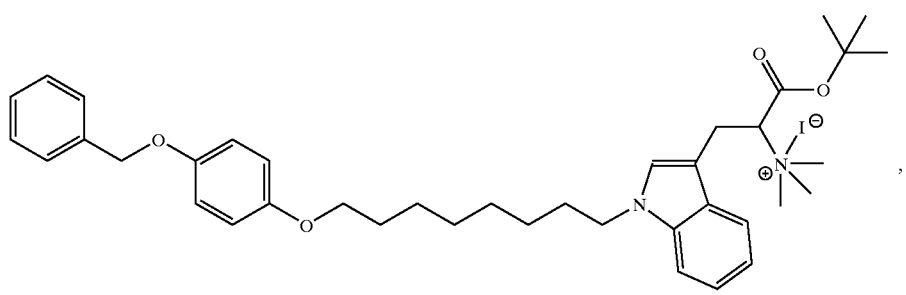
1494
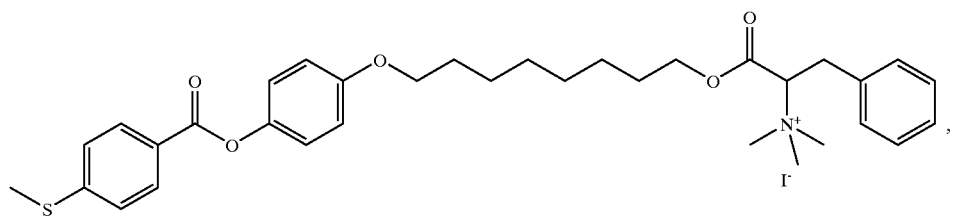
1478
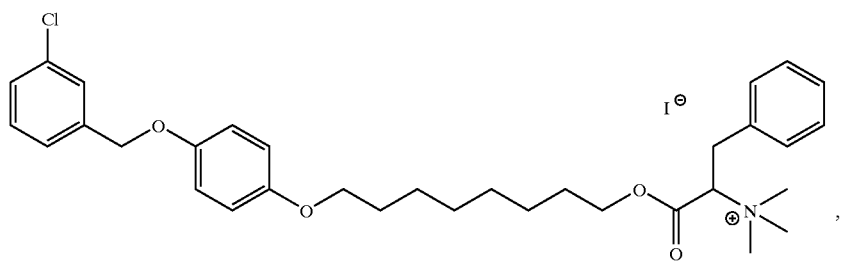
1391
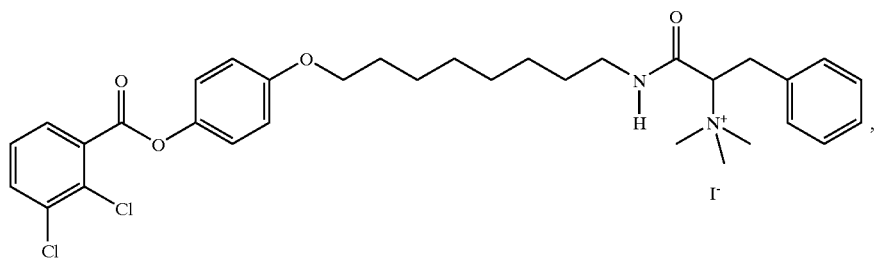
1603

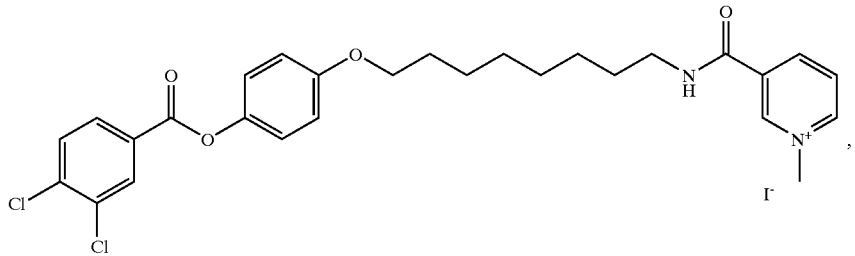
1665
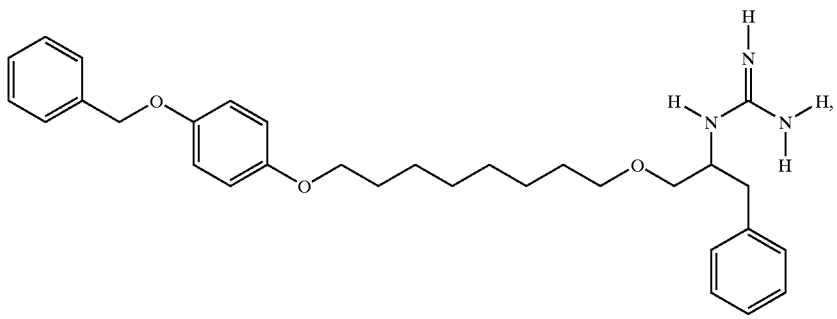
1679
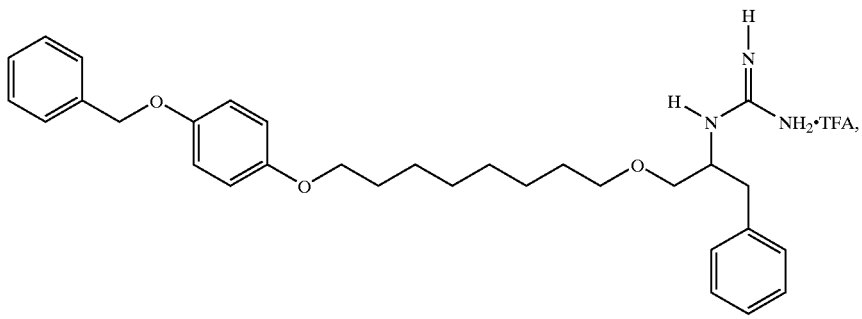
1680'
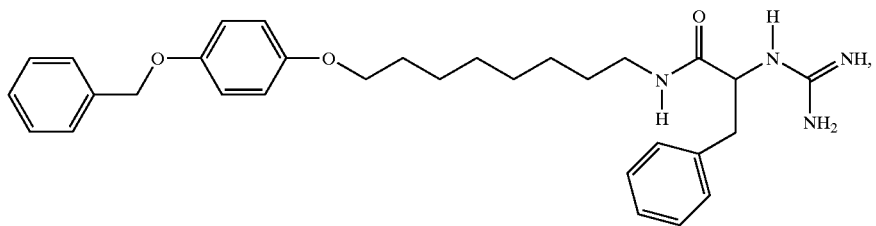
1681'
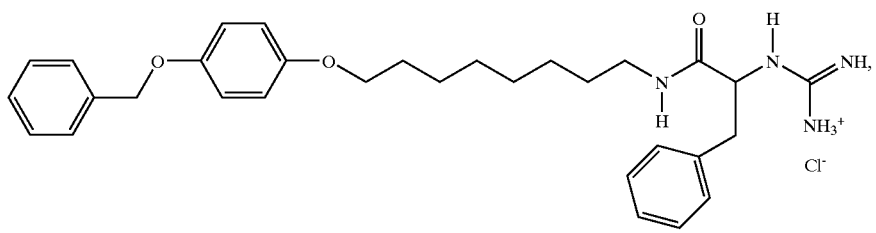
1682'

-continued
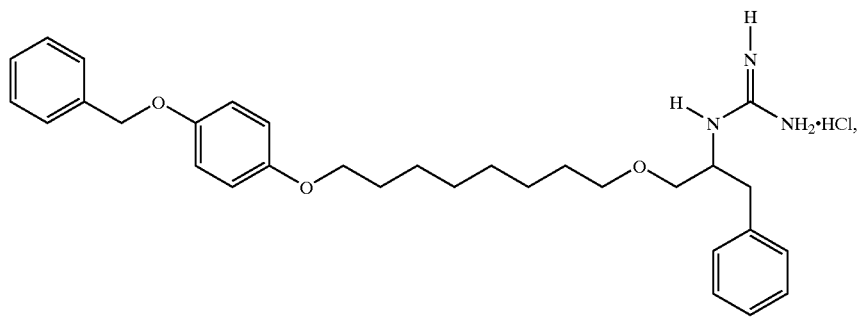
1685'
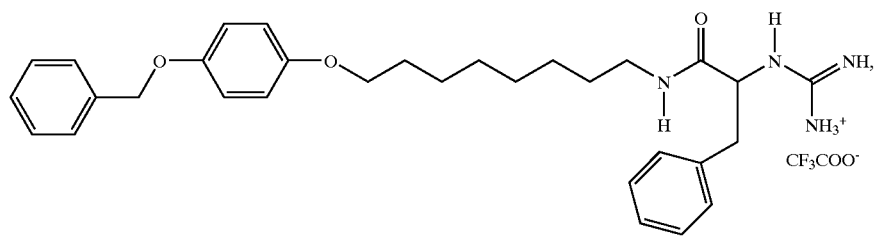
1503'
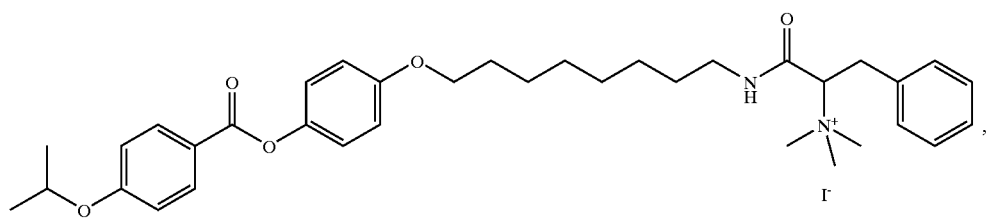
1600
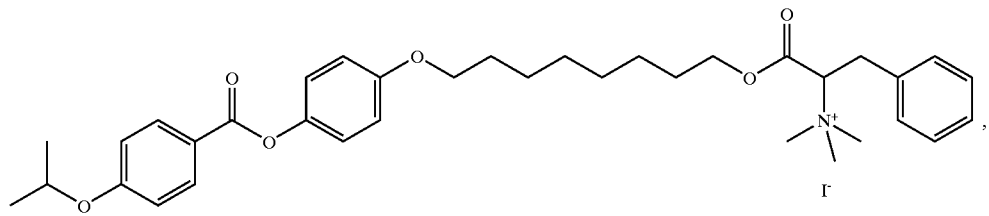
1477
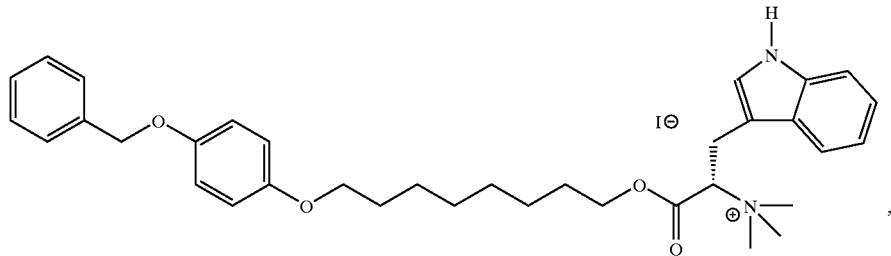
1491'
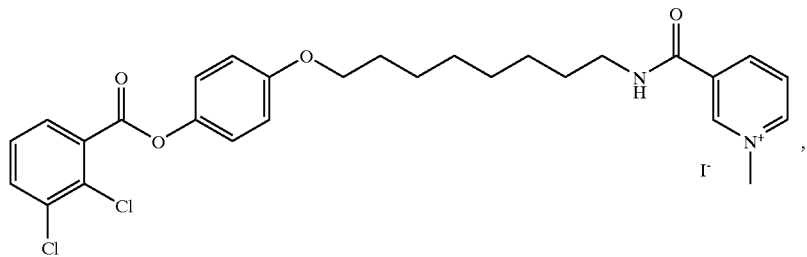
1661

-continued
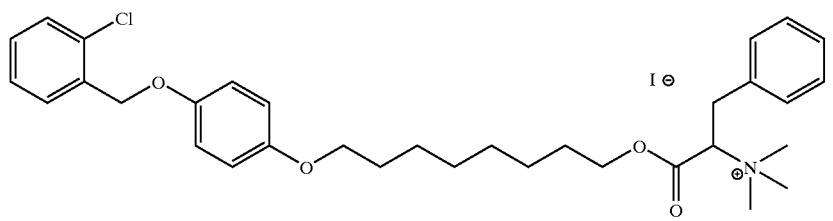
1390
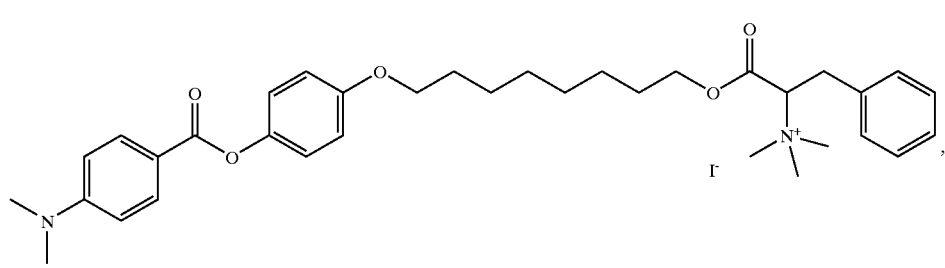
1484
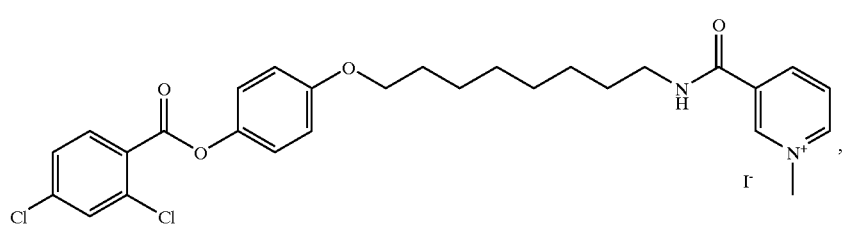
1662
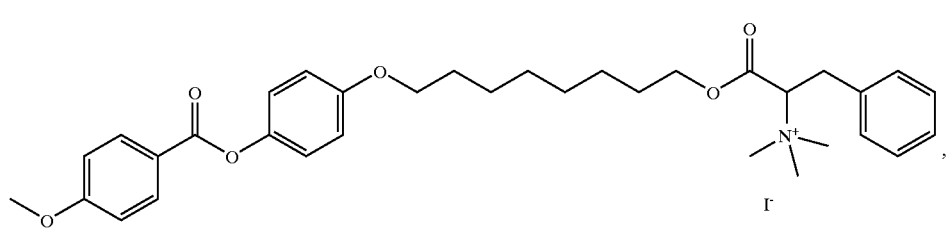
1456
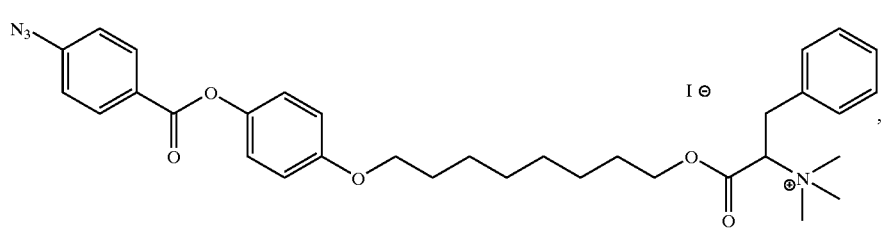
1432
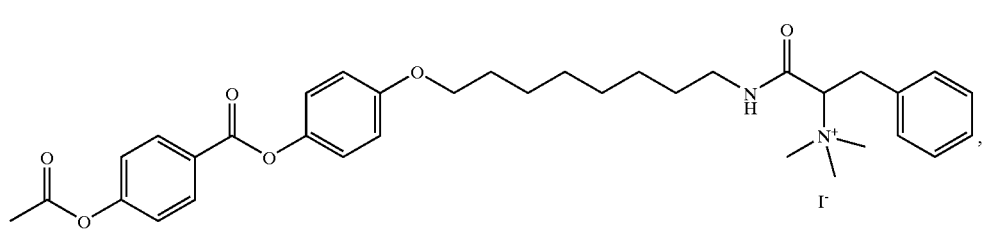
1599

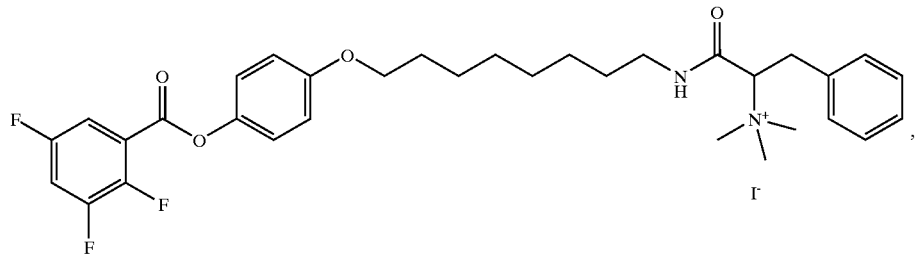
1617
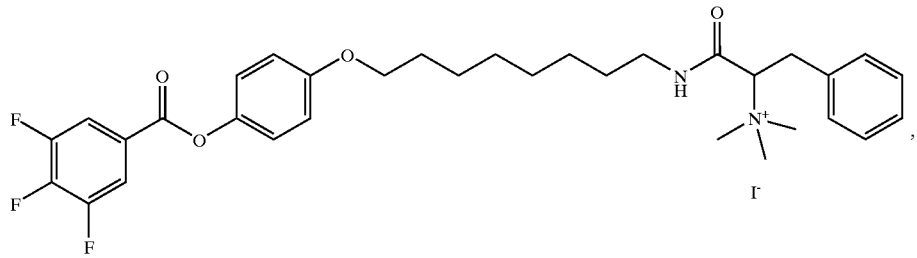
1621
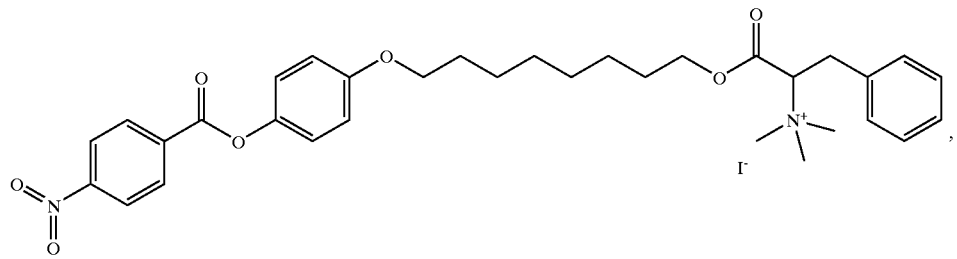
1483
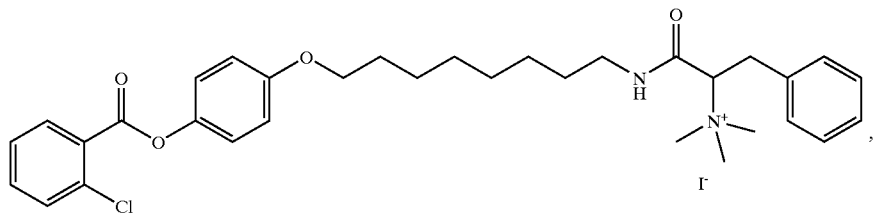
1593
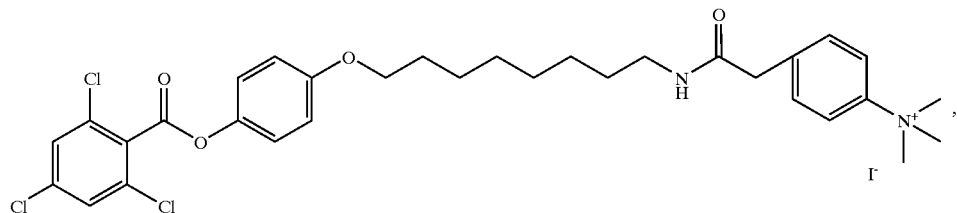
1645
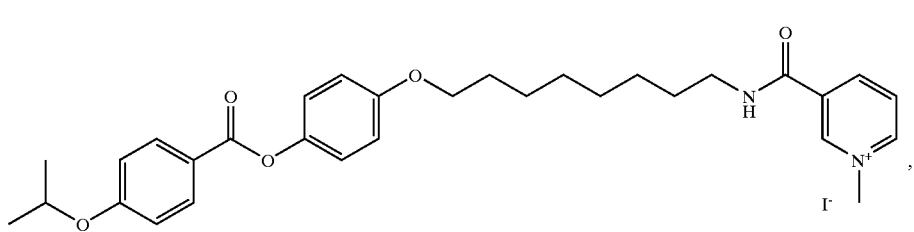
1658

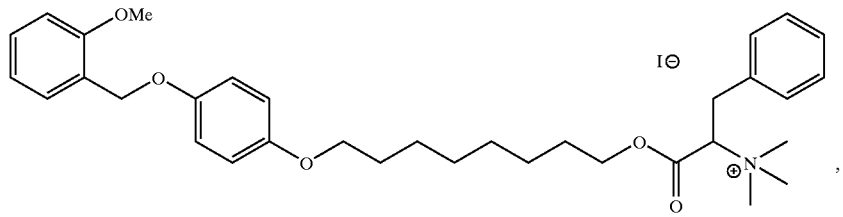
1387
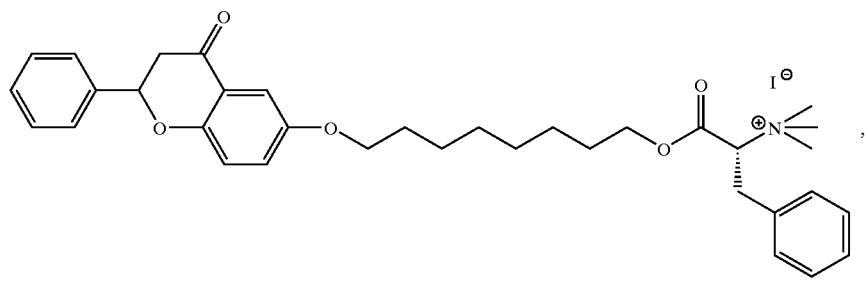
1370'
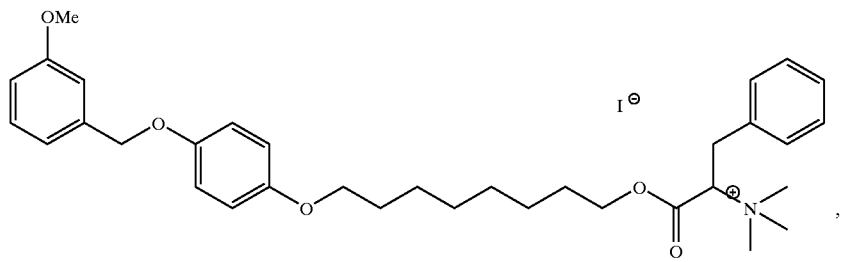
1388
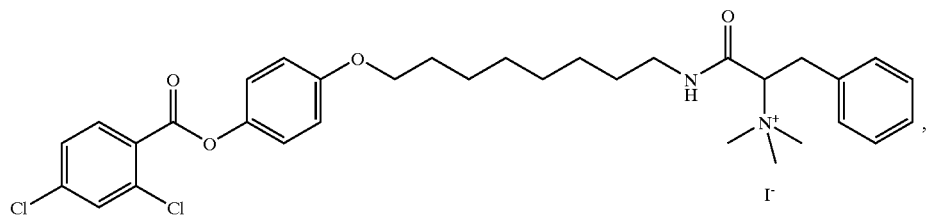
1604
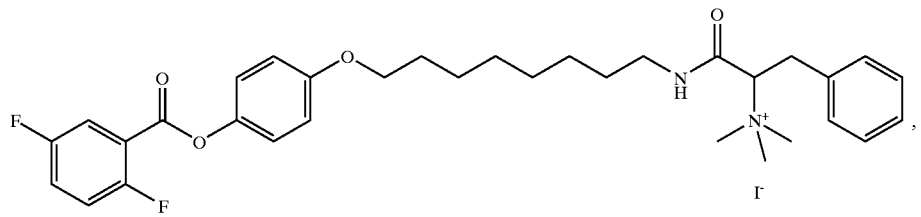
1611
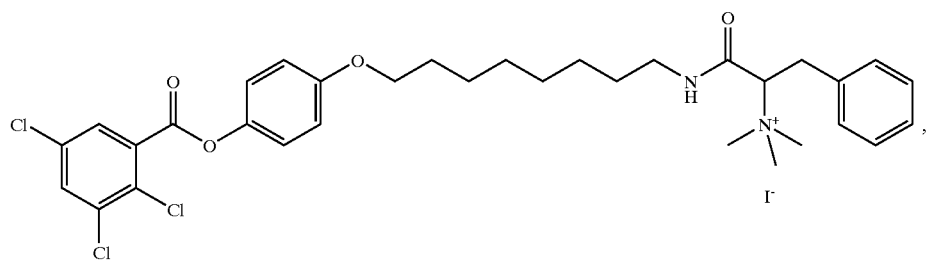
1615

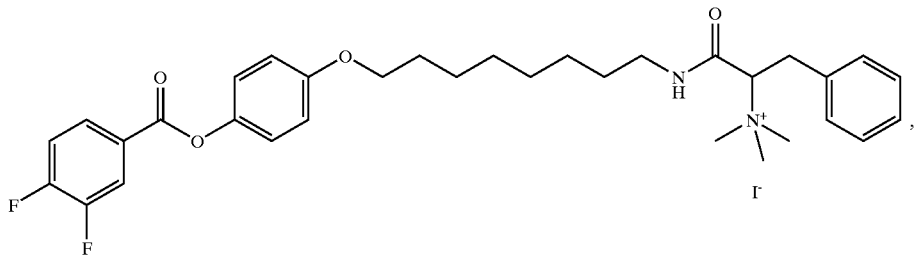
1613
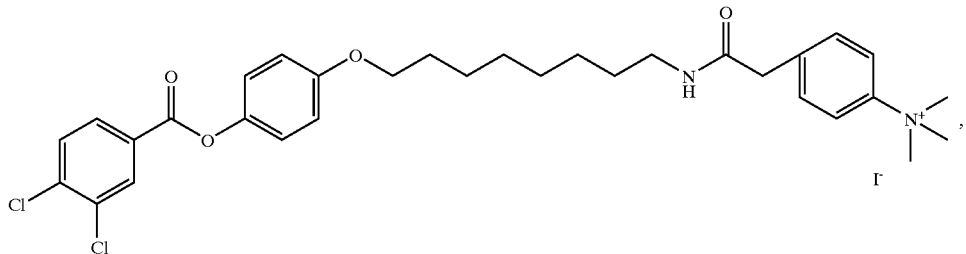
1636
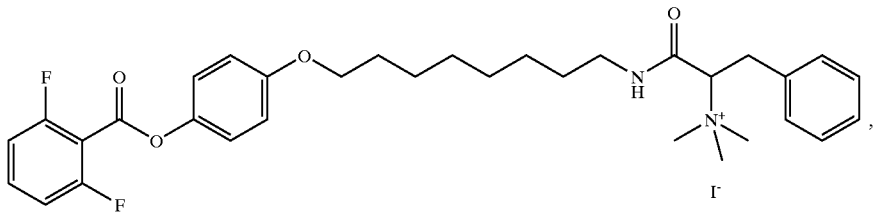
1612
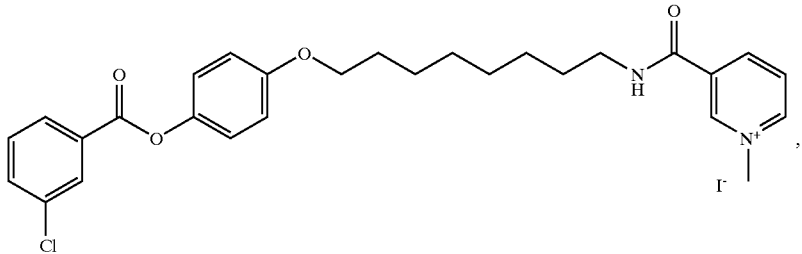
1652
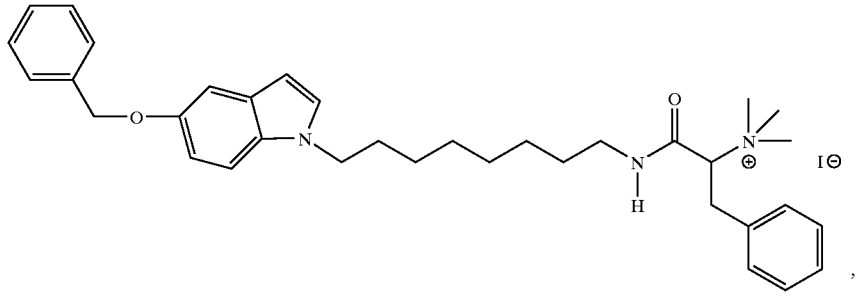
1447'
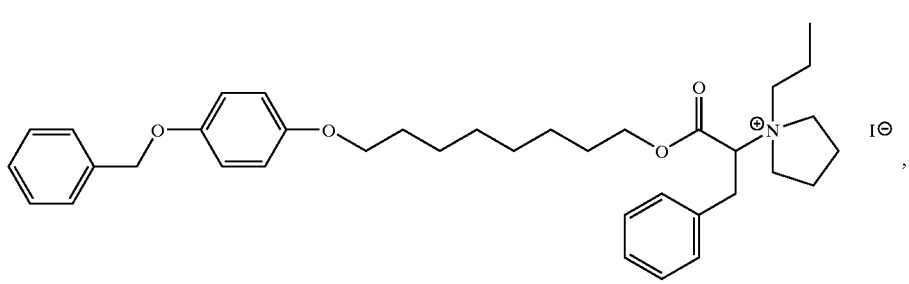
1443'

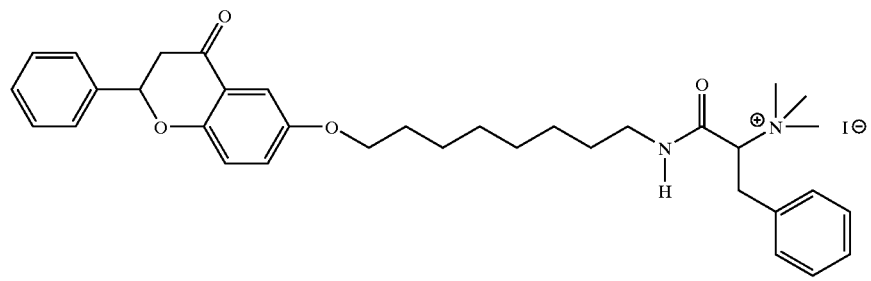
1450'
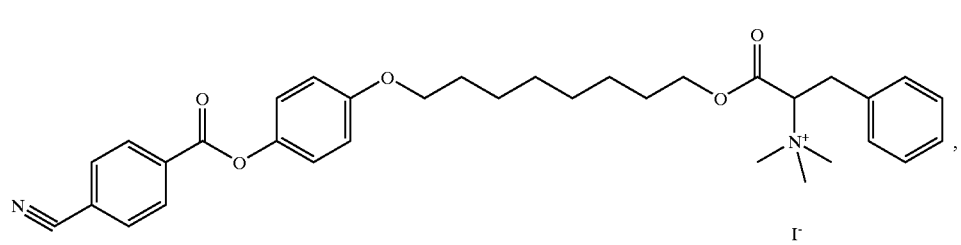
1479
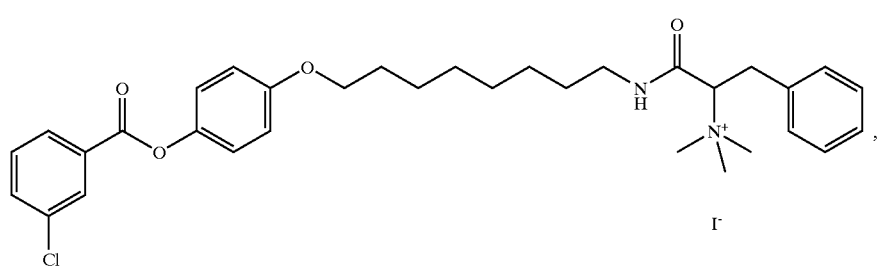
1594
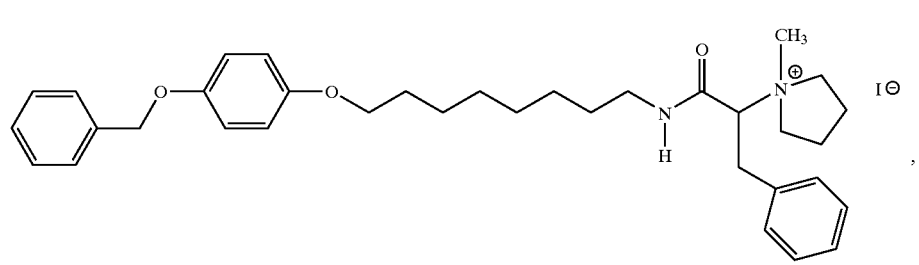
1495'
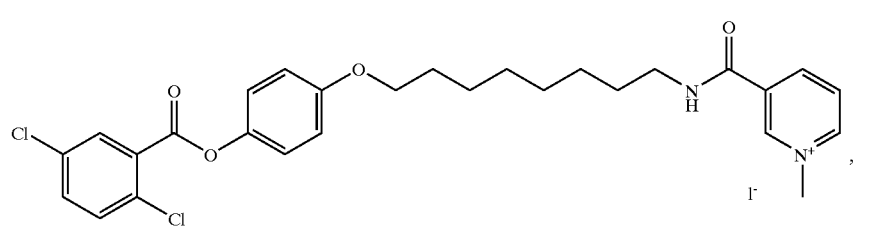
1663
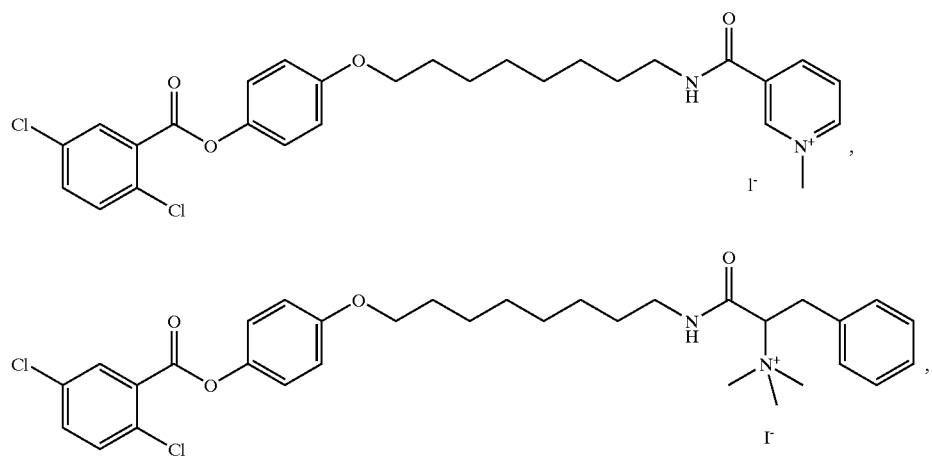
1605

-continued
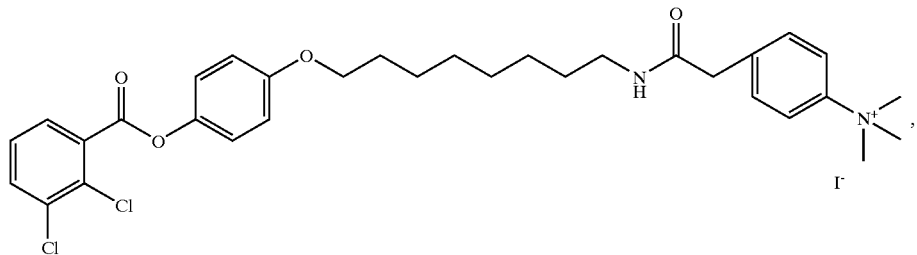
1632
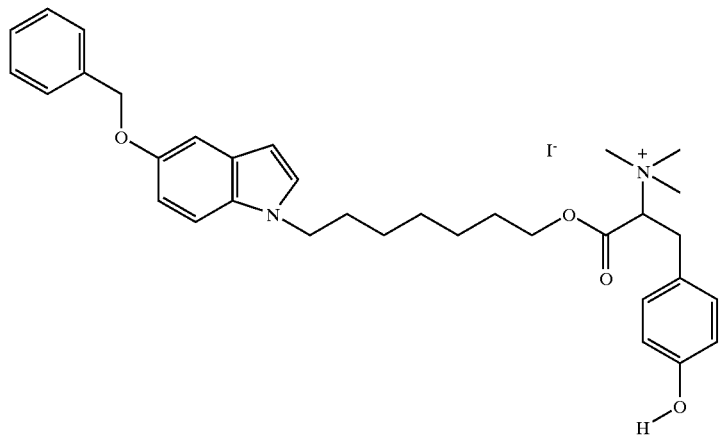
1683
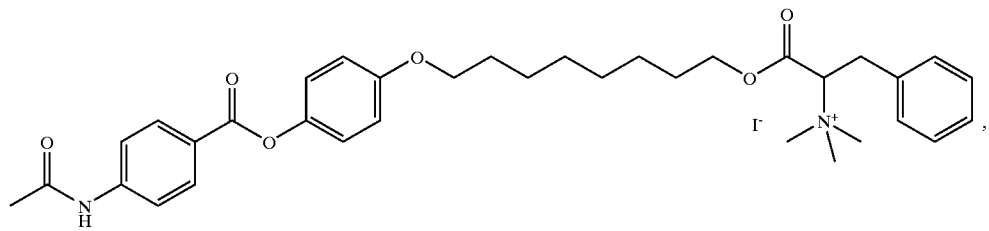
1482
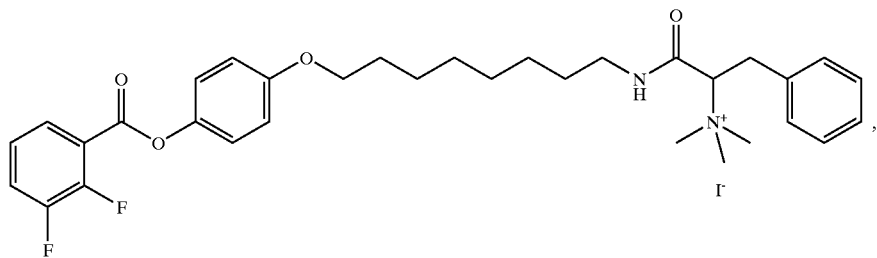
1609
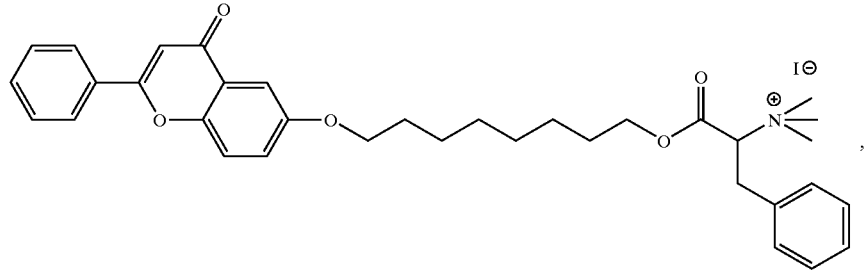
1371'

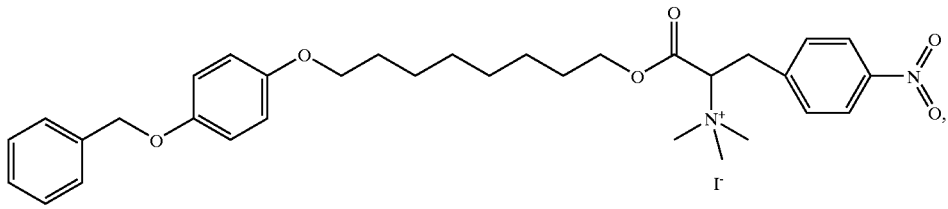 1405
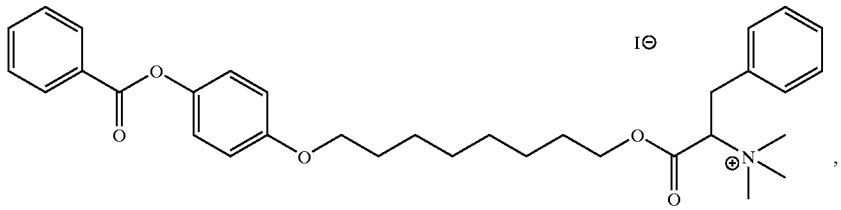 1431
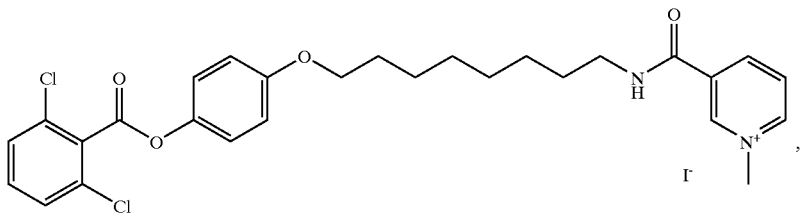 1664
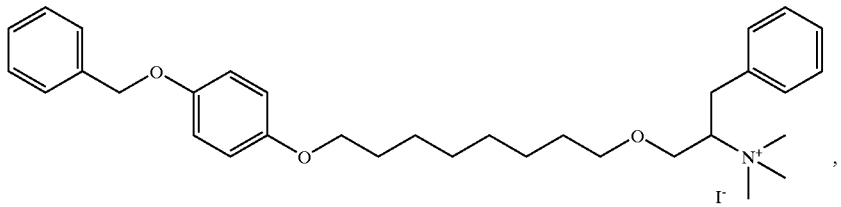 1439
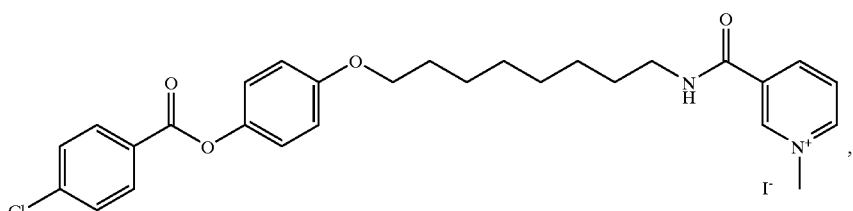 1653
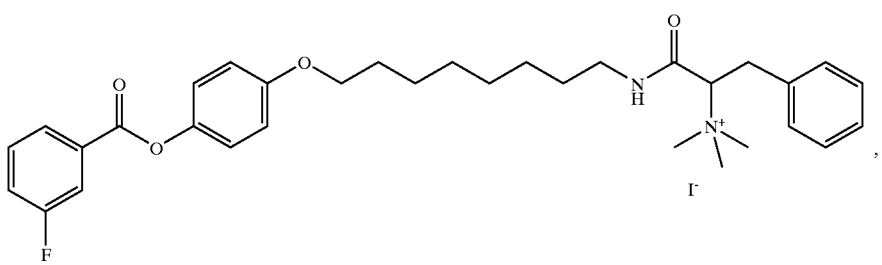 1597
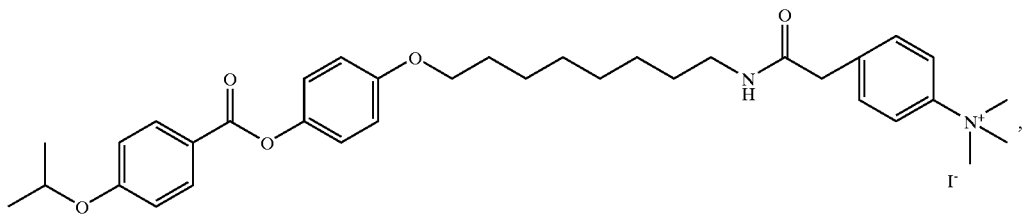 1629

-continued
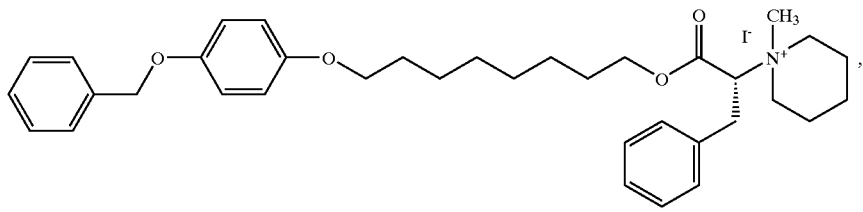
1340'
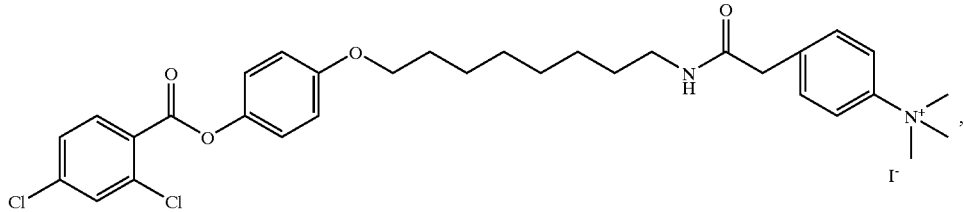
1633
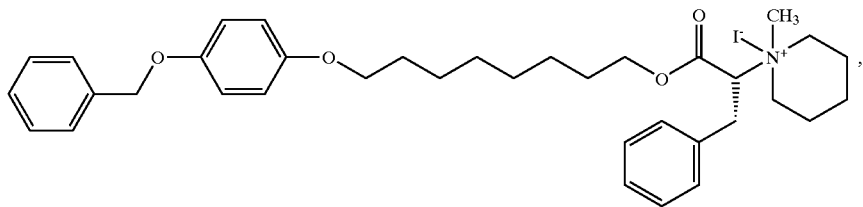
1337'
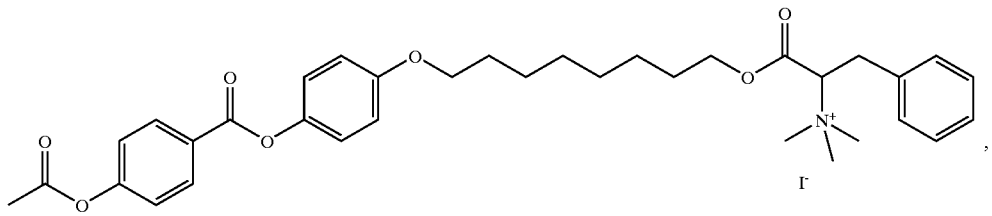
1475
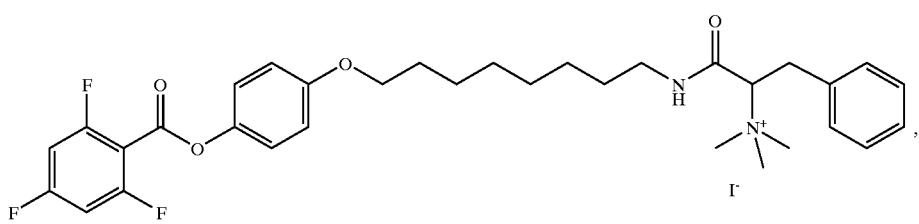
1620
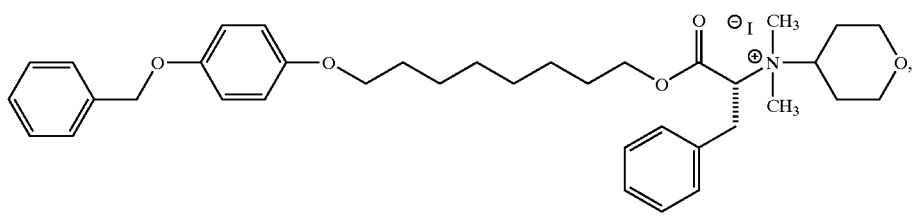
1358'
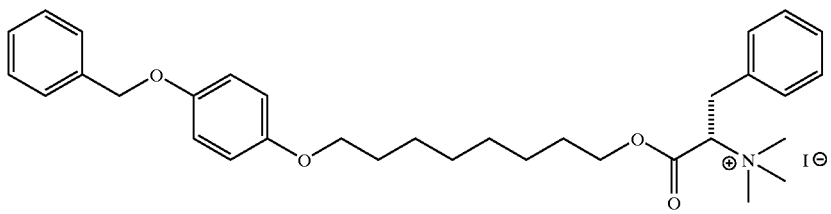
1197'

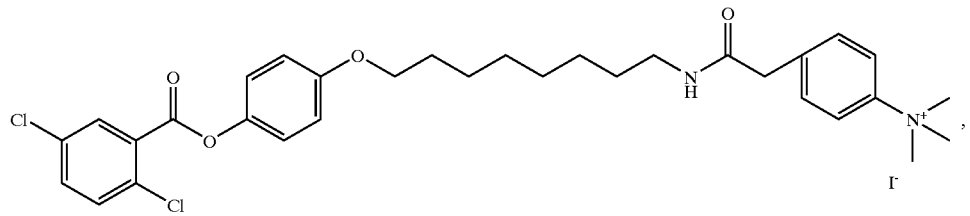
1634
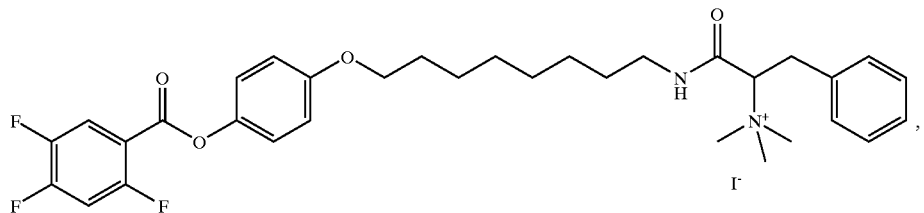
1619
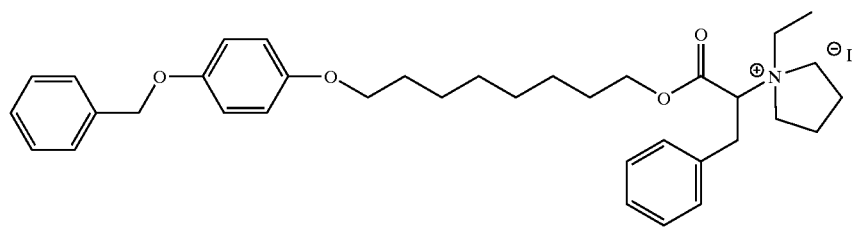
1442'
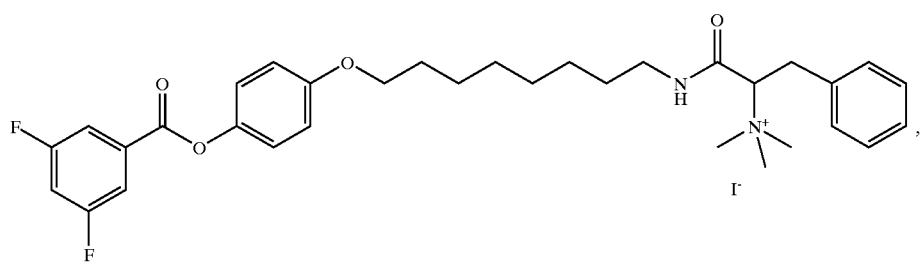
1614
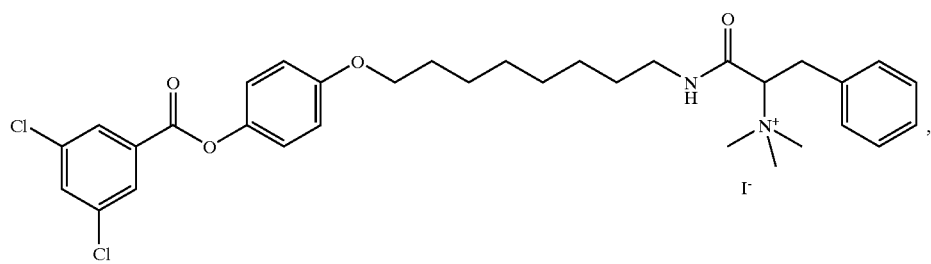
1608
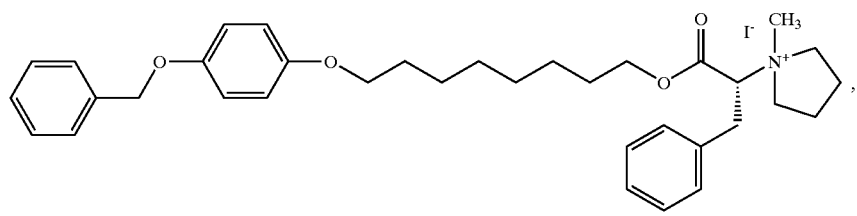
1339'

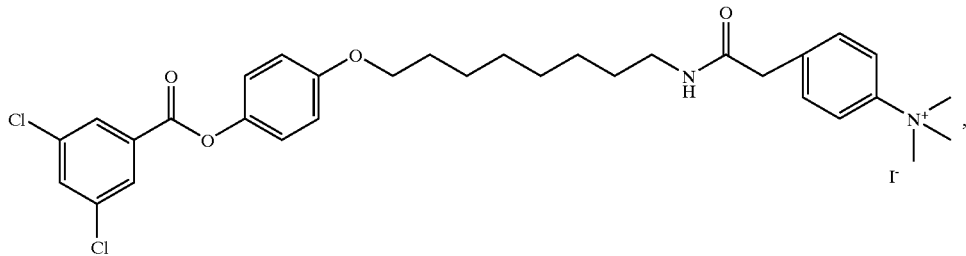
1637
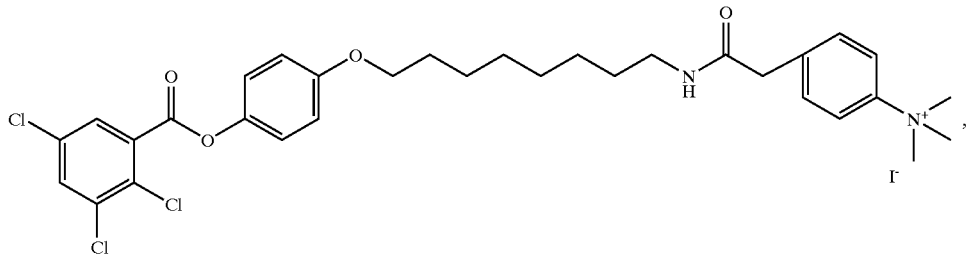
1644
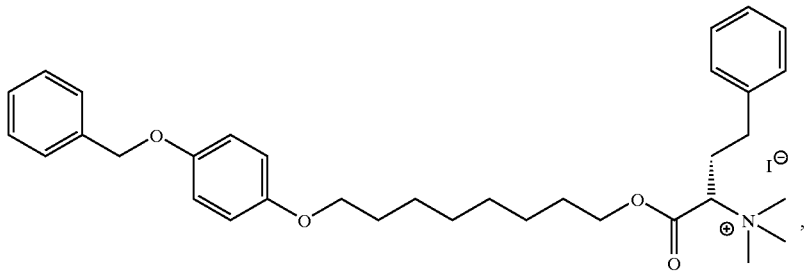
1198'
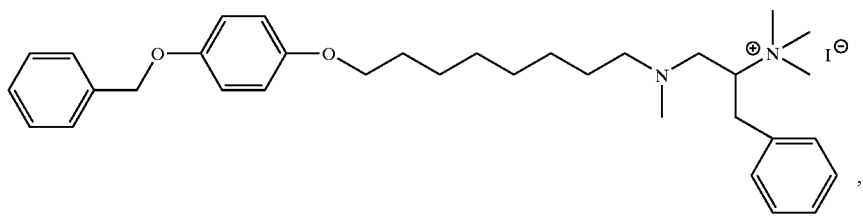
1499'
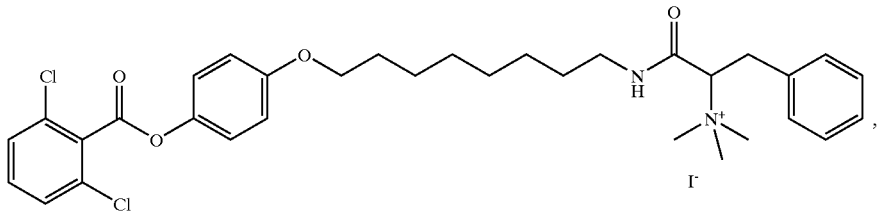
1606
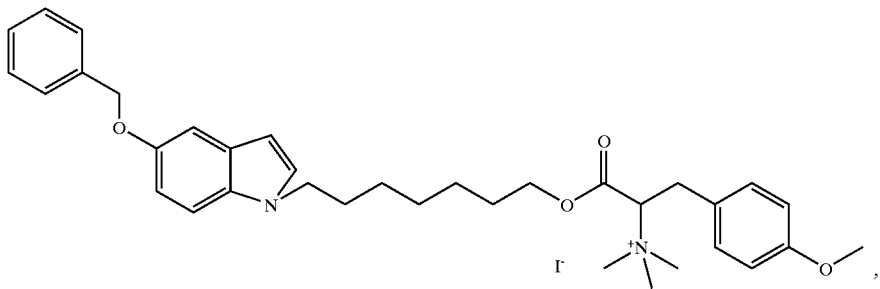
1454

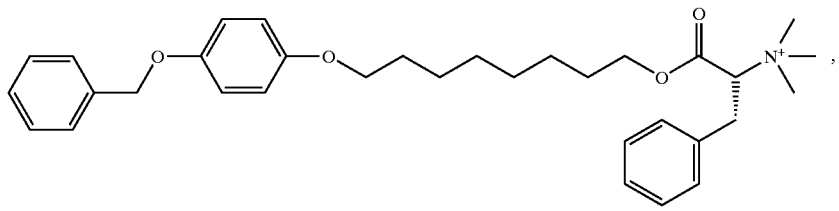
1338
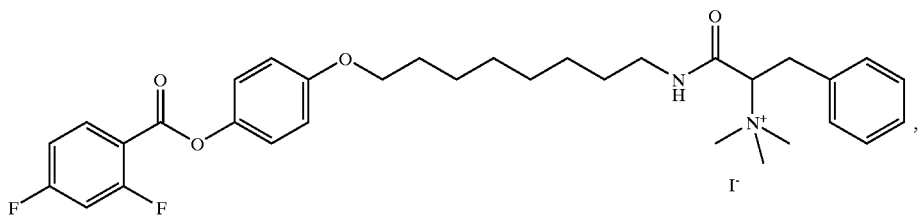
1610
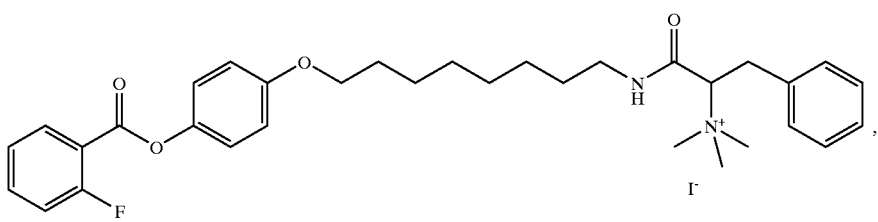
1596
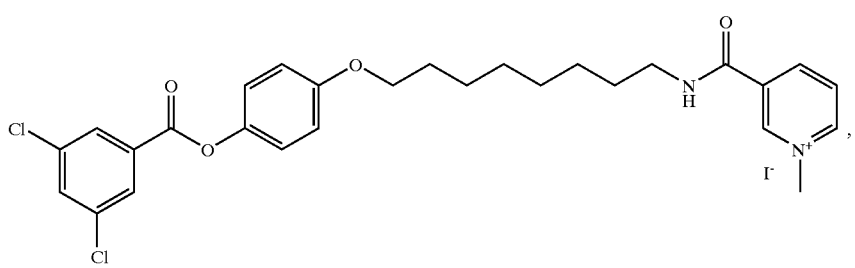
1666
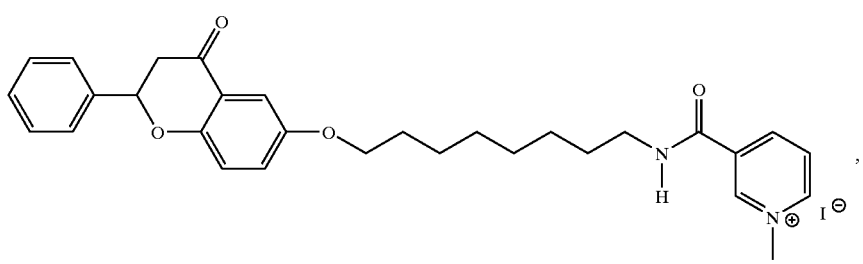
1448
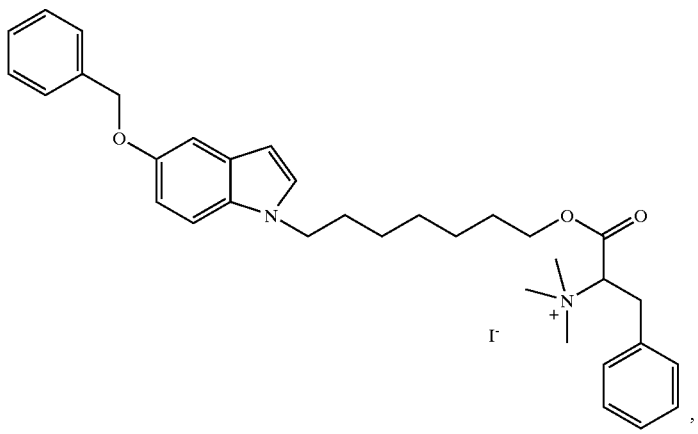
1408

-continued
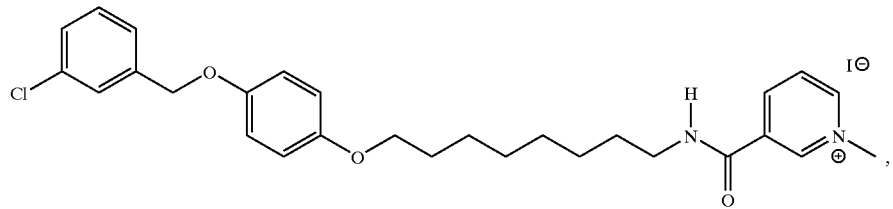
1422
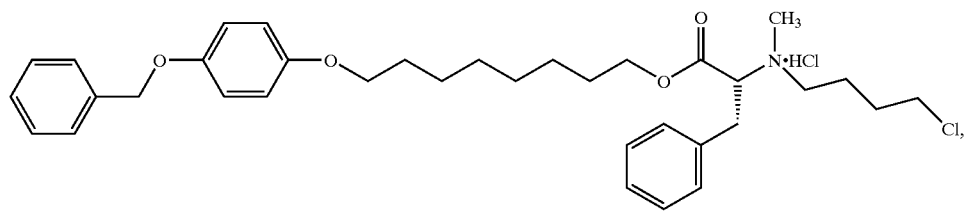
1401'
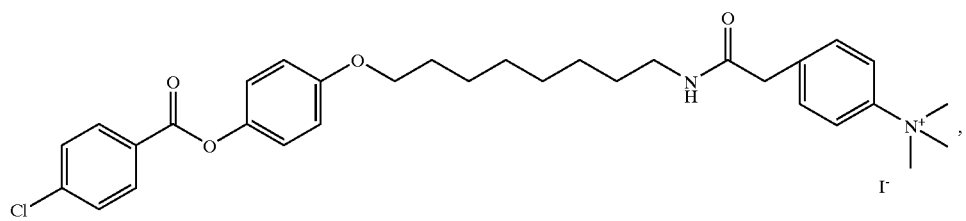
1624
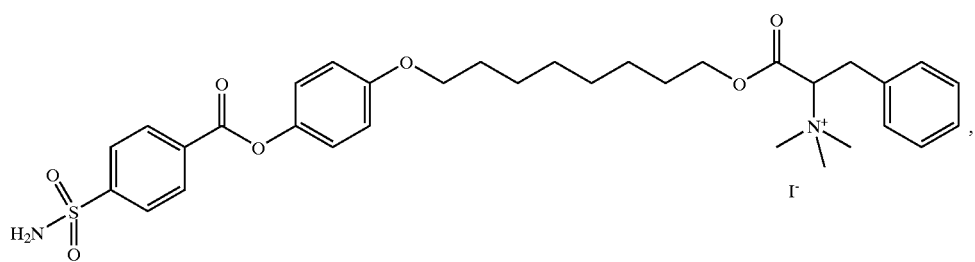
1485
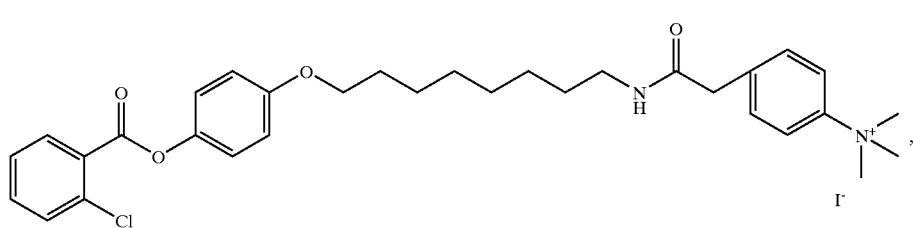
1622
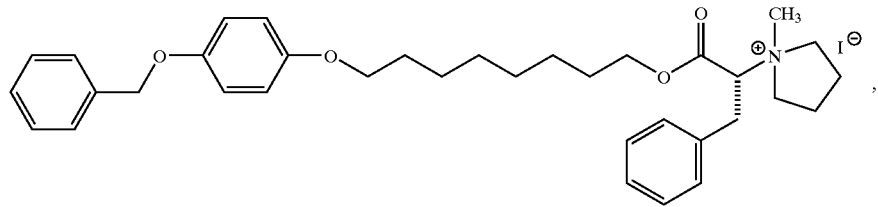
1336'
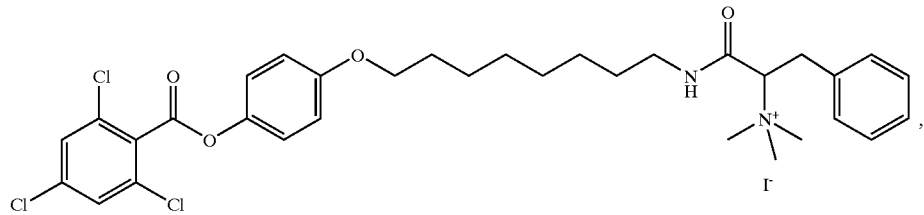
1616

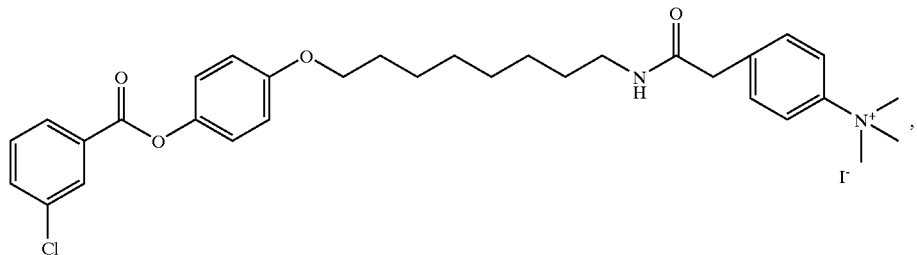
1623
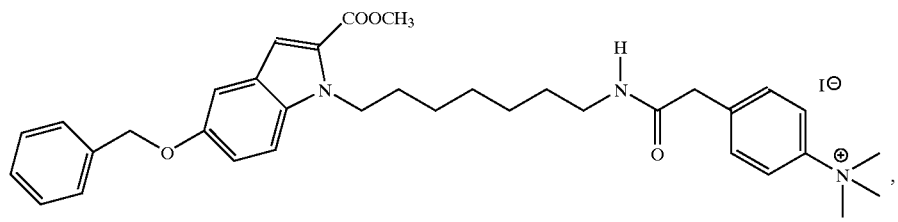
1290
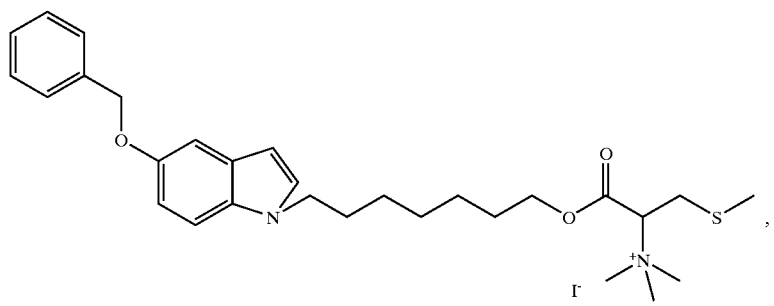
1451
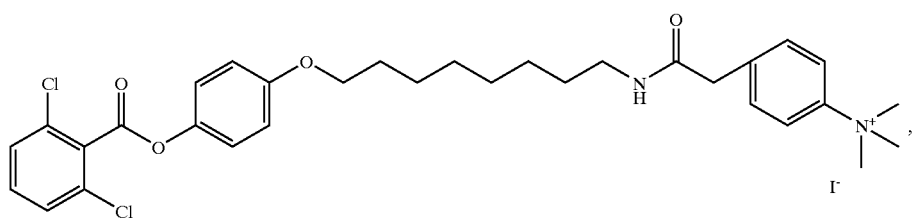
1635
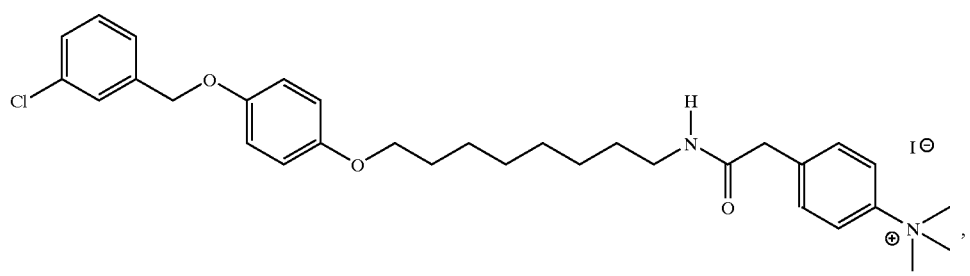
1421
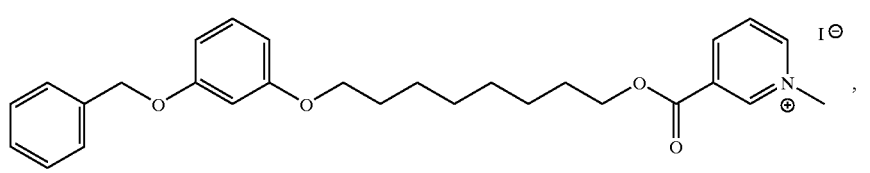
1168

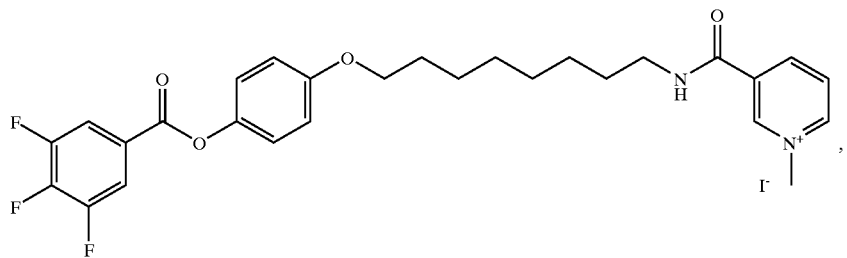
1678
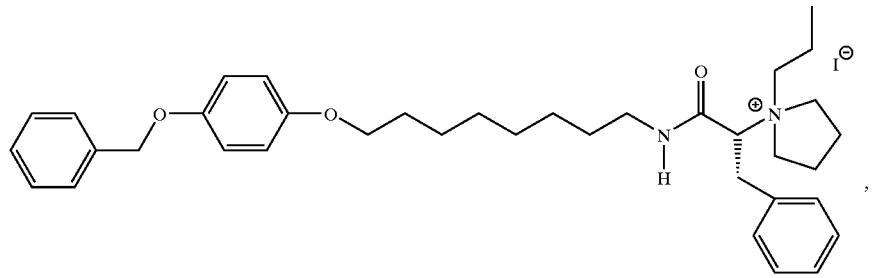
1502'
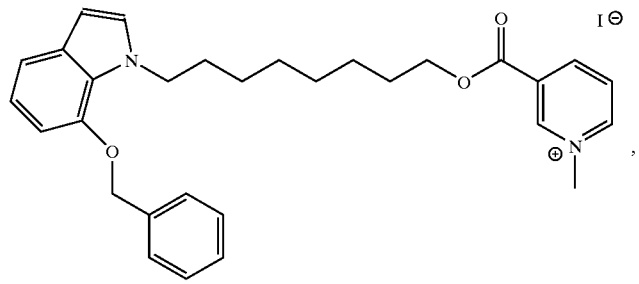
1126
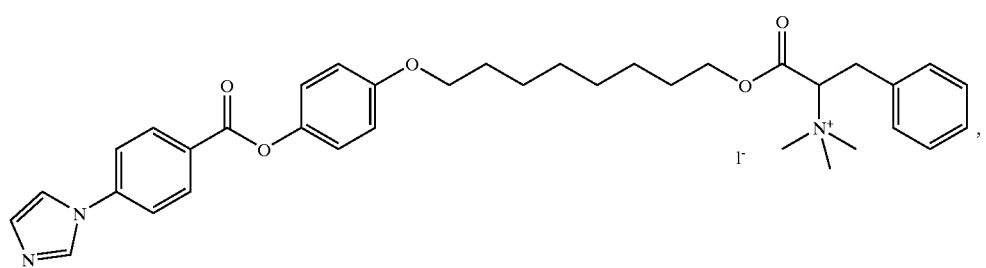
1486
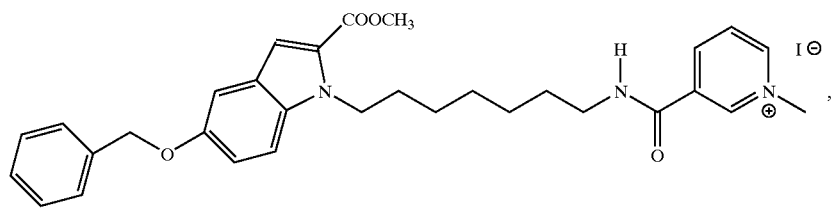
1292
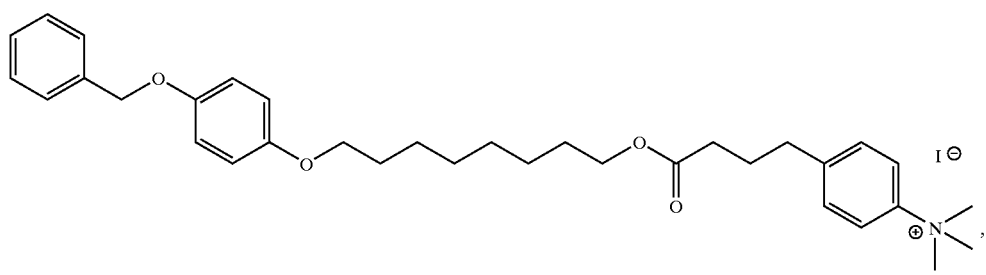
1264

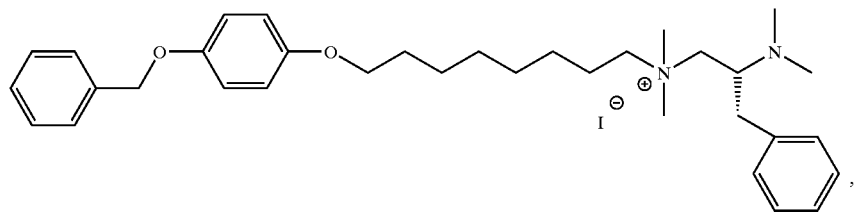 1498'
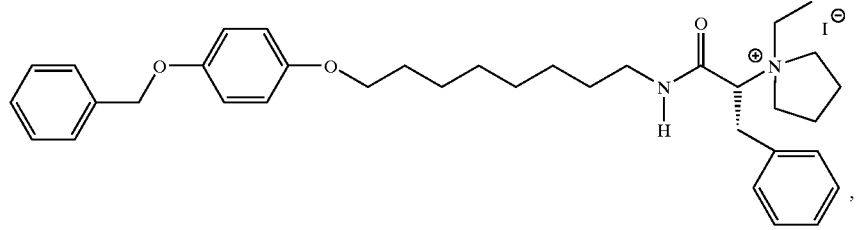 1501'
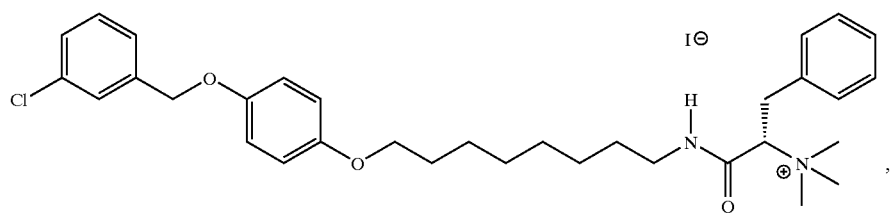 1420'
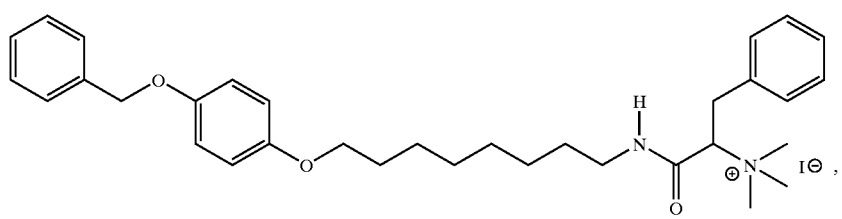 1364
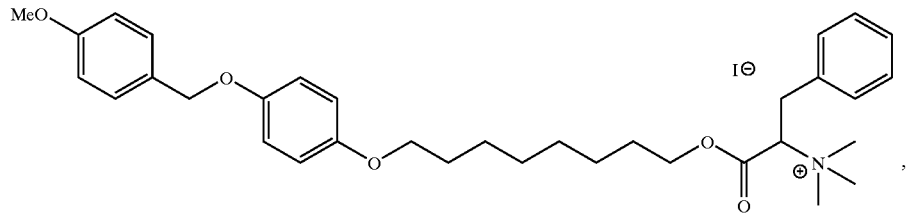 1389
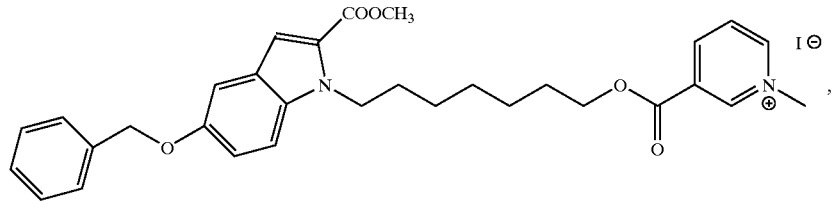 1294
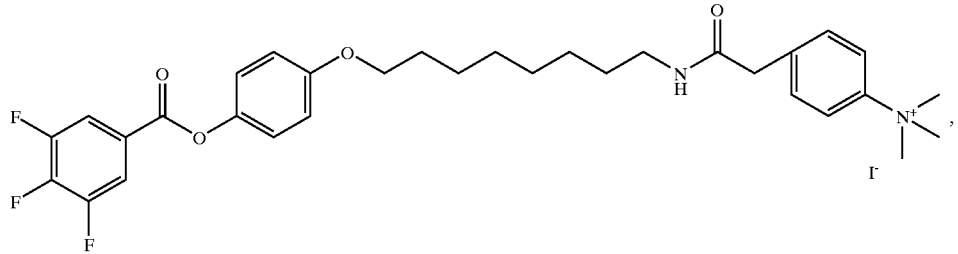 1650

-continued
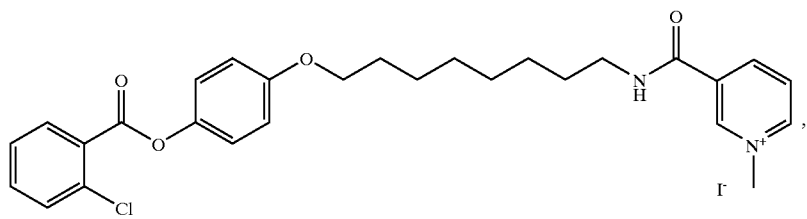
1651
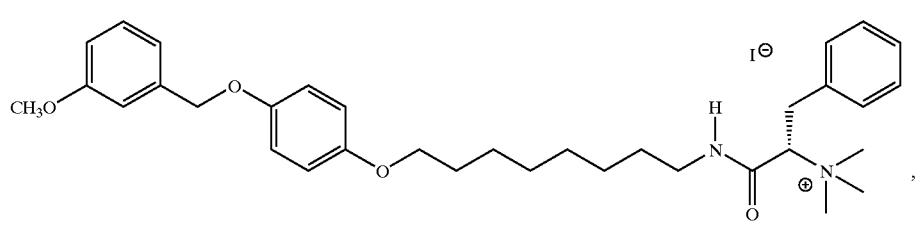
1423'
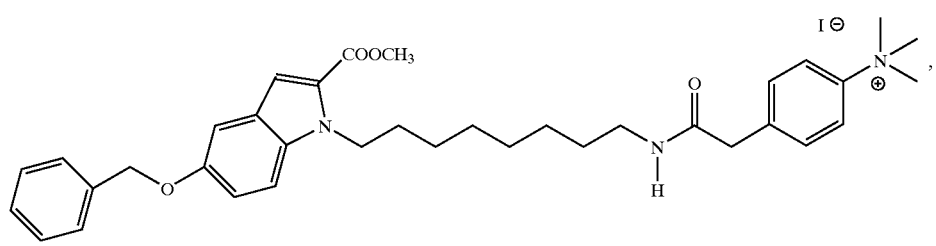
1291
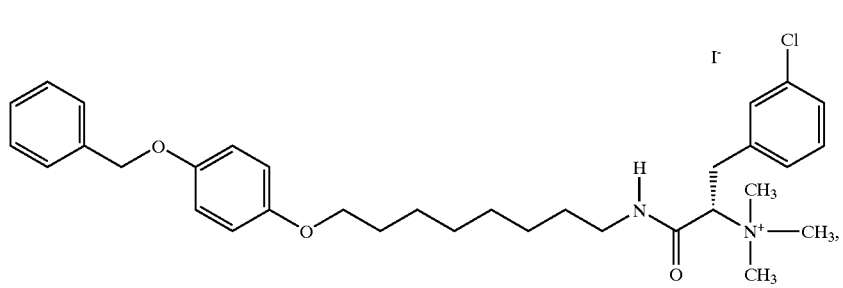
1492'
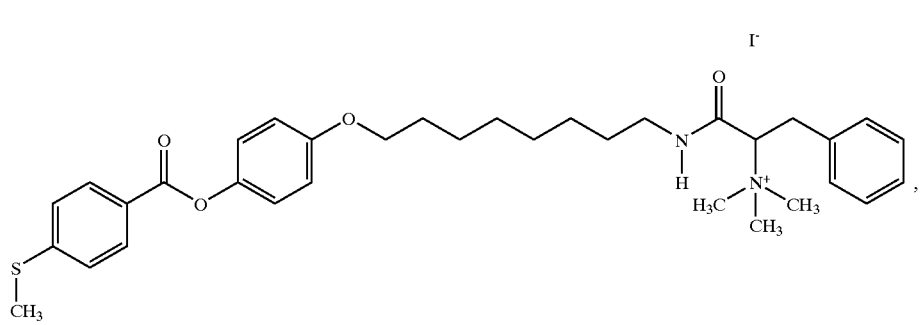
1601'
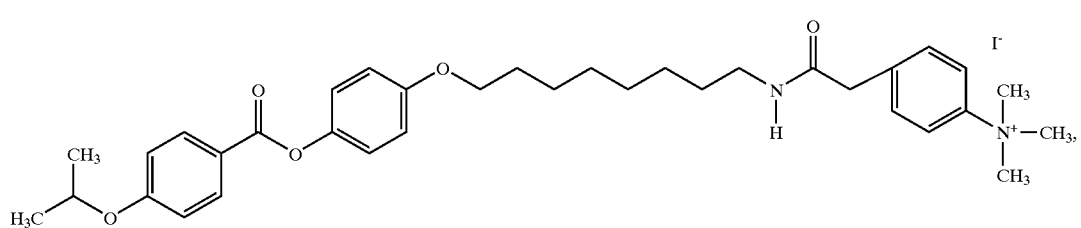
1629

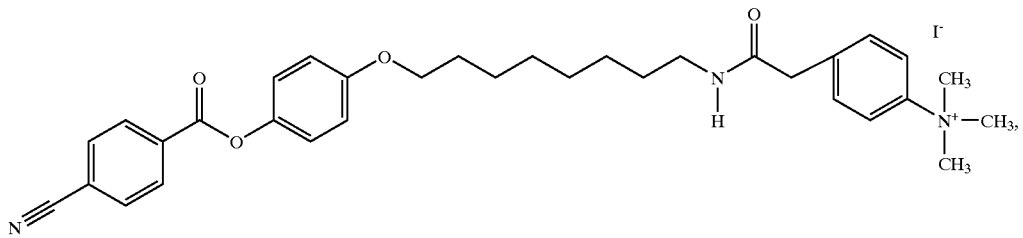
1631
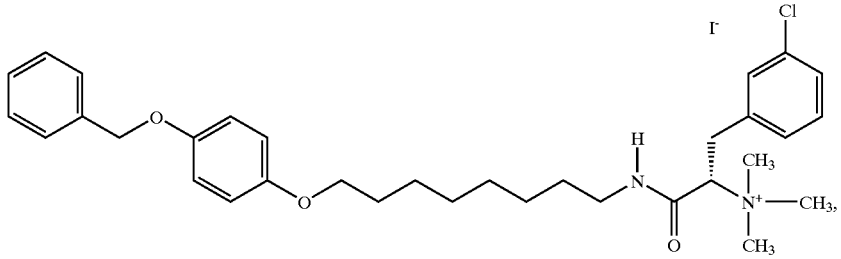
1692'
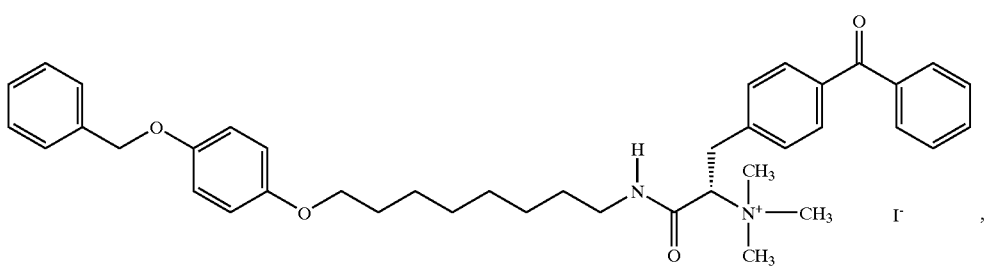
1700'
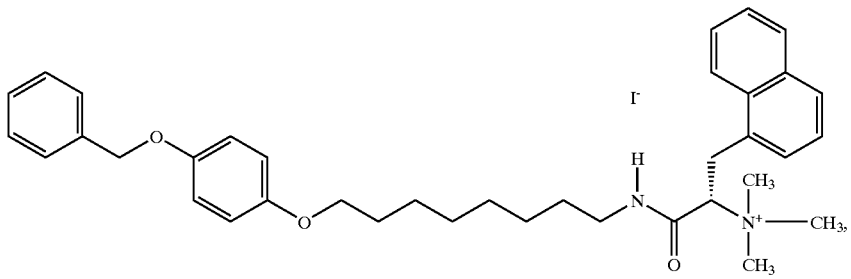
1705'
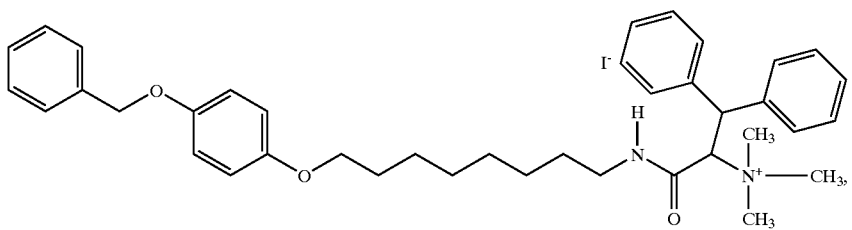
1709'
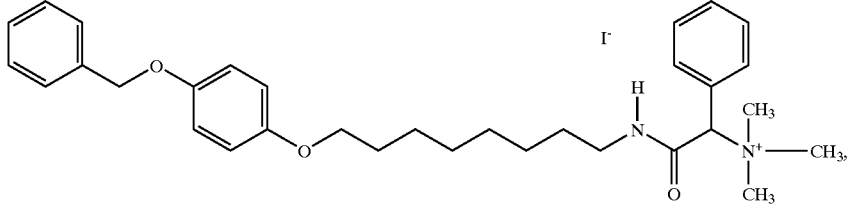
1713'

-continued
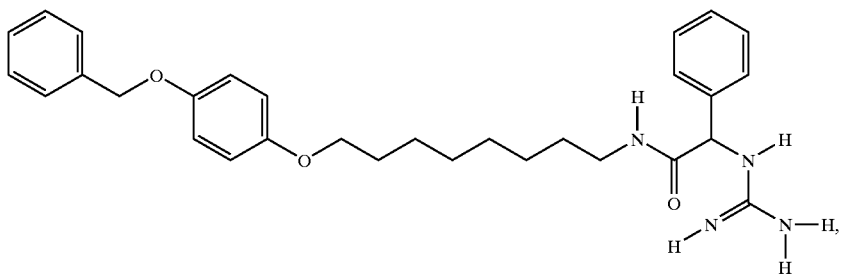
1714'
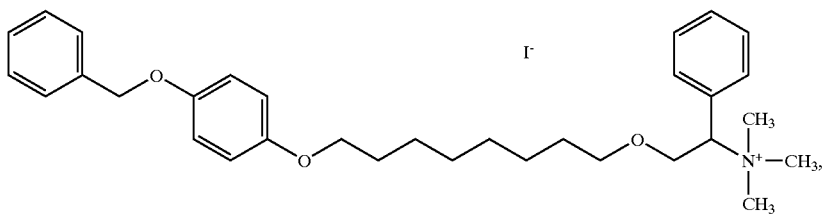
1715'
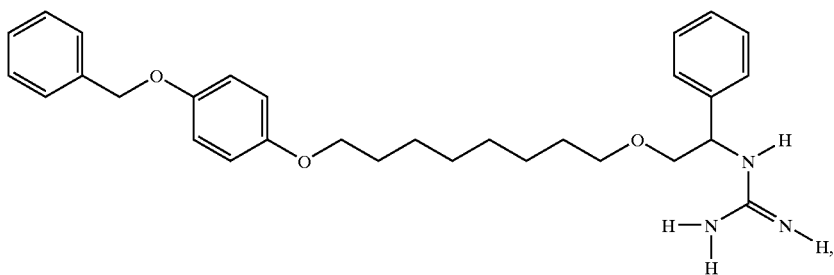
1716'
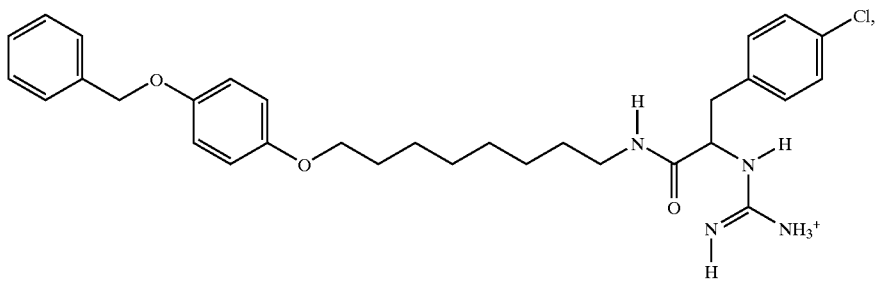
1722'
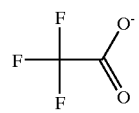
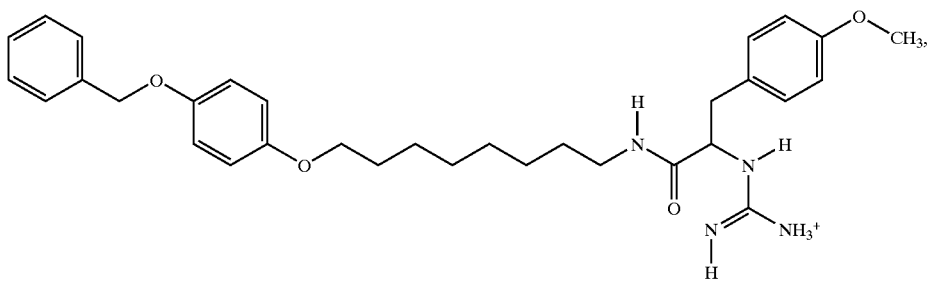
1725'
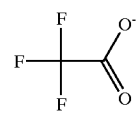

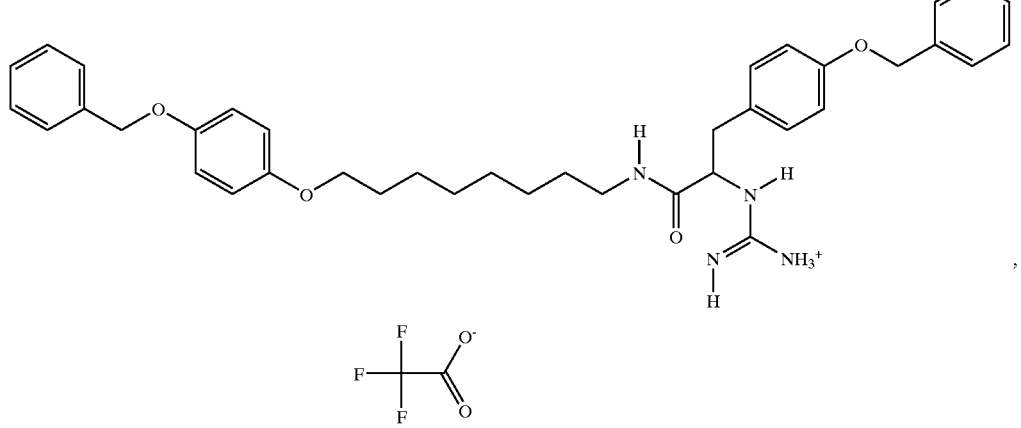
1727'
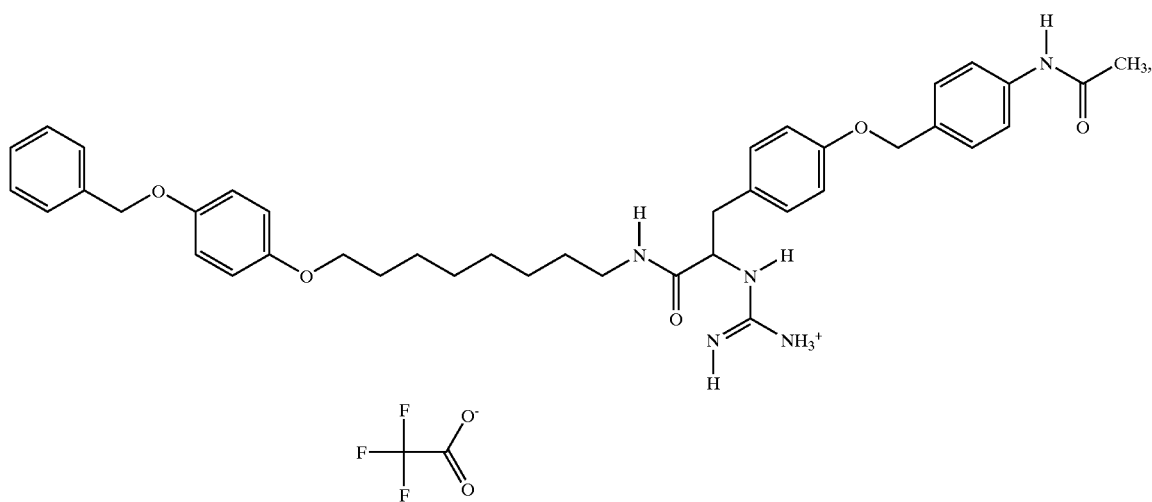
1728'
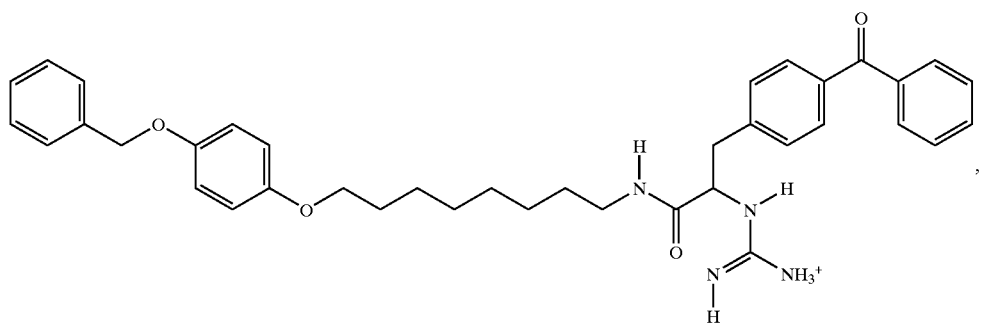
1729'

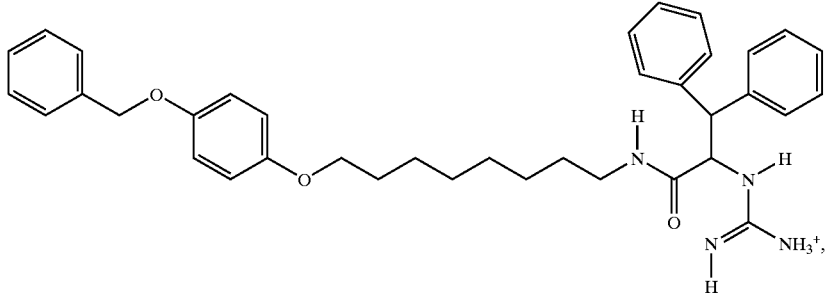
1738'
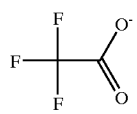
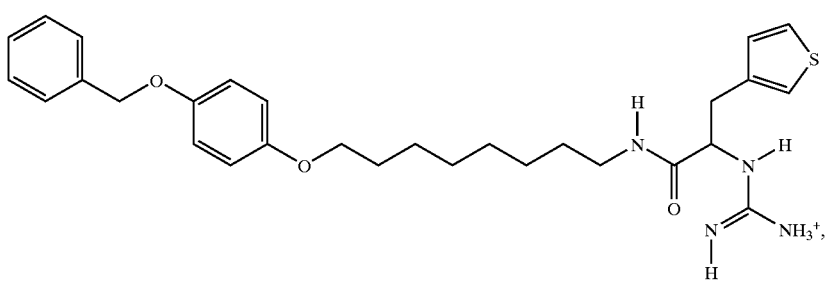
1741'
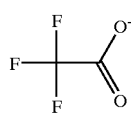
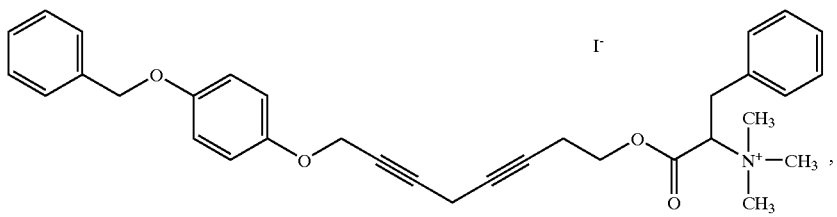
1752'
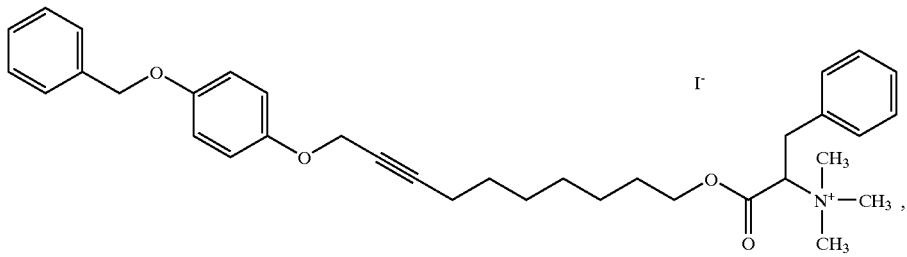
1755'
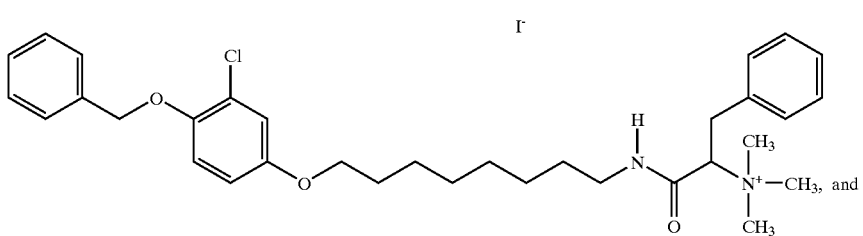
1758'

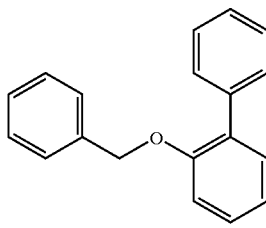
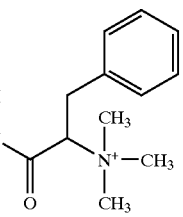

1760' wherein I⁻ is a pharmaceutically acceptable anion.

The compounds described above can have a suitable configuration if an asymmetric center is present. Thus, the compounds may be in R, S, or a mixture of R and S forms.

Further, in the compounds described above, the amino acids employed may be the natural (L) form or the unnatural (D) form.

Embodiments of the above compounds of formula (I) include:

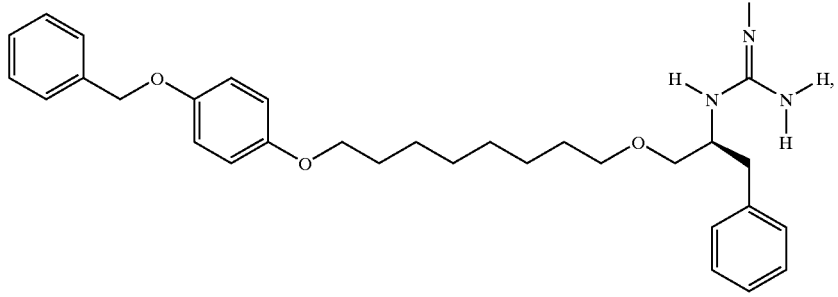

1679

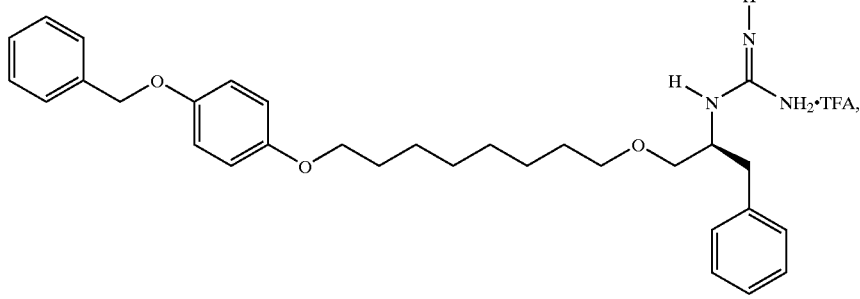

1680

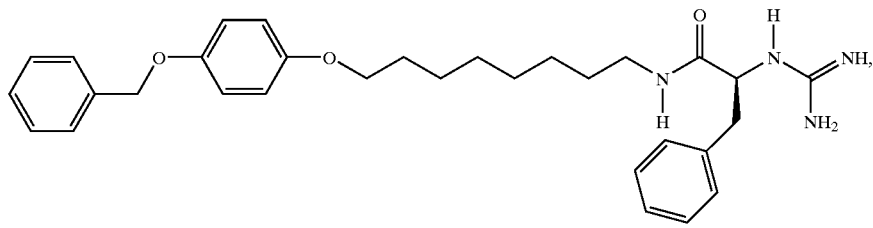

1681

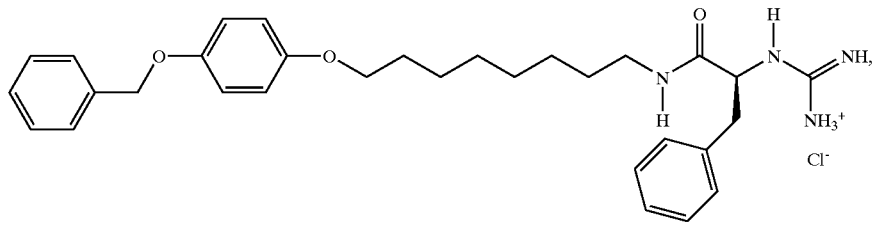

1682

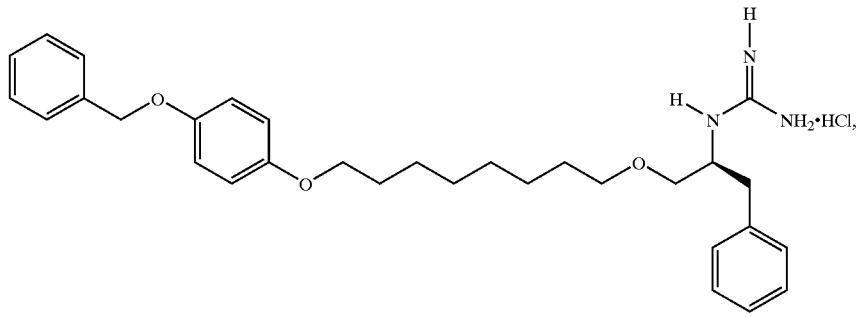
1685
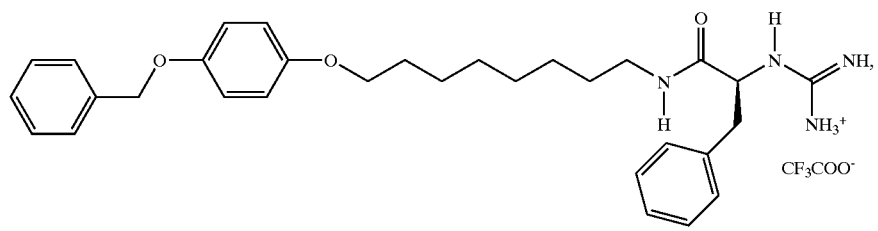
1503
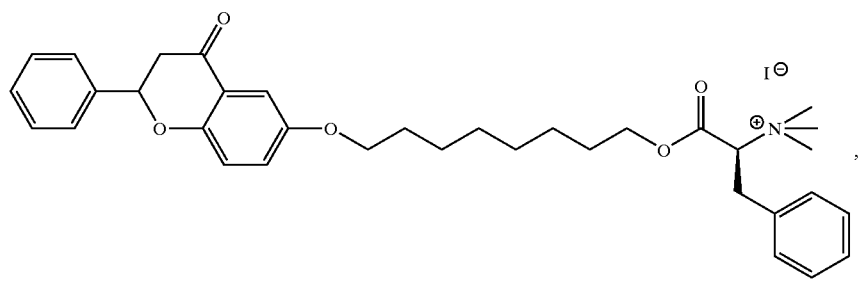
1370
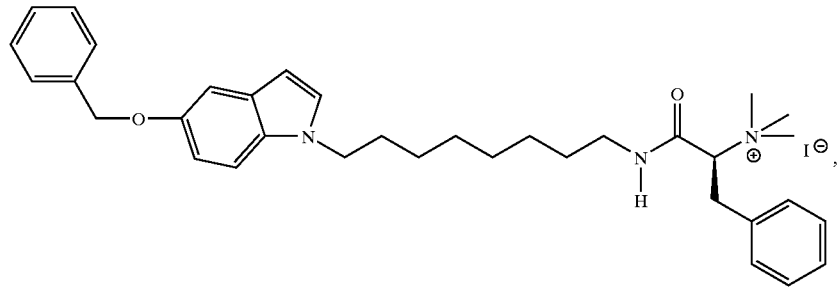
1447
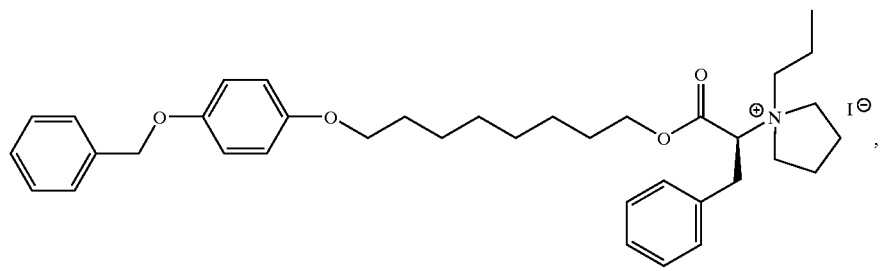
1443'

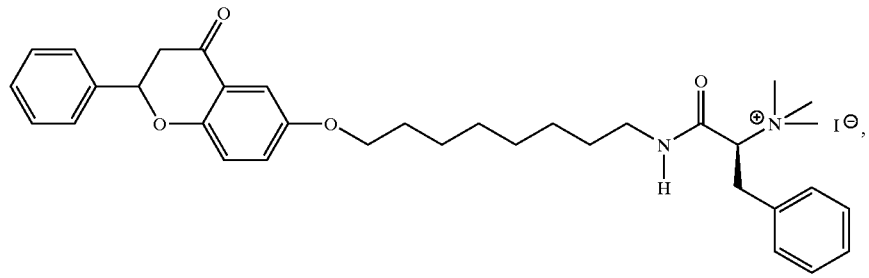
1450′
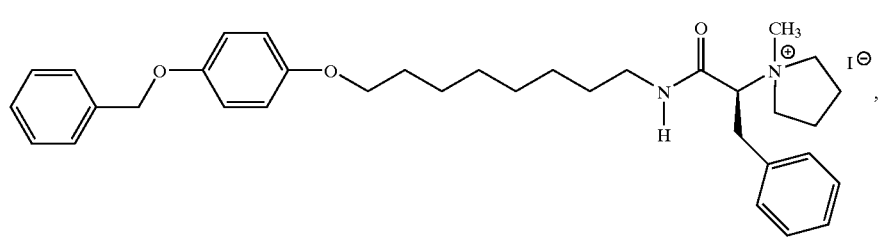
1495′
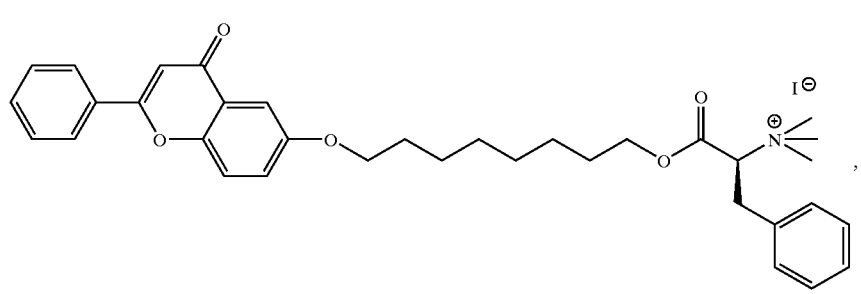
1371
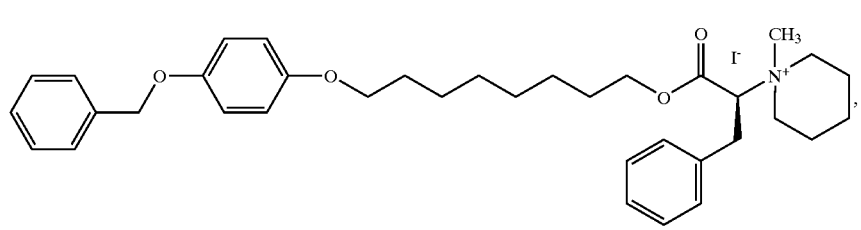
1337
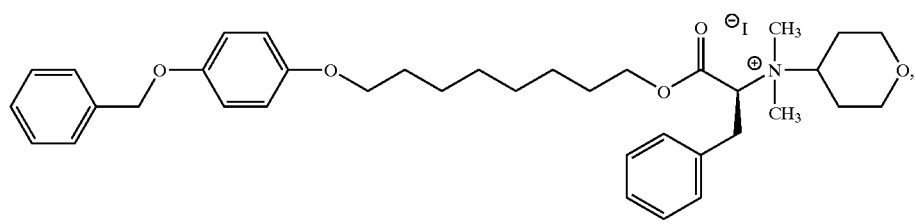
1358
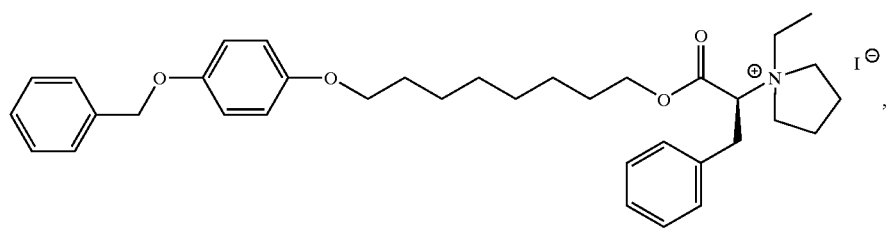
1442

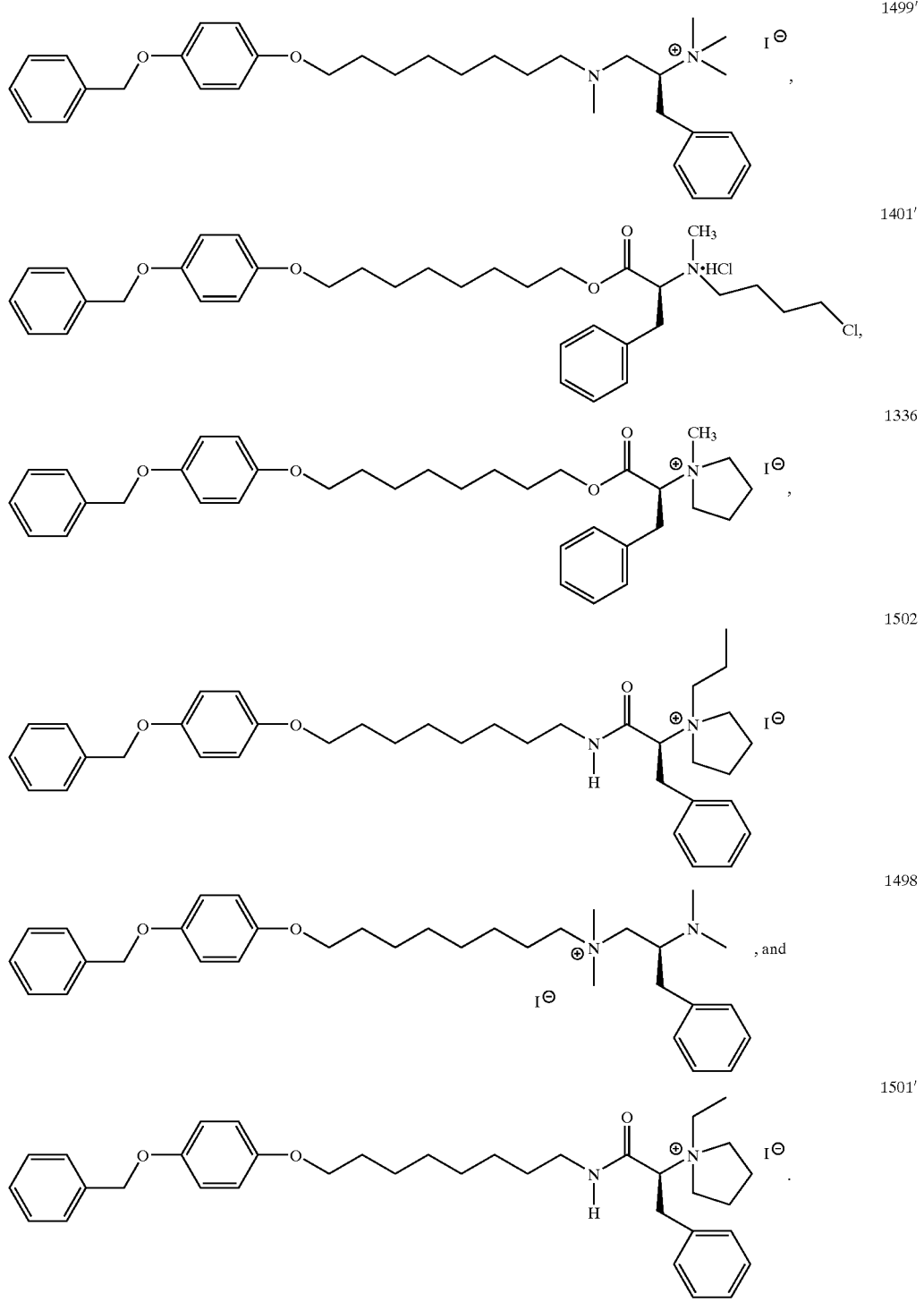

The present invention provides in another embodiment, a compound of the formula A—B—(CH$_2$)$_n$—O—CO—CH$_2$—Ph (NMe$_3$)$^+$I$^-$, wherein A is a phenyl or indole, optionally substituted with a benzyloxy group; B is a covalent bond or oxygen atom, and I$^-$ is a pharmaceutically acceptable anion. For example, A is a phenyl group substituted with benzyloxy, chlorobenzyloxy, or methoxybenzyloxy group. The chloro or methoxy group can be in any of ortho, para, or meta positions. In embodiments, the chloro or methoxy group is in the ortho or para position. A further example includes a compound where A is an indole substituted with benzyloxy.

Specific examples of the compounds of the above embodiment of the present invention include compounds selected from the group consisting of:

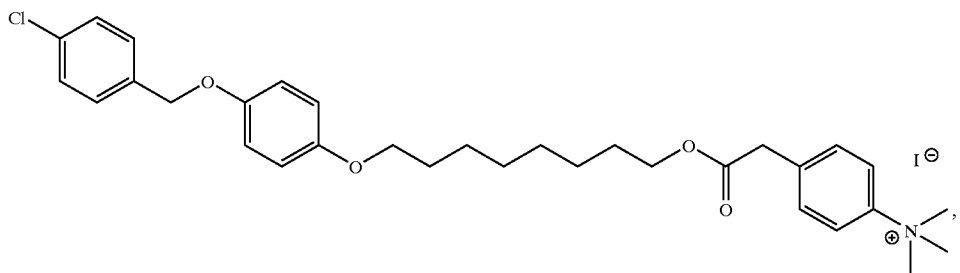
1398
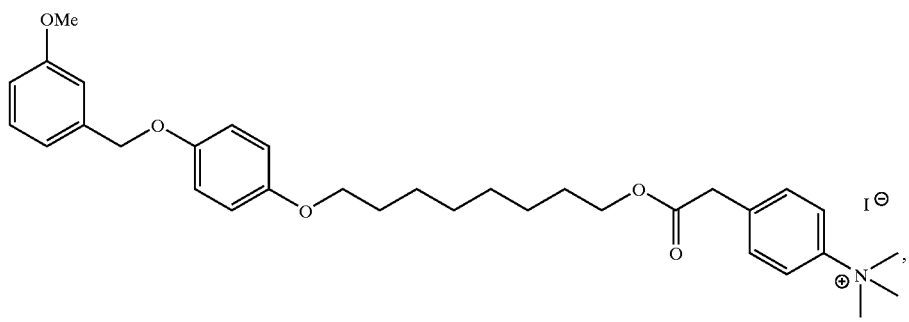
1394
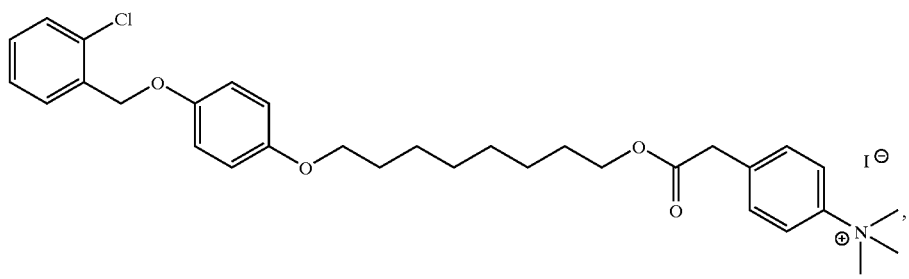
1396
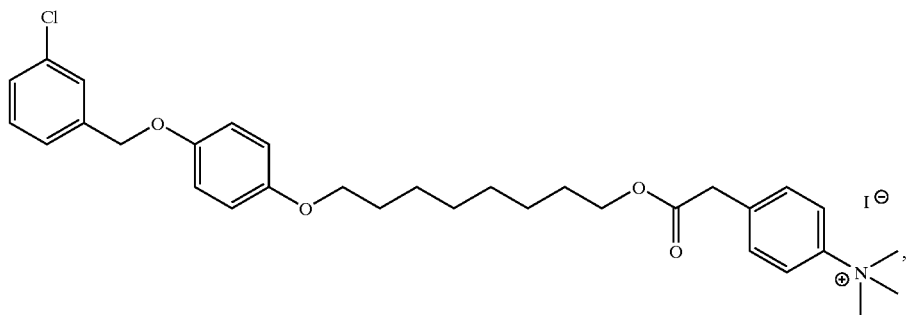
1397
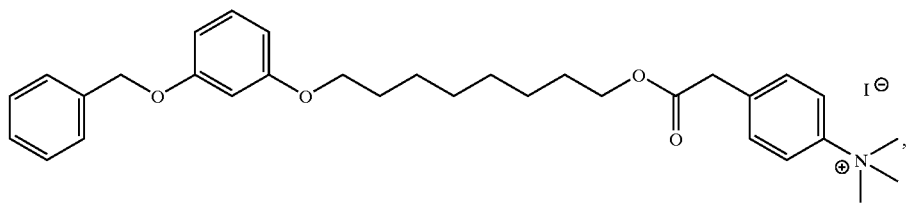
1169

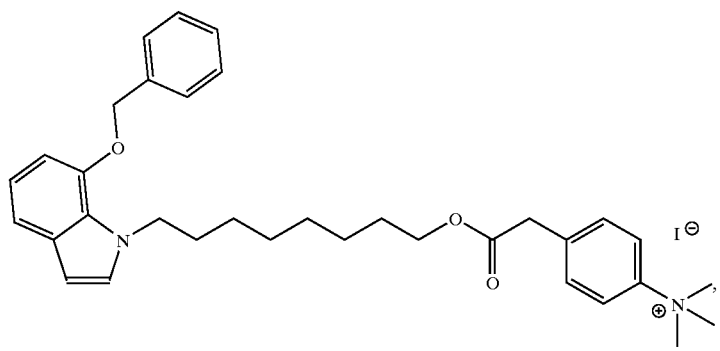
1127
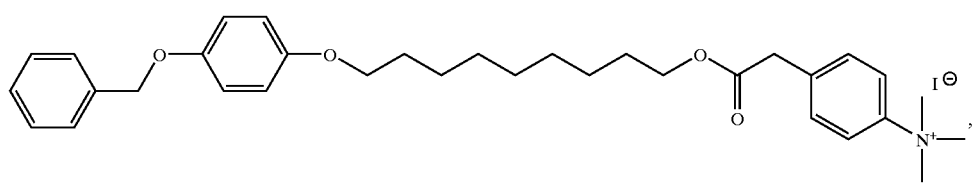
1321
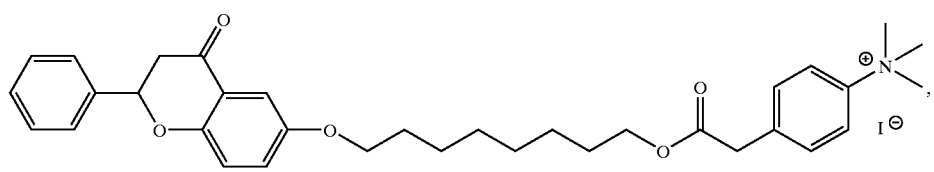
1369
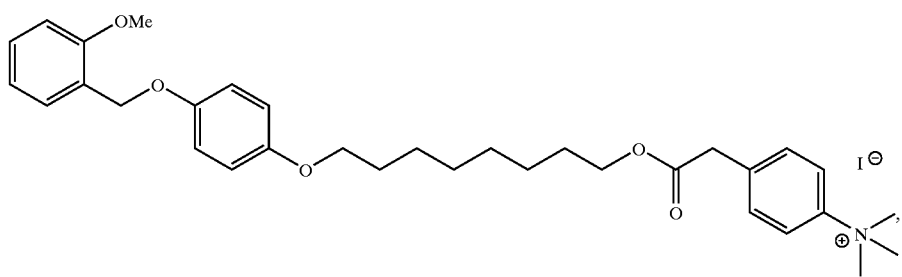
1393
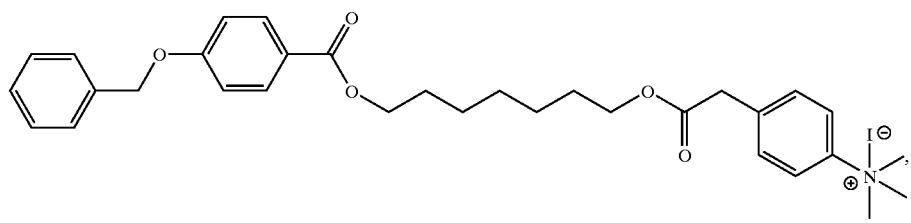
1359
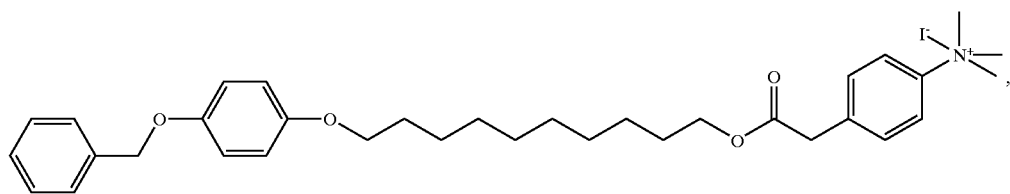
1322

-continued

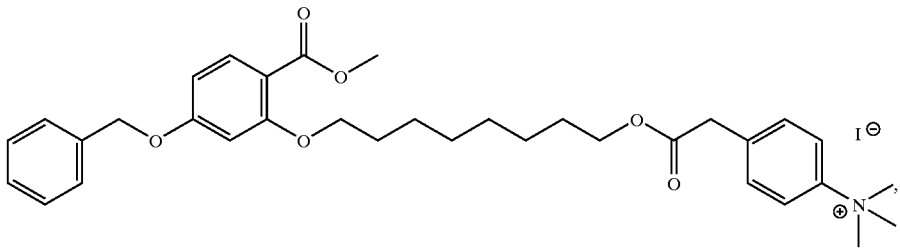
1182

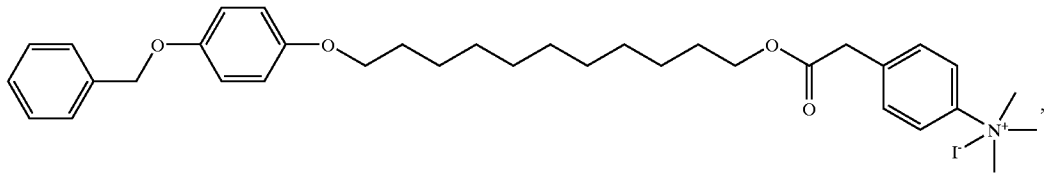
1323

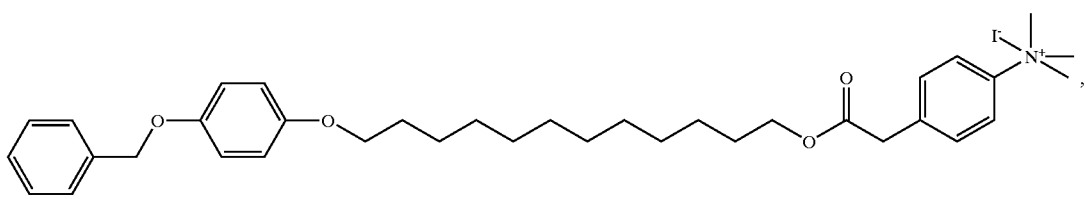
1324

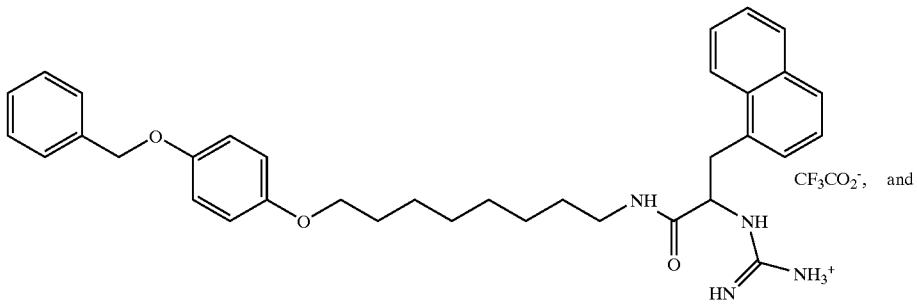
1734

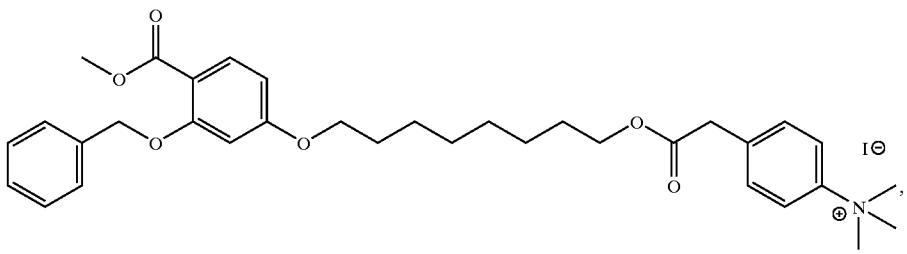
1186 wherein I⁻ is a pharmaceutically acceptable anion.

In a preferred embodiment, the inhibitor of NAD synthetase has the Structure 2':

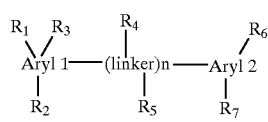

Structure 2' wherein Aryl 1 is indolyl or phenyl; Aryl 2 is phenyl, pyridinyl, indolyl, or quinolinyl; and the linker is $-(CH_2)_n-$, $-(CH_2)_n-O-C(=O)-$, $-O(CH_2)_n-O-C(=O)-$, $-(CH_2)_n-O-C(=O)CH_2-$, or $-O(CH_2)_n-O-C(=O)CH_2-$.

For example, in Structures 2, 2', and 4, $R_1-R_3$ are independently selected from the group consisting of H, aryloxy, hydroxyaryl, aryl $C_1-C_6$ alkoxy, $C_1-C_6$ alkoxy, $C_1-C_6$ alkoxycarbonyl, $C_1-C_6$ alkyl, $C_1-C_6$ alkylcarbonyl, arylcarbonyl, nitro, halo, carboxy, halo $C_1-C_6$ alkyl, perhalo $C_1-C_6$ alkyl, triphenymethoxy, phenylcarbonylamino, $C_1-C_6$ alkoxycarbonyl $C_2-C_6$ alkenyl, arylcarbonyl $C_2-C_6$ alkenyl, benzofuranyl carbonyl, $C_1-C_6$ alkylbenzylfuranyl carbonyl, arylaminocarbonyl, arylcarbonyloxy, aminocarbonyl, $C_1-C_6$ alkoxycarbonylamino, phthalidimido, morpholino, pyrrolidinyl, phenylhydantoinyl, and acetylpiperazinyl; and $R_6-R_7$ are independently selected from the group consisting of H, $C_1-C_6$ alkylamino, $C_1-C_6$ dialkylamino, $C_1-C_6$ trialkylammonium, $C_1-C_6$ N-alkyl, and $C_1-C_6$ alkoxycarbonyl. In an embodiment, $R_3-R_4$ are independently H.

In some embodiments, Aryl 1 is indolyl. In some other embodiments, Aryl 1 is phenyl. In certain embodiments, Aryl 2 is phenyl. In certain other embodiments, Aryl 2 is pyridinyl. In further embodiments, Aryl 2 is quinolinyl. In other embodiments, Aryl 2 is indolyl.

In certain embodiments, particularly where Aryl 1 is indolyl or phenyl, more particularly indolyl, $R_1$–$R_3$ are independently selected from the group consisting of H, phenoxy, hydroxyphenyl, benzyloxy, methoxy, methoxycarbonyl, isopropyl, butyl, acetyl, phenylcarbonyl, nitro, fluoro, carboxy, trifluoromethyl, triphenylmethoxy, phenylcarbonylamino, methoxycarbonyl ethenyl, phenylcarbonyl ethenyl, benzofuranyl carbonyl, butylbenzylfuranyl carbonyl, phenylaminocarbonyl, phenylcarbonyloxy, aminocarbonyl, methoxycarbonylamino, phthalidimido, morpholino, pyrrolidinyl, phenylhydantoinyl, and acetylpiperazinyl.

In other embodiments, particularly where Aryl 1 is phenyl, $R_1$–$R_3$ are independently selected from the group consisting of H, phenoxy, hydroxyphenyl, benzyloxy, acetyl, phenylcarbonyl, nitro, phenylcarbonyl ethenyl, benzofuranyl carbonyl, butylbenzylfuranyl carbonyl, phenylaminocarbonyl, phenylcarbonyloxy, aminocarbonyl, and methoxycarbonylamino.

Other examples of inhibitors of NAD synthetase has the Structure 300:

Structure 300

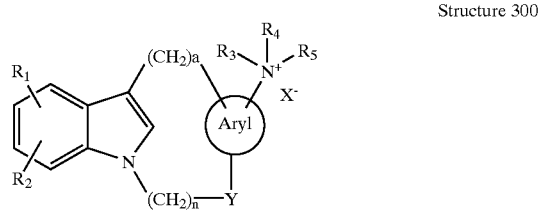

wherein Y is C, N, O, S, ester, amide, or ketone, n is an integer of from 1 to 12, a is an integer from 1–3, and $R_1$–$R_5$ each, independently, is H, unsubstituted or substituted cyclic group or an aliphatic group, a branched or an unbranched group, or an alkyl, alkenyl, or alkynyl, or an aryl group.

A further example of the inhibitor of NAD synthetase has the Structure 400:

Structure 400

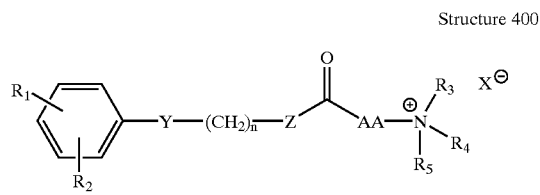

wherein Y is C, N, O, S, ester, amide, or ketone; Z is C, N, O, or S; AA is a natural or unnatural stereoisomer of an α-, β, γ, or δ-amino acid in which the carboxyl carbonyl is attached to Z, and the amino grouping may be a primary, secondary, tertiary, or quaternary ammonium compound; n is an integer of from 1 to 12; and $R_1$–$R_5$ each, independently, is H, unsubstituted or substituted cyclic group or an aliphatic group, a branched or an unbranched group, or an alkyl, alkenyl, alkynyl, aryl, aryl alkyl, or aryl alkoxy group.

In Structures 300 and 400, $R_1$–$R_2$ may also be H, hydroxyl, ketone, nitro, amino, amidino, guanidino, carboxylate, amide, ester, sulfonate, halogen, alkoxy, or aryloxy group.

Particular examples of inhibitors of NAD synthetase are 5940, 5949, 5951, 5409, 5948, 5270, 5939, 5947, 5953, and 5274:

5940

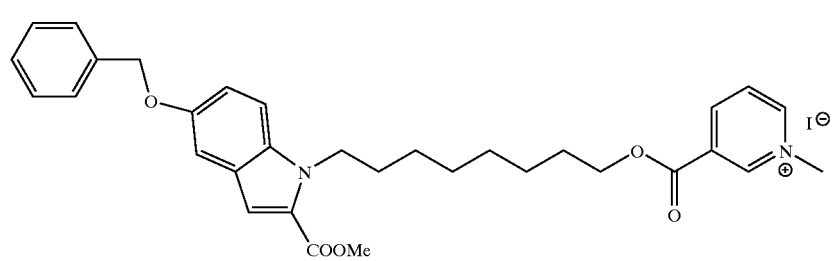

5949

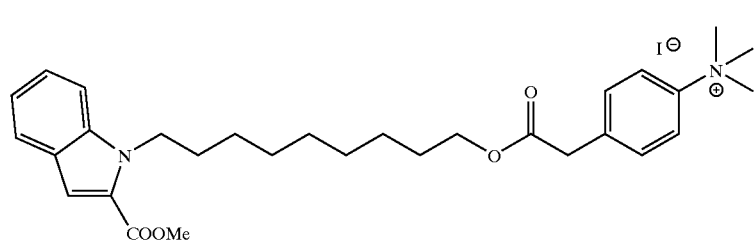

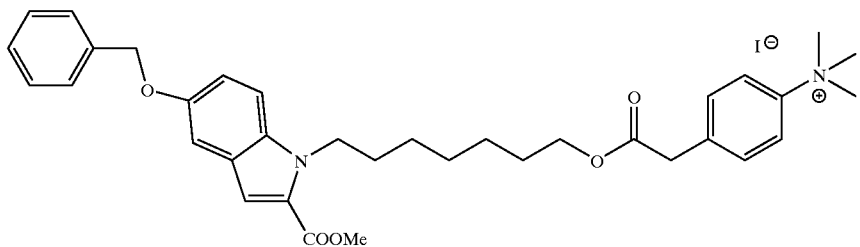
5951
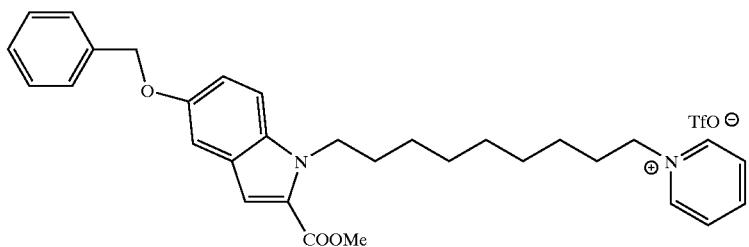
5409
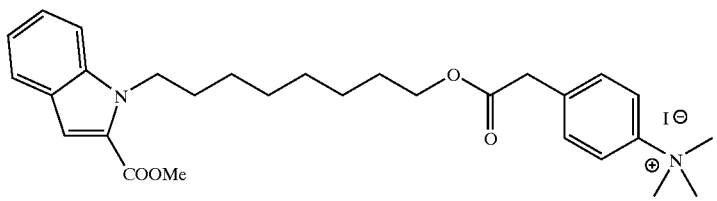
5948
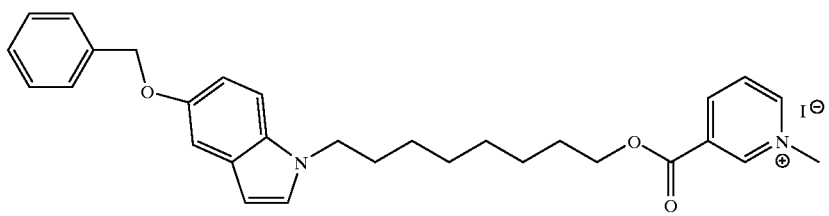
5270
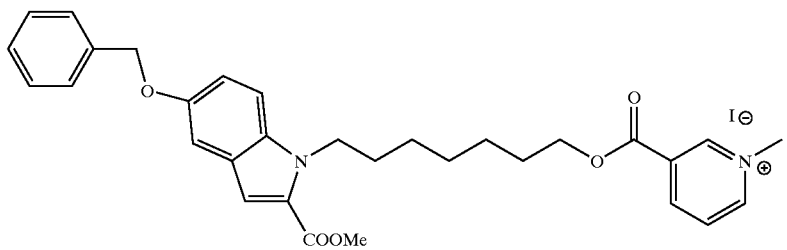
5939
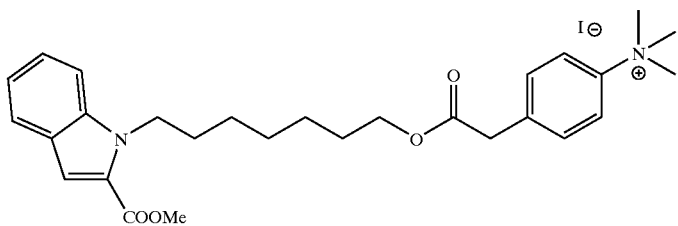
5947

-continued

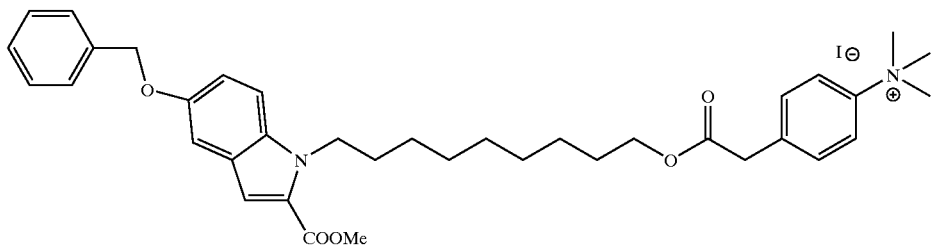

5953

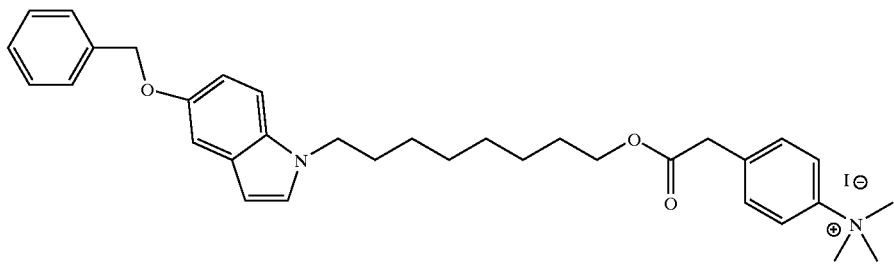

5274

The present invention further provides a method for treating or preventing a microbial (e.g., bacterial or fungal) infection in a mammal comprising administering to said mammal an effective amount of a compound that binds to the dimer interface of the NAD synthetase enzyme of the microbe (bacterium or fungus).

In the method of killing yeast, as well as in the method of decreasing the growth of yeast, the NAD synthetase enzyme inhibitor is a compound that selectively binds with catalytic sites or subsites on a yeast NAD synthetase enzyme to reduce or eliminate the production of NAD by the yeast. In such methods, it is particularly preferably that there is little or no inhibitory activity on the host cell. For example, when the method is utilized to inhibit yeast activity in a mammal, it is preferred that there is little or no attendant affect on the NAD synthetase activity of the host. In one embodiment, the host is a mammal. In a further embodiment, the host is a plant.

In one embodiment, the invention provides administering an antifungal agent to a mammal in need of such treatment or prevention. In one embodiment, the fungal agent that causes the infection is yeast. In separate embodiments of the methods of administering, the antifungal agent comprises one or more compounds disclosed herein.

Further provided by the invention herein is preferably a method of killing yeast with an amount of yeast NAD synthetase enzyme inhibitor compound to reduce or eliminate the production of NAD whereby the yeast is killed. The present invention further provides a method of decreasing yeast growth, comprising contacting the yeast with an amount of yeast NAD synthetase enzyme inhibitor effective to reduce or eliminate the production of NAD whereby yeast growth is decreased is also provided.

The present invention provides, in an embodiment, a method for increasing production of a food animal comprising administering to the food animal an effective amount of at least one inhibitor of NADs of a microbe capable of infecting the food animal.

In another embodiment, the present invention provides a method for the treatment or prevention of infection by a spore-forming bacterium in an animal comprising treating an environment of the animal with an effective amount of at least one inhibitor of NADs of the spore-forming bacterium. In a further embodiment, the present invention provides a method for killing the vegetative cell of a spore-forming bacterium in an environment comprising treating the environment with an effective amount of at least one inhibitor of NADs of the bacterium. An example of a spore-forming bacterium is a biological warfare agent, e.g., *Bacillus anthracis*.

In still another embodiment, the present invention provides a method for treating a fungal or bacterial disease in a plant comprising treating the plant or an environment of the plant with an effective amount of at least one inhibitor of NADs of the fungus or bacterium. In a further embodiment, the present invention provides a method for a treating plant comprising the treating the plant, or an environment thereof, with a pesticidal effective amount of at least one inhibitor of NADs of a pest. An example of the plant is a food crop.

In yet another embodiment, the present invention provides a method for disinfecting, sterilizing, or decontaminating an object comprising treating the object with an effective amount of at least one inhibitor of NADs of a microbe. The microbe is a microorganism, e.g., bacterium or fungus. An example of a fungus is mold or yeast.

Any suitable object can be disinfected, sterilized, or decontaminated. Examples of suitable objects include an article of clothing, an animal, an organ of an animal, a structure, an equipment, a furniture, an environment, a food crop, a chicken, a chicken skin, and an egg, e.g., egg shell. In accordance with the present invention, the environment being disinfected, sterilized, or decontaminated can be land, air, or water, or a combination thereof.

An example of the environment includes a medical environment. Thus, for example, a medical device, medical equipment, hospital, or surgical room can be disinfected. Medical personnel also can be disinfected or decontaminated. In accordance with the present invention, medical devices such as implantable medical devices, e.g., catheters can be disinfected, sterilized, or decontaminated. Medical equipment such as a surgical equipment may also be disinfected, sterilized, or decontaminated. Further, the organs of animals, including human, can be disinfected or decontaminated. An example of an organ is the digestive tract.

In a further embodiment, the present invention provides a method for controlling insect population in an environment comprising treating the environment with an effective amount of at least one inhibitor of NADs of the insect. Any suitable environment can be treated. For example, a household environment or an agricultural environment can be treated.

For the treatment of food animals to increase production, the inhibitor or antimicrobial agent may be mixed with animal feed at a typical concentration of 1–500 mg per kg of feed. Alternatively, similar concentrations may be added to the animals' drinking water. Further alternatively, the antimicrobial agent may be administered as an oral pill or may be injected, either intramuscularly or intravenously.

The method of the present invention in an embodiment is useful in the prophylaxis or therapy of biological warfare agents, including, but not limited to, the spore-forming bacterium such as *Bacillus anthracis* or a microorganism carrying the virulent gene of a spore-forming bacteria such as *Bacillus anthracis*. In *Bacillus anthracis* and other spore-forming bacteria, NADs is required for outgrowth of the germinated spore. Since inhibitors of NADs also prevent vegetative growth, this represents two different points of attack on the life cycle of these bacteria and should provide extremely effective prophylaxis and/or therapy.

In the treatment of plants, in a typical application, the antimicrobial agent in a suitable vehicle is sprayed onto growing plants to either prevent or treat fungal and/or bacterial diseases. Alternatively, application may be made by deposition of solutions or solid preparations on the soil near growing plants.

In an application of NADs inhibitors as pesticides for controlling pests and insects in the household and/or for agricultural uses, NADs inhibitors with pesticidal or insecticidal activities and in a suitable vehicle, e.g., organic or aqueous vehicle, are sprayed in areas of homes that are commonly treated with existing insecticidal preparations. In a typical agricultural application, the pesticidal or insecticidal agent in a suitable vehicle is sprayed onto growing plants to either prevent or treat infestation by insects. Alternatively, pesticidal or insecticidal application to plants may be made by deposition on the soil near growing plants.

In a typical application for disinfection, sterilization or decontamination of structural surfaces, a solution of the microbicidal compound in a suitable vehicle would be painted, sprayed, or soaked (by immersion into a solution) onto the surface of the object. For treatment of the soil or ground, a solution of the microbicidal agent in a suitable vehicle may be sprayed onto or soaked into the ground, or a solid form may be mixed with the soil. The microbicidal agent may also be added to contaminated water supplies in sufficient concentration (1–100 micromolar) to cause sterilization. In processing, handling, and packaging animal foods, such as eggs or chickens, a solution of the microbicidal compound in a suitable vehicle may be painted, sprayed, or soaked (by immersion into a solution) onto the surface of the food. Numerous related beneficial applications are possible, including decontamination of chicken skins, e.g., to reduce *Salmonella typhimurium*, egg shells (carriers of *Salmonella*), and disinfection of other foods.

In the field of sterilization, disinfecting and decontamination including, microbicidal concentrations of NADs inhibitors have the potential for use in a variety of situations benefiting from sterilization or decontamination, including the treatment of clothing, surfaces of structures, equipment, furniture, and natural environmental surfaces such as the ground and water supplies.

A typical application for disinfection of implantable devices would involve soaking the device in a solution of the microbicidal compound. Alternatively, the implantable device may be manufactured to contain a releasable or bioactive form of the microbicidal compound, either by mechanical entrapment in the polymeric material composing the surface of the device or by covalent chemical attachment to the polymeric material composing the surface of the device. For treatment of transplantable organs, the organ may be immersed in a solution of the microbicidal agent contained in a suitable vehicle. Whole body washing can be accomplished by thoroughly wiping the body with a solution of the microbicidal agent, or by immersion of the body in a suitable solution.

Control of dental caries and/or gum disease may be accomplished by washing of the oral cavity with a suitable solution of the microbicidal agent, or by incorporation into a toothpaste used in brushing the teeth.

Numerous medical applications and devices requiring disinfection or decontamination are possible such as pacemakers, defibrillators, artificial hearts or parts thereof, whole body washing of infected patients, treatment of transplantable organs for transplantation, decontamination of surgical rooms and surgical equipment, and control of dental caries or gum disease.

Decontamination associated with spore-forming bacteria such as *Bacillus anthracis*, inhibitors of germination may cause damage to the spore and should be bactericidal to the vegetative cell. Thus these inhibitors may be used to decontaminate a variety of environments including, but not limited to, environmental surfaces and drinking water.

In the treatment, prevention, or control of fungal and bacterial diseases in plants and foodcrops, the inhibitor can be carried in a suitable vehicle and sprayed onto the plants to either prevent or treat fungal and/or bacterial diseases. Alternatively, application may be made by deposition of solutions or solid preparations on the soil near growing plants.

Numerous medical applications requiring disinfection or decontamination are possible. These include digestive tract decontamination in humans related to surgery (see G. Ramsay and R. H. van Saene, "Selective gut decontamination in intensive care and surgical practice: where are we [Review]," World Journal of Surgery, 22(2):164–70, February 1998; and G. Basha et al., "Local and systemic effects of intraoperative whole-colon washout with 5 percent povidone-iodine," British Journal of Surgery. 86(2):219–26, February 1999), the disinfection of, or impregnation of NADs inhibitors into, materials used in implantable devices such as intravenous catheters (see O. Traore et al., "Comparison of in-vivo antibacterial activity of two skin disinfection procedures for insertion of peripheral catheters: povidone iodine versus chlorhexidine," Journal of Hospital Infection. 44(2):147–50, February 2000; and T. S. Elliott, "Role of antimicrobial central venous catheters for the prevention of associated infections," [Review] Journal of antimicrobial Chemotherapy. 43(4):441–6, April 1999), pacemakers, defibrillators, artificial hearts or parts thereof, whole body washing of infected patients, treatment of transplantable organs for transplantation, decontamination of surgical rooms and surgical equipment, and control of dental caries or gum disease (see B. M. Eley, "Antibacterial agents in the control of supragingival plaque—a review," British Dental Journal, 186(6):286–96, Mar. 27, 1999).

It is to be understood that this invention is not limited to the specific synthetic methods described herein. It is to be further understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

Throughout this application, where a chemical diagram has a straight line emanating from a chemical structure, such a line represents a $CH_3$ group. For example, in the following diagram:

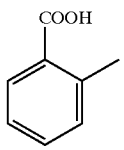

o-methylbenzoic acid is represented.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. The term "cycloalkyl" intends a cyclic alkyl group of from three to eight, preferably five or six carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing from one to six, more preferably from one to four, carbon atoms.

The term "alkylene" as used herein refers to a difunctional saturated branched or unbranched hydrocarbon chain containing from 1 to 24 carbon atoms, and includes, for example, methylene (—$CH_2$—), ethylene (—$CH_2$—$CH_2$—), propylene (—$CH_2$—$CH_2$—$CH_2$—), 2-methylpropylene [—$CH_2$—CH($CH_3$)—$CH_2$—], hexylene [—($CH_2$)$_6$—] and the like. The term "cycloalkylene" as used herein refers to a cyclic alkylene group, typically a 5- or 6-membered ring.

The term "alkene" as used herein intends a mono-unsaturated or di-unsaturated hydrocarbon group of 2 to 24 carbon atoms. Asymmetric structures such as (AB)C=C(CD) are intended to include both the E and Z isomers. This may be presumed in structural formulae herein wherein an asymmetric alkene is present.

The term "alkynyl" as used herein refers to a branched or unbranched unsaturated hydrocarbon group of 1 to 24 carbon atoms wherein the group has at least one triple bond.

The term "cyclic" as used herein intends a structure that is characterized by one or more closed rings. As further used herein, the cyclic compounds discussed herein may be saturated or unsaturated and may be heterocyclic. By heterocyclic, it is meant a closed-ring structure, preferably of 5 or 6 members, in which one or more atoms in the ring is an element other than carbon, for example, sulfur, nitrogen, etc.

The term "bicyclic" as used herein intends a structure with two closed rings. As further used herein, the two rings in a bicyclic structure can be the same or different. Either of the rings in a bicyclic structure may be heterocyclic.

By the term "effective amount" of a compound as provided herein is meant a sufficient amount of the compound to provide the desired treatment or preventive effect. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount may be determined by one of ordinary skill in the art using only routine experimentation. It is preferred that the effective amount be essentially non-toxic to the subject, but it is contemplated that some toxicity will be acceptable in some circumstances where higher dosages are required.

By "pharmaceutically acceptable carrier" is meant a material that is not biologically or otherwise undesirable, i.e., the material may be administered to an individual along with the compounds of the invention without causing any undesirable biological effects or interacting in a deleterious manner with any of the other components of the pharmaceutical composition in which it is contained.

As used herein, "NAD synthetase enzyme" is defined as the enzyme that catalyzes the final reaction in the biosynthesis of NAD, namely, the transformation of NaAD into NAD. As used herein, the term "catalytic sites" are defined as those portions of the NAD synthetase enzyme that bind to substrates, and cofactors, including nicotinic acid dinucleotide (NaAD), NAD, adenosine triphosphate (ATP), adenosine monophosphate (AMP), pyrophosphate, magnesium and ammonia in bacteria or microbes. The term "receptor site" or "receptor subsite" relates to those portions of the bacterial NAD synthetase enzyme in which the bacterial NAD synthetase enzyme inhibitors disclosed herein are believed to bind. For the purposes of this disclosure, the terms "catalytic site," "receptor site" and "receptor subsite" may be used interchangeably. The inhibitors may also inhibit the NAD synthetase enzyme by mechanisms not involving binding of the inhibitor to catalytic sites.

As used herein, the term "antimicrobial compound" denotes a material that kills or deactivates microbes so as to reduce or eliminate the harmful effects of the bacteria on a subject or in a system. Microbes are microorganisms which are too small to be seen by the naked eye, e.g., bacteria, fungi, viruses, and protozoa, preferably bacteria and fungi. For example, antibacterials are known in the art as "bacteriostatic agents" or "bateriocidal agents." The bacteria so affected can be gram positive, gram negative or a combination thereof. The terms "antimicrobial compound" and "broad spectrum antibiotic" denote a material that kills or deactivates a wide variety of microbes, including, but not limited to, one of more of, gram positive or gram negative bacteria, *Staphylococcus aureus, Streptococcus pyogenes, Streptococcus viridans, Enterococcus*, anaerobic *Streptococcus, Pneumococcus, Gonococcus, Meningococcus, Mima, Bacillus anthracis, C. diphtheriae, List. monocytogenes, Streptobacillus monohiliformis, Erysipelothrix insidiosa, E. coli, A. aerogenes, A. faecalis, Proteus mirabilis, Pseudomonas aeruginosa, K pneumoniae, Salmonella, Shigella, H. influenzae, H. ducreyi, Brucella, Past. pestis, Past. tularensis, Past. multocida, V. comma, Actinobacillus mallei, Pseud. pseudomallei, Cl. tetani, Bacteroides, Fusobacterium fusiforme, M. tuberculosis*, atypical *mycobacteria, Actinomyces israelii, Nocardia, T. pallidum, T. pernue, Borrelia recurrentis, Peptospira, Rickettsia*, and *Mycoplasma pneumoniae*.

In accordance with the desirability for developing improved antimicrobials, e.g., antibacterial and antimicrobial agents, with the invention herein novel compounds have been identified that inhibit bacterial NAD synthetase enzymatic activity. Such activity translates into effectiveness as bacteriocidal agents, as well as effectiveness a broad spectrum antibiotic materials. Novel compounds have been developed that inhibit a previously unrecognized target in prokaryotic organisms, such as bacteria, to block essential biological function and thereby cause bacterial death or deactivation of the microbes. Specifically, the invention herein has identified an enzyme found in both gram positive and gram negative bacteria, NAD synthetase enzyme, which can be utilized as a target for drug design to provide protection from and/or treatment for bacterial and other microbial infections.

The NAD synthetase enzyme catalyzes the final step in the biosynthesis of nicotinamide adenine dinucleotide (NAD). Bacterial NAD synthetase is an ammonia-dependent amidotransferase belonging to a family of "N-type" ATP pyrophosphatases; this family also includes asparagine synthetase and argininosuccinate synthetase. NAD synthetase enzyme catalyzes the last step in both the de novo and salvage pathways for $NAD^+$ biosynthesis, which involves the transfer of ammonia to the carboxylate of nicotinic acid adenine dinucleotide (NaAD) in the presence of ATP and $Mg^{+2}$. The overall reaction is illustrated in FIG. 1. Unlike eukaryotic NAD synthetase e.g., that found in mammals, which can utilize glutamine as a source of nitrogen, prokaryotic NAD synthetase in bacteria utilizes ammonia as the sole nitrogen source. Through x-ray crystallography and other methods, the invention has identified marked differences in the structures of eukaryotic and prokaryotic forms of the NAD synthetase enzyme. For example, *B. subtilis* NAD synthetase enzyme, which in the invention has been crystallized and used in the drug design methodologies herein, is a dimeric material with molecular weight around 60,500. In marked contrast, the eukaryotic form of NAD synthetase found in mammals is multimeric and has a molecular weight of at least 10 times larger.

By utilizing the significant differences between the eukaryotic and prokaryotic forms of NAD synthetase enzyme, the invention herein provides novel compounds that can be utilized as antimicrobial agents that specifically target the prokaryotic NAD synthetase enzyme without significantly affecting a mammalian host. With the invention herein, it has been found that by specifically inhibiting bacterial NAD synthetase enzymatic activity, bacteria can be deprived of the energy necessary to thrive and replicate. Accordingly, through the invention disclosed and claimed herein, antibacterial drugs may be developed that preferentially attack the bacteria to kill or deactivate it so as to reduce or eliminate its harmful properties, without appreciably affecting mammalian NAD synthetase enzymatic activity at the same dosage. Moreover, the invention provides methods of treating microbial infections in a mammal, e.g., human. Because of the differences in structure between bacterial and mammalian NAD synthetase enzyme, it would not be expected that the compounds of the invention would inhibit or otherwise affect mammalian NAD synthetase enzyme in the same manner as the compounds act on bacteria.

Figure 2:
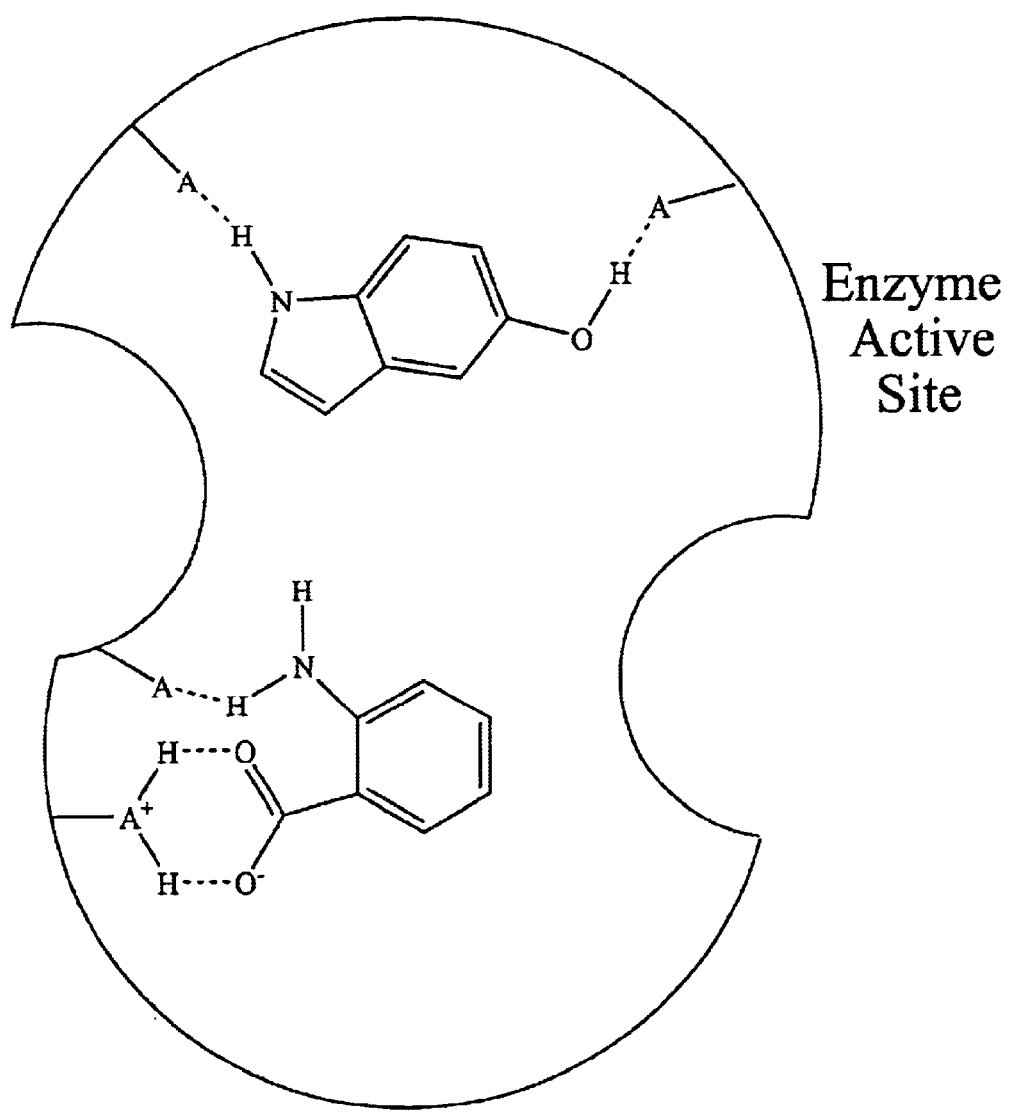
FIG. 2 schematically illustrates catalytic sites on a bacterial NAD synthetase enzyme.

Without being bound by theory, through chemical analysis and x-ray crystallography methods, characterized at least two separate catalytic subsites on the bacterial NAD synthetase enzyme in which it is possible to bind at least one or more small molecules ("active molecules") have been characterized. These sites are illustrated in FIG. 2.

Figure 3:
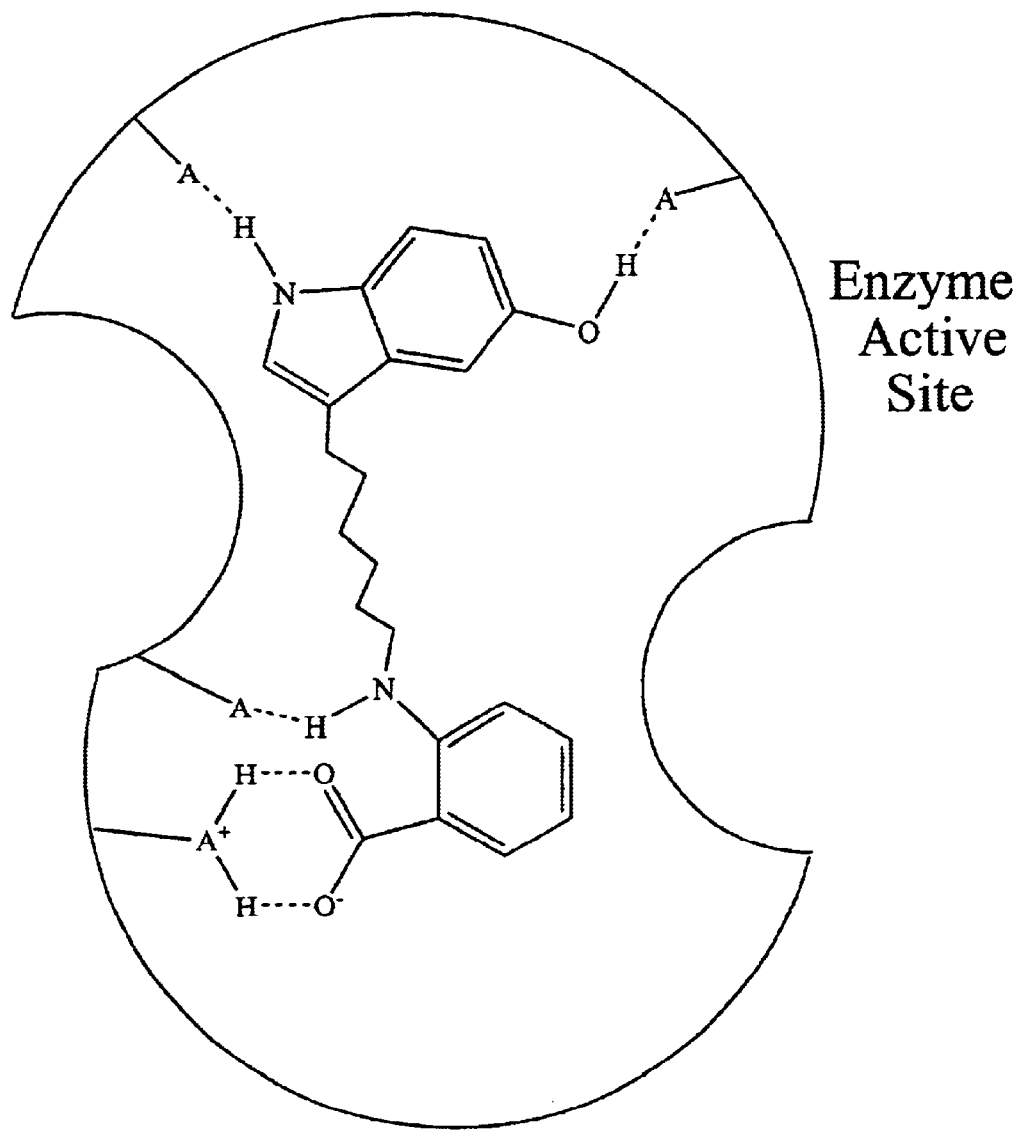
FIG. 3 schematically illustrates the blocking of catalytic sites of a bacterial NAD synthetase enzyme.

Because of the specific structure of these catalytic sites, it may be possible to identify small molecules that will demonstrate affinity for at least one of the sites. Small molecules of the proper configuration, the configuration being determined by the structure of the catalytic site(s), may bind with a receptor site or sites on the microbial, e.g., bacterial NAD synthetase enzyme, thereby blocking the catalytic activity of the enzyme. FIG. 3 illustrates a bacterial NAD synthetase enzyme in which the catalytic sites are blocked by an example of a compound of the present invention.

Under such circumstances, it is hypothesized that, for example, spore-forming bacteria will be unable to undergo germination and outgrowth, and the essential cellular respiratory functions of the vegetative bacteria will be halted, thereby causing cellular death or deactivation, e.g., gram positive and gram negative bacteria and other microbes will be killed or prevented from growing. Accordingly, the invention has found that compounds that exhibit inhibitory activity against the bacterial NAD synthetase enzyme will also exhibit therapeutic activity as antibacterial and antimicrobial compounds, as well as broad spectrum antibiotic materials.

With embodiments of the invention described herein, it is possible to synthesize novel tethered dimeric compounds that exhibit activity as microbial NAD synthetase enzyme inhibitors. By linking one or more active molecules through a linker molecule, one or more ends of the tethered dimer can bind in the respective receptor sites or subsites to thereby render the bacterial NAD synthetase enzyme inactive. When more than one active molecule is used, each active molecule can be the same or different. The term "active molecules" as used herein refers to small molecules that may be used alone or tethered together through a linker (tether) fragment to form a tethered dimeric compound. v Further, under some circumstances, different active molecules will be more likely to bind to different locations in the receptor site of a bacterial NAD synthetase enzyme because of the differing chemical make-up of each of these sites. Therefore, in one embodiment, it may be beneficial to tether at least two different active molecules to each other wherein each active molecule demonstrates selective affinity for a different subsite in the receptor. Using the tethered dimers herein it may be possible to drastically enhance the potency of NAD synthetase enzyme inhibition, as compared to blocking a single site on the bacterial NAD synthetase enzyme. As used herein, the term "selective affinity" means that the active molecule shows enhanced tendency to bind with one subsite with the receptor in the bacterial NAD synthetase enzyme because of a chemical complementarity between the receptor subsite and the active molecule. A tethered dimer compound is illustrated below.

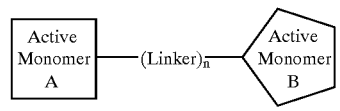

In one embodiment, a dimeric inhibitor compound will bind with, for example, the sites of catalytic activity on the bacterial NAD synthetase enzyme, thereby preventing the production of NAD/NADH by the bacteria. By varying the length of the linker molecule, or the distance between the two active molecules, the affinity of the inhibitor compound for the NAD synthetase enzyme maybe varied.

In practice of the invention relating to the design of novel NAD synthetase enzyme inhibitor compounds, a software program can be utilized which facilitates the prediction of the binding affinities of molecules to proteins so as to allow identification of commercially available small molecules with the ability to bind to at least one receptor subsite in the bacterial NAD synthetase enzyme. An example of one such computer program is DOCK, available from the Department of Pharmaceutical Chemistry at the University of California, San Francisco. DOCK evaluates the chemical and geometric complementarity between a small molecule and a macromolecular binding site.

The active molecules specifically disclosed herein may be used, as well as any pharmaceutically acceptable salts thereof. As noted, pharmaceutically acceptable salts of the compounds set out herein below are also contemplated for use in this invention. Such salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water, alone or in combination with an inert, water-miscible organic solvent, at a temperature of from about 0° C. to about 100° C., preferably at room temperature. The molar ratio of the compounds to base used are chosen to provide the ratio desired for any particular salts. For preparing, for example, the ammonium salts of the free acid starting material—a particular preferred embodiment—the starting material can be treated with approximately one equivalent of pharmaceutically acceptable base to yield a neutral salt. When calcium salts are prepared, approximately one-half a molar equivalent of base is used to yield a neutral salt, while for aluminum salts, approximately one-third a molar equivalent of base will be used.

Compounds prepared in accordance with the design and synthesis methods of this invention are especially attractive because they may preferably be further optimized by incorporation of substituents on either the active molecule and/or the linking group. These latter modifications can also preferably be accomplished using the combinatorial methods disclosed herein.

In a preferred embodiment, the invention provides administering a broad spectrum antibiotic to a mammal in need of such treatment or prevention. In a further preferred embodiment, the microbial infection is a bacterial infection. In yet another embodiment of the invention, the bacterial infection is caused by a bacterium that is a gram negative or gram positive bacteria. The bacterial infection may preferably be caused by an antibiotic resistant strain of bacteria.

Further provided by the invention herein is preferably a method of killing a prokaryote with an amount of prokaryotic NAD synthetase enzyme inhibitor compound to reduce or eliminate the production of NAD whereby the prokaryote is killed. A method of decreasing prokaryotic growth, comprising contacting the prokaryote with an amount of a prokaryotic NAD synthetase enzyme inhibitor effective to reduce or eliminate the production of NAD whereby prokaryotic growth is decreased is also provided. In the method of killing a prokaryote, as well as in the method of decreasing prokaryotic growth, the compound comprises one or more compounds provided herein.

In the method of killing a prokaryote, as well as in the method of decreasing prokaryotic growth, the prokaryote is a bacterium. Further preferably, the bacterium is a gram negative or a gram positive bacteria. Still preferably, the prokaryote is an antibiotic resistant strain of bacteria.

Also in the method of killing a prokaryote, as well as in the method of decreasing prokaryotic growth, the NAD synthetase enzyme inhibitor is a compound that selectively binds with catalytic sites or subsites on a bacterial NAD synthetase enzyme to reduce or eliminate the production of NAD by the bacteria.

In the methods discussed above, the compound is preferably administered by oral, rectal, intramuscular, intravenous, intravesicular or topical means of administration. The compounds of this invention can be administered to a cell of a subject either in vivo or ex vivo. For administration to a cell of the subject in vivo, as well as for administration to the subject, the compounds of this invention can be administered orally, parenterally (e.g., intravenously), by intramuscular injection, by intraperitoneal injection, subcutaneous injection, transdermally, extracorporeally, topically, mucosally or the like.

Depending on the intended mode of administration, the compounds of the present invention can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected composition, possibly in combination with a pharmaceutically acceptable carrier and, in addition, may include other medicinal agents, pharmaceutical agents, carriers, adjuvants, diluents, etc.

Parenteral administration of the compounds of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, subcutaneous, intramuscular, intraperitoneal, intravenous and intratracheal routes. One approach for parenteral administration involves use of a slow release or sustained release system such that a constant dosage is maintained. These compounds can be present in a pharmaceutically acceptable carrier, which can also include a suitable adjuvant. By "pharmaceutically acceptable," it is meant a material that is not biologically or otherwise undesirable, i.e., the material maybe administered to an individual along with the selected compound without causing substantial deleterious biological effects or interacting in a deleterious manner with any of the other components of the composition in which it is contained.

Routes of administration for the compounds herein are preferably in a suitable and pharmacologically acceptable formulation. When administered to a human or an animal subject, the bacterial NAD synthetase enzyme inhibitor compounds of the libraries herein are preferably presented to animals or humans orally, rectally, intramuscularly, intravenously, intravesicularly or topically (including inhalation). The dosage preferably comprises between about 0.1 to about 15 g per day and wherein the dosage is administered from about 1 to about 4 times per day. The preferred dosage may also comprise between 0.001 and 1 g per day, still preferably about 0.01, 0.05, 0.1, and 0.25, 0.5, 0.75 and 1.0 g per day. Further preferably, the dosage may be administered in an amount of about 1, 2.5, 5.0, 7.5,10.0, 12.5 and 15.0 g per day. The dosage may be administered at a still preferable rate of about 1, 2, 3, 4 or more times per day. Further, in some circumstances, it may be preferable to administer the compound of the invention continuously, as with, for example, intravenous administration. The exact amount of the compound required will vary from subject to subject, depending on the species, age, weight and general condition of the subject, the particular compound used, its mode of administration and the like. Thus, it is not possible to specify an exact amount for every compound. However, an appropriate amount can be determined by one of ordinary skill in the art using only routine experimentation given the teachings herein.

If ex vivo methods are employed, cells or tissues can be removed and maintained outside the subject's body according to standard protocols well known in the art. The compounds of this invention can be introduced into the cells via known mechanisms for uptake of small molecules into cells (e.g., phagocytosis, pulsing onto class I MHC-expressing cells, liposomes, etc.). The cells can then be infused (e.g. in a pharmaceutically acceptable carrier) or transplanted back into the subject per standard methods for the cell or tissue type. Standard methods are known for transplantation or infusion of various cells into a subject.

It is further provided a method of disinfecting a material contaminated by a microbe, comprising contacting a contaminated material with a bacterial NAD synthetase enzyme inhibitor compound in an amount sufficient to kill or deactivate the microbe. In yet another embodiment, the compound utilized for contacting comprises one or more compounds provided herein.

In yet a further embodiment of the invention herein, the compounds of the present invention are effective as disinfectant materials for, for example, hard or soft surfaces, fabrics, and other contaminated materials such as those in hospitals, households, schools, nurseries, and any other location. In yet another embodiment, the invention provides a method for disinfecting comprising contacting a bacterial contaminated material with a bacterial NAD synthetase enzyme inhibitor compound.

The inhibitors of NAD synthetase according to the present invention can be employed in a variety of processes for the treatment of humans, animals and plants as well as decontamination, sterilization and/or disinfectant techniques. The present invention further provides a method for preventing germination of spore-forming bacteria and/or the vegetative growth of bacteria, fungi and/or molds comprising administering an effective amount of at least one inhibitor of NAD synthetase, e.g. prophylactically or therapeutically, e.g., to at least one of a human, a mammal, or an animal.

The present invention further provides a method for preparing a compound of the formula A:

    (A)

wherein $Ar_1$, $Ar_2$, and $Ar_3$ are independently aryl or heteroaryl, optionally substituted with one or more substituents selected from the group consisting of $C_1$–$C_6$ alkyl, $C_1$–$C_6$ alkoxy, $C_1$–$C_6$ haloalkyl, $C_1$–$C_6$ hydroxyalkyl, $C_1$–$C_6$ alkoxy $C_1$–$C_6$ alkyl, halo, amino $C_1$–$C_6$ alkylamino, $C_1$–$C_6$ dialkylamino, $C_1$–$C_6$ trialkylamino, $C_1$–$C_6$ alkylamino $C_1$–$C_6$ alkyl, $C_1$–$C_6$ dialkylamino $C_1$–$C_6$ alkyl, $C_1$–$C_6$ trialkylamino $C_1$–$C_6$ alkyl, azido, amine oxide, hydroxy, carboxyl, $C_1$–$C_6$ alkylcarbonyl, $C_1$–$C_6$ alkylcarbonyl $C_1$–$C_6$ alkyl, $C_1$–$C_6$ alkylcarbonyloxy, $C_1$–$C_6$ alkylcarbonyloxy $C_1$–$C_6$ alkyl, $C_1$–$C_6$ alkyloxycarbonyl $C_1$–$C_6$ alkyl, $C_1$–$C_6$ alkyloxycarbonyl, $C_1$–$C_6$ alkylthio, nitro, nitrosyl, cyano, hydroxyamino, sulfonamido, $C_1$–$C_6$ dialkyl sulfonamido, $C_1$–$C_6$ alkylcarbonylamino, formyl, formylamino, mercaptyl, and heterocyclyl; optionally, a ring nitrogen atom of heteroaryl $Ar_1$, $Ar_2$, or $Ar_3$ may be quaternized;

X is selected from the group consisting of a covalent bond, $(CH_2)_mO$, $O(CH_2)_m$, $(CH_2O)_m$, $(OCH_2)_m$, $(CH_2CH_2O)_m$, $(OCH_2CH_2)_m$, $C(=O)O$, $OC(=O)$, $OC(=O)O$, $(CH_2)_mS$, $S(CH_2)_m$, $(CH_2S)_m$, $(SCH_2)_m$, NH, NR, $^+NR_2$, $C(=O)NH$, $C(=O)NR$, $NHC(=O)$, $NRC(=O)$, $CH(OH)$, and $CH(OR)$, wherein R is $C_1$–$C_6$ alkyl and m is 0–5;

$Q_1$ is (i) a $C_1$–$C_6$ alkylenyl, $C_1$–$C_6$ alkylenyl carbonyloxy $C_1$–$C_6$ alkyl, or $C_1$–$C_6$ alkylenyl carbonylamino $C_1$–$C_6$ alkyl group, optionally having a substituent selected from the group consisting of amino, $C_1$–$C_6$ alkylamino, $C_1$–$C_6$ haloalkylamino, $C_1$–$C_6$ haloalkyl $C_1$–$C_6$ alkyl amino, $C_1$–$C_6$ hydroxyalkylamino, $C_1$–$C_6$ hydroxyalkyl $C_1$–$C_6$ alkylamino, $C_1$–$C_6$ dialkylamino, $C_1$–$C_6$ trialkylamino, and a heterocyclic containing a nitrogen atom which may be optionally quaternized;

and n is from 1 to 15;

comprising (i) providing a compound of the formula B:

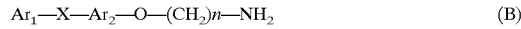    (B)

and (ii) reacting the compound of formula B with a compound of formula C:

    (C);

wherein $Q_1$ is optionally protected.

In an embodiment, the compound of formula B may be prepared by reacting a compound of formula D: $Ar_1$—X—$Ar_2$—OH (D) with a compound of formula E: Hal—$(CH_2)$n—NPhth (E); wherein "Hal" stands for a halogen atom and "NPhth" stands for phthalidimide linked to $(CH_2)n$ at the nitrogen atom, to obtain a compound of formula F:

    (F);

and hydrolyzing the compound of formula F.

In accordance with another embodiment, the present invention provides a method for preparing a compound of the formula G:

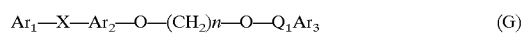    (G)

wherein $Ar_1$, $Ar_2$, and $Ar_3$ are independently aryl or heteroaryl, optionally substituted with one or more substituents selected from the group consisting of $C_1$–$C_6$ alkyl, $C_1$–$C_6$ alkoxy, $C_1$–$C_6$ haloalkyl, $C_1$–$C_6$ hydroxyalkyl, $C_1$–$C_6$ alkoxy $C_1$–$C_6$ alkyl, halo, amino, $C_1$–$C_6$ alkylamino, $C_1$–$C_6$ dialkylamino, $C_1$–$C_6$ trialkylamino, $C_1$–$C_6$ alkylamino $C_1$–$C_6$ alkyl, $C_1$–$C_6$ dialkylamino $C_1$–$C_6$ alkyl, $C_1$–$C_6$ trialkylamino $C_1$–$C_6$ alkyl, azido, amine oxide, hydroxy, carboxyl, $C_1$–$C_6$ alkylcarbonyl, $C_1$–$C_6$ alkylcarbonyl $C_1$–$C_6$ alkyl, $C_1$–$C_6$ alkylcarbonyloxy, $C_1$–$C_6$ alkylcarbonyloxy $C_1$–$C_6$ alkyl, $C_1$–$C_6$ alkyloxycarbonyl $C_1$–$C_6$ alkyl, $C_1$–$C_6$ alkyloxycarbonyl, $C_1$–$C_6$ alkylthio, nitro, nitrosyl, cyano, hydroxyamino, sulfonamido, $C_1$–$C_6$ dialkyl sulfonamido, $C_1$–$C_6$ alkylcarbonylamino, formyl, formylamino, mercaptyl, and heterocyclyl; optionally, a ring nitrogen atom of heteroaryl $Ar_1$, $Ar_2$, or $Ar_3$ may be quaternized;

X is selected from the group consisting of a covalent bond, $(CH_2)_mO$, $O(CH_2)_m$, $(CH_2O)_m$, $(OCH_2)_m$, $(CH_2CH_2O)_m$, $(OCH_2CH_2)_m$, $C(=O)O$, $OC(=O)$, $OC(=O)O$, $(CH_2)_mS$, $S(CH_2)_m$, $(CH_2S)_m$, $(SCH_2)_m$, NH, NR, $^+NR_2$, $C(=O)NH$, $C(=O)NR$, $NHC(=O)$, $NRC(=O)$, $CH(OH)$, and $CH(OR)$, wherein R is $C_1$–$C_6$ alkyl and m is 0–5;

$Q_1$ is (i) a $C_1$–$C_6$ alkylenyl, $C_1$–$C_6$ alkylenyl carbonyloxy $C_1$–$C_6$ alkyl, or $C_1$–$C_6$ alkylenyl carbonylamino $C_1$–$C_6$ alkyl group, optionally having a substituent selected from the group consisting of amino, $C_1$–$C_6$ alkylamino, $C_1$–$C_6$ haloalkylamino, $C_1$–$C_6$ haloalkyl $C_1$–$C_6$ alkyl amino, $C_1$–$C_6$ hydroxyalkylamino, $C_1$–$C_6$ hydroxyalkyl $C_1$–$C_6$ alkylamino, $C_1$–$C_6$ dialkylamino, $C_1$–$C_6$ trialkylamino, and a heterocyclic containing a nitrogen atom which may be optionally quaternized;

and n is from 1 to 15;

comprising (i) providing a compound of the formula H:

$$Ar_1\text{---}X\text{---}Ar_2\text{---}O\text{---}(CH_2)n\text{---}OH \quad (H)$$

and (ii) reacting the compound of formula H with a compound of formula J:

$$HO\text{---}Q_1Ar_3 \quad (J);$$

wherein $Q_1$ is optionally protected.

In accordance with an embodiment, the compound of formula H may be prepared by reacting a compound of formula D:

$$Ar_1\text{---}X\text{---}Ar_2\text{---}OH \quad (D)$$

with a compound of formula K:

$$Hal\text{---}(CH_2)n\text{---}OH \quad (K)$$

wherein "Hal" stands for a halogen atom, e.g., cl, Br, or I to obtain a compound of formula L:

$$Ar_1\text{---}X\text{---}Ar_2\text{---}O\text{---}(CH_2)n\text{---}OH \quad (L).$$

In a preferred embodiment, the present invention provides a method for preparing the above compounds wherein n is from 7 to 13 relating to compounds of formulas A and G. In accordance with an embodiment, $Ar_1$, $Ar_2$, and $Ar_3$ are aryl, particularly phenyl. In an embodiment, X is $CH_2O$. In accordance with an embodiment of the method, $Q_1$ is a $C_1$–$C_6$ alkylenyl, optionally having a substituent selected from the group consisting of amino, $C_1$–$C_6$ alkylamino, $C_1$–$C_6$ haloalkylamino, $C_1$–$C_6$ haloalkyl $C_1$–$C_6$ alkyl amino, $C_1$–$C_6$ hydroxyalkylamino, $C_1$–$C_6$ hydroxyalkyl $C_1$–$C_6$ alkylamino, $C_1$–$C_6$ dialkylamino, $C_1$–$C_6$ trialkylamino, and a heterocyclic containing a nitrogen atom which may be optionally quaternized, preferably $Q_1$ is $C_1$–$C_3$ alkylenyl, having a substituent selected from the group consisting of amino, $C_1$–$C_6$ alkylamino. $C_1$–$C_6$ dialkylamino, and $C_1$–$C_6$ trialkylamino.

The present invention further provides a pharmaceutical composition comprising at least one of the compounds described along with a pharmaceutically acceptable carrier.

The pharmaceutically acceptable carriers described herein, for example, vehicles, adjuvants, excipients, or diluents, are well-known to those who are skilled in the art and are readily available to the public. It is preferred that the pharmaceutically acceptable carrier be one which is chemically inert to the active compound and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols and polyethylene glycols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stablizers, and preservatives. The compound can be administered in a physiologically acceptable diluent in a pharmaceutical carrier, such as a sterile liquid or mixture of liquids, including water, saline, aqueous dextrose and related sugar solutions, an alchohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly (ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, and synthetic oils. Specific examples of oils include peanut, soybean, sesame, cottonseed, forn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamino salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolyproplene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, eds., pages 238–250 (1982), and *ASHP Handbook on Injectable Drugs*, Toissel, 4th ed., pages 622–630 (1986).

The present invention further provides a method for treating or preventing a microbial (e.g., bacterial or fungal) infection in a mammal comprising administering to said mammal an effective amount of at least one of the compounds described above. The present invention also provides a method for treating or preventing tuberculosis.

The present invention further provides a method for combating agroterrorism involving an infective agent on an object comprising treating the object with an amount of a compound effective to inhibit the NAD synthetase of the infective agent. Agroterrorism is defined as the intentional introduction of animal or plant pests or the cultivation or production of pathogenic bacteria, fungi, parasites, protozoans, viruses, or their toxic products for the purpose of causing poultry, livestock, crop, soil, or human disease, poisoning, or death. This could occur through introducing pests intended to kill food crops, spreading virulent disease among confined feedlots where animals are given high protein rations for preparing them for slaughter, poisoning civil or agricultural water sources or food supplies, or using food-borne pathogens to cause human disease. Food-borne pathogens are microorganisms that cause illness through the ingestion of food.

The following examples further illustrate the invention but, of course, should not be construed as in any way limiting its scope.

EXAMPLE 1

This Example illustrates a method of preparing compounds of the present invention in accordance with an embodiment of the invention.

Experimental Procedures

Melting points were determined using an Electrothermal 9100 apparatus and are uncorrected. IR spectra were taken with Brucker Vector-22 and Bomen MB-104 instruments. All $^1$H and $^{13}$C NMR spectra were recorded on a Brucker 300 MHz spectrometer using TMS as internal standard. The values of chemical shifts (δ) are given in ppm and coupling constants (J) in Hz. Elemental analyses were performed by Atlantic Microlab, Norcross, Ga. Reactions were monitored by TLC (Whatmann, Silica gel, UV254, 25 μM plates) and flash column chromatography was done using 'BAKER' silica gel (40 μM) in solvent systems indicated. The solvents used for reactions were purchased as anhydrous in Sure-Seal™ bottles from Aldrich chemical company. All other reagents were used as received.

Synthesis of Compound 1364 (Scheme 1)

Compound 2

To a solution of 4-(benzyloxy)phenol 1 (0.40 g, 2.0 mmol) in 10 mL of DMF was added solid NaH (60% in mineral oil, 88 mg, 2.2 mmol), and the mixture was stirred at r.t for 30 min under a nitrogen atmosphere. N-(8-Bromooctyl) phthalimide (0.74 g, 2.2 mmol) was added and the mixture stirred at room temperature for 3 h. The reaction mixture was quenched with water (20 mL) and extracted with EtOAc (2×20 mL). The organic layer was washed with water (2×10 mL) and brine (10 mL), Removal of solvent from the dried ($Na_2SO_4$) extract gave the crude product. It was crystallized from MeOH to afford 2 (0.71 g, 78% yield) as a white solid. m.p: 74–75° C. (MeOH)., $^1$H-NMR ($CDCl_3$) δ 1.26–1.48 (m, 8H), 1.59–1.79 (m, 4H), 3.67 (t, 2H, J=7.28 Hz), 3.88 (t, 2H, J=6.53 Hz), 5.00 (s, 2H), 6.81 (d, 2H, J=9.14 Hz), 6.89 (d, 2H, J=9.15 Hz), 7.27–7.45 (m, 5H), 7.66–7.73 (m, 2H) and 7.81–7.86 (m, 2H); $^{13}$CNMR ($CDCl_3$) δ 25.9, 26.7, 28.5, 29.1, 29.2, 29.3, 37.9, 68.4, 70.6, 115.3, 115.7, 123.1, 127.4, 127.8, 128.5, 132.1, 133.8, 137.3, 152.7, 153.4 and 168.4; IR (neat): 1693 $cm^{-1}$; MS ($ES^+$): 458 (M+1).

Compound 3

To a solution of 2 (11.1 g, 24.3 mmol) in $CH_2Cl_2$ (120 mL) and MeOH (16 mL) was added anhydrous hydrazine (2.29 mL, 72.9 mmol) at r.t. under a nitrogen atmosphere. The reaction mixture was stirred overnight at r.t. Formation of white precipitate, which is a by-product occurred. The precipitate was filtered and washed with $NH_4OH$ saturated $CHCl_3$:MeOH (10:1). The filtrate was evaporated to get rid of methanol, then re-dissolved in $NH_4OH$ saturated $CHCl_3$ (400 mL), washed with 1N NaOH (3×60 mL), water (2×60 mL), and brine (2×60 mL). After drying over $Na_2SO_4$, the organic layer was concentrated to about 250 mL, and 1N HCl (60 mL) was added to the above solution, resulting in the formation of a white precipitate. This was filtered and washed with water and $CHCl_3$. After drying under vacuum hydrochloride salt 3 (6.8 g, 77% yield) was obtained as a white solid., m.p. 180–182° C., $^1$H-NMR (DMSO-$d_6$) δ 1.22–1.44 (m, 8H), 1.48–1.61 (m, 2H), 1.61–1.72 (m, 2H), 2.67–2.81 (m, 2H), 3.86 (t, 2H, J=6.38 Hz), 5.02 (s, 2H), 6.83 (d, 2H, J=9.10 Hz), 6.92 (d, 2H, J=9.09 Hz), 7.28–7.45 (m, 5H) and 7.98 (bs 3H); $^{13}$CNMR ($CDCl_3$) δ 25.5, 2.58, 26.9 (2C), 28.5, 28.6, 28.8, 67.7, 69.6, 115.2, 115.6, 127.6, 127.7, 128.4, 137.4, 152.2 and 152.8; IR (neat): 3440 $cm^{-1}$; MS ($ES^+$): 328 (M+).

Scheme 1

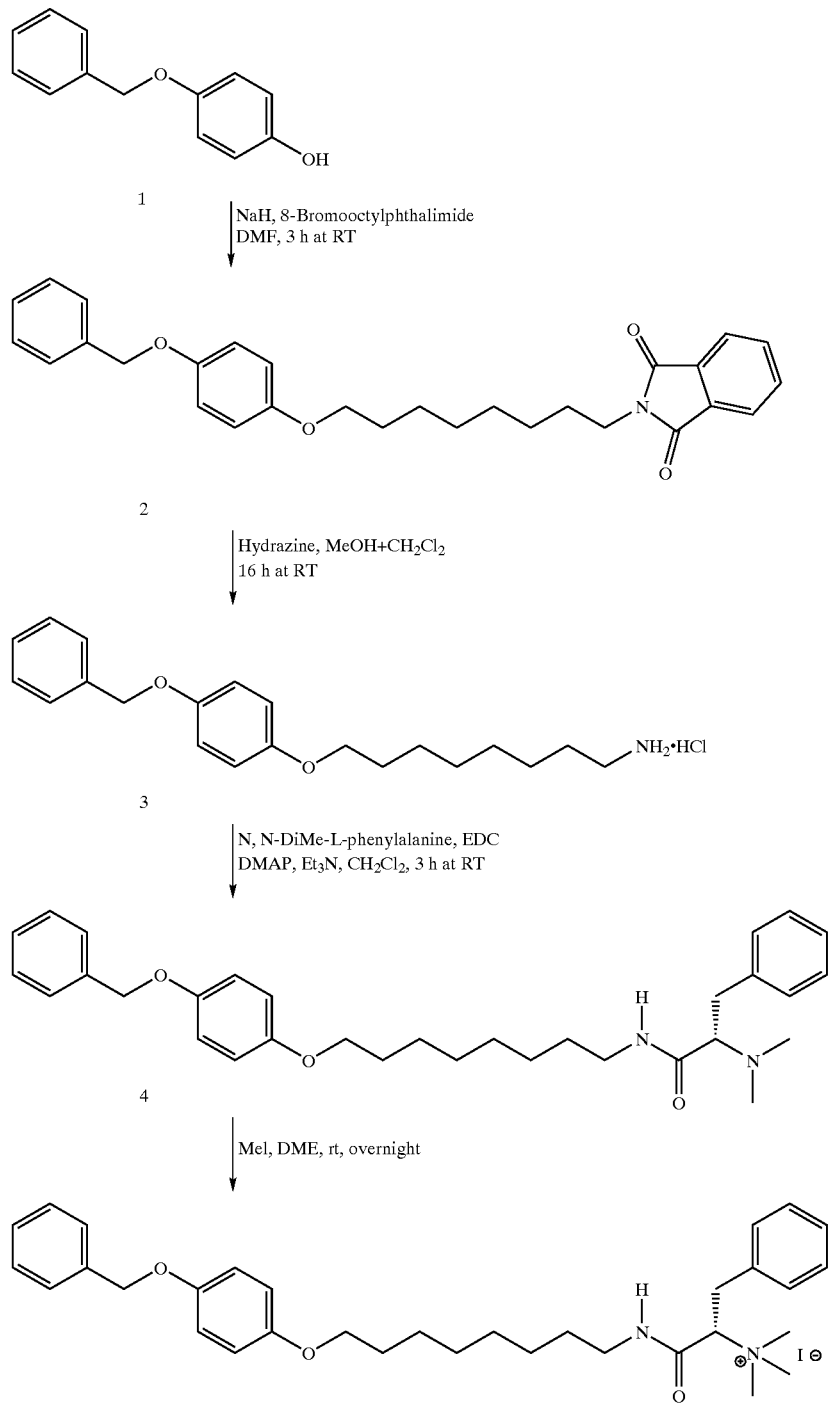

1364

Compound 4

Compound 3 (hydrochloride salt) (0.95 g, 2.6 mmol) was suspended in CH$_2$Cl$_2$ (15 mL) and cooled to 0° C. Et$_3$N (0.44 mL, 3.12 mmol) was added and stirred for 5 min. Then N,N-dimethyl-L-phenylalanine (0.61 g, 3.12 mmol), 1-ethyl-3-(3-dimethylaminopropyl)carbodiimide (EDC) (0.60 g, 3.12 mmol) and DMAP (0.036 g, 0.3 mmol) were added. The reaction mixture was stirred at r.t. overnight. The reaction mixture was diluted with CH$_2$Cl$_2$ (50 mL) and washed with 1M NaHCO$_3$ (2×20 mL), water (2×20 mL), and brine (20 mL). Removal of solvent from the dried (Na$_2$SO$_4$) extract gave the crude product, which was purified by flash column chromatography (20×4 cm) over silica gel using 1% MeOH in CHCl$_3$ to afford the pure amide 4 (1.35 g, 103% yield) as a white solid., mp: 61–62° C., $^1$H-NMR (CDCl$_3$) δ 1.18–1.35 (m, 6H), 1.35–1.49 (m, 4H), 1.67–1.81 (m, 2H), 2.29 (s, 6H), 2.81–2.92 (m, 1H), 3.08–3.26 (m, 4H), 3.88 (t, 2H, J=6.52 Hz), 4.99 (s, 2H), 6.73 (bs, 1H), 6.81 (d, 2H, J=9.17 Hz), 6.89 (d, 2H, J=9.18 Hz) and 7.12–7.45 (m, 10H); $^{13}$CNMR (CDCL$_3$) δ 25.8, 26.7, 29.1, 29.2, 29.3, 29.5, 32.7, 38.9, 42.2, 68.4, 70.5, 71.0, 115.2, 115.6, 125.9, 127.3, 127.7, 128.2, 128.4, 129.1, 137.2, 140.0, 152.7, 153.4 and 171.9; MS (ES$^+$): 503 (M+1); Anal. Calcd for C$_{32}$H$_{42}$N$_2$O$_3$.0.5H$_2$O: C, 75.16; H, 8.47; N 5.48. found: C, 75.15; H, 8.23 and N 5.42.

Compound 1364

To a solution of compound 4 (0.096 g, 0.19 mmol) in anhydrous DME (3 mL) was added iodomethane (0.35 mL, 5.6 mmol). The reaction mixture was heated at 80° C. for 12 h with stirring and cooled to room temperature. After evaporation, the crude product was purified by flash silica gel column (10×2 cm) chromatography over silica gel using, stepwise, CHCl$_3$:MeOH (30:1 followed by 10:1) to afford pure 1364 (0.095 g, 77% yield).m.p.: 98–99° C., $^1$H-NMR (CDCl$_3$) δ 0.95–1.31(m, 8H), 1.31–1.45 (m, 2H), 1.66–1.79 (m, 3H), 2.85–2.99 (m, 1H), 3.03–3.15 (m, 1H), 3.15–3.33 (m, 2H), 3.48 (s, 9H), 3.88 (t, 3H, J=6.52 Hz), 5.00 (s, 2H), 5.74 (dd, 1H, J$_1$=11.2 Hz, J$_2$=4.57 Hz), 6.83 (d, 2H, J=9.17 Hz), 6.90 (d, 2H, J=9.17 Hz), 7.22–7.43 (m, 10H) and 7.78 (t, 1H, J=5.58 Hz); $^{13}$CNMR (CDCl$_3$) δ 20; IR (neat):3245, 1679 cm$^{-1}$; MS (ES$^+$): 517(M+); Anal. Calcd for C$_{33}$H$_{45}$IN$_2$O$_3$: C, 61.49; H, 7.04; N, 4.35. found: C, 61.20; H, 6.89 and N, 4.23.

Synthesis of 1439 (Scheme 2)

Compound 5

To a solution of 4-(benzyloxy)phenol 1 (2.4 g, 12 mmol) in DMF (32 mL) was added sodium hydride (0.528 g, 13.2 mmol, 60% in mineral oil), and the mixture was stirred under N$_2$ at r.t. for 30 min. 8-Bromo-1-octanol (2.25 mL, 13.2 mmol) was added and the reaction mixture was further stirred at r.t. for 5 h. TLC (30% EtOAc in hexanes) showed that reaction was complete. After being quenched with saturated ammonium chloride solution and ice, the mixture was extracted with EtOAc (3×60 mL). The combined organic layer was then washed with 1N. NaOH solution (2×40 mL), water (2×40 mL) and brine (2×40 mL). After drying (Na$_2$SO$_4$) the organic layer was evaporated and concentrated to around 20 mL, when a white solid began precipitating. The mixture was cooled, filtered, and the filter washed with hexane to give 2.2 g white solid. The filtrate was further cooled to give another 0.8 g of 5 (76.9% yield) as a white solid.,mp. 94–95° C. $^1$H-NMR (CDCl$_3$) δ 1.28–1.51 (m, 8H), 1.51–1.63 (m, 3H), 1.69–1.81 (m, 2H), 3.62 (t, 2H, J=6.58 Hz), 3.88 (t, 2H, J=6.52 Hz), 5.00 (s, 2H), 6.82 (d, 2H, J=9.09 Hz), 6.89 (d, 2H, J=9.21 Hz) and 7.26–7.45 (m, 5H); $^{13}$C-NMR (CDCl$_3$) δ 25.6, 25.9, 29.3, 32.6, 62.9, 68.5, 70.6, 115.3, 115.7, 127.4, 127.8, 128.4, 137.2, 152.7 and 153.4; IR (KBr): 3303 cm$^{-1}$; MS (ES$^+$): 329 (M+1); Anal. Calcd for C$_{21}$H$_{28}$O$_3$: C, 76.78; H, 8.60. found: C, 76.64 and H, 8.58.

Scheme 2

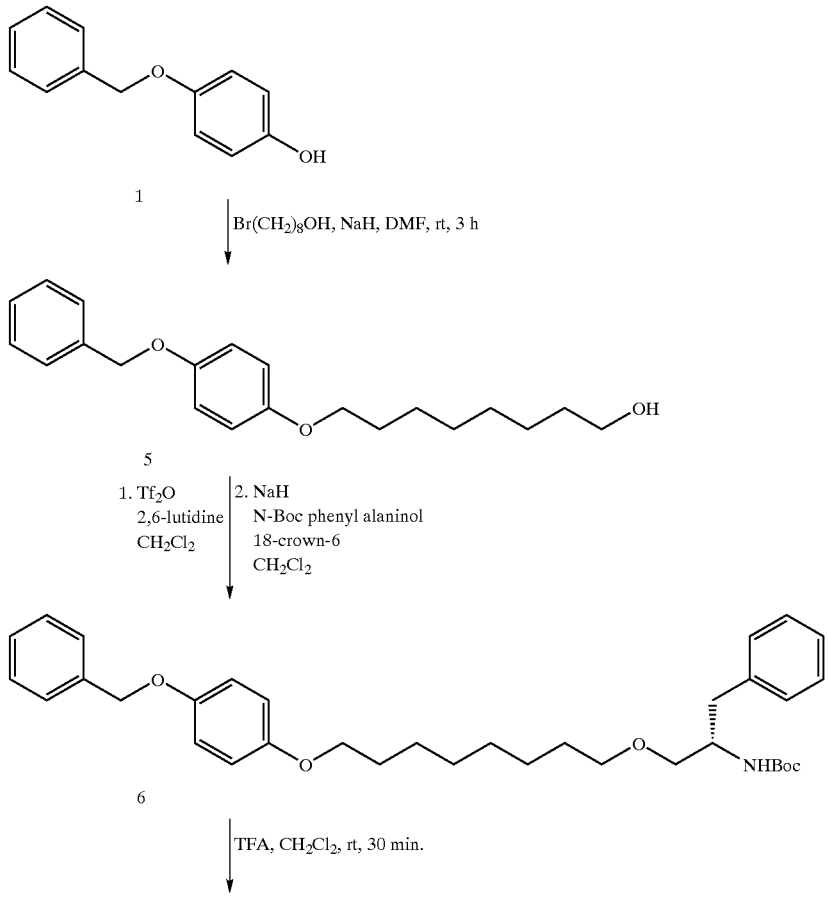

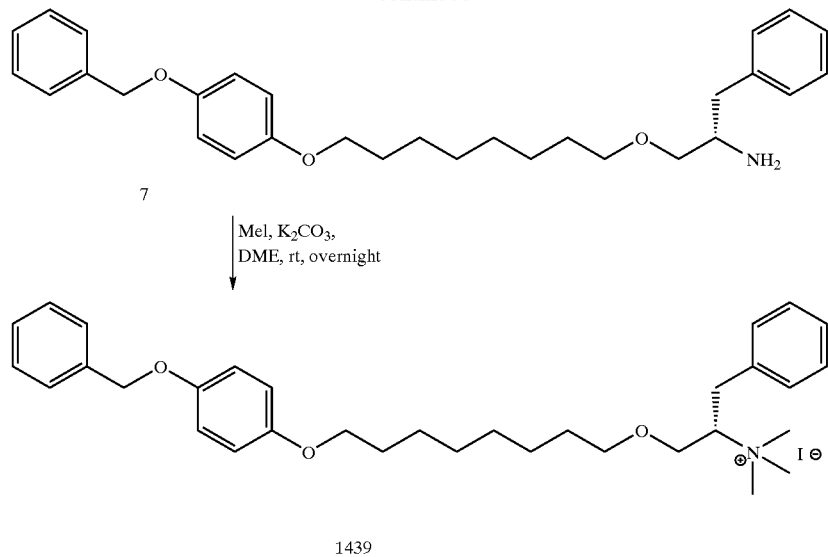

1439

Compound 6

To a cooled solution (0° C.) of alcohol 5 (1 g, .3.05 mmol) in CH$_2$Cl$_2$ (40 mL) was added 2,6-lutidine (0.46 mL, 3.955 mmol), followed by triflic anhydride (0.62 mL, 3.687 mmol). After stirred at 0° C. for 15 min. TLC (EtOAc:Hexanes 1:3) showed the reaction is complete. The reaction mixture was then washed with water (2×20 mL), brine (20 mL) and dried (Na$_2$SO$_4$). The solvent was completely removed and the product triflate was dried at high vacuum for 10 min. Triflate was then dissolved in CH$_2$Cl$_2$ (10 mL) and added in 10 minutes to a solution of N-Boc phenyl alaminol (1.53 g, 6.095 mmol) and NaH (0.305 g, 60% in mineral oil, 7.625 mmol) in CH$_2$Cl$_2$ (30 mL) kept at 0° C. Reaction bubbled vigorously. It was stirred for 5 minutes and 18-crown-6 (0.081 g, 0.307 mmol) was added and the reaction mixture was allowed to attain room temperature and stirred at room temp for 30 minutes. TLC (25% EtOAc in hexanes) showed that the reaction is complete. Reaction was then washed with water (2×20 mL) and brine (20 mL). Removal of solvent from the dried (Na$_2$SO$_4$) extract gave the crude product which was purified by f column chromatography over silica gel (20×4 cm) using 10% EtOAc in hexanes as eluent to afford the pure ether 6 (1.39 g, 81.28% yield) as a white solid. mp.65–66° C. $^1$H-NMR (CDCl$_3$) δ 1.28–1.39 (m, 6H), 1.42 (s, 9H), 1.39–1.51 (m, 2H), 1.51–1.64 (m, 2H), 1.69–1.81 (m, 2H), 2.75–2.94 (m, 2H), 3.23–3.32 (m, 2H), 3.32–3.45 (m, 2H), 3.88 (t, 2H, J=6.52 Hz), 4.88 (d, 1H, J=8.04 Hz), 4.98 (s, 2H), 6.81 (d, 2H J=9.26 Hz), 6.88 (d, 2H, J=9.21 Hz) and 7.15–7.43 (m, 10H); $^{13}$CNMR (CDCl$_3$) δ 25.9, 26.1, 28.3 (2C), 29.29, 29.33, 29.5, 37.7, 51.5, 68.4, 70.3, 70.5, 71.1, 79.1, 115.2, 115.6, 126.1, 127.3, 127.7, 128.2, 128.4, 129.4, 137.2, 138.2, 152.7, 153.4 and 155.3; IR (neat):1685, 3373 cm$^{-1}$; MS (ES$^+$): 562 (M+1); Anal. Calcd for C$_{35}$H$_{47}$NO$_5$: C, 74.83; H, 8.43; N, 2.49. found: C, 74.59; H, 8.39 and N, 2.56.

Compound 7

To a solution of Boc-protected ether 6 (1.00 g, 1.782 mmol) in CH$_2$Cl$_2$ (5 mL) at room temperature a solution of TFA (5 mL) in CH$_2$Cl$_2$ (5 mL) was added and stirred at room temperature for 30 min. TLC (10% MeOH in CHCl$_3$) showed that the reaction is complete. Solvent and TFA were removed completely under vacuum and residue was dissolved in CH$_2$Cl$_2$ (20 mL). It was washed with sat. Na$_2$CO$_3$ (2×10 mL), water (2×10 mL) and brine (10 mL). Removal of solvent from the dried (Na$_2$SO$_4$) extract gave the crude product. Purified by column chromatography over silica gel (15×3 cm) using 10% MeOH in CHCl$_3$ to obtain the pure amine 7 (0.711 g, 86.51% yield) as a colorless oil. $^1$H-NMR (CDCl$_3$) δ 1.28–1.38 (m, 6H), 1.38–1.50 (m, 4H), 1.50–1.64 (m, 2H), 1.67–1.79 (m, 2H), 2.52 (dd, 1H, J1=13.19 Hz, J2=7.29 Hz), 2.76 (dd, 1H, J$_1$=13.34 Hz, J$_2$=4.45 Hz), 3.15–3.27 (m, 2H), 3.33–3.48 (m, 3H), 3.86 (t, 2H, J=6.44 Hz), 4.96 (s, 2H), 6.80 (d, 2H, J=9.12 Hz), 6.87 (d, 2H, J=8.92 Hz) and 7.15–7.43 (m, 10H); $^{13}$CNMR (CDCl$_3$) δ 25.8, 25.9, 29.2 (2C), 29.3, 29.5, 40.6, 52.2, 68.3, 70.4, 71.1, 75.2, 115.1, 115.6, 126.1, 127.3, 127.7, 128.3, 128.4, 129.1, 137.2, 138.8, 152.6 and 153.3; MS (ES$^+$): 462 (M+1); Anal. Calcd for C$_{30}$H$_{39}$NO$_3$: C, 78.05; H, 8.52; N, 3.03. found: C, 77.83; H, 8.56 and N, 3.02.

Compound 1439

To a solution of the amine 7 (0.7 g, 1.518 mmol) in DME (15 mL) was added potassium carbonate (1.25 g, 9.057 mmol) and iodomethane (1.4 mL, 22.4 mmol). The reaction mixture was stirred at room temperature overnight. TLC (10% MeOH in CHCl$_3$) showed that the reaction is complete. Precipitation of the product was observed. CHCl$_3$ was added to the reaction mixture until all the product went into a solution. K$_2$CO$_3$ was removed by filtration through celite 521. The filtrate was concentrated on a rotary evaporator until solid began precipitating out. This was filtered and washed with DME and ethyl acetate to obtain pure 1439 (0.518 g, 54.08% yield) as a white solid., mp. 128–129° C. $^1$H-NMR (CDCl$_3$) δ 1.29–1.40 (m, 6H), 1.40–1.52 9 m, 2H), 1.52–1.63 (m, 2H), 1.69–1.81 (m, 2H), 3.12 (t, 1H, J=12.26 Hz), 3.22–3.43 (m, 4H), 3.58 (s, 9H), 3.84–3.95 (m, 3H), 4.25–4.33 (m, 1H), 5.00 (s, 2H), 6.81 (d, 2H, J=9.15 Hz), 6.90 (d, 2H, J=9.14 Hz) and 7.21–7.45 (m, 10H); $^{13}$CNMR (CDCl$_3$) δ 25.9, 26.1, 29.18, 29.2, 29.24, 29.3, 31.3, 53.4, 65.1, 68.4, 70.5, 71.7, 73.8, 115.2, 115.6, 127.3, 127.5, 127.7, 128.4, 129.0, 129.4, 134.7, 137.1, 152.7 and 153.3; MS (ES$^+$): 504 (M+); Anal. Calcd for C$_{33}$H$_{46}$INO$_3$: C, 62.75; H, 7.34; N, 2.22. found: C, 62.40; H, 7.17 and N, 2.17.

Synthesis of Guanidine 1503
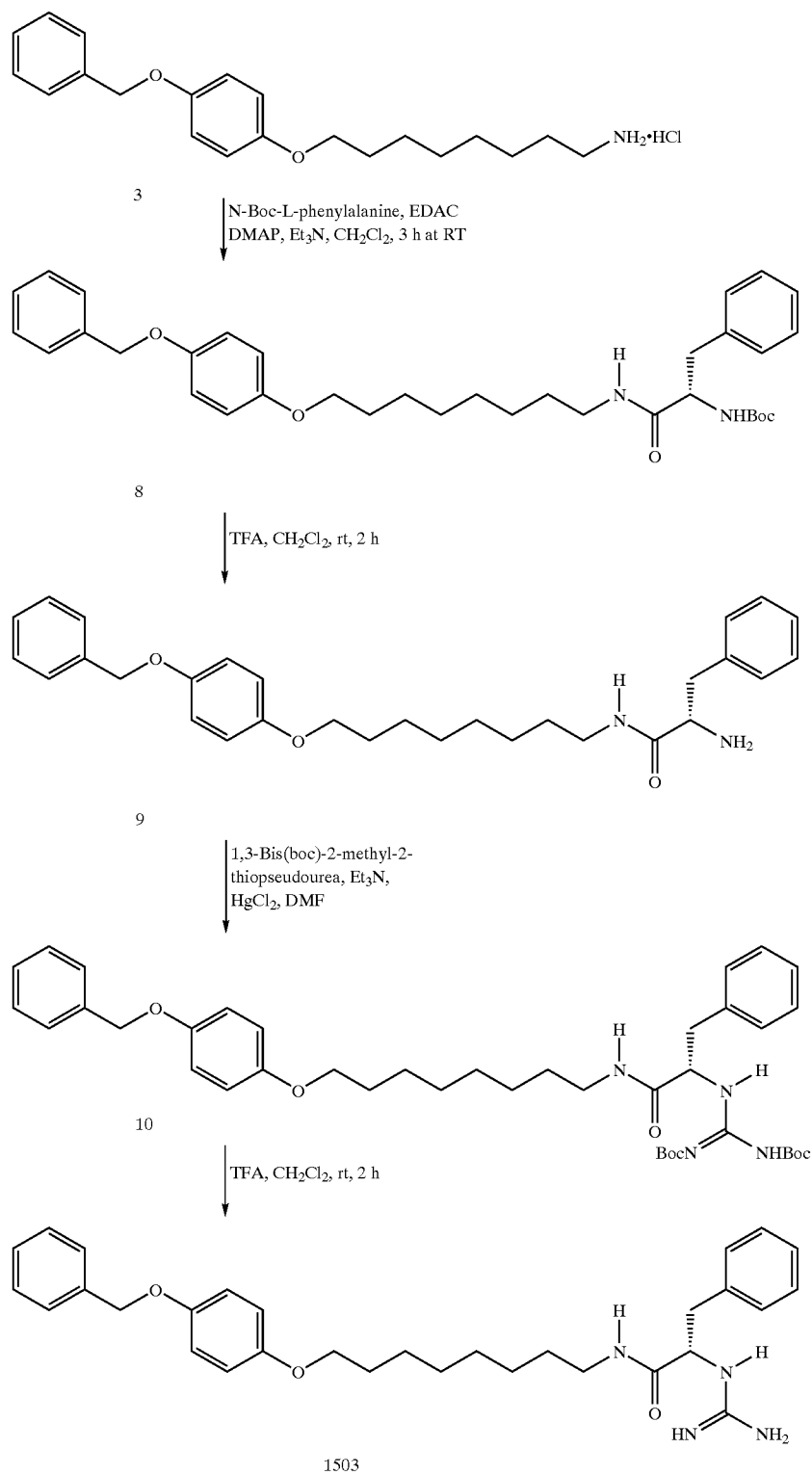
Compound 8
Compound 3 (free amine, 1.0 g, 3.05 mmol), N-Boc-L-phenylalanine (0.89 g, 3.35 mmol), 1-[3-[(dimethylamino)propyl]-3-ethylcarbodiimide hydrochloride (0.72 g, 3.66 mmol), and DMAP (0.036 g, 0.30 mmol) was dissolved in 20 mL of anhydrous $CH_2Cl_2$. The mixture was stirred at room temperature for 3 h, diluted with CHCl$_3$ (50 mL) and washed with 5% NaHCO$_3$ solution (2×30 mL) followed by brine (1×30 mL). The organic layer was dried over sodium sulfate and evaporated under reduced pressure. The product was purified by flash silica gel column chromatography using hexanes/CHCl$_3$/MeOH (3/1/0.1) to afford 8 (1.5 g, 86% yield) as a white solid. m.p.: 108–110° C.; $^1$H NMR (CDCl$_3$) δ 1.17–1.45 (m, 10H), 1.41 (s, 9H), 1.69–1.82 (m, 2H), 2.96–3.18 (m, 4H), 3.89 (t, 2H, J=6.5 Hz), 4.26 (q, 1H, J=7.6 Hz,), 5.01 (s, 2H), 5.09 (bs, 1H, —NH), 5.67 (bs, 1H, —NH), 6.82 (d, 2H, J=9.2 Hz), 6.90 (d, 2H, J=9.2 Hz), 7.19–7.41 (m, 10H); $^{13}$C NMR (CDCl$_3$), δ 26.19, 26.87, 28.48, 29.35, 29.44, 29.53, 29.54, 38.98, 39.62, 68.69, 70.87, 115.55, 115.98, 127.67, 128.07, 128.74, 128.86, 129.52, 137.50, 153.03, 153.66, 171.11.; MS (ES+) 575 (M+1), 475 (M+1-Boc); (ES−) 573 (M−1).

Compound 9

To a solution of compound 8 (1.5 g. 2.61 mmol) in 10 mL of anhydrous CH$_2$Cl$_2$ was added 5 mL of trifluoroacetic acid in 5 mL of anhydrous CH$_2$Cl$_2$ at room temperature under argon atmosphere. The mixture was stirred for 30 min and the reaction was quenched by an addition of 10 g of solid NaHCO$_3$. The mixture was partitioned between water (50 mL) and CHCl$_3$ (2×100 mL). The organic layer was dried over sodium sulfate and evaporated under reduced pressure. The product was crystallized from ether to afford 9 (1.2 g, 97% yield) as a white solid. m.p.: 82–84° C.; $^1$H NMR (CDCl$_3$) δ 1.30–1.57 (m, 10H), 1.67–1.77 (m, 2H), 2.68 (dd, 1H, J=9.1, 13.6 Hz), 3.15–3.27 (m, 3H), 3.54 (dd, 1H, J=4.3, 9.1 Hz), 3.85 (t, 2H, J=6.5 Hz), 4.95 (s, 2H), 6.79 (d, 2H, J=9.2 Hz), 6.87 (d, 2H, J=9.2 Hz), 7.17–7.37 (m, 10H); $^{13}$C NMR (CDCl$_3$) δ 25.93, 26.77, 29.15, 29.21, 29.28, 38.98, 41.01, 56.37, 68.40, 70.50, 115.26, 115.68, 126.66, 127.37, 127.77, 128.44, 128.57, 129.25, 137.25, 137.95, 152.74, 153.39, 174.00; MS (ES+) 475 (M+1).

Compound 10

To a stirred solution of compound 9 (0.1 g, 0.21 mmol) in DMF was added triethylamine (0.073 mL, 0.52 mmol) and HgCl$_2$ (0.095 g, 0.35 mmol). The mixture was cooled down to 0° C. and bis-Boc-S-methyl-isothiourea (0.091, 0.31 mmol) was added at once. The mixture was stirred for 3 h and after the filtration of resulting white solid, the filtrate was partitioned between 5% NaHCO$_3$ (50 mL) and EtOAc (3×50 mL). The organic layer was dried over sodium sulfate and evaporated under reduced pressure. The product was purified by silica gel column chromatography using hexanes/EtOAc (15/1 to 7/1) to afford 10 (0.14 g, 93% yield) as a colorless oil; $^1$H NMR (CDCl$_3$) δ 1.20–1.55 (m, 10H), 1.48 (s, 18H), 1.69–1.77 (m, 2H), 3.05–3.18 (m, 4H), 3.88 (t, 2H, J=6.5 Hz), 4.67 (q, 1H, J=7.2 Hz), 5.00 (s, 2H), 6.42 (1H, pseudo t, —NH), 6.82 (d, 2H, J=9.3 Hz), 6.90 (d, 2H, J=9.3 Hz), 7.18–7.44 (m, 10H), 8.81 (d, 1H, J=7.2 Hz, —NH), 11.31 (s, 1H, —NH); $^{13}$C NMR (CDCl$_3$)δ 26.14, 26.28, 26.84, 28.13, 28.39, 29.30, 29.38, 29.48, 37.76, 39.55, 56.06, 68.60, 70.78, 79.45, 83.60, 115.47, 115.90, 126.99, 127.61, 128.00, 128.63, 128.67, 129.66, 137.02, 137.44, 152.79, 152.95, 153.59, 155.90, 163.14, 170.21; MS (ES+) 717 (M+1); (ES−) 715 (M−1).

Compound 1503

To a solution of compound 10 (0.3 g. 0.42 mmol) in 2 mL of anhydrous CH$_2$Cl$_2$ was added 1 mL of trifluoroacetic acid in 1 mL of anhydrous CH$_2$Cl$_2$ at room temperature under argon atmosphere. The mixture was stirred for 1 h and evaporated under reduced pressure. The residue was partitioned between 5% Na$_2$CO$_3$ (50 mL) and EtOAc (3×50 mL). The organic layer was dried over sodium sulfate and evaporated under reduced pressure. The product was purified by silica gel column chromatography using CHCl$_3$/MeOH/30% NH$_4$OH (10/1/0.1) to afford 0.17 g of free base of 1503 as a amorphous solid (79% yield). A solution of free base of 1503 (50 mg) in 3 mL of anhydrous CH$_2$Cl$_2$ was added 50 μL of trifluoroacetic acid and the mixture was evaporated with anhydrous ether (5×10 mL). The resulting white crystal was suspended with ether and collected by filtration to give 1503 (0.045 g, 74% yield). m.p.: 108–113° C.; $^1$H NMR (free base, CDCl$_3$) δ 1.11–1.55 (m, 10H), 1.68–1.77 (m, 2H), 2.85–3.23 (m, 4H), 3.86 (t, 2H, J=6.5 Hz), 4.82 (bs, 1H), 4.97 (s, 2H), 6.80 (d, 2H, J=9.2 Hz), 6.88 (d, 2H, J=9.2 Hz), 7.21–7.41 (m, 10H), 7.95 (bs, 2H, —NH$_2$), 8.23 (bs, 1H, —NH); $^{13}$C NMR (CDCl$_3$) δ 26.17, 26.81, 28.73, 29.31, 29.38, 29.53, 40.13, 68.66, 70.80, 115.49, 115.94, 127.65, 128.02, 128.69, 128.96, 129.30, 135.04, 137.45, 152.98, 153.62, 157.09, 171.22; MS (ES+) 517 (M+1).

Synthesis of Cyclic Guanidine Compound 1686 (Scheme 4)

Compound 1686

A solution of compound 9 (0.05 g, 0.105 mmol) and 2-methylthio-2-imidazoline hydroiodide (0.14 g 0.580 mmol) in anhydrous CH$_3$CN was refluxed for 2 days. The mixture was cooled down and evaporated under reduced pressure. The residue was Scheme 4

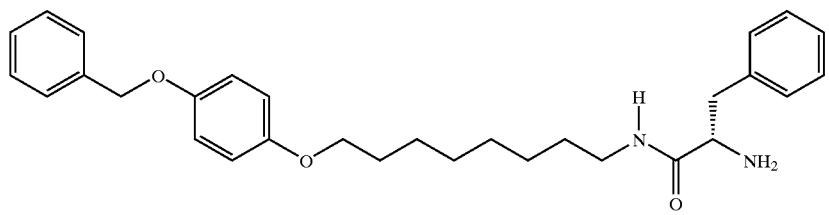

9

2-methylthio-2-imidazoline•HCl
CH$_3$CN, reflux, 2 days

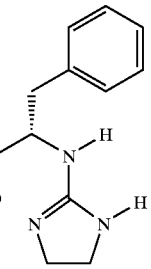

1686 suspended with $CH_2Cl_2$ and any solid was removed by filtration. The filtrate was concentrated and purified by silica gel column chromatography using [$NH_4OH$ saturated $CHCl_3$/MeOH (100/1 to 10/1) and crystallization from ether to give 30 mg of 1686 (0.03 g, 53% yield) as a white solid. $^1H$ NMR (free base, $CDCl_3$, δ ppm) 1.18–1.52 (m, 10H), 1.65–1.79 (m, 2H), 2.74 (dd, 1H, J=9.2, 13.1 Hz), 3.10–3.41 (m, 7H), 3.52 (bs, 1H, —NH), 3.89 (t, 2H, J=6.5 Hz), 3.85–3.94 (m, 1H), 4.82 (bs, 1H), 5.01 (s, 2H), 6.78 (d, 2H, J=9.2 Hz), 6.90 (d, 2H, J=9.2 Hz), 7.22 (m, 1H, —NH), 7.26–7.41 (m, 10H); $^{13}C$ NMR ($CDCl_3$, δ ppm) 26.19, 27.03, 29.41, 29.47, 29.53, 29.59, 39.29, 40.85, 43.69, 62.06, 68.71, 70.85, 115.53, 115.96, 126.69, 127.68, 128.05, 128.69, 128.73, 129.64, 137.49, 139.37, 153.00, 153.64, 160.14, 173.33.; MS (ES+) 543 (M+1); (ES−) 541 (M−1).

Synthesis of Guanidine Compound 1679 (Scheme 5)

Compound 11

To a solution of 7 (0.30 g, 0.65 mmol) in anhydrous DMF (4 mL), $Et_3N$ (0.35 mL, 2.63 mmol) and 1,3-bis(tert-butoxycarbonyl)-2-methyl-2-thiopseudourea (0.208 g, 0.717 mmol) were added and stirred for 5 min at r.t. $HgCl_2$ (0.194 g, 0.715 mmol) was added to the reaction mixture and stirring continued at r.t. for 30 min. TLC (10% MeOH in $CHCl_3$) showed that the reaction is complete. Diluted with EtOAC (20 mL) and the white solid formed was filtered off through celite 521. Filtrate was washed with water (3×5 mL), brine (5 mL) and dried ($Na_2SO_4$). Removal of solvent gave the crude product which was purified by column (15×2 cm) chromatography over silica gel using 10% EtOAc in hexanes as eluent to afford the pure product 11 (0.218 g, 92.8% yield); $^1H$-NMR ($CDCl_3$) δ 1.27–1.43 (m, 8H), 1.47 (s, 9H), 1.50 (m, 9H), 1.53–1.65 (m, 2H), 1.67–1.81 (m, 2H), 2.83–3.02 (m, 2H), 3.25–3.35 (m, 2H), 3.39 (t, 2H, J=6.30 Hz), 3.88 (t, 2H, J=6.53 Hz), 4.41–4.54 (M, 1H), 4.98 (s, 2H), 6.81 (d, 2H, J=9.18 Hz), 6.88 (d, 2H, J=9.21 Hz), 7.15–7.43 (m, 10H), 8.66 (d, 1H, J=8.34 Hz) and 11.48 (s, 1H); $^{13}CNMR$ ($CDCl_3$) δ 25.9, 26.0, 27.9, 28.2, 29.2, 29.3, 29.4, 29.5, 37.2, 51.4, 68.3, 69.4, 70.4, 71.1, 78.7, 82.6, 115.2, 115.6, 126.2, 127.3, 127.7, 128.1, 128.4, 129.5, 137.2, 137.9, 152.6, 152.8, 153.3, 155.5 and 163.6; MS (ES+): 704 (M+1); Anal. Calcd for $C_{41}H_{57}N_3O_7$: C, 69.96; H, 8.16; N, 5.97. found: C, 69.91; H, 8.10; and N, 5.93.

Compound 1679

To a solution of 11 (0.16 g, 0.227 mmol) in $CH_2Cl_2$ (2 mL) a solution of TFA (2 mL) in $CH_2Cl_2$ (2 mL) was added and stirred at r.t. for 3.5 h. TLC (in 10% MeOH in $CHCl_3$) showed that the reaction is complete. Solvent and TFA were completely removed, redissolved in $CH_2Cl_2$ (20 mL), washed with sat. $Na_2CO_3$ (3×5 mL), water (2×5 mL) and brine (5 mL). Removal of solvent from the dried ($Na_2SO_4$) extract gave the crude product which was purified by column (10×2 cm) chromatography over silica gel using 10% MeOH in $CHCl_3$ as eluent to afford the pure guanidine derivative 1679 (0.082 g, 71.65% yield); 1H-NMR ($CDCl_3$) δ 1.17–1.45 (m, 8H), 1.45–1.61 (m, 2H), 1.65–1.81 (m, 2H), 2.73–2.87 (m, 1H), 2.87–3.04 (m, 1H), 3.25–3.43 (m, 3H), 3.43–3.56 (m, 1H), 3.65–3.80 (m, 1H), 3.86 (t, 2H, J=6.46 Hz), 4.96 (s, 2H), 6.80 (d, 2H, J=9.18 Hz), 6.88 (d, 2H, J=8.97 Hz), 7.03 (bs, 1H), 7.16–7.49 (m, 12H, Ar—H and NH2) and 8.09 (d, 1H, 6.54 Hz); $^{13}CNMR$ ($CDCl_3$) δ 25.6, 25.7, 29.0 (2C), 29.1(2C), 37.1, 55.1, 68.2, 70.4, 71.6, 73.9, 115.1, 115.5, 126.8, 127.2, 127.6, 128.3, 128.5, 128.8, 136.4, 137.1, 152.5, 153.2 and 158.8; IR (neat):3155, 3259, 3329 $cm^{-1}$; MS (ES+): 504 (M+1); Anal. Calcd for $C_{33}H_{42}F_3N_3O_5$ (TFA salt): C, 64.17; H, 6.85; N, 6.80. found: C, 64.68; H, 7.06 and N, 6.78.

Scheme 5

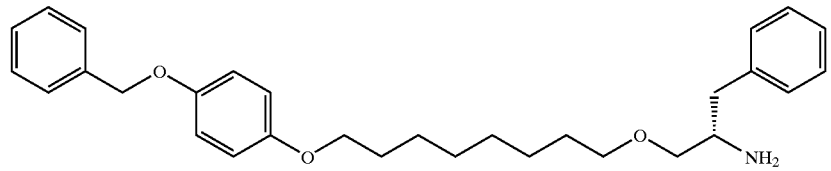

7

1,3-Bis(boc)-2-methyl-2-thiopseudourea, $Et_3N$, $HgCl_2$, DMF

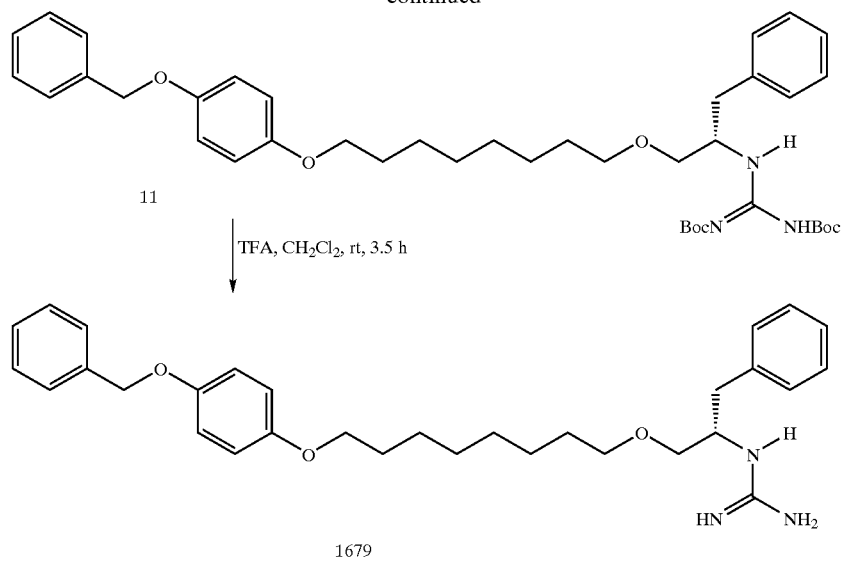

EXAMPLE 2

This example illustrates some of the properties of compounds of the present invention.

Antimicrobial Testing (*P. aeruginosa, E. coli, B. subtilis, S. aureus, S. aureus* (MCR), *A. niger* and *M. flavescens*.)

The MIC test procedures conformed to the present protocol from the National Committee for Clinical Laboratory Standards (NCCLS), and were designed to provide basic antimicrobial data on compounds based on the MIC of the active component.

The test compounds were solubilized, diluted, and pipetted in duplicate into 10 mL sterile culture tubes and dried under vacuum.

Challenge organisms, specified were grown overnight at 37° C. in the appropriate medium (i.e., Mueller-Hinton Broth). These pure broth cultures were diluted 1:1,000 and 2.0 mL were added to the test compound tubes.

Appropriate media controls, challenge organism viability controls, and antibiotic control dilutions (i.e., ampicillin and nystatin), were prepared in the same manner as the test compounds and run against the challenge organisms.

The cultures were incubated overnight at 37° C. and MIC's in μg/ml were indicated by visual determination of the first clear tube.

The minimum inhibitory concentration (MIC) was defined as the concentration of test compound that completely inhibited growth of the challenge organism.

Antimicrobial Testing (*B. anthracis*).

To determine the MIC of each compound in liquid bacterial culture medium against spores of *Bacillus anthracis* Sterne 34F2, an MIC range of 128 μg/mL–0.0156 μg/mL was tested in triplicate using a 48-well, tissue culture plate. Dilutions (of up to 1:7.8) of each compound (stock concentration 1.0 mg/mL in 100% methanol) were made in 2× M–H broth. Spores were suspended to 1×10⁶ spores/400 μl in filter-sterilized MilliQ water.

Potency of Various Compounds to Inhibit Gram-Negative Bacterial Growth or the Growth of Two Fungi In Vitro

| Compound No. | P aeruginosa | E. coli | C. albicans | A. niger |
|---|---|---|---|---|
| 1197 | >50 | >50 | <1.56 | <6.25 |
| 1364 | >50; >50 | <50; >50 | <1.56; <12.56 | >50; >50 |
| 1420 | >50 | >50 | <3.13 | >50 |
| 1423 | >50 | >50 | <3.13 | <50 |
| 1439 | >50 | <12.5 | <3.13 | <25 |
| 1447 | >50; >50 | >50: <50 | <6.25; <3.13 | >50; >50 |
| 1450 | >50 | >50 | <6.25 | >50 |
| 1503 | >50 | >50 | >50 | >50 |
| Ciprofloxacin | <5.0 | <5.0 | — | — |
| Doxycycline | <30 | <1.56 | — | — |
| Amphotericin B | — | — | <1.56 | <1.56 |

All values are reported as μg/mL.

Potency of Various Compounds to Inhibit Bacterial Growth In Vitro

| Compound No. | B. subtilis | S. aureus | S. aureus (MCR) | B. anthracis | M. flavescens |
|---|---|---|---|---|---|
| 1197 | <0.78 | <0.78 | <0.78 | — | — |
| 1364 | <0.39; <6.25 | <0.78; <2.5 | <0.78; <1.56 | — | >50 |
| 1391 | <3.13 | — | <1.56 | — | — |
| 1420 | <0.39 | <1.56 | <0.78 | — | — |
| 1423 | <0.20 | <1.56 | <1.56 | — | — |
| 1439 | <0.39 | <0.78 | <1.56 | 4; 4 | <12.5 |
| 1447 | <1.56; <0.78 | <1.56; <0.78 | <1.56; <1.56 | — | <6.25 |
| 1450 | <3.13 | <3.13 | <3.13 | — | <3.13 |
| 1484 | <3.13 | | <0.78 | — | |
| 1503 | <0.78; <3.13 | <0.78 | <0.78; <1.56 | 8; 16 | >50 |
| 1505 | <0.78 | — | <0.78 | — | — |
| 1594 | >50 | — | <6.25 | 8; 32 | — |
| 1617 | <12.5 | — | <6.25 | 16; — | — |
| 1685 | <3.13 | — | <0.78 | 4; 4 | — |
| Ciprofloxacin | <5.0; <0.5 | <5.0 | <5.0; <0.5 | 0.25; 0.125 | |
| Doxycycline | <1.56 | <1.56 | <30 | — | |
| Ampicillin | <0.5; <0.2 | | >50 | — | |

Values are reported as μg/mL and represent the Minimal Inhibitory Concentration (MIC) for each assay.

Where multiple values are shown (*B.subtilis, S. aureus, S. aureus* (MCR)), these represent two or more tests performed.

For assays using *B. anthracis,* the approximate MICs were determined for various compounds in a standard broth dilution assay using bacterial growth media or by visually inspecting the samples for turbidity (appearance of bacterial outgrowth) when bacteria were cultured in mammalian cell culture media.

Cytotoxicity in Murine 3T3 Cells

Methods

Prior to conducting the assay, cell number, serum concentration, and medium conditions were optimized. Then using the assay conditions as described below, cells were seeded on day 1 and allowed to adhere for at least 1 hour. Test articles were added to achieve a final concentration of 10, 50 and 100 μM in the cultures (Note: in an initial assay, a concentration of 500 μM was included but due to solubility issues as well as marked cytotoxicity, this concentration was excluded from the final assay). The initial solubilization of the test articles was in 50:50 methanol:water (v/v). (Note: Compound 1364 went into solution on day 1, but precipitated on day 2. The organic solvent was increased from 50% to 66%.(v/v)). Compound 1439 never went into solution at 50% organic. Compound 1503b went into solution at 50% organic. Maximum concentration of methanol did not exceed 1.6% in the final assay. On day 1, compounds 1439 and 1364 required sonication before solubility was reached). The cells plus compound were incubated overnight at 37° C., under a 5% $CO_2$/95% $O_2$ atmosphere. On day 2, the cells in the positive control wells were lysed with 0.9% Triton X-100 for 45 minutes to establish maximum levels of LDH release. The plates were centrifuged at 250× g for 5 minutes, the supernatants transferred to a new assay plate, and the LDH was measured. The assay plates were read at OD 490 nm.

| Experimental Conditions | |
|---|---|
| Assay Conditions | |
| Culture Medium | DMEM, 10% calf serum |
| Control: Maximum LDH release | Lysis with Triton X-100 at 0.9% |
| Control: Spontaneous LDH release | Cells with no compound added |
| Control: LDH standard | Bovine heart LDH (included in kit) |
| Incubation Conditions | 37° C. for 20 hrs; 5% $CO_2$/95% $O_2$ |
| Compound Concentrations | 10 μM, 50 μM, 100 μM |
| Enzyme Assay | Promega Cytotox 96 Cytotoxicity Assay |

Abbreviations: DMEM Dulbecco's Modified Eagle's Medium

Cytotoxicity in Rabbit Primary Renal Cells

Isolation of Proximal Tubules and Culture Conditions

Rabbit renal proximal tubules were isolated using the iron oxide perfusion method and grown in 35-mm tissue culture dishes under improved conditions. The cell culture medium was a 1:1 mixture of DMEM/Ham's F-12 (without D-glucose, phenol red, or sodium pyruvate) supplemented with 15 mM HEPES buffer, 2.5 mM L-gluatmine, 1 μM pyridoxine HCL, 15 mM sodium bicarbonate, and 6 mM lactate. Hydrocortisone (50 nM), selenium (5 ng/mL), human transferrin (5 μg/mL), bovine insulin (10 nM) and L-ascorbic acid-2-phosphate (50 μM) were added to fresh culture medium immediately prior to daily media change.

Treatment of RPRC

All numbered compounds were diluted in methanol and the final concentration of methanol in RPRC was less then 0.1% (v/v). 4-BOP also was dissolved in methanol while TMAI was dissolved in ethanol and ciprofloxacin was dissolved in media. These concentrations of solvents did not cause any increases in RPRC death alone.

Measurement of RPRC Death

Cell death was monitored in RPRC by assessment of both annexin V and PI staining using flow cytometry. Briefly, RPRC were exposed to the indicated concentrations of compounds for 24 hr. Media was removed and RPRC washed twice with phosphate-buffered saline (PBS) and incubated in a binding buffer (10 mM HEPES, 140 mM NaCL, 5 mM KCL, 1 mM $MgCl_2$, 1.8 mM $CaCl_2$, pH=7.4) containing annexin V-FITC (1 μmol) and PI (25 μg/mL). After a 10 min incubation, RPRC were washed three times in the binding buffer and were released from the monolayers by gentle scrapping with a rubber policeman. Annexin V and PI staining were measured using a BectonDickson FacsCalibur flow cytometer (San Jose, Calif.). An equal number of cells (10,000) were counted for sample and apoptotic cells were defined as those that stained positive for annexin V-FITC only. RPRC undergoing necrotic cell death stained for PI only. Late apoptotic cells (RPRC dying initially by apoptosis and/or necrotic cell death that exhibited more extensive degradation of the plasma membrane over time) were defined as those that stained positive for both annexin V and PI.

Data Analysis

RPRC isolated from one rabbit represented one experiment (n=1). Data were analyzed and are reported as means±standard error of the mean of at least 3 separate experiments.

| Effect of Various Compounds on Mammalian Cell Growth In Vitro | | | |
|---|---|---|---|
| Compound No. | % CELLULAR NECROSIS (FIBROBLASTS)[1] | % CELLULAR NECROSIS (RPRC)[2] | % APOPTOSIS (RPRC)[3] |
| Control | | 2 ± 1 | 7 ± 1 |
| TMAI | — | 2 ± 1 | 5 ± 1 |
| Cipro | — | 4 ± 1 | 9 ± 3 |
| 1617 | — | 18 ± 2 | 23 ± 3 |
| 1594 | — | 29 ± 4 | 13 ± 2 |
| 1439 | 73 | 62 ± 2 | 10 ± 1 |
| 1364 | 62 | 63 ± 2 | 15 ± 3 |

[1]at 100 μM
[2]at 300 μM
[3]at peak effect (30 μM)
RPRC—rabbit primary renal cells
TMAI—tetramethylammonium iodide
Reference value 1 μM = approximately 0.6 to 0.7 μg/mL for compounds 1364, 1439, 1594 and 1617 contingent upon the molecular weight of the compound.

EXAMPLE 3

This Example illustrates the NAD synthetase enzyme inhibiting activity of some compounds of the present invention.

Prokaryotic NAD Synthetase Enzyme Activity Assay

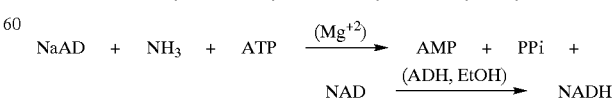

The coupled assay—production of NAD was monitored through conversion to NADH by alcohol dehydrogenase. [NADH] was monitored by 2 parallel methods: the change in absorbance at 340 nm, and fluorescence at 460 nm (excitation 320 nm). The assay condition were as follows: Total volume=200 μL; 58.5 mM HEPPS, pH 8.5; 18.5 mM NH₄Cl; 9.75 mM MgCl₂; 1% (v/v) EtOH; 0.3% BOG (w/v); 40 μg/mL ADH; 0.1 mM NaAD; 0.2 mM ATP; 2.0 μg/mL NAD synthetase; 2.5% (v/v) DMSO. Controls were included for determining inhibitor background, precipitation, and ADH inhibition.

| Compound No. | IC₅₀ (μM) | | | |
|---|---|---|---|---|
| | Mean | SD | SEM | N |
| 1126 | 36.2 | | | 1 |
| 1127 | 23.0 | 1.8 | 0.37 | 23 |
| 1168 | 36.2 | | | 1 |
| 1169 | 36.2 | | | 1 |
| 1182 | 42.1 | 3.2 | 1.84 | 3 |
| 1186 | 46.1 | | | 2 |
| 1197 | 20.8 | 2.7 | 0.57 | 23 |
| 1264 | 38.1 | | | 2 |
| 1290 | 36.2 | | | 1 |
| 1291 | 36.2 | | | 1 |
| 1292 | 36.2 | | | 1 |
| 1294 | 36.2 | | | 1 |
| 1321 | 22.0 | 1.8 | 1.27 | 2 |
| 1322 | 26.5 | 4.8 | 3.41 | 2 |
| 1323 | 48.2 | | | 1 |
| 1324 | 50.7 | | | 1 |
| 1336 | 19.4 | 1.1 | 0.57 | 4 |
| 1337 | 20.3 | 2.0 | 0.99 | 4 |
| 1338 | 23.0 | 2.6 | 1.28 | 4 |
| 1339 | 19.8 | 1.7 | 0.85 | 4 |
| 1340 | 19.3 | 1.6 | 0.79 | 4 |
| 1358 | 46.6 | | 0.00 | 2 |
| 1359 | 42.2 | 6.6 | 3.80 | 3 |
| 1364 | 48.4 | 14.7 | 4.90 | 9 |
| 1369 | 29.2 | 3.0 | 1.71 | 3 |
| 1370 | 16.9 | 0.9 | 0.45 | 4 |
| 1371 | 19.1 | 1.2 | 0.67 | 3 |
| 1387 | 20.5 | 5.8 | 2.58 | 5 |
| 1388 | 14.5 | 4.0 | 2.32 | 3 |
| 1389 | 45.5 | 8.5 | 4.93 | 3 |
| 1390 | 14.2 | 3.1 | 0.85 | 13 |
| 1391 | 11.5 | 2.9 | 0.60 | 24 |
| 1393 | 36.7 | 4.9 | 2.81 | 3 |
| 1394 | 22.5 | 4.0 | 2.32 | 3 |
| 1396 | 15.1 | 2.8 | 1.25 | 5 |
| 1397 | 16.9 | 3.0 | 1.76 | 3 |
| 1398 | 16.0 | 2.2 | 1.29 | 3 |
| 1401 | >100 μM | | | |
| 1405 | 18.8 | | | 2 |
| 1408 | 30.5 | 5.3 | 3.03 | 3 |
| 1420 | 31.3 | 9.6 | 5.54 | 3 |
| 1421 | 34.8 | 2.8 | 1.98 | 2 |
| 1422 | 27.9 | 3.9 | 2.73 | 2 |
| 1423 | 32.9 | 12.8 | 7.36 | 3 |
| 1431 | 18.2 | 1.9 | 1.09 | 3 |
| 1432 | 16.6 | 3.3 | 0.99 | 11 |
| 1439 | 22.7 | 5.1 | 1.81 | 8 |
| 1442 | 21.4 | 1.9 | 1.38 | 2 |
| 1443 | 27.9 | 17.0 | 9.80 | 3 |
| 1447 | 22.1 | 6.2 | 2.06 | 9 |
| 1448 | 30.7 | 0.5 | 0.32 | 2 |
| 1450 | 31.7 | 9.0 | 4.03 | 5 |
| 1451 | 34.2 | 0.6 | 0.43 | 2 |
| 1454 | 23.9 | 2.7 | 1.90 | 2 |
| 1456 | 17.0 | 2.3 | 0.67 | 12 |
| 1475 | 22.6 | | | 1 |
| 1477 | 14.0 | 2.9 | 0.93 | 10 |
| 1478 | 15.8 | 10.5 | 3.17 | 11 |
| 1479 | 18.6 | 0.6 | 0.42 | 2 |
| 1482 | 26.2 | 8.3 | 5.88 | 2 |
| 1483 | 16.0 | 1.7 | 0.85 | 4 |
| 1484 | 14.8 | 6.3 | 1.89 | 11 |
| 1485 | 34.8 | | | 1 |
| 1486 | 37.8 | | | 1 |
| 1491 | 19.9 | 5.6 | 1.68 | 11 |

-continued

| Compound No. | IC₅₀ (μM) | | | |
|---|---|---|---|---|
| | Mean | SD | SEM | N |
| 1494 | 12.5 | 5.6 | 1.68 | 11 |
| 1495 | 33.4 | 19.1 | 7.21 | 7 |
| 1498 | 39.4 | | | 1 |
| 1499 | 26.8 | | | 1 |
| 1501 | 38.2 | | | 1 |
| 1502 | 35.6 | | | 1 |
| 1503 | 12.7 | 3.4 | 0.72 | 23 |
| 1505 | 6.6 | 1.5 | 0.41 | 14 |
| 1593 | 18.1 | 3.3 | 2.33 | 2 |
| 1594 | 25.0 | 6.8 | 4.77 | 2 |
| 1596 | 28.0 | | | 1 |
| 1597 | 21.3 | | | 1 |
| 1599 | 44.0 | | | 1 |
| 1600 | 28.7 | 8.6 | 2.73 | 10 |
| 1603 | 34.9 | 12.2 | 3.39 | 13 |
| 1604 | 21.1 | 4.1 | 2.92 | 2 |
| 1605 | 21.0 | | | 1 |
| 1606 | 39.1 | | | 1 |
| 1608 | 26.3 | | | 1 |
| 1609 | 20.7 | | | 1 |
| 1610 | 30.4 | | | 1 |
| 1611 | 23.3 | 8.0 | 5.68 | 2 |
| 1612 | 26.2 | 12.0 | 8.48 | 2 |
| 1613 | 19.1 | 3.0 | 2.12 | 2 |
| 1614 | 23.1 | | | 1 |
| 1615 | 22.3 | 7.1 | 5.05 | 2 |
| 1616 | 38.5 | | | 1 |
| 1617 | 31.4 | 14.8 | 8.55 | 3 |
| 1619 | 22.3 | | | 2 |
| 1620 | 21.9 | | | 2 |
| 1621 | 25.5 | 14.8 | 14.81 | 1 |
| 1622 | 34.2 | | | 1 |
| 1623 | 33.9 | | | 1 |
| 1624 | 31.2 | | | 1 |
| 1629 | 21.1 | | | 1 |
| 1632 | 18.5 | | | 1 |
| 1633 | 20.4 | | | 1 |
| 1634 | 21.2 | | | 1 |
| 1635 | 35.1 | | | 1 |
| 1636 | 19.0 | 2.5 | 1.75 | 2 |
| 1637 | 23.3 | | | 1 |
| 1644 | 23.9 | | | 1 |
| 1645 | 18.1 | 5.4 | 3.80 | 2 |
| 1650 | >50 μM | | | |
| 1651 | 47.7 | | | |
| 1652 | 17.9 | | | |
| 1653 | 19.5 | | | |
| 1658 | 16.8 | 2.4 | 1.72 | 2 |
| 1661 | 23.7 | 7.8 | 3.20 | 6 |
| 1662 | 23.2 | 5.5 | 1.95 | 8 |
| 1663 | 18.4 | | | 1 |
| 1664 | 19.9 | | | 1 |
| 1665 | 19.6 | 2.5 | 0.79 | 10 |
| 1666 | 27.7 | | | 1 |
| 1678 | 36.5 | | | 1 |
| 1679 | 10.4 | 2.2 | 0.75 | 9 |
| 1680 | 10.1 | 1.2 | 0.37 | 11 |
| 1681 | 12.9 | 1.4 | 0.46 | 9 |
| 1682 | 17.6 | 3.7 | 1.38 | 7 |
| 1683 | 20.2 | | | 1 |
| 1685 | 9.9 | 1.7 | 0.60 | 8 |

All references, including publications, patent applications, and patents, cited herein are hereby incorporated by reference to the same extent as if each reference were individually and specifically indicated to be incorporated by reference and were set forth in its entirety herein.

The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of formula (I):

$$Ar_1-X-Ar_2-Y-L-Z-Q \qquad (I)$$

wherein

Q is $Q_1Ar_3$ or $Ar_3Q_1$;

$Ar_1$, $Ar_2$, and $Ar_3$ are aryl, optionally substituted with one or more substituents selected from the group consisting of $C_1-C_6$ alkyl, $C_1-C_6$ alkoxy, $C_1-C_6$ haloalkyl, $C_1-C_6$ hydroxyalkyl, $C_1-C_6$ alkoxy $C_1-C_6$ alkyl, halo, amino, $C_1-C_6$ alkylamino, $C_1-C_6$ dialkylamino, $C_1-C_6$ trialkylamino, $C_1-C_6$ alkylamino $C_1-C_6$ alkyl, $C_1-C_6$ dialkylamino $C_1-C_6$ alkyl, $C_1-C_6$ trialkylamino $C_1-C_6$ alkyl, azido, amine oxide, hydroxy, carboxyl, $C_1-C_6$ alkylcarbonyl, $C_1-C_6$ alkylcarbonyl $C_1-C_6$ alkyl, $C_1-C_6$ alkylcarbonyloxy, $C_1-C_6$ alkylcarbonyloxy $C_1-C_6$ alkyl, $C_1-C_6$ alkyloxycarbonyl $C_1-C_6$ alkyl, $C_1-C_6$ alkyloxycarbonyl, $C_1-C_6$ alkylthio, nitro, nitrosyl, cyano, hydroxylamino, sulfonamido, $C_1-C_6$ dialkyl sulfonamido, $C_1-C_6$ alkylcarbonylamino, formyl, formylamino, mercaptyl, and heterocyclyl;

X, Y, and Z are independently selected from the group consisting of a covalent bond, $(CH_2)mO$, $O(CH_2)m$, $(CH_2O)m$, $(OCH_2)m$, $(CH_2CH_2O)m$, $(OCH_2CH_2)m$, $C(=O)O$, $OC(O)$, $OC(O)O$, $(CH_2)_mS$, $S(CH_2)m$, $(CH_2S)m$, $(SCH_2)m$, NH, NR, $+NR_2$, $C(O)NH$, $C(=O)NR$, $NHC(=O)$, $NRC(=O)$, $CH(OH)$, and $CH(OR)$, wherein R is $C_1-C_6$ alkyl and m is +0–5;

L is $\{(CR_1R_2)q-(W)t(CR_3R_4)r\}p$, wherein $R_1$–$R_4$ are independently selected from the group consisting of H, $C_1-C_6$ alkyl, $C_1-C_6$ alkoxy, $C_1-C_6$ haloalkyl, $C_1-C_6$ hydroxyalkyl, $C_1-C_6$ alkoxy $C_1-C_6$ alkyl, halo, amino, $C_1-C_6$ alkylamino, $C_1-C_6$ dialkylamino, azido, hydroxy, aldehyde, $C_1-C_6$ acetal, $C_1-C_6$ ketal, $C_1-C_6$ alkylcarbonyl, $C_1-C_6$ alkylcarbonyl $C_1-C_6$ alkyl, $C_1-C_6$ alkylcarbonyloxy, $C_1-C_6$ alkylcarbonyloxy $C_1-C_6$ alkyl, $C_1-C_6$ alkylthio, nitro, nitrosyl, cyano, sulfonamido, $C_1-C_6$ alkylcarbonylamino, and heterocyclyl; W is a moiety selected from the group consisting of alicyclic ring, aromatic ring, heterocyclic ring, combinations of alicyclic, heterocyclic, and/or aromatic rings, $C_2-C_6$ alkenyl, dienyl, $C_2-C_6$ alkynyl, $C_1-C_6$ alkoxy, $C_2-C_6$ alkenyloxy, $C_2-C_6$ alkynyloxy, anhydrido, enol, ketene, amino, imino, hydrazinyl, epoxy, episulfide, amido, amine oxide, urea, urethane, ester, thioester, carbonate, carbonyl, thiocarbonyl, sulfonyl, diazo, sulfonamido, ether oxygen, ether sulfur, thionyl, silyl, peroxide, lactam, lactone, phenylene, monosaccharide, di-, tri-, and higher polysaccharides, nucleic acid, amino acid, phosphonyl, phosphoryl, and combinations thereof; q, r, and t are independently 0–20; q, r, and t are not simultaneously 0; and p is 1–6; L, optionally, further including O, N, or S; and $Q_1$ is (i) a $C_1-C_6$ alkylenyl, $C_1-C_6$ alkylenyl carbonyloxy $C_1-C_6$ alkyl, or $C_1-C_6$ alkylenyl carbonylamino $C_1-C_6$ alkyl group, optionally having one or more substituents selected from the group consisting of amino, $C_1-C_6$ alkylamino, $C_1-C_6$ haloalkylamino, $C_1-C_6$ haloalkyl $C_1-C_6$ alkyl amino, $C_1-C_6$ hydroxyalkylamino, $C_1-C_6$ hydxoxyalkyl $C_1-C_6$ alkylamino, $C_1-C_6$ dialkylamino, $C_1-C_6$ trialkylamino, and heterocyclic containing a nitrogen atom which may be optionally quaternized, (ii) a $C_2-C_6$ alkylenyl; (iii) methylenyl with the proviso that Z is other than covalent bond or O(C=O) when Q is $Q_1Ar_3$ wherein $Ar_3$ is a phenyl para substituted with amino, methylamino, dimethylamino, or trimethylamino or $Ar_3$ is a pyridyl or N-methyl pyridyl; (iv) a covalent bond with the proviso that when $Ar_3$ is pyridyl, N-methyl pyridyl, or phenyl para substituted with trimethylaminomethyl group, Z is other than a covalent bond or O(C=O); (v) a group containing amidine or guanidine function wherein the amidine or guanidine may be optionally N-substituted with a $C_1-C_6$ alkyl; or (vi) a zwitterion;

wherein hetrocyclyl moieties are selected from the group consisting of five and six membered closed ring structures where one or more ring atoms is other than carbon, or a pharmaceutically acceptable salt thereof.

2. The compound of claim 1, wherein $Ar_1$, $Ar_2$, and $Ar_3$ are independently phenyl or substituted phenyl.

3. The compound of claim 2, wherein $Ar_1$ is phenyl or phenyl substituted with one or more substituents selected from the group consisting of $C_1-C_6$ alkyl, $C_1-C_6$ alkoxy, $C_1-C_6$ haloalkyl, $C_1-C_6$ hydroxyalkyl, $C_1-C_6$ alkoxy $C_1-C_6$ alkyl, halo, amino, $C_1-C_6$ alkylamino, $C_1-C_6$ dialkylamino, $C_1-C_6$ trialkylamino, $C_1-C_6$ alkylamino $C_1-C_6$ alkyl, $C_1-C_6$ dialkylamino $C_1-C_6$ alkyl, $C_1-C_6$ trialkylamino $C_1-C_6$ alkyl, azido, amine oxide, hydroxy, carboxyl, $C_1-C_6$ alkylcarbonyl, $C_1-C_6$ alkylcarbonyl $C_1-C_6$ alkyl, $C_1-C_6$ alkylcarbonyloxy, $C_1-C_6$ alkylcarbonyloxy $C_1-C_6$ alkyl, $C_1-C_6$ alkyloxycarbonyl $C_1-C_6$ alkyl, $C_1-C_6$ alkyloxycarbonyl, $C_1-C_6$ alkylthio, nitro, nitrosyl, cyano, hydroxylamino, sulfonamido, $C_1-C_6$ dialkyl sulfonamido, $C_1-C_6$ alkylcarbonylamino, formyl, formylamino, mercaptyl, and heterocyclyl.

4. The compound of claim 3, wherein $Ar_1$ is phenyl or phenyl substituted with one or more substituents selected from the group consisting of $C_1-C_6$ alkoxy, halo, amino, $C_1-C_6$ alkylamino, $C_1-C_6$dialkylamino, azido, $C_1-C_6$ alkylcarbonyloxy, $C_1-C_6$ alkylthio, nitro, cyano, sulfonamido, $C_1-C_6$ dialkyl sulfonamido, $C_1-C_6$ alkylcarbonylamino, and heterocyclyl.

5. The compound of claim 2, wherein $Ar_2$ is phenyl, optionally substituted with one or more substituents selected from the group consisting of $C_1-C_6$ alkyl, $C_1-C_6$ alkoxy, $C_1$–$C_6$ haloalkyl, $C_1$–$C_6$ hydroxyalkyl, $C_1$–$C_6$ alkoxy $C_1$–$C_6$ alkyl, halo, amino, $C_1$–$C_6$ alkylamino, $C_1$–$C_6$ dialkylamino, $C_1$–$C_6$ trialkylamino, $C_1$–$C_6$ alkylamino $C_1$–$C_6$ alkyl, $C_1$–$C_6$ dialkylamino $C_1$–$C_6$ alkyl, $C_1$–$C_6$ trialkylamino $C_1$–$C_6$ alkyl, azido, amine oxide, hydroxy, carboxyl, $C_1$–$C_6$ alkylcarbonyl, $C_1$–$C_6$ alkylcarbonyl $C_1$–$C_6$ alkyl, $C_1$–$C_6$ alkylcarbonyloxy, $C_1$–$C_6$ alkylcarbonyloxy $C_1$–$C_6$ alkyl, $C_1$–$C_6$ alkyloxycarbonyl $C_1$–$C_6$ alkyl, $C_1$–$C_6$ alkyloxycarbonyl, $C_1$–$C_6$ alkylthio, nitro, nitrosyl, cyano, hydroxylamino, sulfonamido, $C_1$–$C_6$ dialkyl sulfonamido, $C_1$–$C_6$ alkylcarbonylamino, formyl, formylamino, mercaptyl, and heterocyclyl.

6. The compound of claim 1, wherein $Ar_3$ is phenyl, optionally substituted with one or more substituents selected from the group consisting of $C_1$–$C_6$ alkyl, $C_1$–$C_6$ alkoxy, $C_1$–$C_6$ haloalkyl, $C_1$–$C_6$ hydroxyalkyl, $C_1$–$C_6$ alkoxy $C_1$–$C_6$ alkyl, halo, amino, $C_1$–$C_6$ alkylamino, $C_1$–$C_6$ dialkylamino, $C_1$–$C_6$ trialkylamino, $C_1$–$C_6$ alkylamino $C_1$–$C_6$ alkyl, $C_1$–$C_6$ dialkylamino $C_1$–$C_6$ alkyl, $C_1$–$C_6$ trialkylamino $C_1$–$C_6$ alkyl, azido, amine oxide, hydroxy, carboxyl, $C_1$–$C_6$ alkylcarbonyl, $C_1$–$C_6$ alkylcarbonyl $C_1$–$C_6$ alkyl, $C_1$–$C_6$ alkylcarbonyloxy, $C_1$–$C_6$ alkylcarbonyloxy $C_1$–$C_6$ alkyl, $C_1$–$C_6$ alkyloxycarbonyl $C_1$–$C_6$ alkyl, $C_1$–$C_6$ alkyloxycarbonyl, $C_1$–$C_6$ alkylthio, nitro, nitrosyl, cyano, hydroxylamino, sulfonamido, $C_1$–$C_6$ dialkyl sulfonamido, $C_1$–$C_6$ alkylcarbonylamino, formyl, formylamino, mercaptyl, and heterocyclyl.

7. The compound of claim 6, wherein $Ar_3$ is phenyl, optionally substituted with one or more substituents selected from the group consisting of $C_1$–$C_6$ alkoxy and $C_1$–$C_6$ trialkylamino.

8. The compound of claim 1, wherein Q is $Ar_3Q_1$.

9. The compound of claim 8, wherein $Q_1$ is $C_1$–$C_6$ alkylenyl carbonyloxy $C_1$–$C_6$ alkyl, optionally having a $C_1$–$C_6$ trialkylamino group.

10. The compound of claim 8, wherein $Q_1$ is trimethylamino ethylenyl carbonyloxy t-butyl.

11. The compound of claim 8, wherein $Q_1$ is $C_1$–$C_6$ alkylenyl, optionally having a trialkylamino or a heterocyclic containing a quaternized nitrogen atom.

12. The compound of claim 8, wherein $Q_1$ is a covalent bond.

13. The compound of claim 8, wherein $Q_1$ is a zwitterion.

14. The compound of claim 8, wherein $Q_1$ is a group containing amidine or guanidine function wherein the amidine or guanidine may be optionally N-substituted with a $C_1$–$C_6$ alkyl.

15. The compound of claim 1, wherein t is 0.

16. The compound of claim 15, wherein $R_1$–$R_4$ are H.

17. The compound of claim 16, wherein q and r are independently 1–7.

18. The compound of claim 1, wherein said compound is selected from the group consisting of:

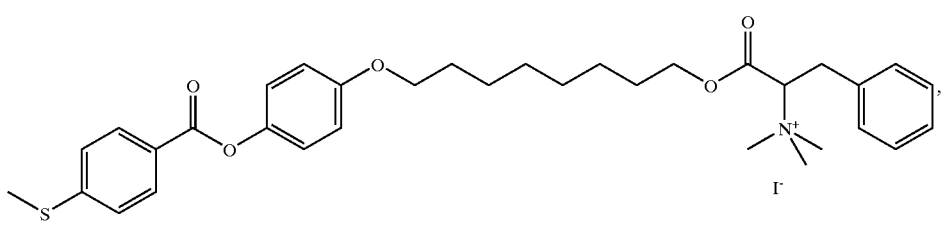

1478

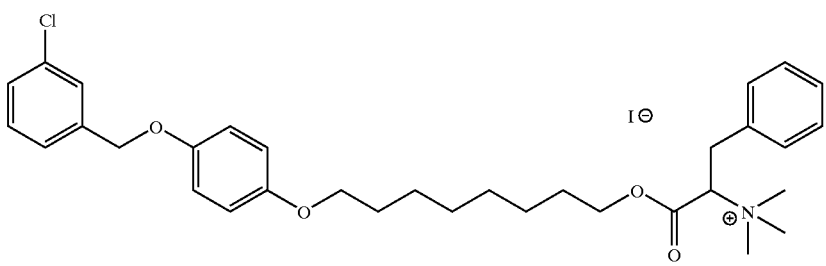

1391

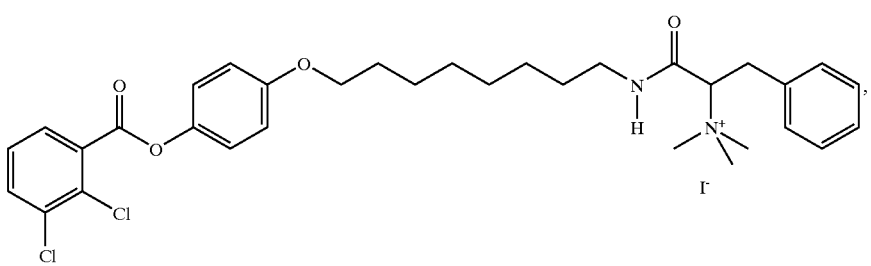

1603

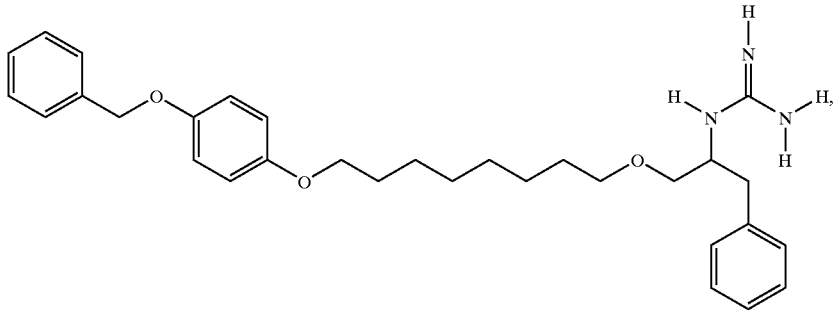
1679
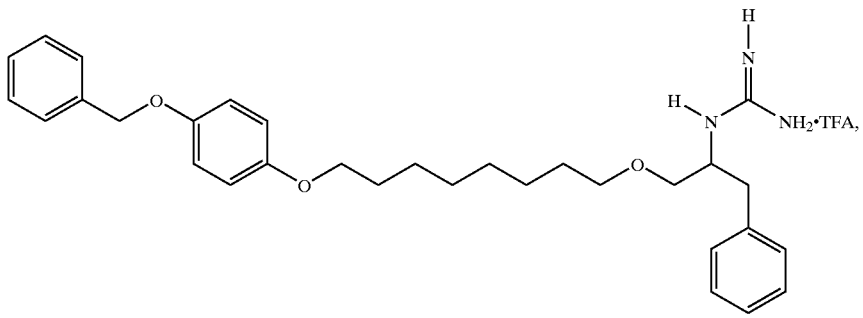
1680'
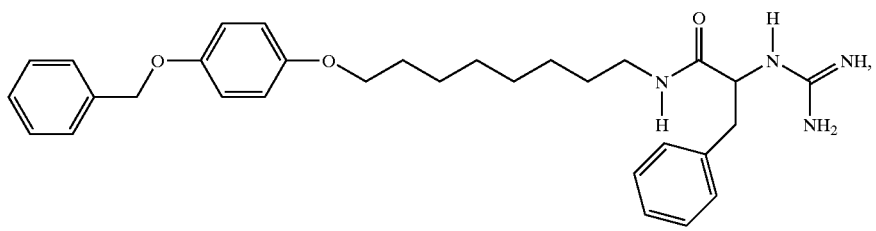
1681'
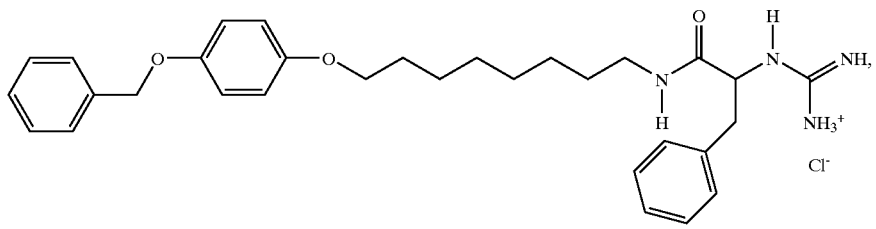
1682'
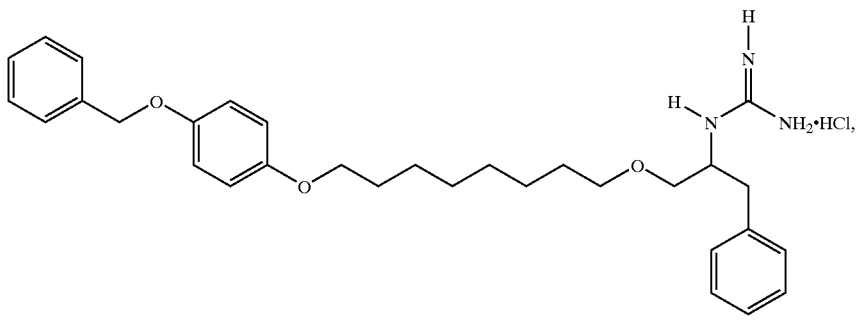
1685'

-continued
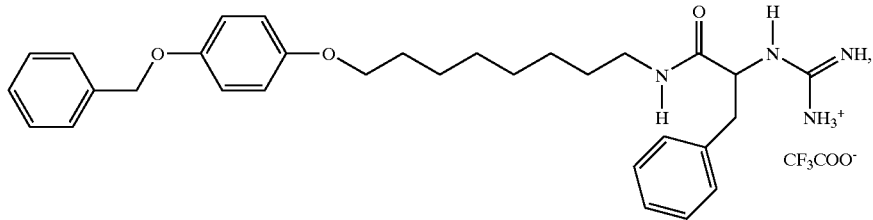
1503'
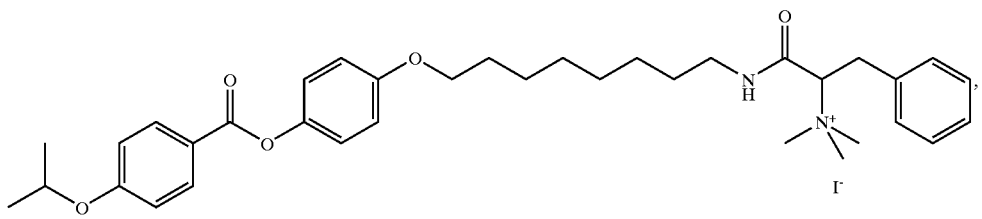
1600
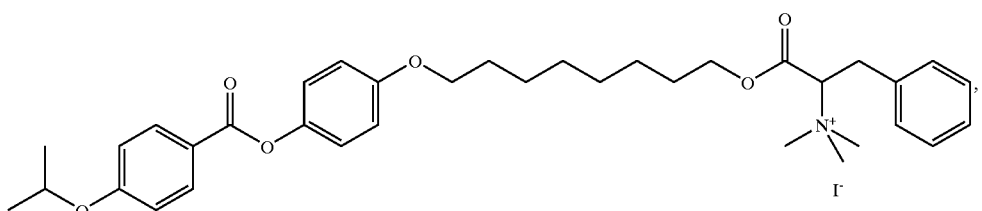
1477
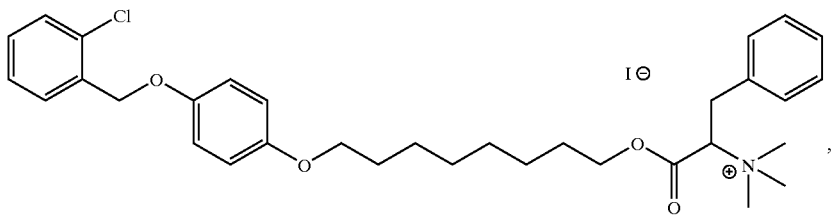
1390
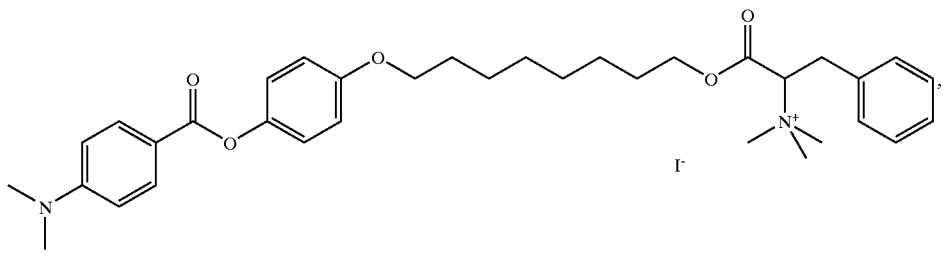
1484
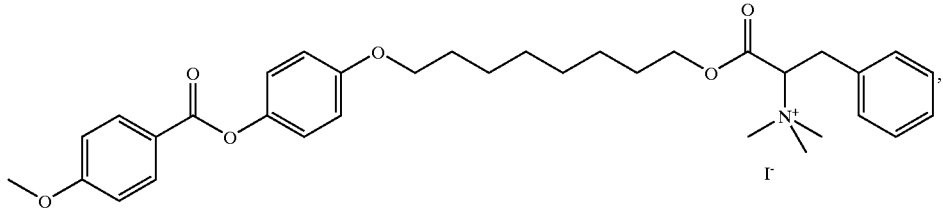
1456
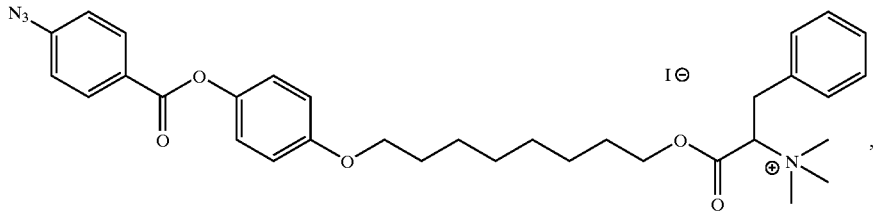
1432

-continued
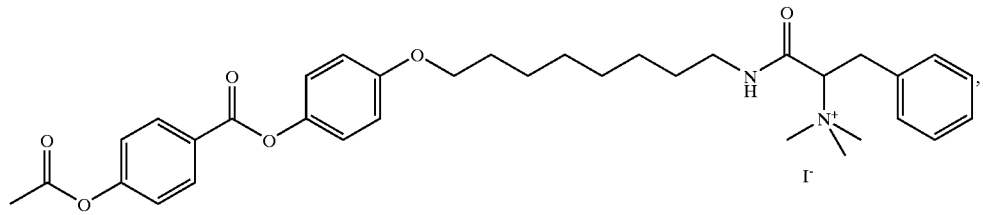
1599
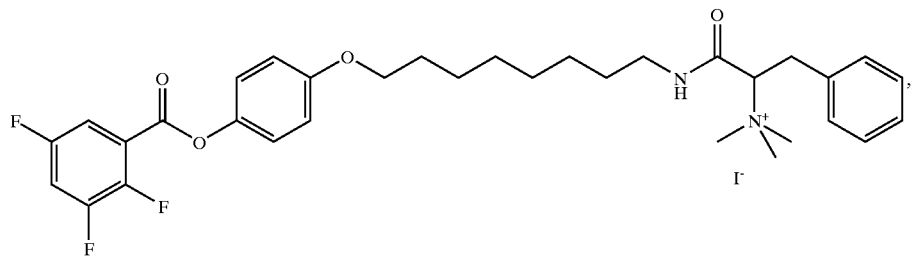
1617
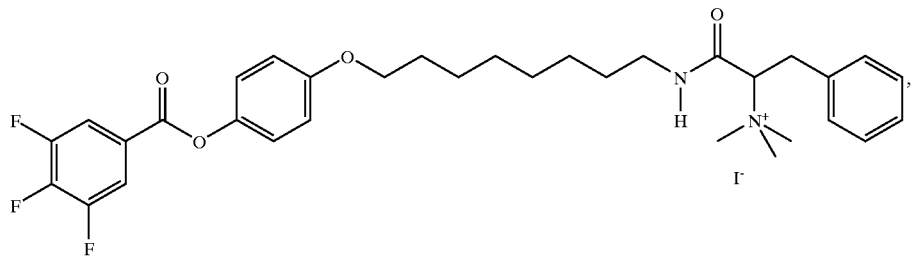
1621
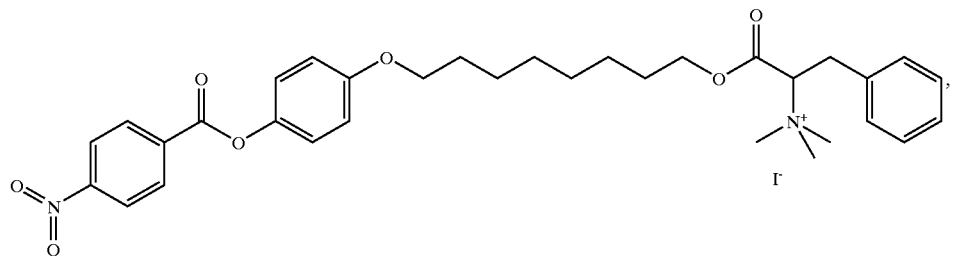
1483
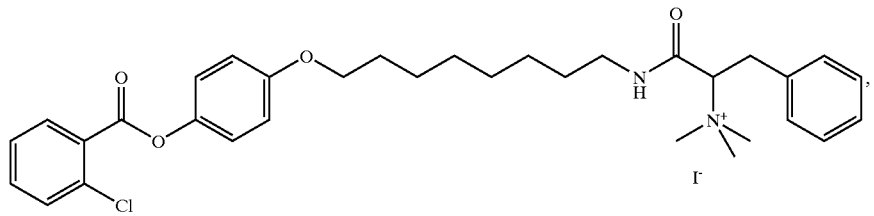
1593
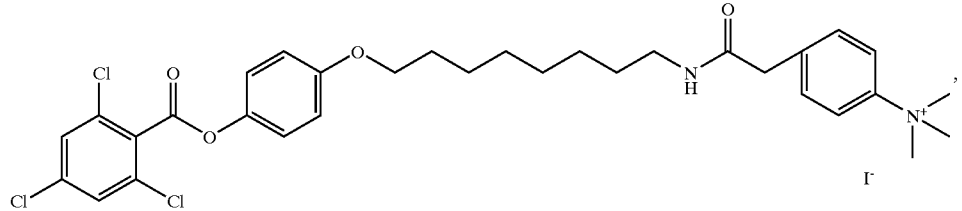
1645

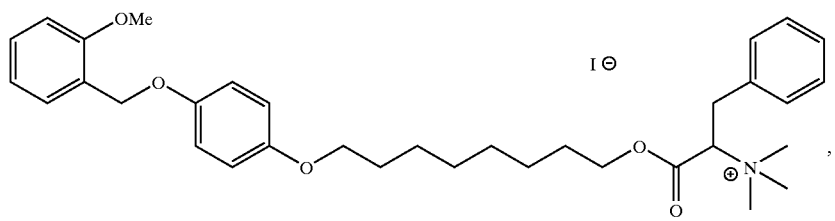
1387
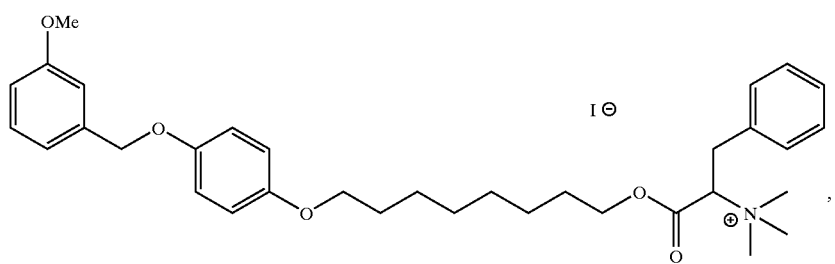
1388
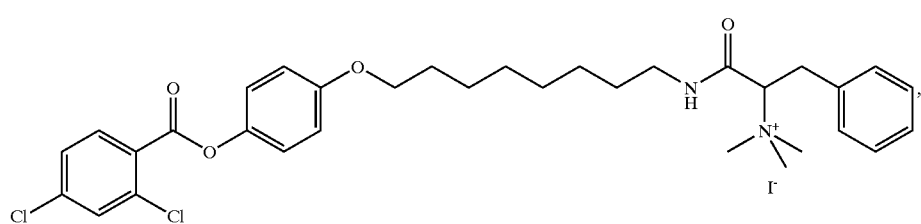
1604
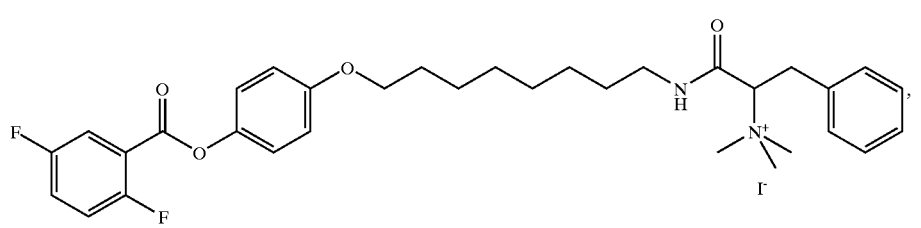
1611
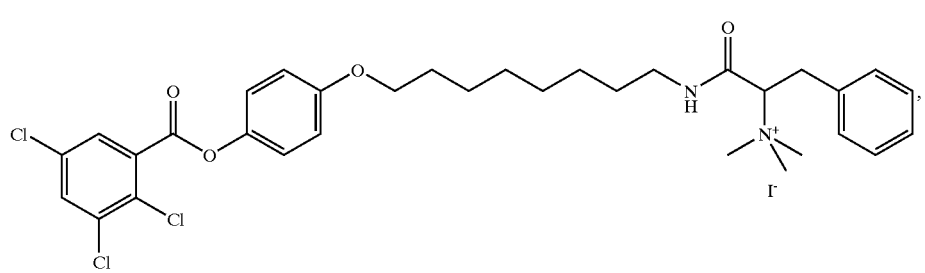
1615
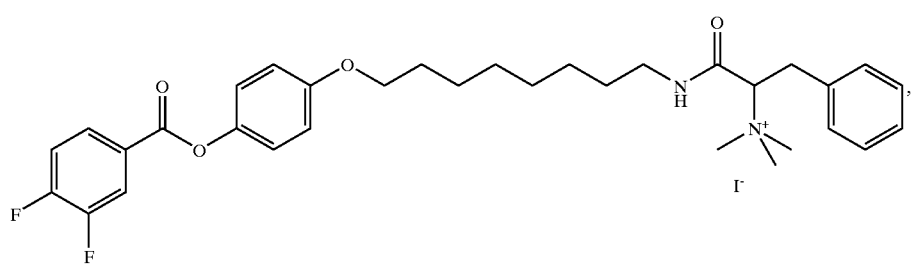
1613

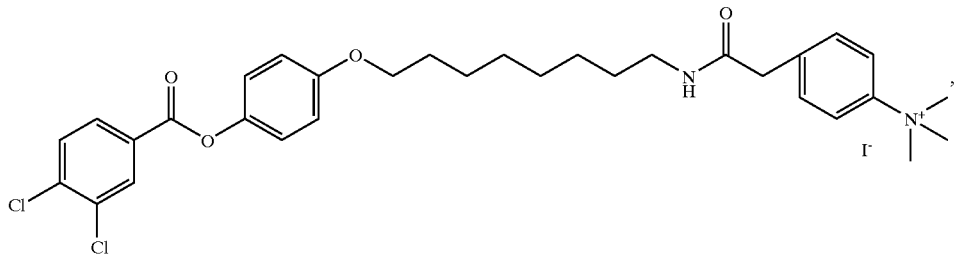
1636
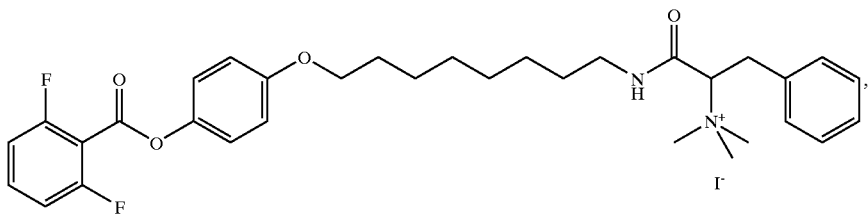
1612
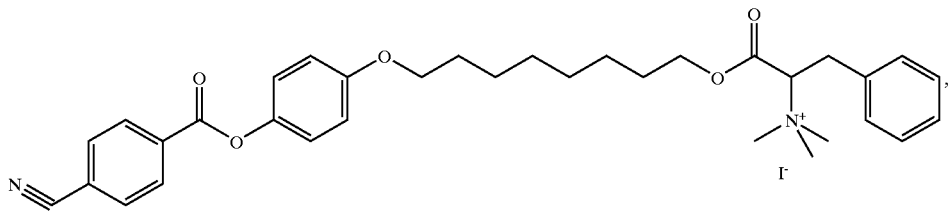
1479
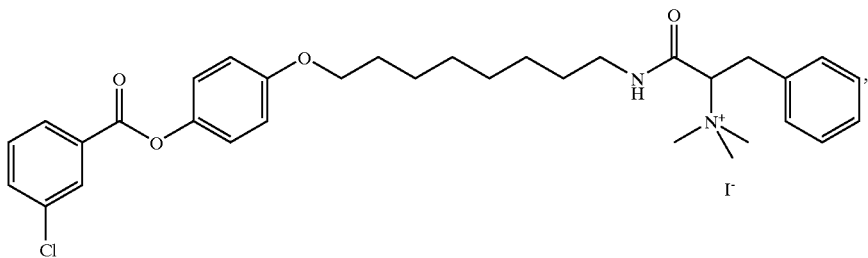
1594
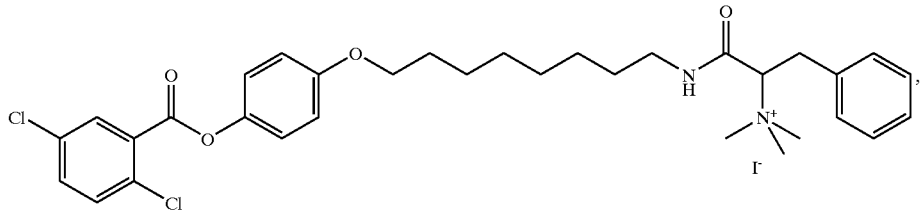
1605
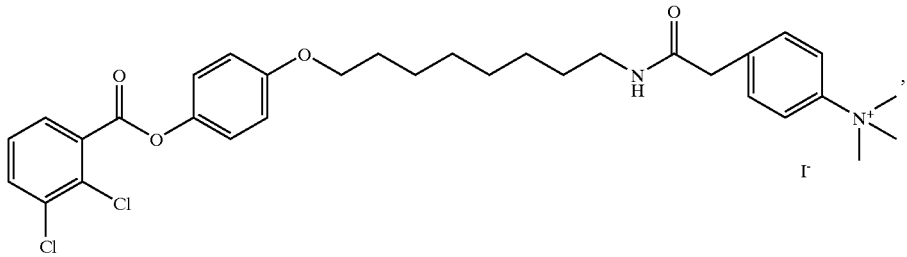
1632

-continued
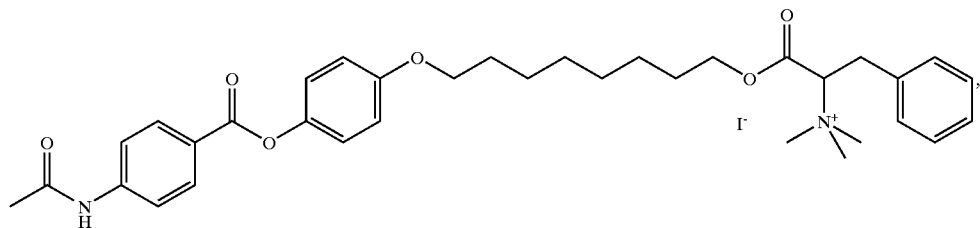
1482
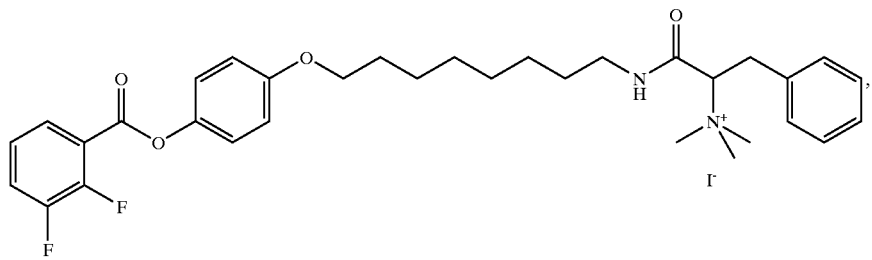
1609
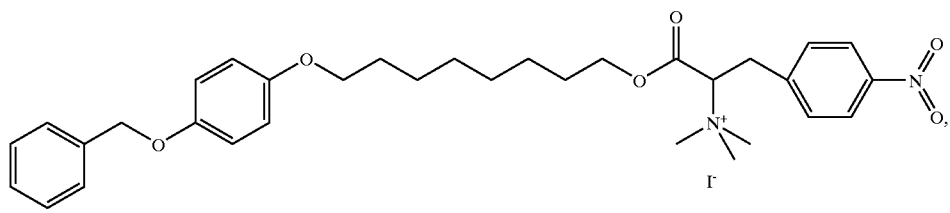
1405
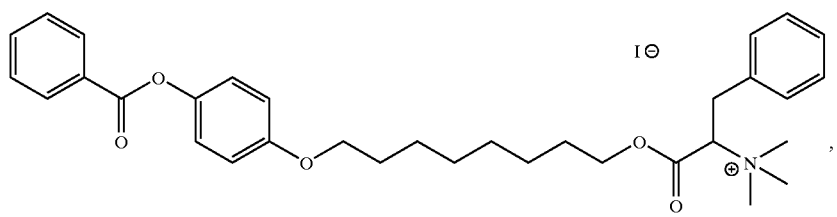
1431
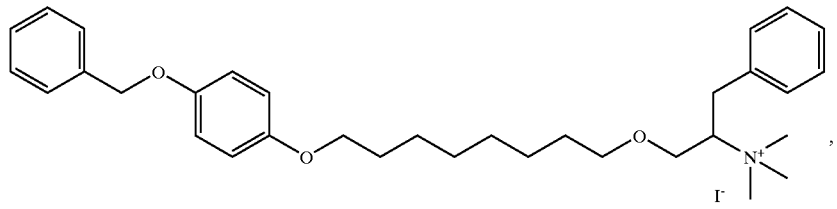
1439
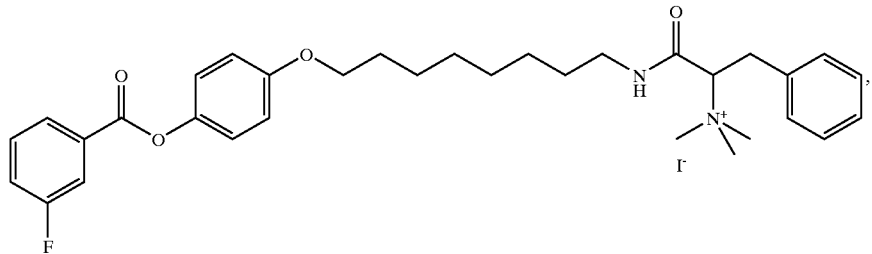
1597
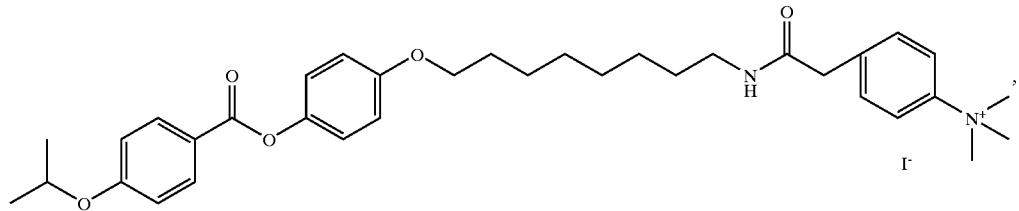
1629

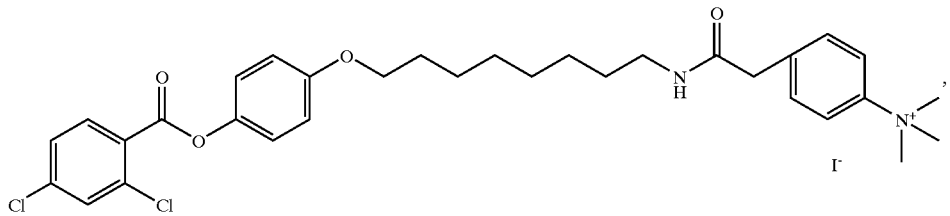
1633
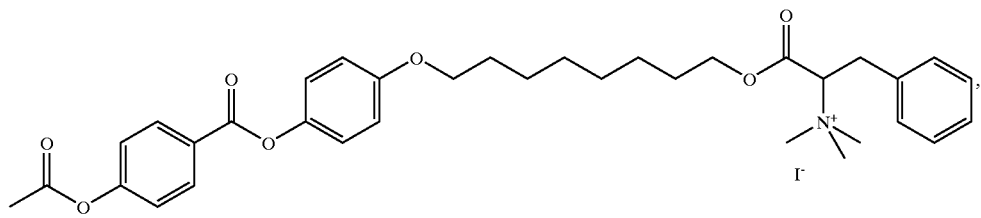
1475
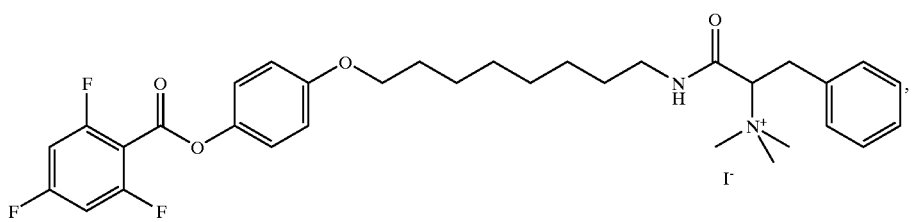
1620
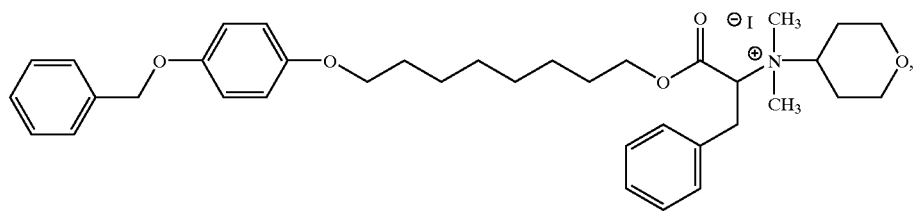
1358'
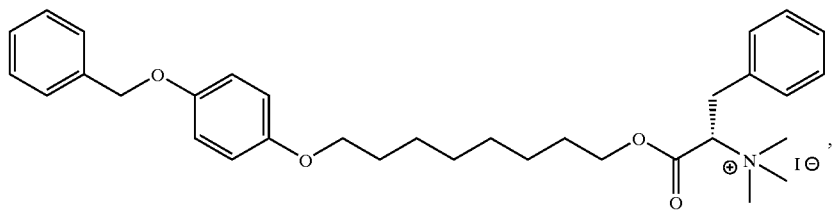
1197'
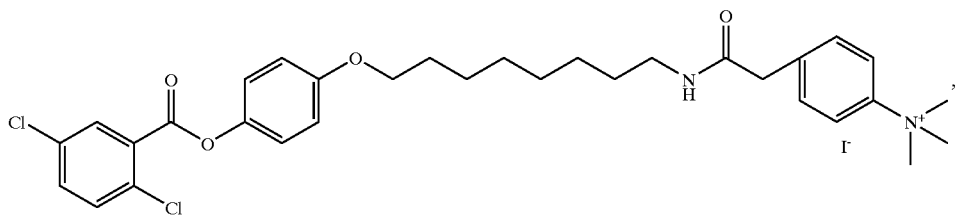
1634
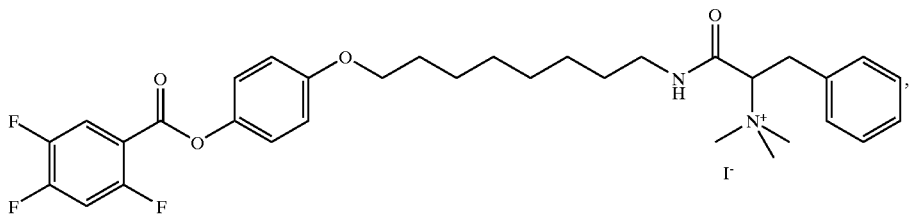
1619

-continued
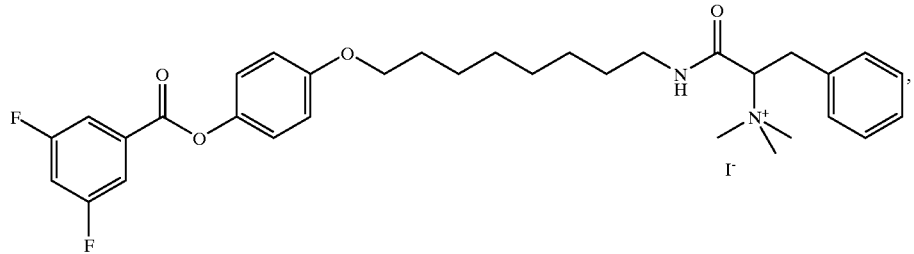
1614
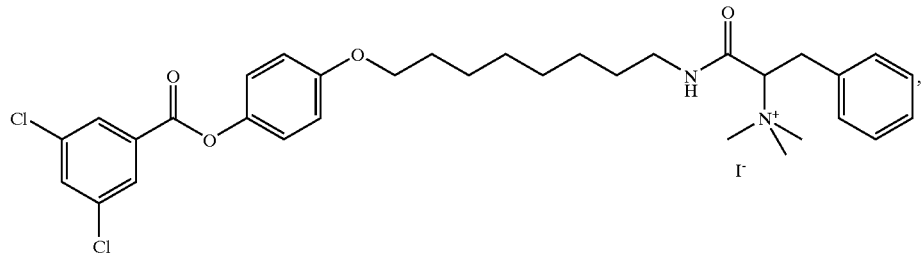
1608
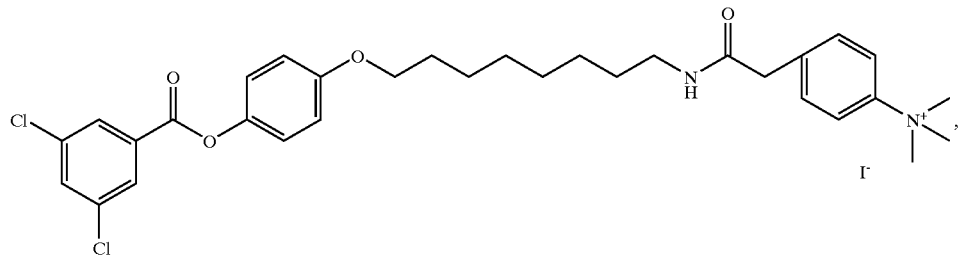
1637
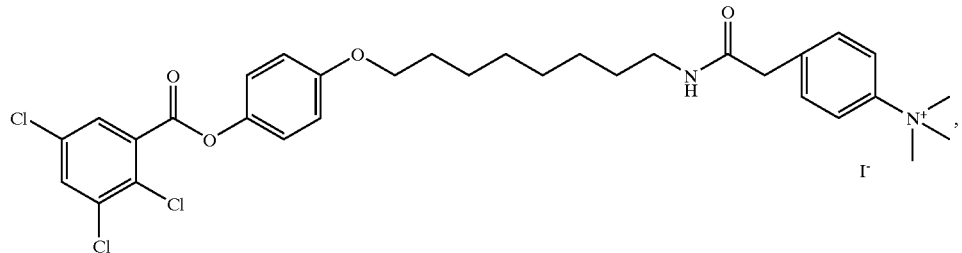
1644
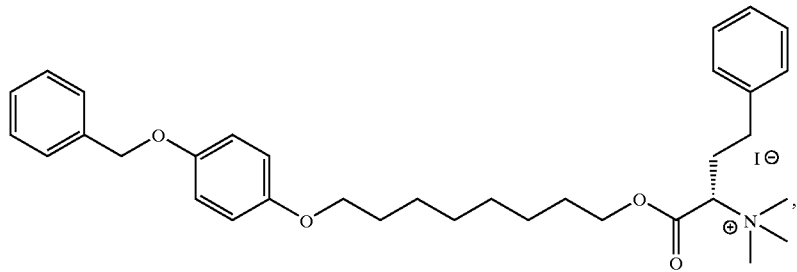
1198'
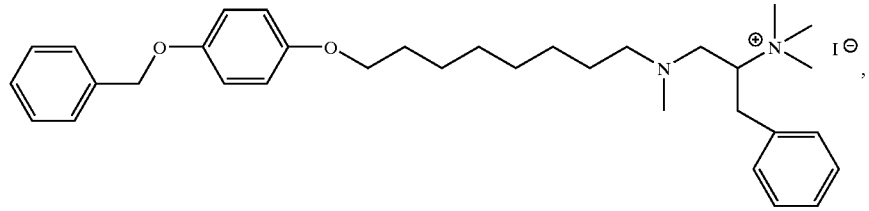
1499'

-continued

1606

1338'

1610

1596

1401'

1624

1485

-continued
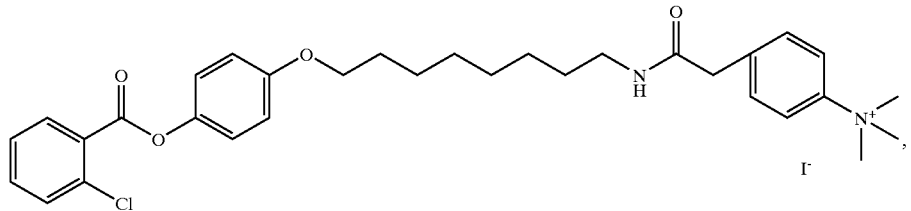
1622
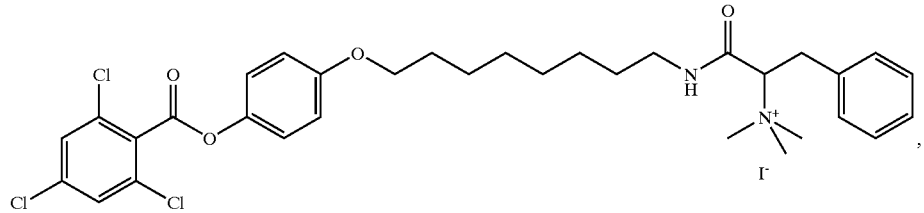
1616
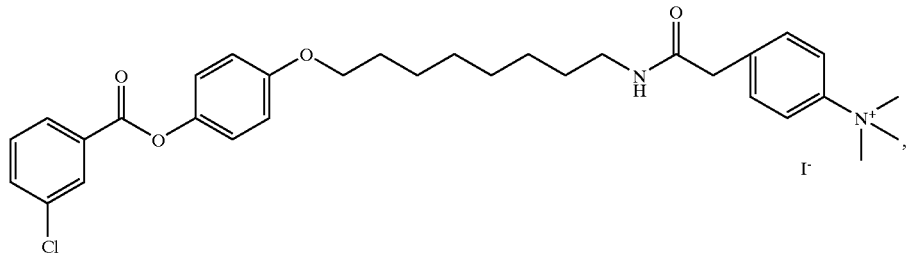
1623
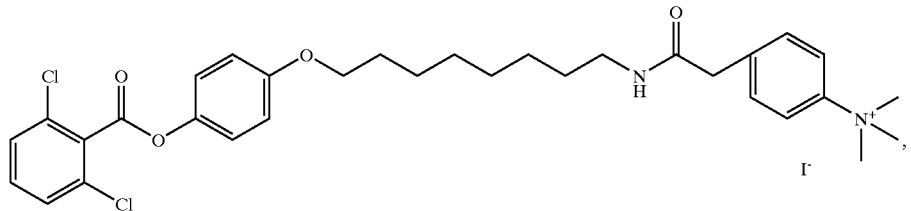
1635
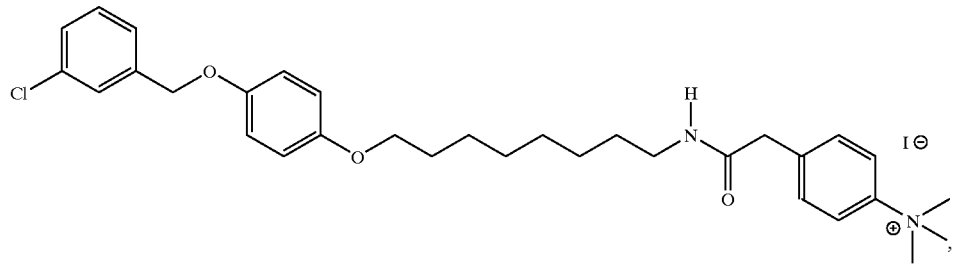
1421
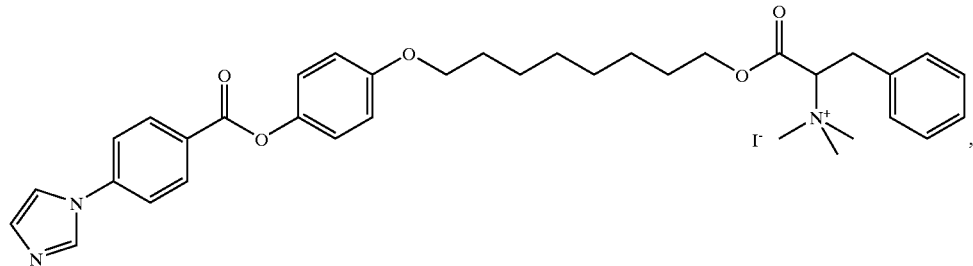
1486

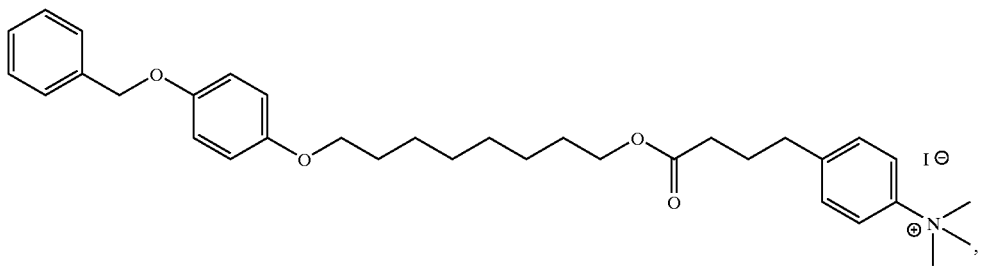
1264
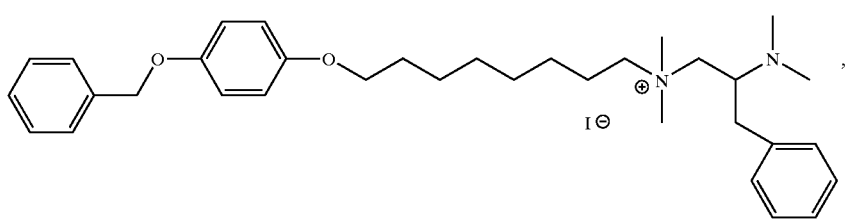
1498'
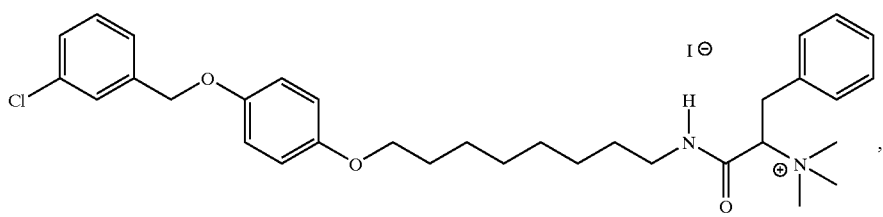
1420'
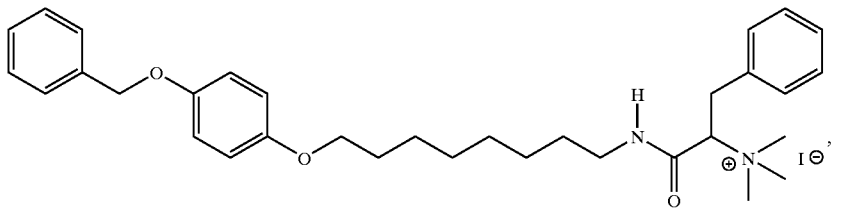
1364
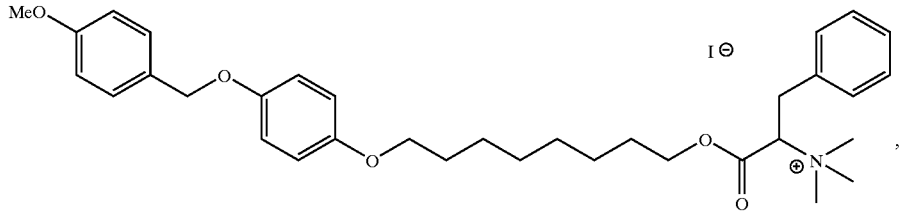
1389
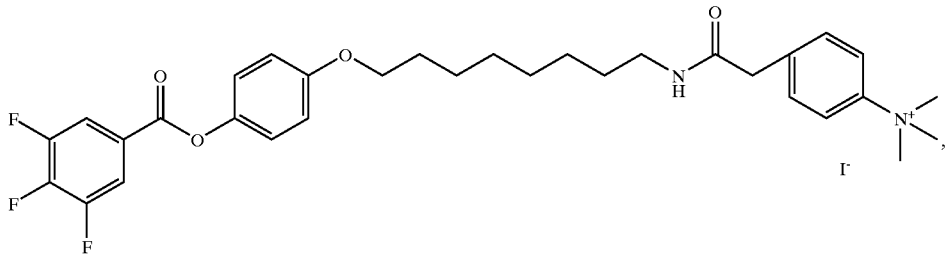
1650
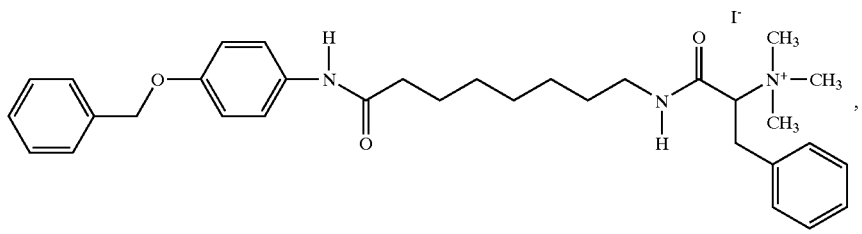
1403

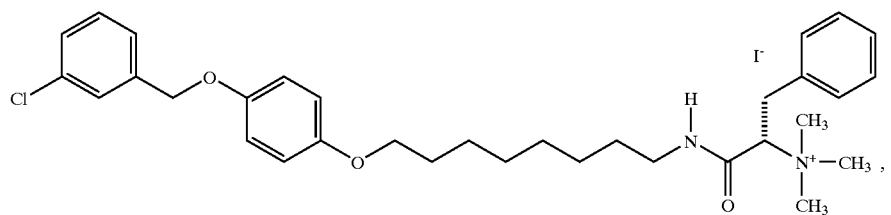
1424
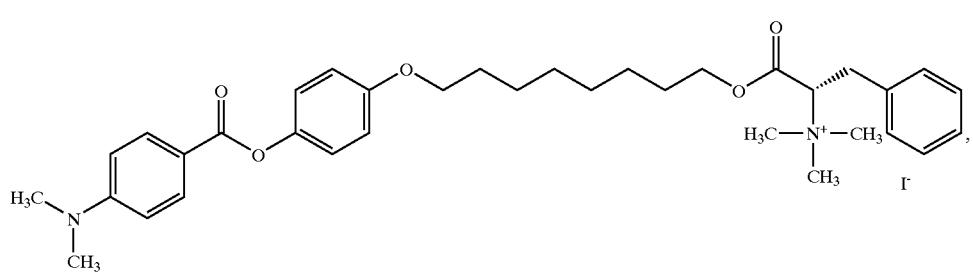
1484'
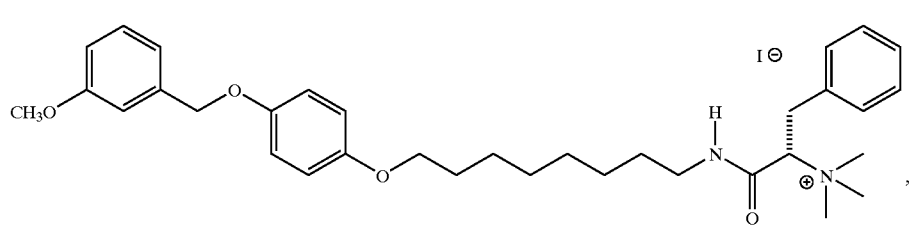
1423'
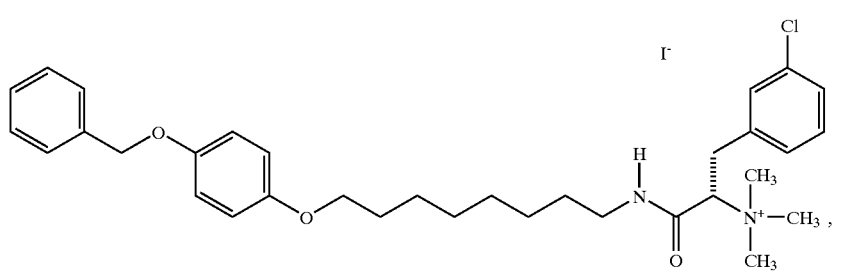
1492'
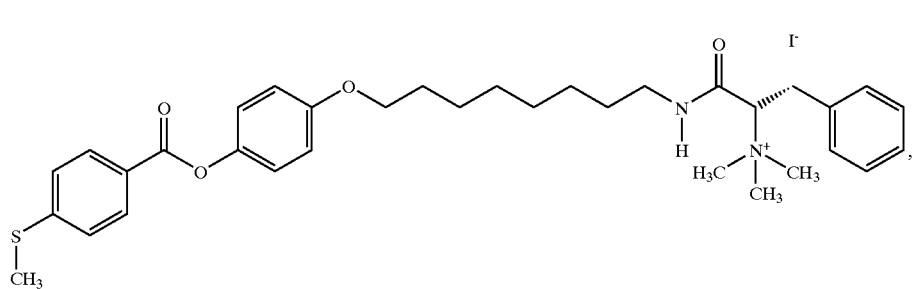
1601'
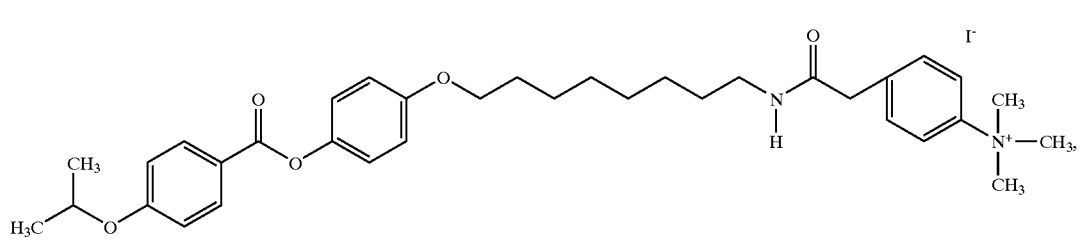
1629

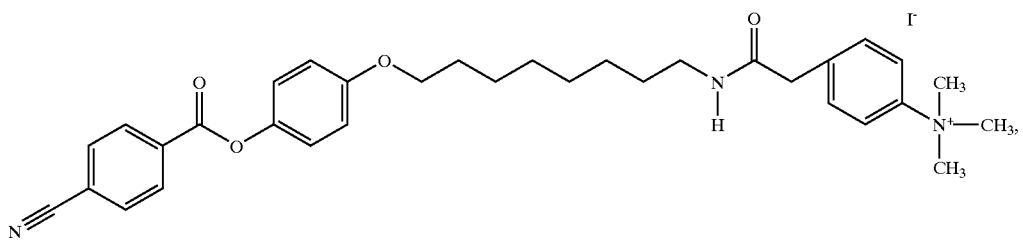
1631
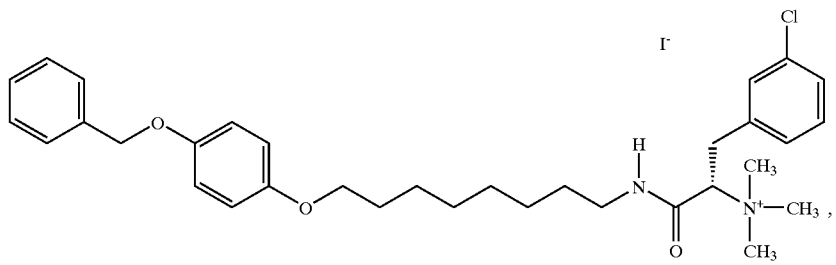
1692'
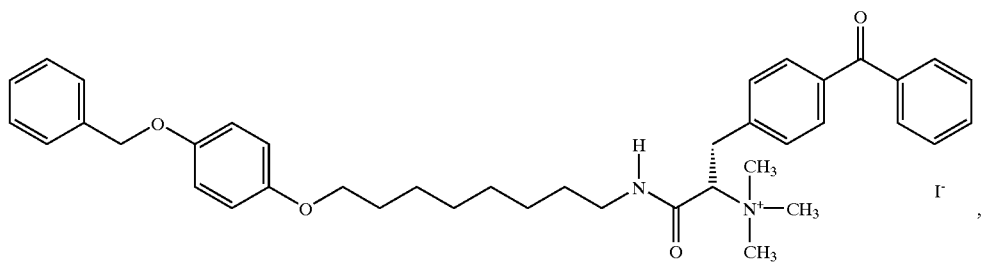
1700'
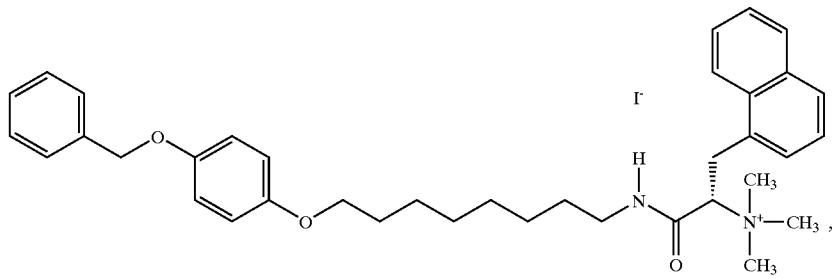
1705'
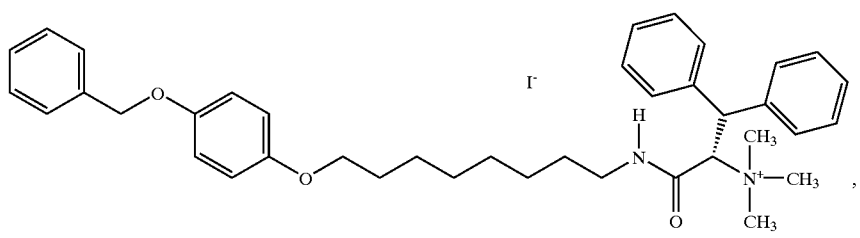
1709'
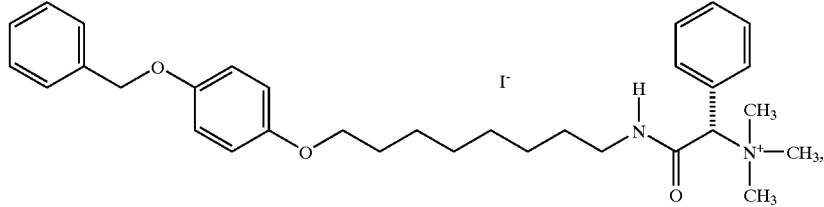
1713'

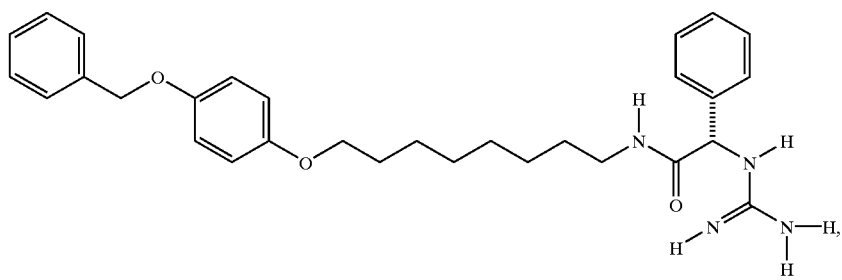
1714'
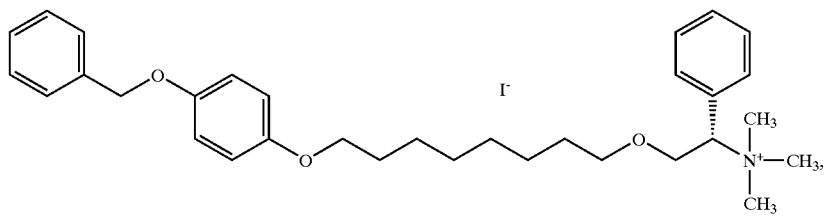
1715'
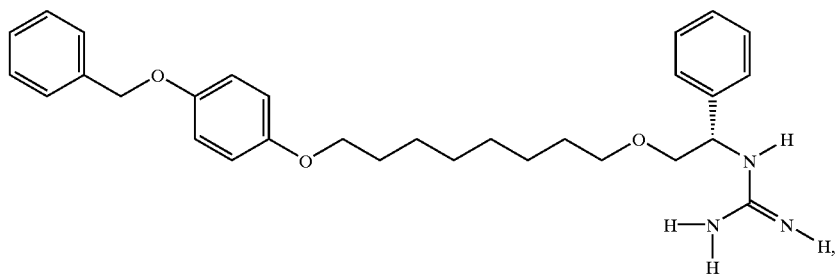
1716'
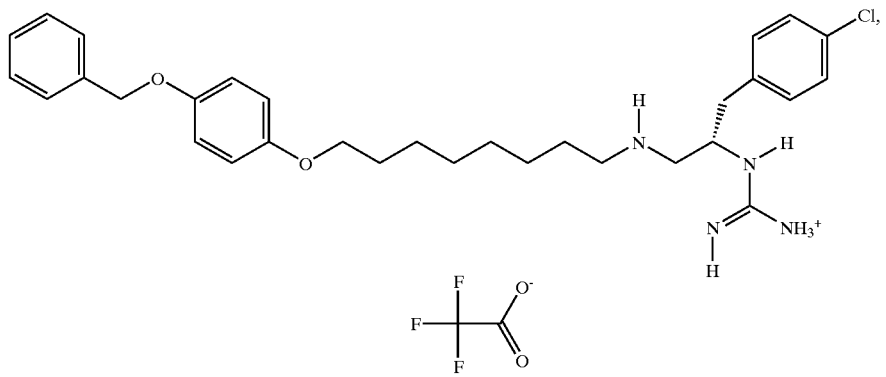
1722'
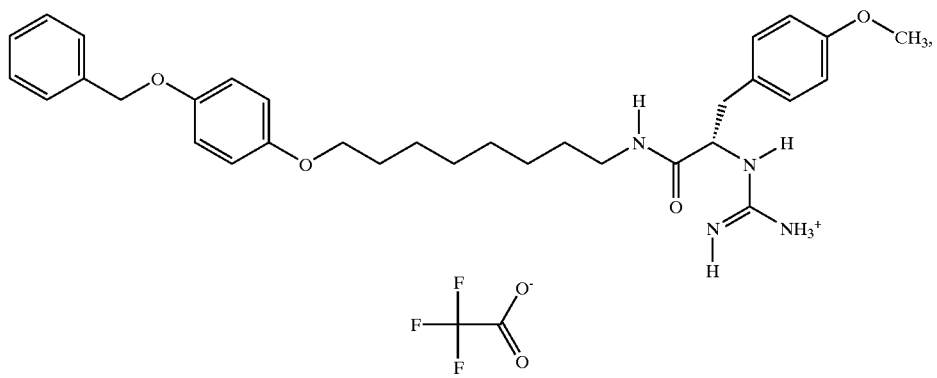
1725'

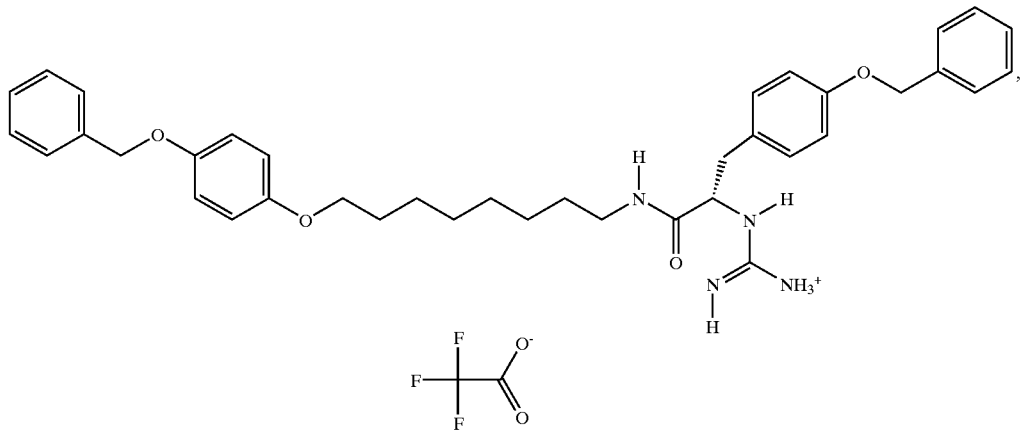
1727'
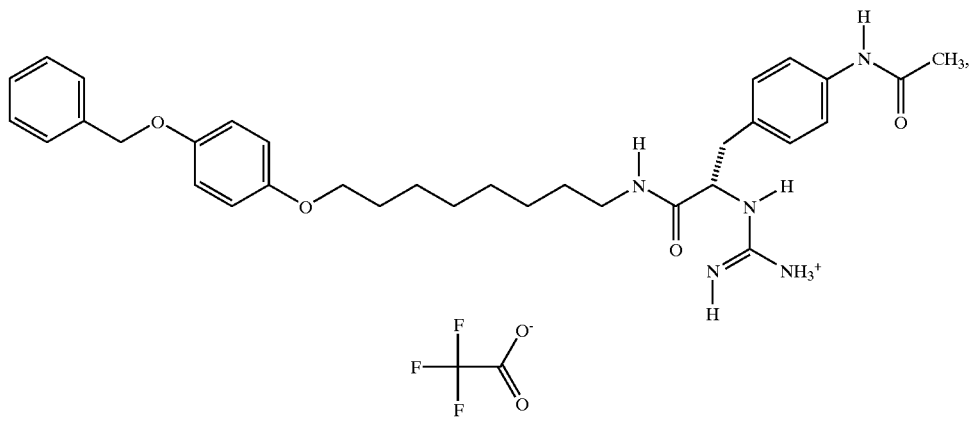
1728'
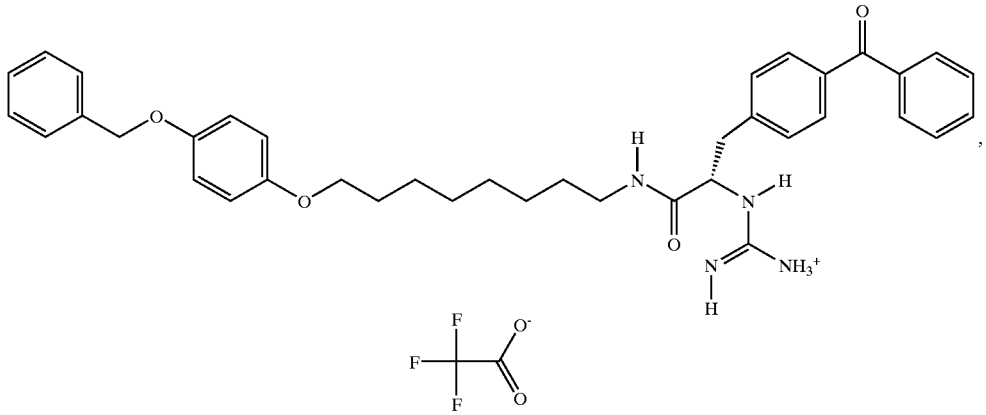
1729'

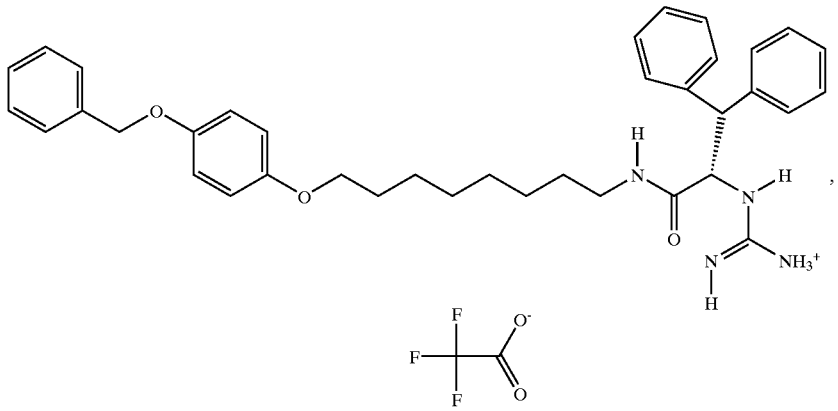
1738'
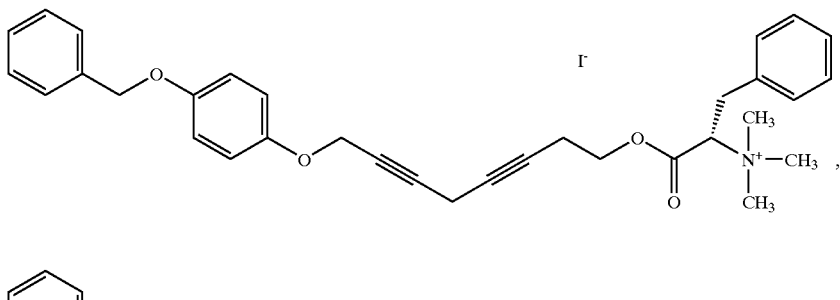
1752'
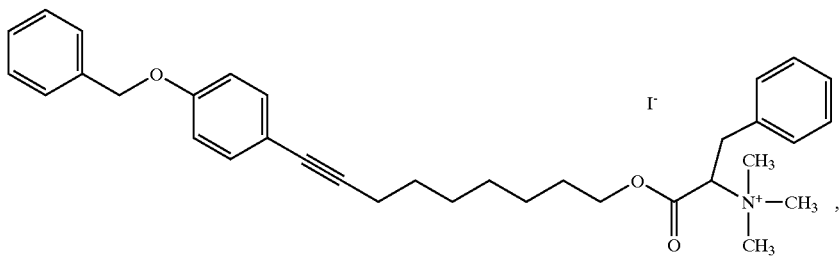
1755
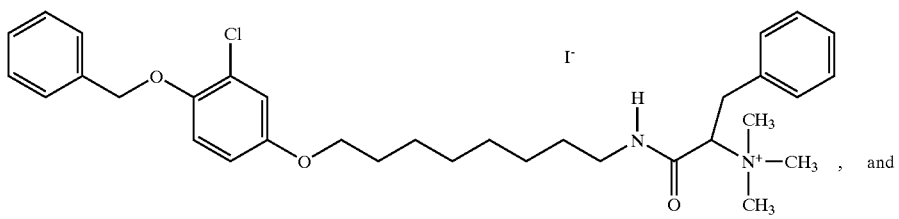
1758
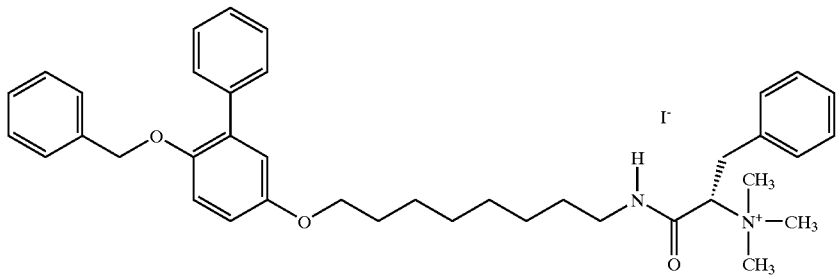
1760'
wherein X⁻ or I⁻ is a pharmaceutically acceptable anion.
19. A compound of the formula A—B—(CH$_2$)$_n$—O—CO—CH$_2$—Ph(NMe$_3$)$^+$X⁻, wherein A is a phenyl, optionally substituted with a benzyloxy group; B is a covalent bond or oxygen atom; n is 1–15; and I- is a pharmaceutically acceptable anion.

20. The compound of claim 19, selected from the group consisting of
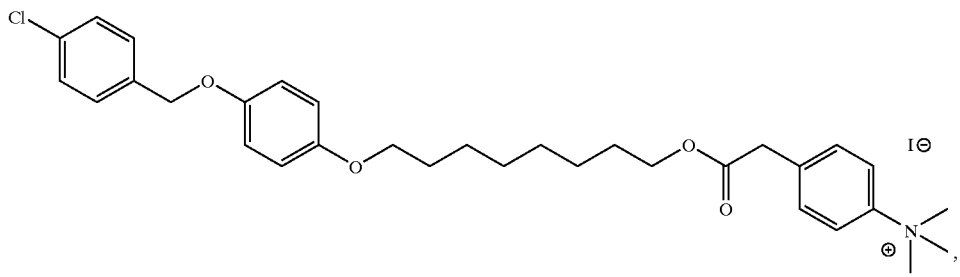
1398
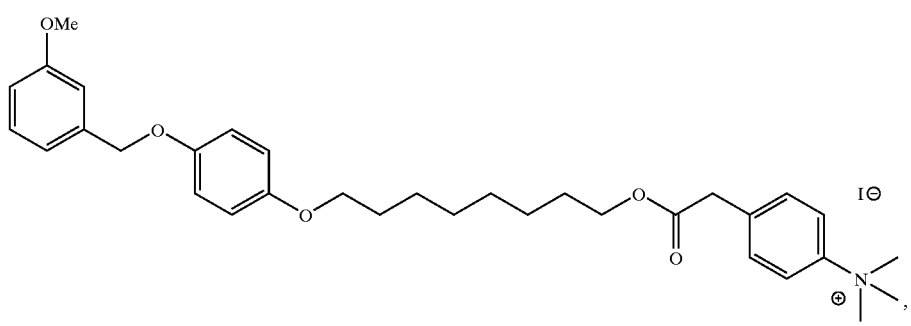
1394
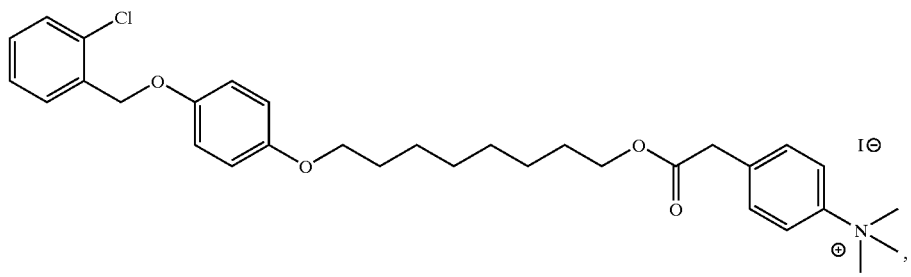
1396
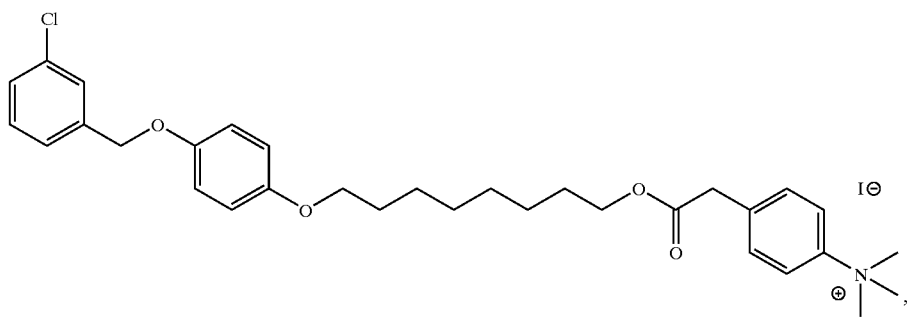
1397
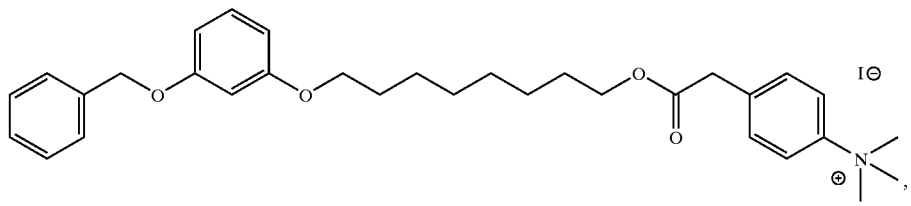
1169

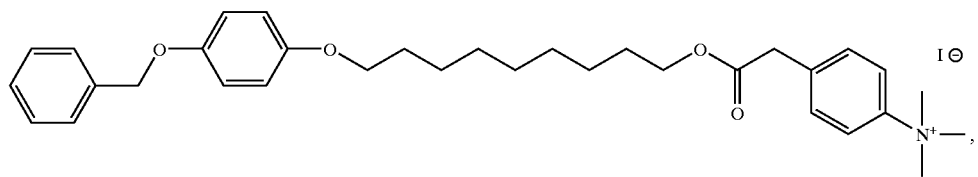
1321
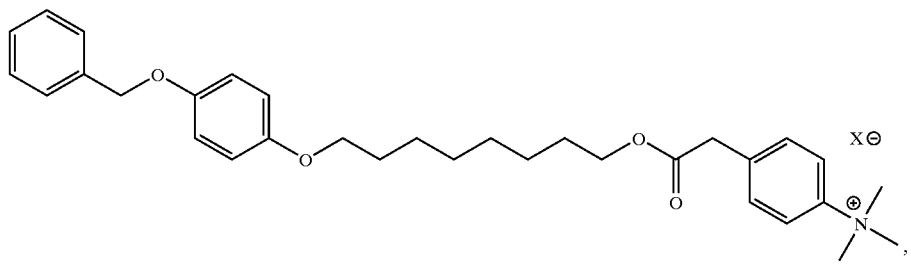
1108
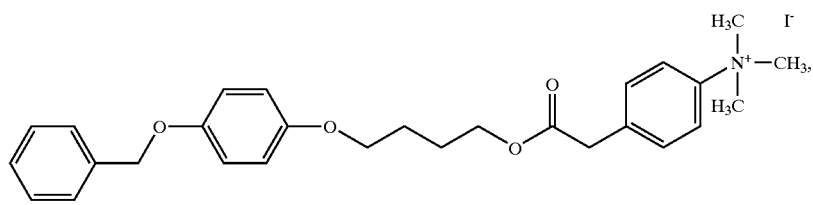
1317
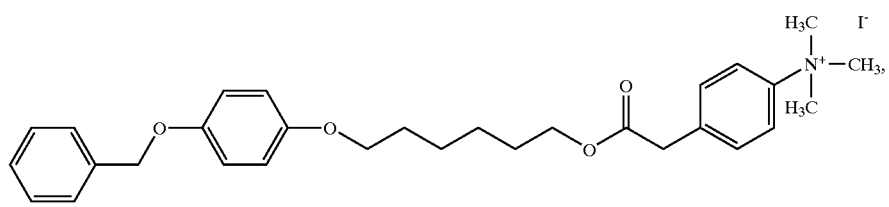
1319
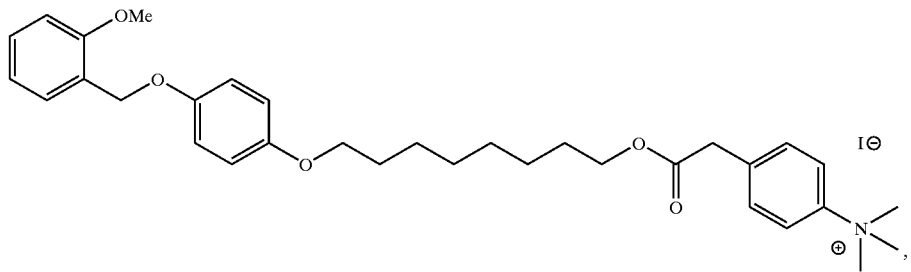
1393
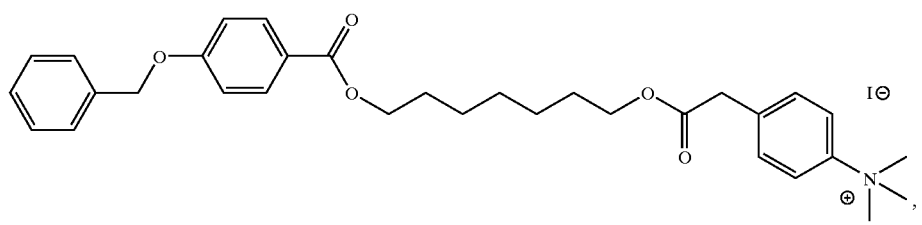
1359

1322

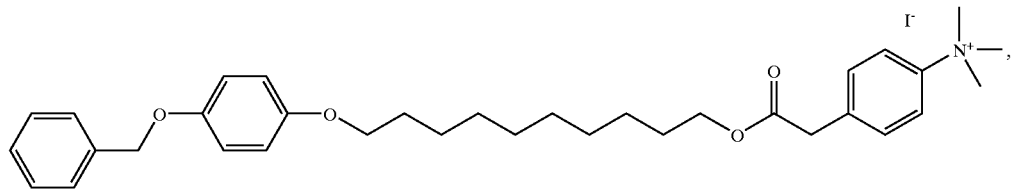

1182

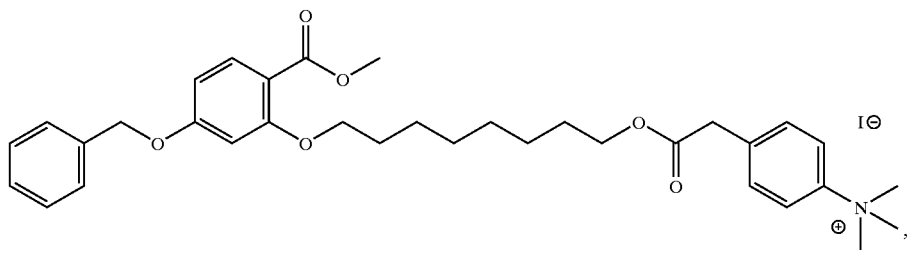

1323

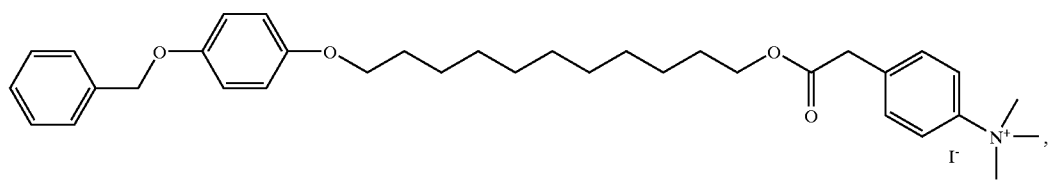

1324

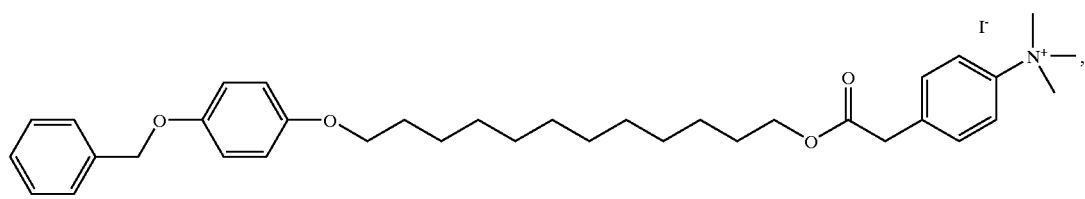

1186

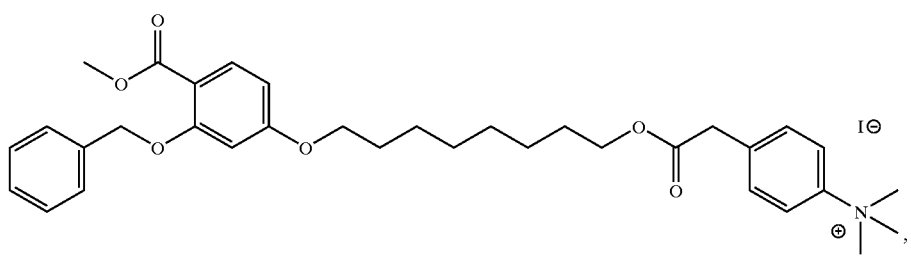

wherein I– is a pharmaceutically acceptable anion.

21. The compound of claim 20, wherein the pharmaceutically acceptable anion is iodide.

22. A pharmaceutical composition comprising a compound of claim 1 and a pharmaceutically acceptable carrier.

23. The compound of claim 20, wherein the pharmaceutically acceptable anion is iodide.

24. A method for treating a microbial infection in a mammal comprising administering to said mammal an effective amount of a compound of claim 1.

25. A pharmaceutical composition comprising a compound of claim 19 and a pharmaceutically acceptable carrier.

26. A method for treating a microbial infection in a mammal comprising administering to said mammal an effective amount of a compound of claim 19.

27. A method for preparing a compound of the formula A:

$$Ar_1-X-Ar_2-O-(CH_2)n-NHCO-Q_1Ar_3 \quad (A)$$

wherein

Ar1, Ar2 and Ar3 are aryl, optionally substituted with one or more substituents selected from the group consisting of $C_1$–$C_6$ alkyl, $C_1$–$C_6$ alkoxy, $C_1$–$C_6$ haloalkyl, $C_1$–$C_6$ hydroxyalkyl, $C_1$–$C_6$ alkoxy $C_1$–$C_6$alkyl, halo, amino, $C_1$–$C_6$ alkylamino, $C_1$–$C_6$ dialkylamino, $C_1$–$C_6$trialkylamino, $C_1$–$C_6$ alkylamino $C_1$–$C_6$ alkyl, $C_1$–$C_6$ dialkylamino $C_1$–$C_6$ alkyl, $C_1$–$C_6$ trialkylamino $C_1$–$C_6$ alkyl, azido, amine oxide, hydroxy, carboxyl, $C_1$–$C_6$ alkylcarbonyl, $C_1$–$C_6$ alkylcarbonyl $C_1$–$C_6$ alkyl, $C_1$–$C_6$ alkylcarbonyloxy, $C_1$–$C_6$ alkylcarbonyloxy $C_1$–$C_6$ alkyl, $C_1$–$C_6$ alkyloxycarbonyl $C_1$–$C_6$ alkyl, $C_1$–$C_6$ alkyloxycarbonyl, $C_1$–$C_6$ alkylthio, nitro, nitrosyl, cyano, hydroxylamino, sulfonamido, $C_1$–$C_6$ dialkyl sulfonamido, $C_1$–$C_6$ alkylcarbonylamino, formyl, formylamino, mercaptyl, and heterocyclyl, wherein heterocyclyl is selected from the group consisting of five and six membered closed ring structures where one or more ring atoms is other than carbon;

X is selected from the group consisting of a covalent bond, $(CH_2)mO$, $O(CH_2)m$, $(CH_2O)m$, $(OCH_2)m$, $(CH_2CH_2)m$, $(OCH_2CH_2)m$, $C(O)O$, $OC(O)$, $OC(O)O$, $(CH_2)mS$, $S(CH_2)m$, $(CH_2S)m$, $(SCH_2)m$, NH, NR, $^+NR_2$, $C(=O)NH$, $C(O)NR$, $NHC(O)$, $NRC(=O)$, $CH(OH)$, and $CH(OR)$, wherein R is $C_1-C_6$ alkyl and m is 0–5;

$Q_1$ is (I) a $C_1-C_6$ alkylenyl, $C_1-C_6$ alkylenyl carbonyloxy $C_1-C_6$alkyl, or $C_1-C_6$ alkylenyl carbonylamino $C_1-C_6$ alkyl group, optionally having a substituent selected from the group consisting of amino, $C_1-C_6$ alkylamino, $C_1-C_6$ haloalkylamino, $C_1-C_6$ haloalkyl $C_1-C_6$ alkyl amino, $C_1-C_6$ hydroxyalkylamino, $C_1-C_6$ hydroxyalkyl $C_1-C_6$ alkylamino, $C_1-C_6$ dialkylamino, $C_1-C_6$ trialkylamino, and a heterocyclic containing a nitrogen atom which may be optionally quaternized;

and n is from 1 to 15;

comprising (i) providing a compound of the formula B:

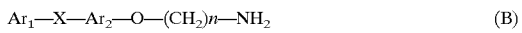

$$Ar_1-X-Ar_2-O-(CH_2)n-NH_2 \quad (B)$$

and (ii) reacting the compound of formula B with a compound of formula C:

$$HOOC-Q_1Ar_3 \quad (C);$$

wherein $Q_1$ is optionally protected.

28. The method of claim 27, wherein the compound of formula B is prepared by reacting a compound of formula D:

$$Ar_1-X-Ar_2-OH \quad (D)$$

with a compound of formula E:

$$Hal-(CH_2)n-NPhth \quad (E)$$

wherein "Hal" stands for a halogen atom and "NPhth" stands for phthalidimide linked to $(CH_2)n$ at the nitrogen atom, to obtain a compound of formula F:

$$Ar_1-X-Ar_2-O-(CH_2)n-NPhth \quad (F);$$

and hydrolyzing the compound of formula F.

29. The method of claim 27, wherein n is from 7 to 13.
30. The method of claim 28, wherein n is from 7 to 13.
31. The method of claim 27, wherein $Ar_1$, $Ar_2$, and $Ar_3$ are phenyl.
32. The method of claim 27, wherein X is $CH_2O$.
33. The method of claim 27, wherein $Q_1$ is a $C_1-C_6$ alkylenyl, optionally having a substituent selected from the group consisting of amino, $C_1-C_6$ alkylamino, $C_1-C_6$ haloalkylamino, $C_1-C_6$ haloalkyl $C_1-C_6$ alkyl amino, $C_1-C_6$ hydroxyalkylamino, $C_1-C_6$ hydroxyalkyl $C_1-C_6$ alkylamino, $C_1-C_6$ dialkylamino, $C_1-C_6$ trialkylamino, and a heterocyclic containing a nitrogen atom which may be optionally quaternized.

34. A method for preparing a compound of the formula G:

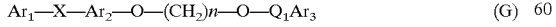

$$Ar_1-X-Ar_2-O-(CH_2)n-O-Q_1Ar_3 \quad (G)$$

wherein $Ar_1$, $Ar_2$, and $Ar_3$ are aryl, optionally substituted with one or more substituents selected from the group consisting of $C_1-C_6$ alkyl, $C_1-C_6$ alkoxy, $C_1-C_6$ haloalkyl, $C_1-C_6$ hydroxyalkyl, $C_1-C_6$ alkoxy $C_1-C_6$ alkyl, halo, amino, $C_1-C_6$ alkylamino, $C_1-C_6$ dialkylamino, $C_1-C_6$ trialkylamino, $C_1-C_6$ alkylamino $C_1-C_6$ alkyl, $C_1-C_6$ dialkylamino $C_1-C_6$ alkyl, $C_1-C_6$ trialkylamino $C_1-C_6$ alkyl, azido, amine oxide, hydroxy, carboxyl, $C_1-C_6$ alkylcarbonyl, $C_1-C_6$ alkylcarbonyl $C_1-C_6$ alkyl, $C_1-C_6$ alkylcarbonyloxy, $C_1-C_6$ alkylcarbonyloxy $C_1-C_6$ alkyl, $C_1-C_6$ alkyloxycarbonyl $C_1-C_6$ alkyl, $C_1-C_6$ alkyloxycarbonyl, $C_1-C_6$ alkylthio, nitro, nitrosyl, cyano, hydroxylamino, sulfonamido, $C_1-C_6$ dialkyl sulfonamido, $C_1-C_6$ alkylcarbonylamino, formyl, formylamino, mercaptyl, and heterocyclyl, wherein hetrocyclyl is selected from the group consisting of five and six membered closed ring structures where one or more ring atoms is other than carbon; optionally, a ring nitrogen atom of heteroaryl $Ar_1$ or $Ar_2$ may be quaternized;

X is selected from the group consisting of a covalent bond, $(CH_2)mO$, $O(CH_2)m$, $(CH_2O)m$, $(OCH_2)m$, $(CH_2CH_2O)m$, $(OCH_2CH_2)m$, $C(O)O$, $OC(O)$, $OC(O)O$, $(CH_2)mS$, $S(CH_2)m$, $(CH_2S)m$, $(SCH_2)m$, NH, NR, $^+NR_2$, $C(O)NH$, $C(=O)NR$, $NHC(O)$, $NRC(=O)$, $CH(OH)$, and $CH(OR)$, wherein R is $C_1-C_6$ alkyl and m is 0–5;

$Q_1$ is (i) a $C_1-C_6$ alkylenyl, $C_1-C_6$ alkylenyl carbonyloxy $C_1-C_6$ alkyl, or $C_1-C_6$ alkylenyl carbonylamino $C_1-C_6$ alkyl group, optionally having a substituent selected from the group consisting of amino, $C_1-C_6$ alkylamino, $C_1-C_6$ haloalkylamino, $C_1-C_6$ haloalkyl $C_1-C_6$ alkyl amino, $C_1-C_6$ hydroxyalkylamino, $C_1-C_6$ hydroxyalkyl $C_1-C_6$ alkylamino, $C_1-C_6$ dialkylamino, $C_1-C_6$ trialkylamino, and a heterocyclic containing a nitrogen atom which may be optionally quaternized;

and n is from 1 to 15;

comprising (i) providing a compound of the formula H:

$$Ar_1-X-Ar_2-O-(CH_2)n-OH \quad (H)$$

and (ii) reacting the compound of formula H with a compound of formula J:

$$HO-Q_1Ar_3 \quad (J);$$

wherein $Q_1$ is optionally protected.

35. The method of claim 34, wherein the compound of formula H is prepared by reacting a compound of formula D:

$$Ar_1-X-Ar_2-OH \quad (D)$$

with a compound of formula K:

$$Hal-(CH_2)n-OH \quad (K)$$

wherein "Hal" stands for a halogen atom, to obtain a compound of formula L:

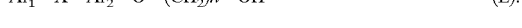

$$Ar_1-X-Ar_2-O-(CH_2)n-OH \quad (L).$$

36. The method of claim 34, wherein n is from 7 to 13.
37. The method of claim 35, wherein n is from 7 to 13.
38. The method of claim 34, wherein $Ar_1$, $Ar_2$, and $Ar_3$ are phenyl.
39. The method of claim 34, wherein X is $CH_2O$.
40. The method of claim 34, wherein $Q_1$ is a $C_1-C_6$ alkylenyl, optionally having a substituent selected from the group consisting of amino, $C_1-C_6$ alkylamino, $C_1-C_6$ haloalkylamino, $C_1-C_6$ haloalkyl $C_1-C_6$ alkyl amino, $C_1-C_6$ hydroxyalkylamino, $C_1-C_6$ hydroxyalkyl $C_1-C_6$ alkylamino, $C_1-C_6$ dialkylamino, $C_1-C_6$ trialkylamino, and a heterocyclic containing a nitrogen atom which may be optionally quaternized.

41. A method of killing a prokaryote present in a human or other animal, a crop, a soil or an environment, comprising contacting the human or other animal, crop, soil or environment with an effective amount of the compound of claim 1 to reduce or eliminate the production of NAD.

42. A method of killing a prokaryote present in a human or other animal, a crop, a soil or an environment, comprising contacting the human or other animal, crop, soil or environment with an effective amount of the compound of claim 19 to reduce or eliminate the production of NAD.

43. A method of decreasing prokaryotic growth present in a human or other animal, a crop, a soil or an environment, comprising contacting the human or other animal, crop, soil or environment with an effective amount of a compound of claim 1 to reduce or eliminate the production of NAD.

44. A method of decreasing prokaryotic growth present in a human or other animal, a crop, a soil or an environment, comprising contacting the human or other animal, crop, soil or environment with an effective amount of a compound of claim 19 to reduce or eliminate the production of NAD.

45. The method of claim 41, wherein the prokaryote is a bacterium.

46. The method of claim 42, wherein the prokaryote is a bacterium.

47. The method of claim 43, wherein the prokaryote is a bacterium.

48. The method of claim 45, wherein the bacterium is a gram negative or a gram positive bacterium.

49. The method of claim 46, wherein the bacterium is a gram negative or a gram positive bacterium.

50. The method of claim 47, wherein the bacterium is a gram negative or a gram positive bacterium.

51. The method of claim 45, wherein the prokaryote is an antibiotic resistant strain of a bacterium.

52. The method of claim 46, wherein the prokaryote is an antibiotic resistant strain of a bacterium.

53. The method of claim 47, wherein the prokaryote is an antibiotic resistant strain of a bacterium.

54. A disinfecting, sterilizing, or decontaminating composition comprising a compound of claim 1 and a suitable carrier.

55. A disinfecting, sterilizing, or decontaminating composition comprising a compound of claim 19 and a suitable carrier.

56. A method of disinfecting, sterilizing, or decontaminating a material in need thereof comprising contacting the material with a compound of claim 1.

57. A method of disinfecting, sterilizing, or decontaminating a material in need thereof comprising contacting the material with a compound of claim 19.

58. A method of killing a fungus comprising contacting the fungus with an amount of a compound of claim 1 to reduce or eliminate the production of NAD.

59. A method of killing a fungus comprising contacting the fungus with an amount of a compound of claim 19 to reduce or eliminate the production of NAD.

60. A method of decreasing fungus growth comprising contacting the fungus with an effective amount of a compound of claim 1 to reduce or eliminate the production of NAD.

61. A method of decreasing fungus growth comprising contacting the fungus with an effective amount of a compound of claim 19 to reduce or eliminate the production of NAD.

62. A method of increasing production of a food animal comprising administering to the food animal an effective amount of a compound of claim 1 to inhibit the NAD synthetase of a microbe capable of infecting the food animal.

63. A method of increasing production of a food animal comprising administering to the food animal an effective amount of a compound of claim 19 to inhibit the NAD synthetase of a microbe capable of infecting the food animal.

64. A method for the treatment of infection by a spore-forming bacterium in an animal comprising contacting an environment of the animal with an effective amount of a compound of claim 1 to inhibit the NAD synthetase of the spore-forming bacterium.

65. A method for the treatment of infection by a spore-forming bacterium in an animal comprising contacting an environment of the animal with an effective amount of a compound of claim 19 to inhibit the NAD synthetase of the spore-forming bacterium.

66. A method of killing the vegetative cell of a spore-forming bacterium in an environment comprising treating the environment with an effective amount of a compound of claim 1 to inhibit the NAD synthetase of the bacterium.

67. A method of killing the vegetative cell of a spore-forming bacterium in an environment comprising treating the environment with an effective amount of a compound of claim 19 to inhibit the NAD synthetase of the bacterium.

68. A method of treating a microbial infection or disease in a plant comprising contacting the plant or an environment of the plant with an effective amount of a compound of claim 1 to inhibit the NAD synthetase of the microbe.

69. A method of treating a microbial infection or disease in a plant comprising contacting the plant or an environment of the plant with an effective amount of a compound of claim 19 to inhibit the NAD synthetase of the microbe.

70. A method for a treating harm to a plant due to a pest comprising contacting the plant, or an environment thereof; with a pesticidal effective amount of a compound of claim 1 to inhibit the NAD synthetase of a pest.

71. A method for a treating harm to a plant due to a pest comprising contacting the plant, or an environment thereof; with a pesticidal effective amount of a compound of claim 19 to inhibit the NAD synthetase of a pest.

72. A method of controlling insect population in an environment comprising contacting the environment with an effective amount of a compound of claim 1 to inhibit the NAD synthetase of the insect.

73. A method of controlling insect population in an environment comprising contacting the environment with an effective amount of a compound of claim 19 to inhibit the NAD synthetase of the insect.

74. The compound of claim 18, which is selected from the group consisting of:

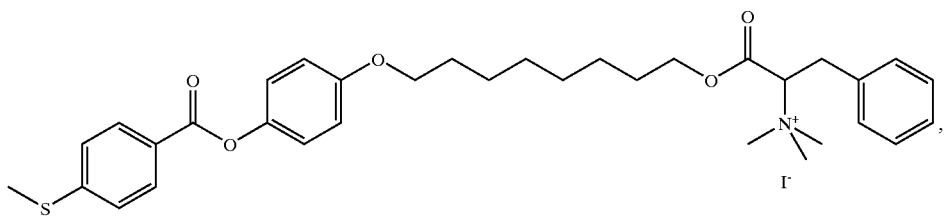
1478
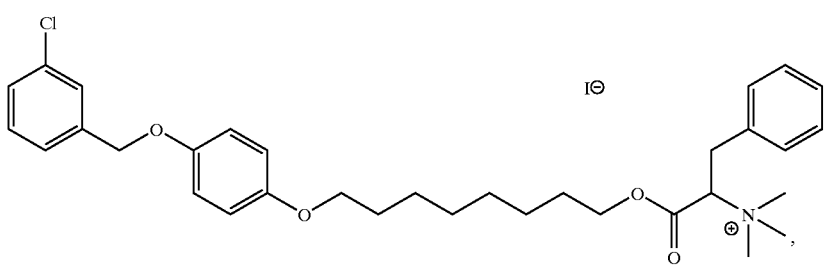
1391
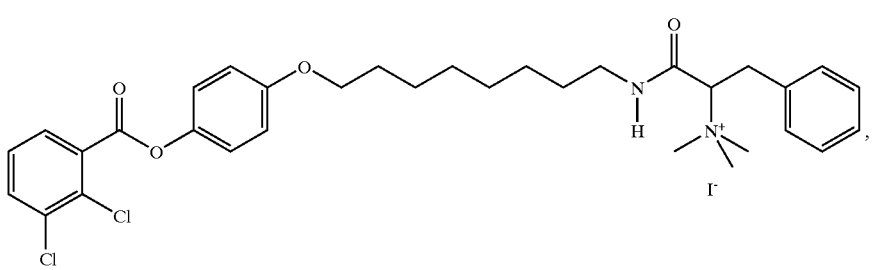
1603
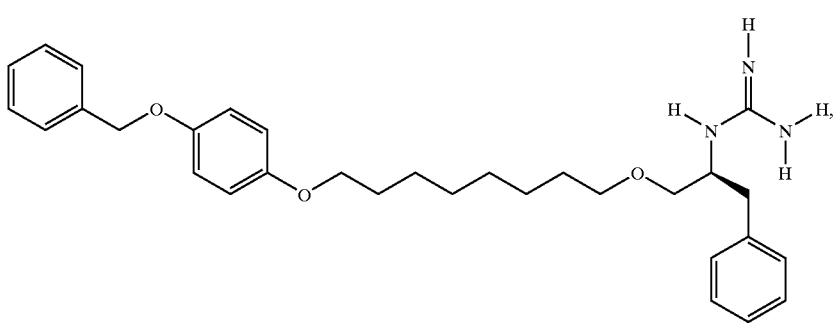
1679
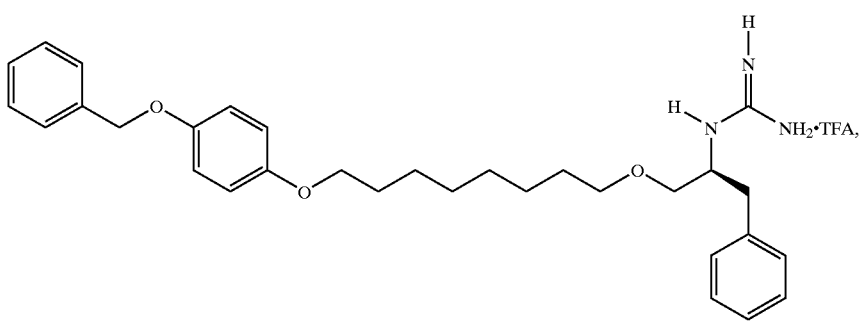
1680'
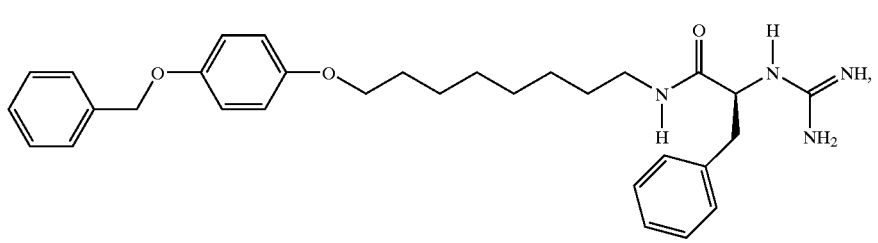
1681'

-continued
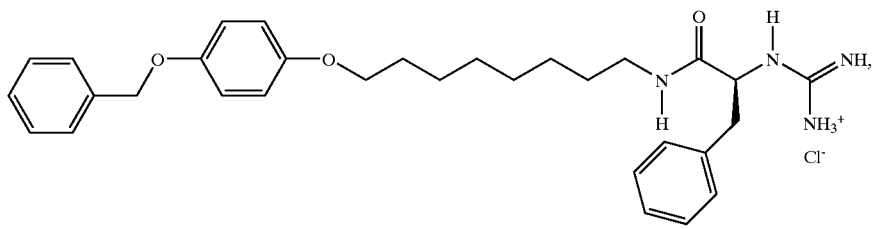
1682'
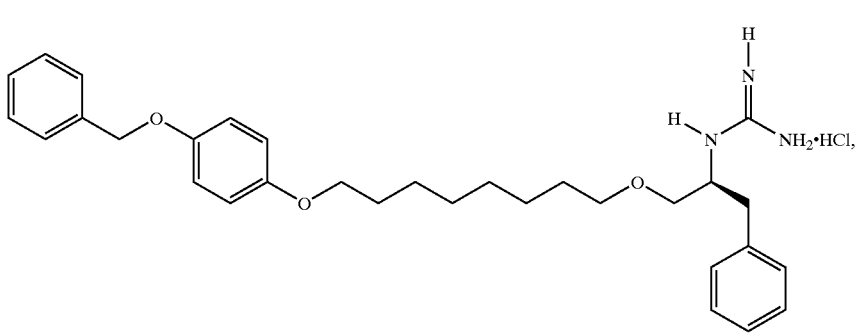
1685'
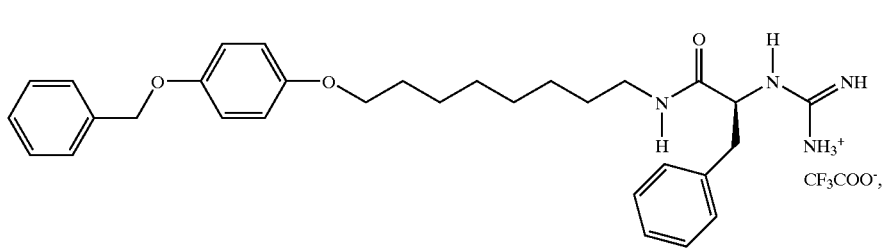
1503'
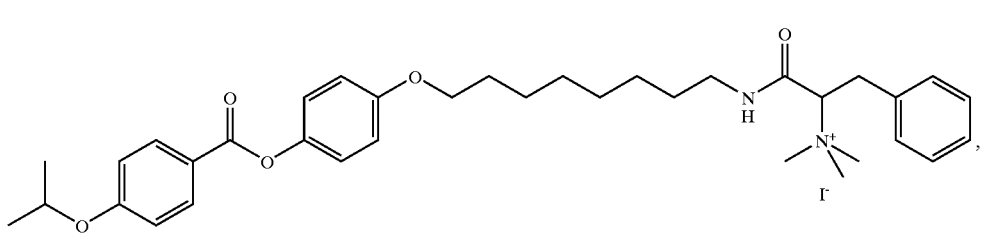
1600
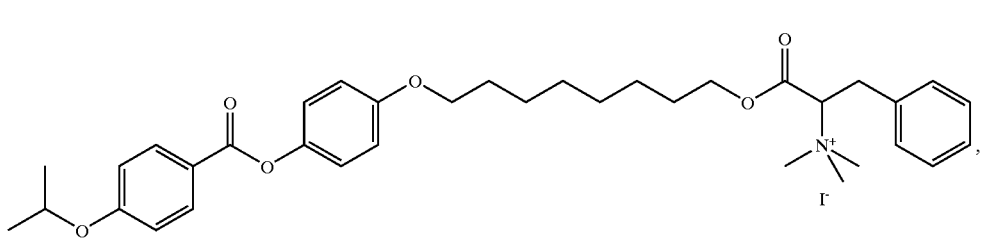
1477
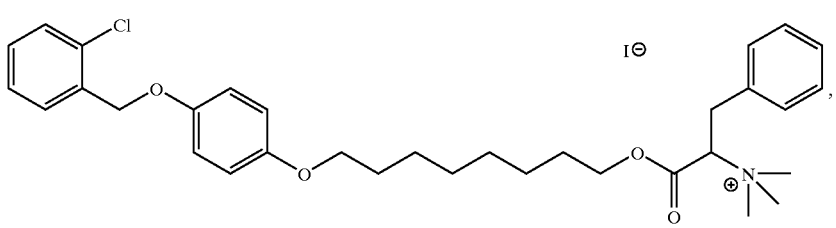
1390

-continued
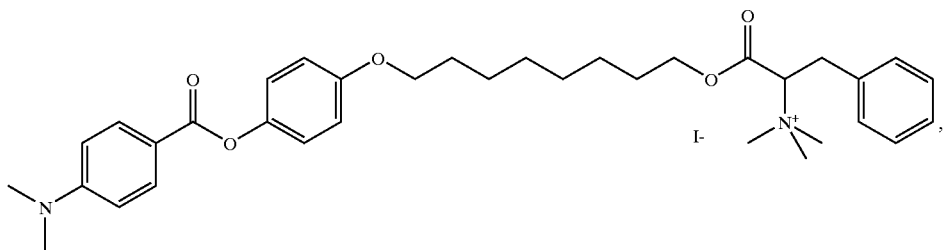
1484
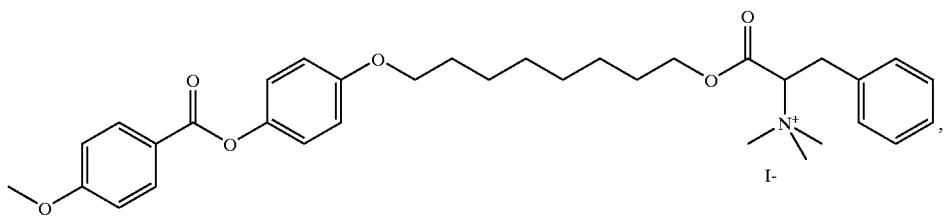
1456
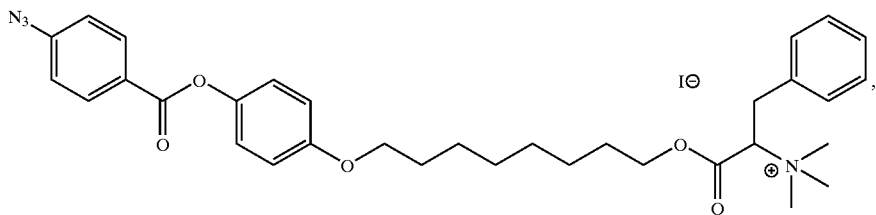
1432
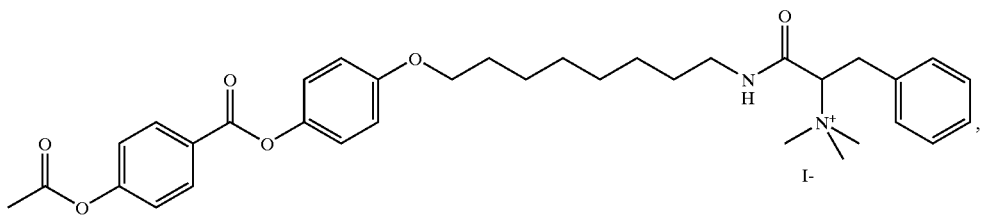
1599
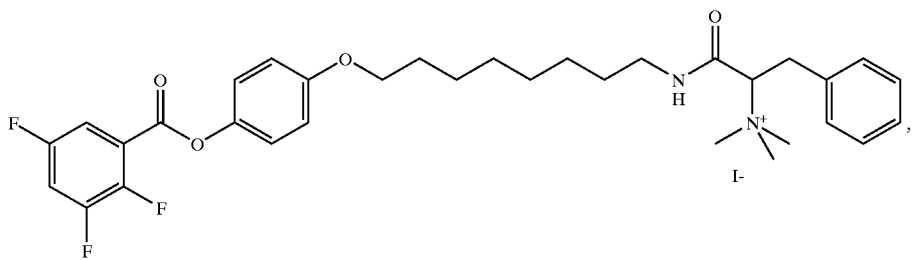
1617
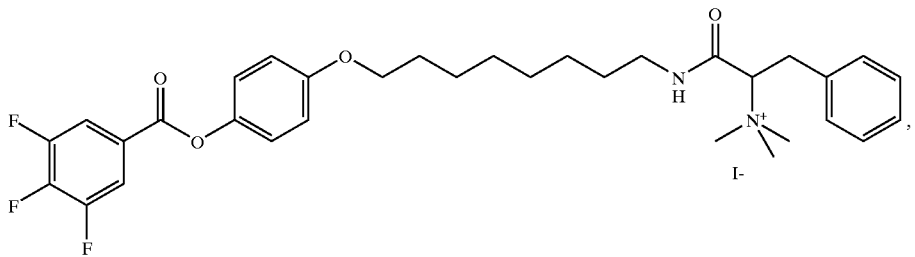
1621

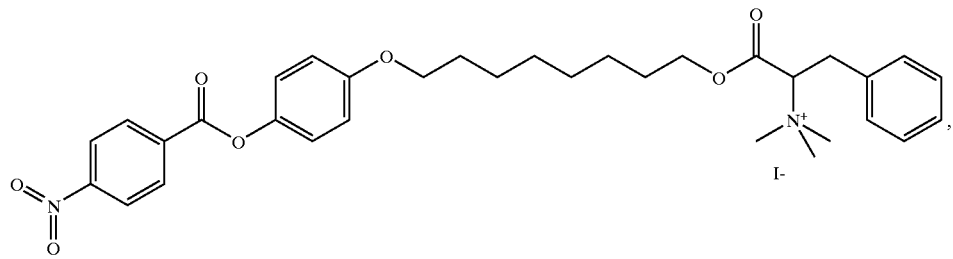
1483
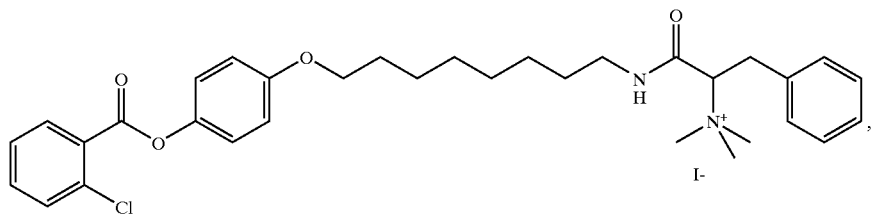
1593
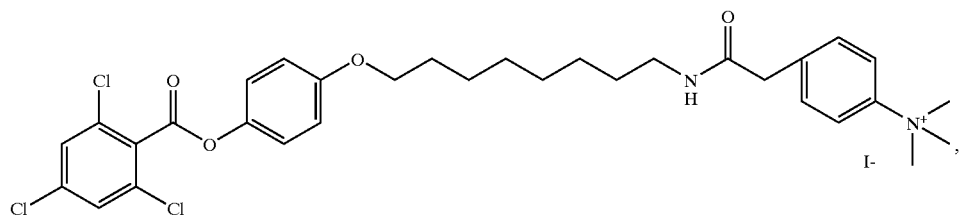
1645
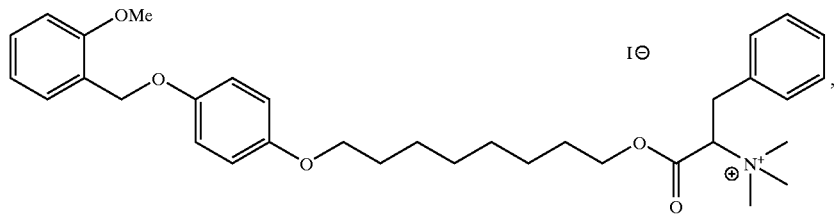
1387
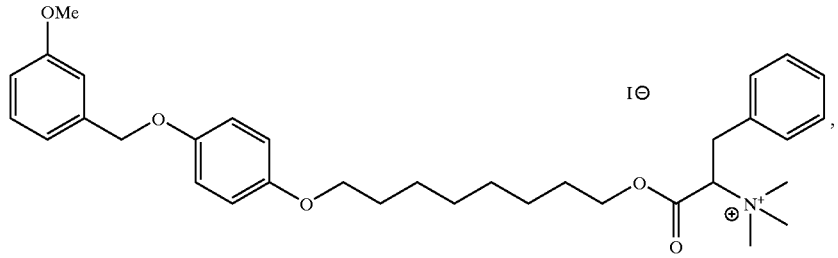
1388
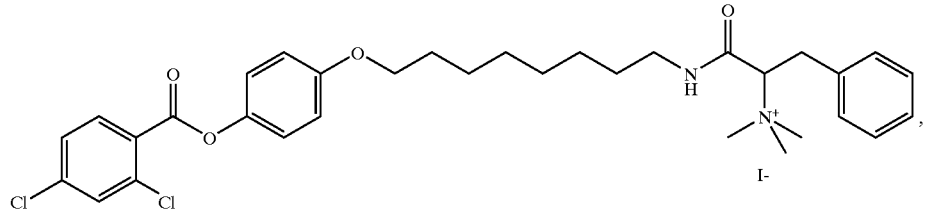
1604
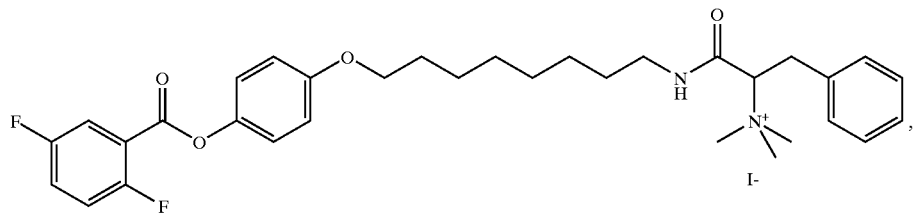
1611

-continued
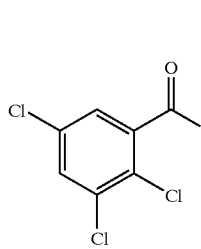 1615
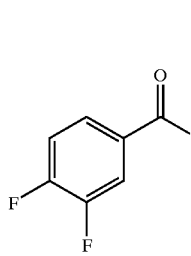 1613
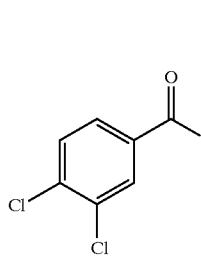 1636
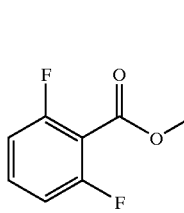 1612
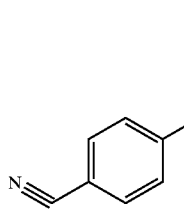 1479
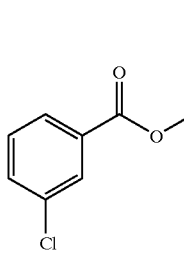 1594

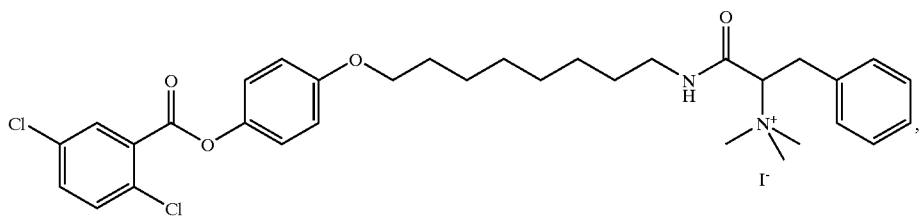
1605
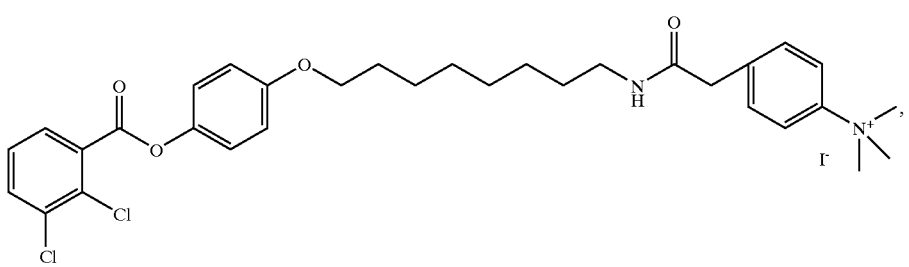
1632
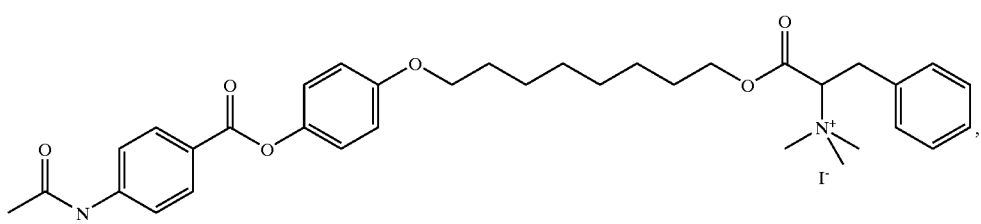
1482
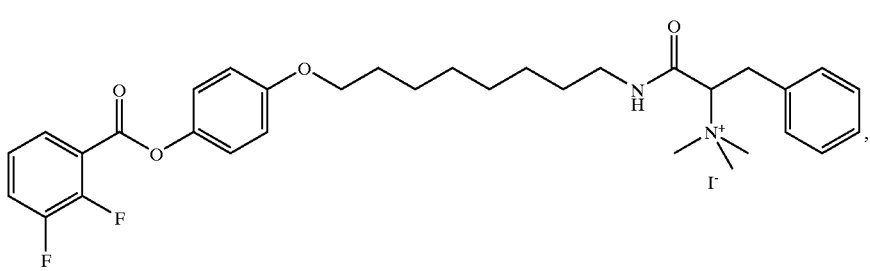
1609
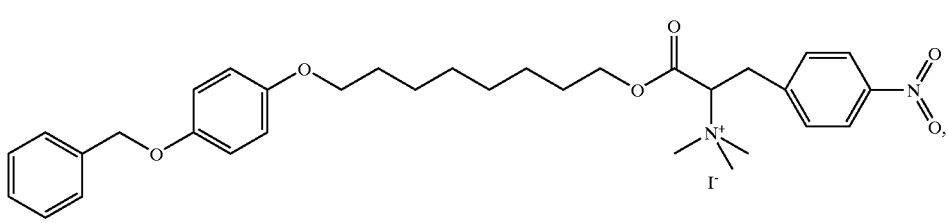
1405
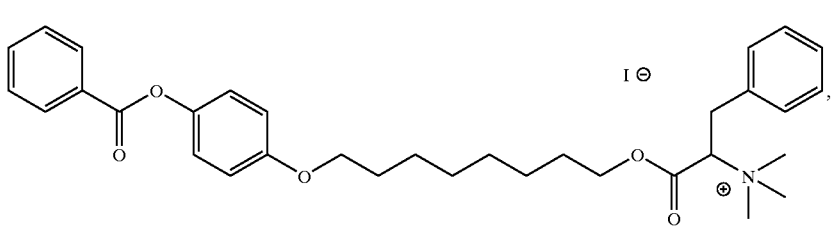
1431
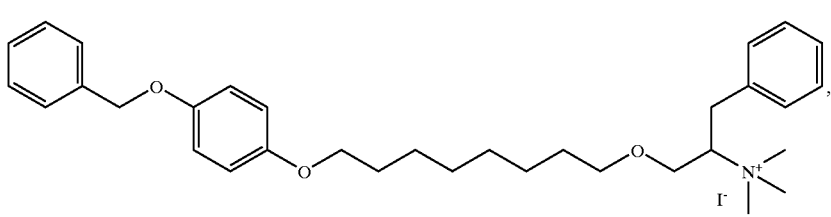
1439

-continued
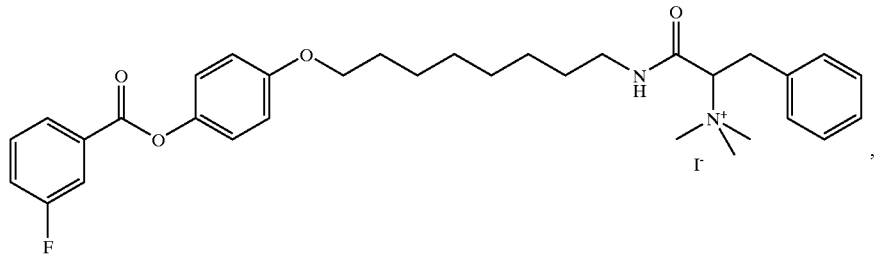
1597
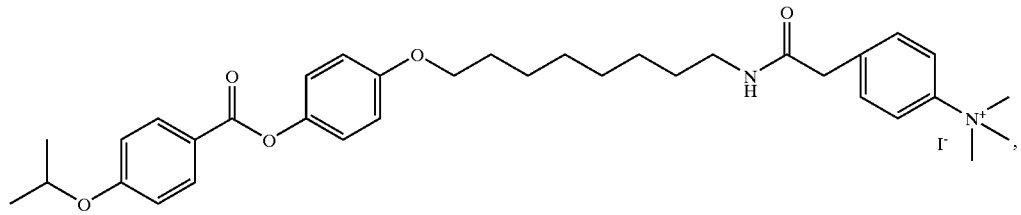
1629
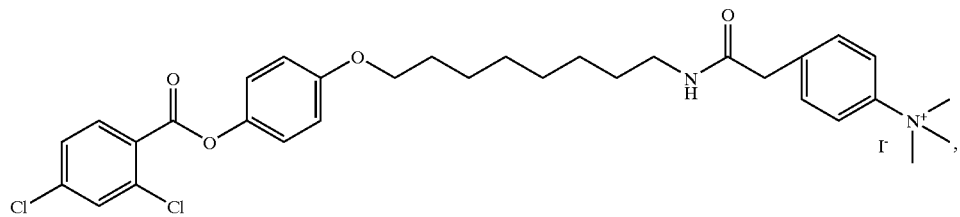
1633
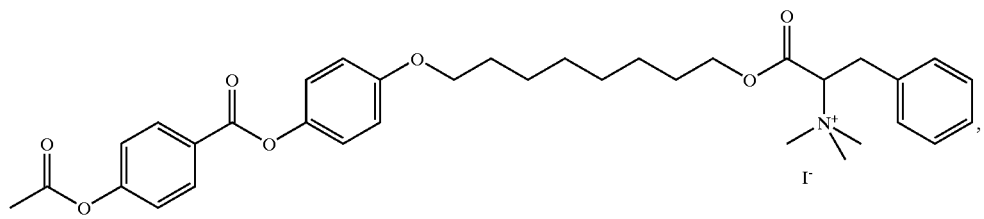
1475
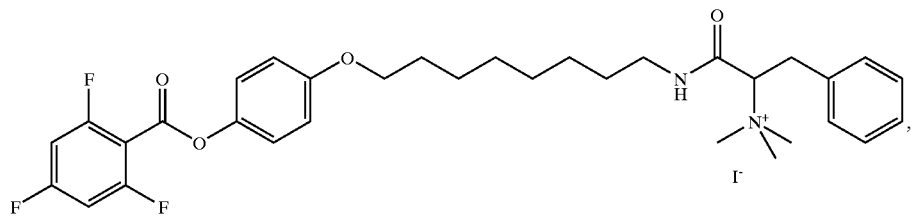
1620
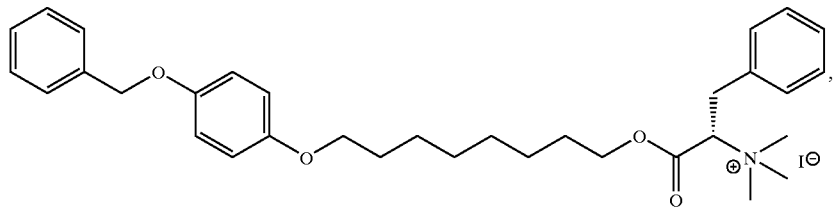
1197'
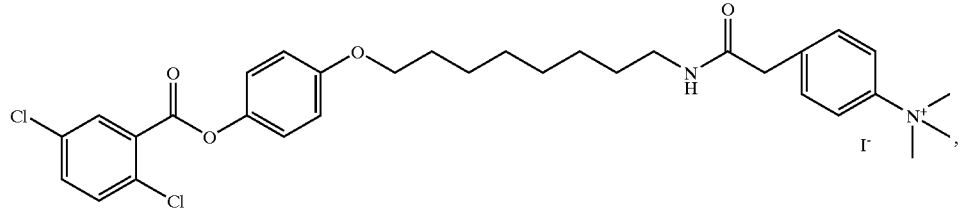
1634

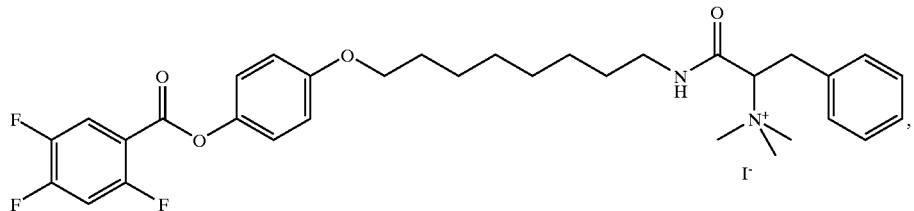
1619
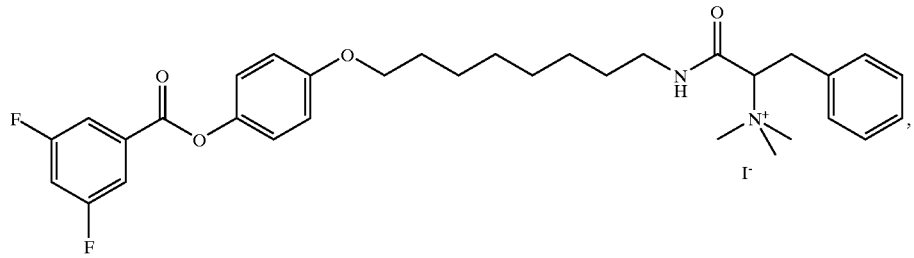
1614
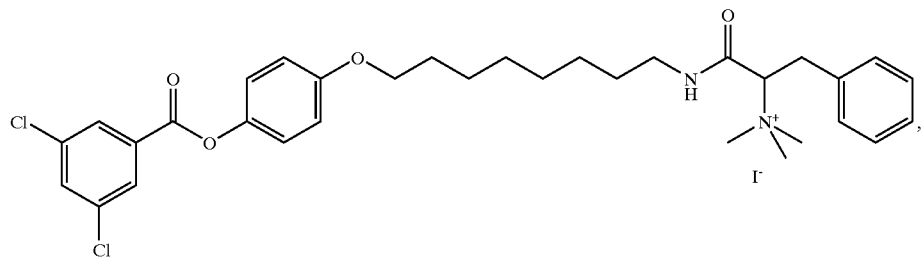
1608
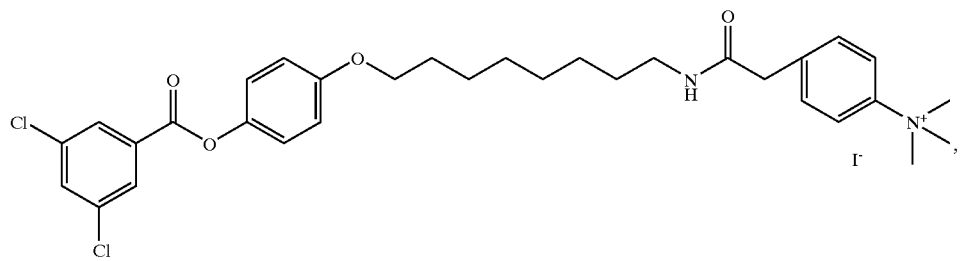
1637
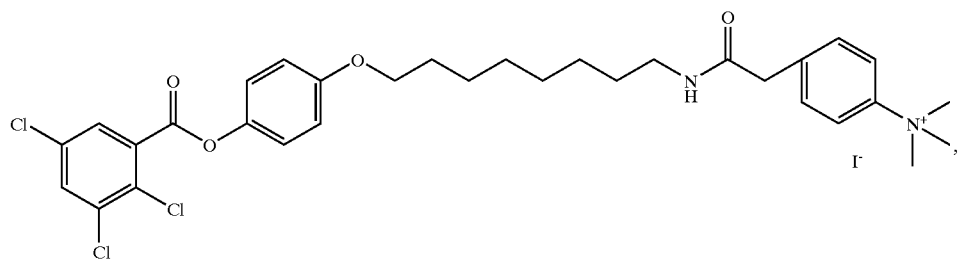
1644
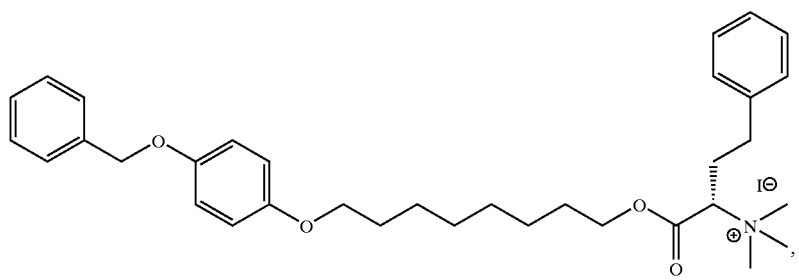
1198′

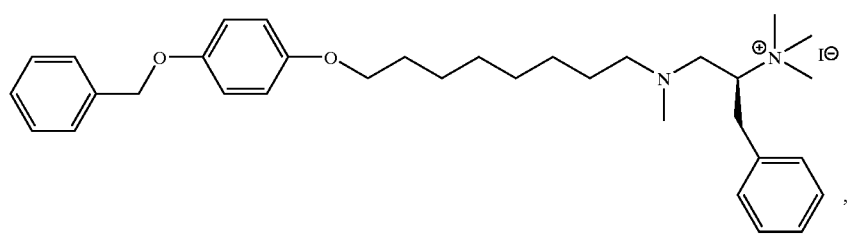
1499'
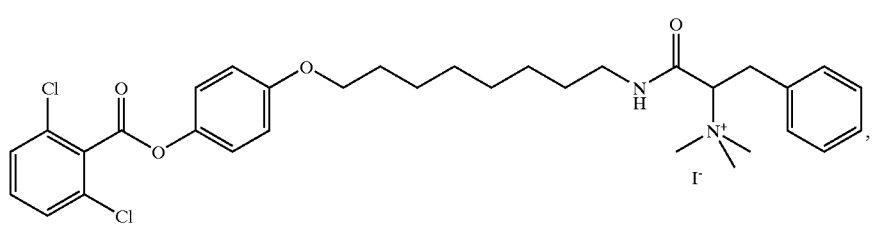
1606
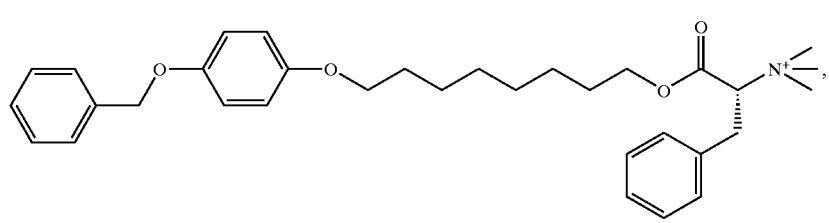
1338'
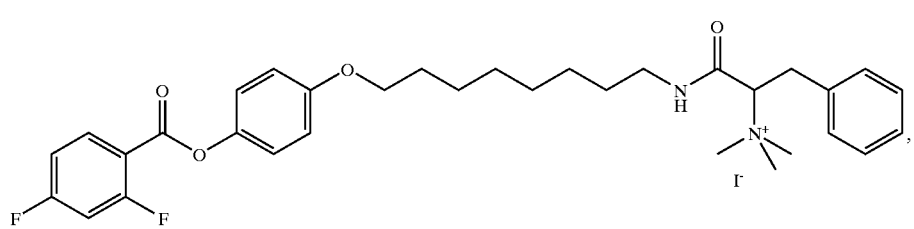
1610
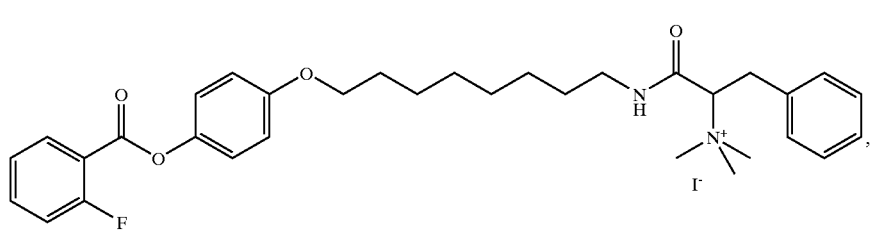
1596
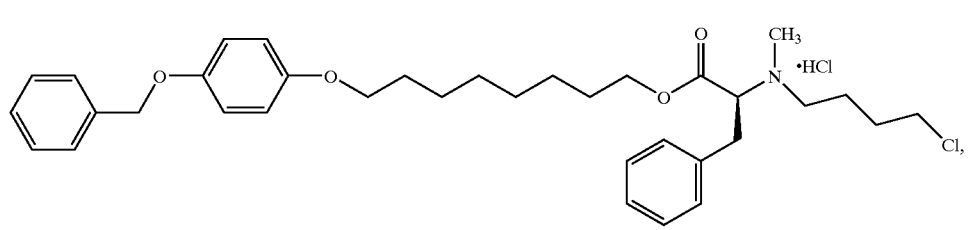
1401'
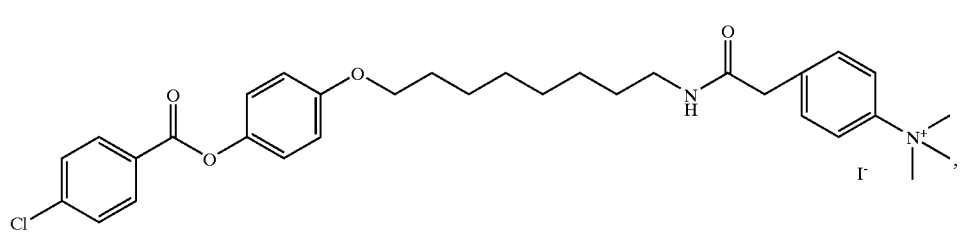
1624

-continued
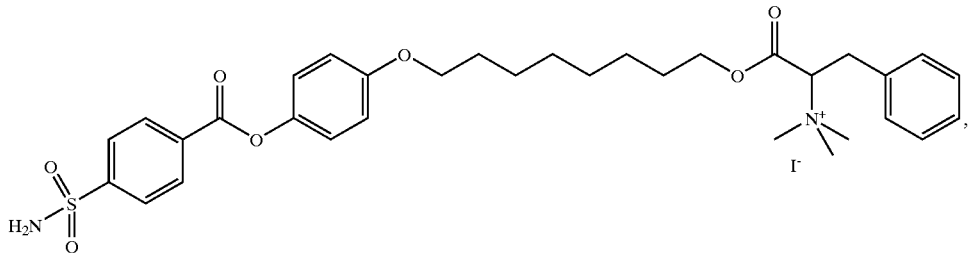
1485
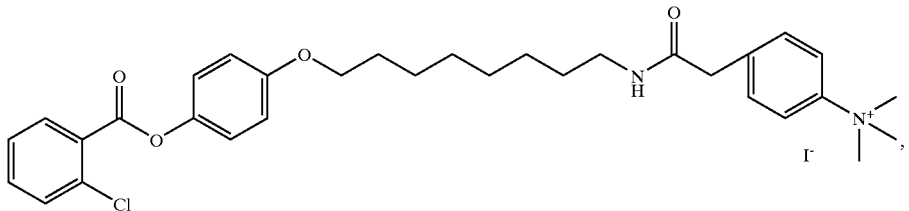
1622
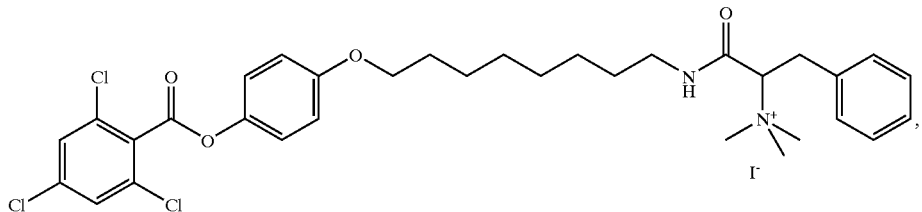
1616
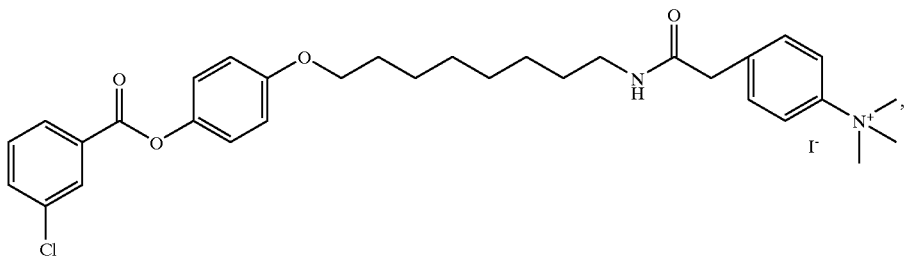
1623
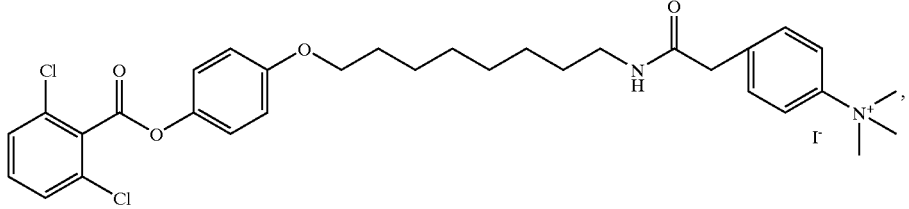
1635
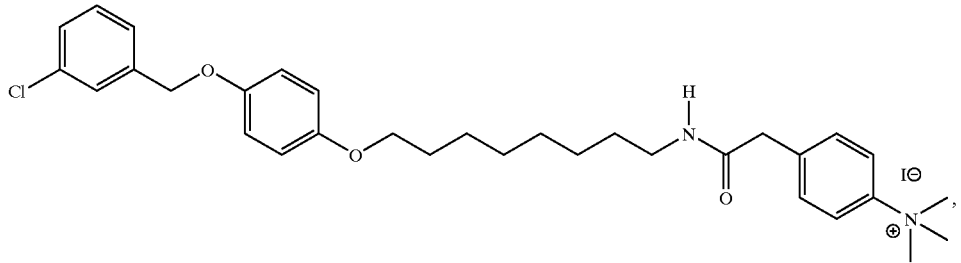
1421

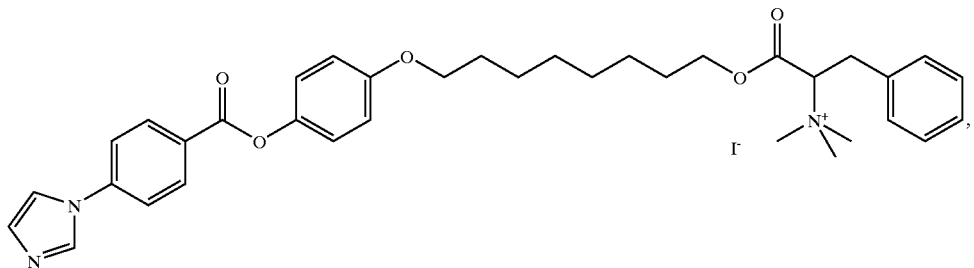
1486
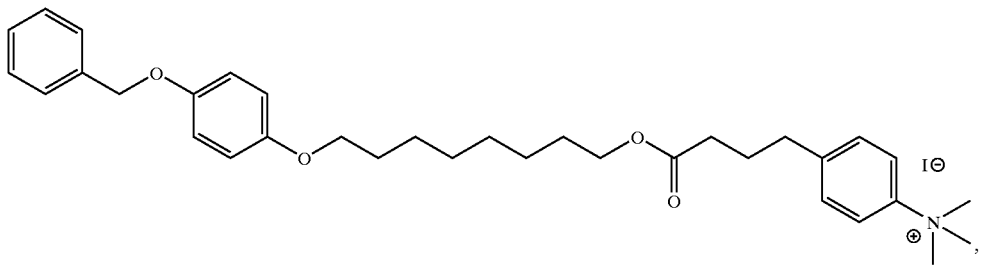
1264
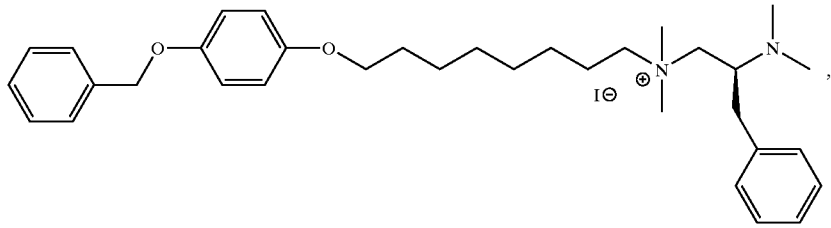
1498′
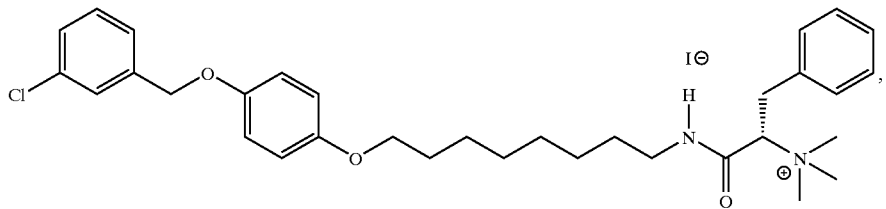
1420′
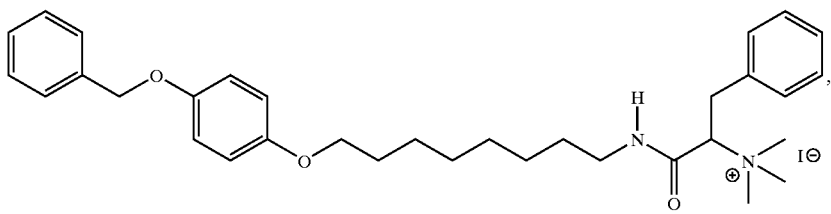
1364
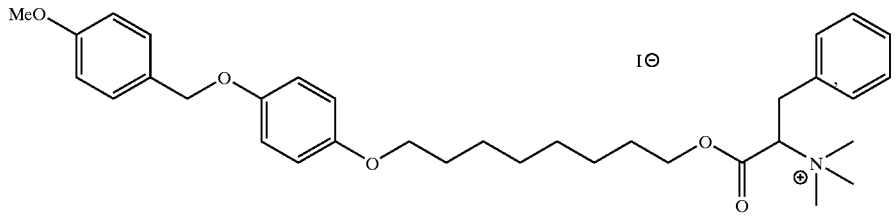
1389

-continued
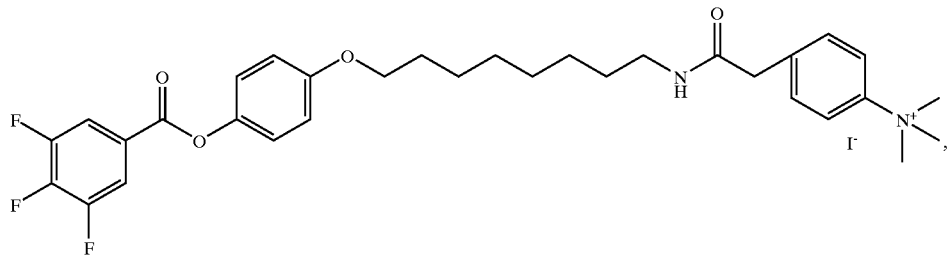
1650
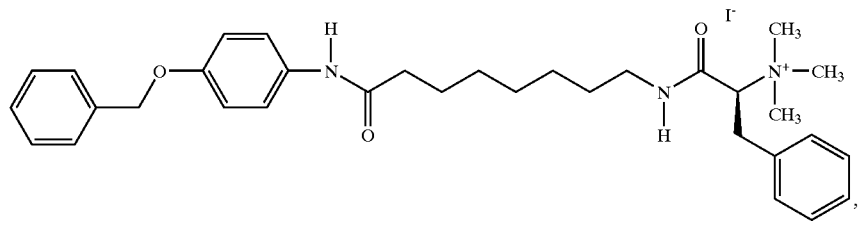
1403
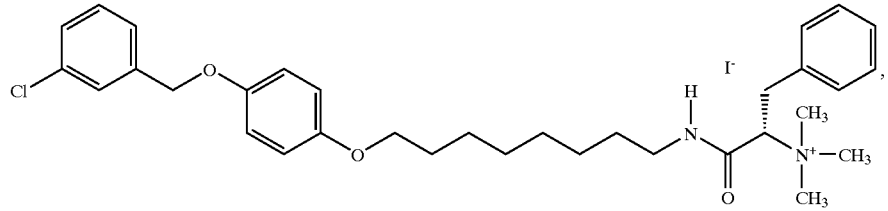
1424'
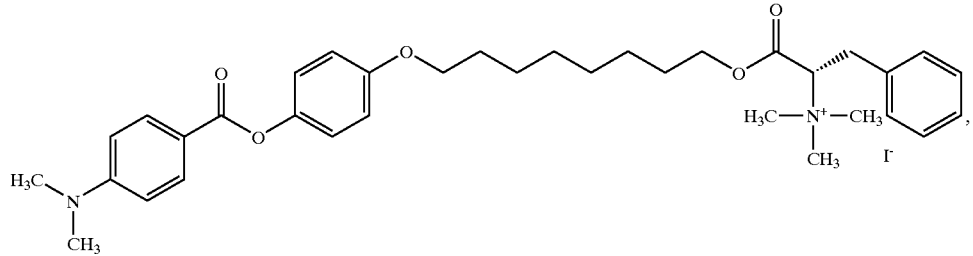
1484'
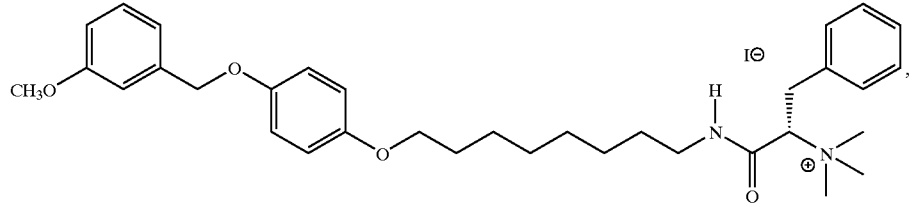
1423'
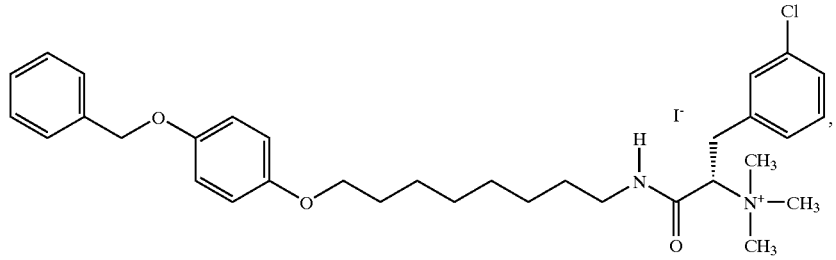
1492'

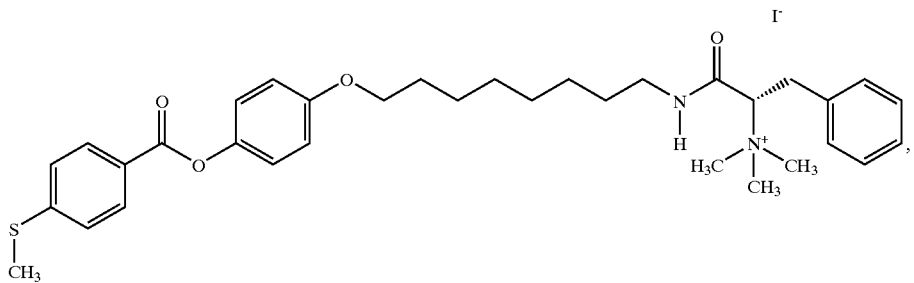
1601'
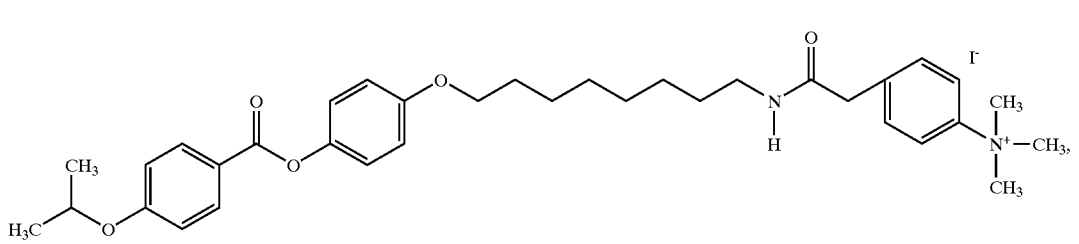
1629
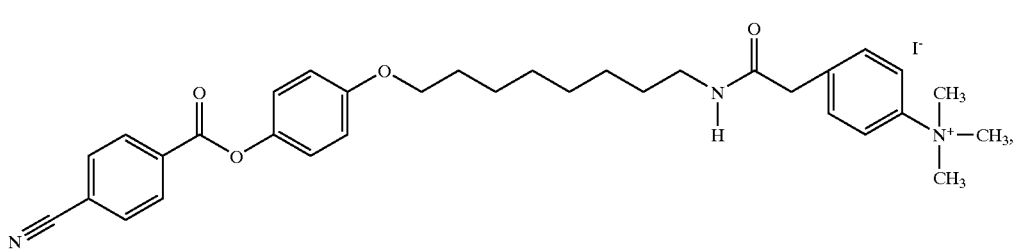
1631
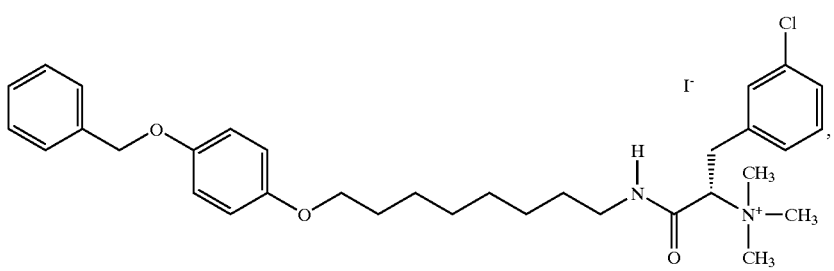
1692'
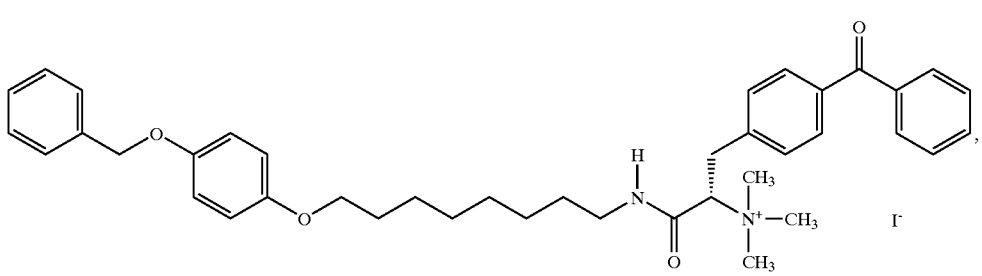
1700'
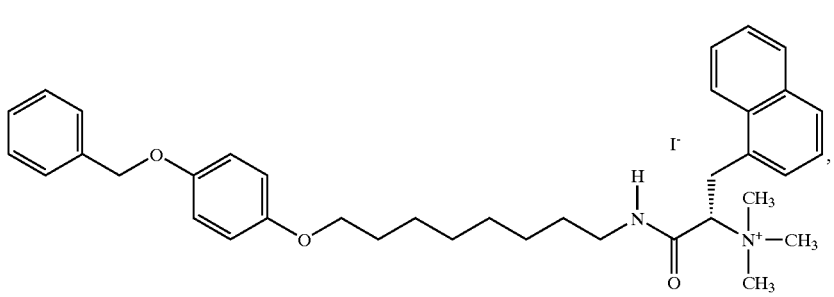
1705'

-continued
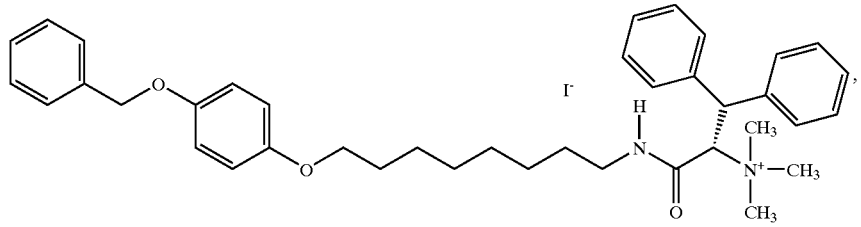
1709'
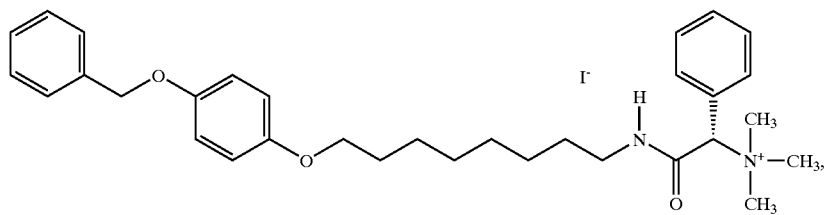
1713'
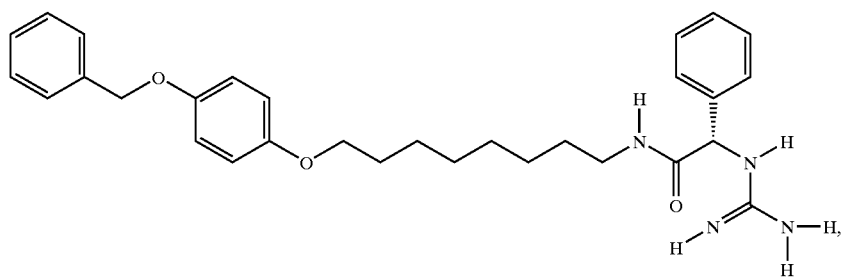
1714'
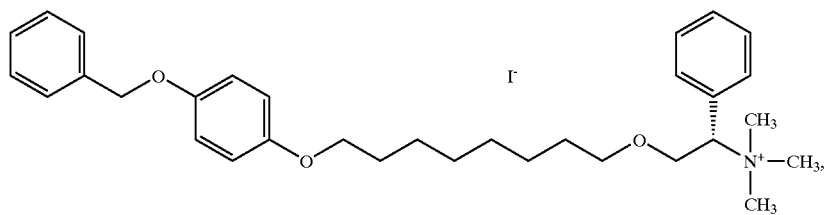
1715'
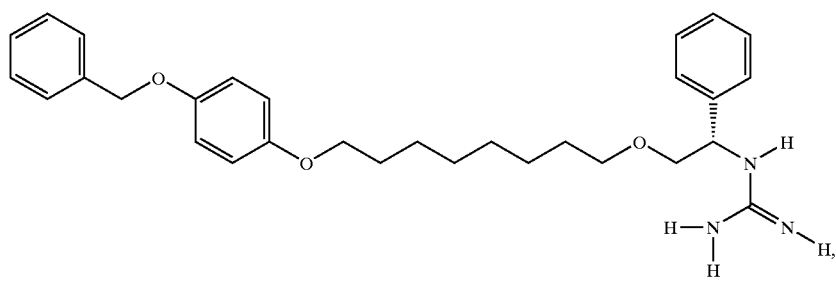
1716'
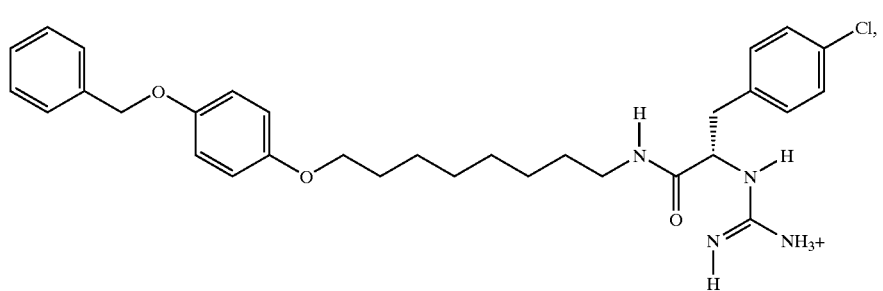
1722'
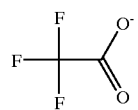

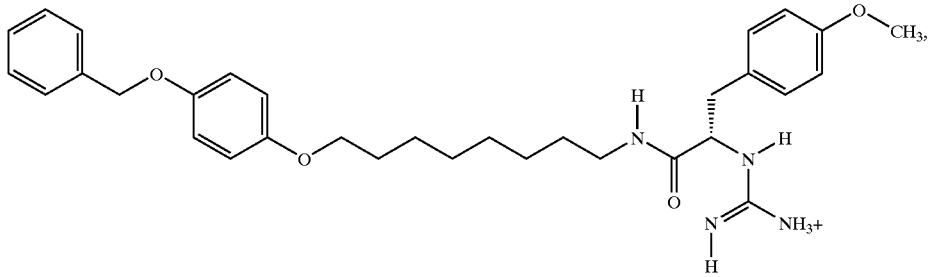
1725'
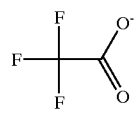
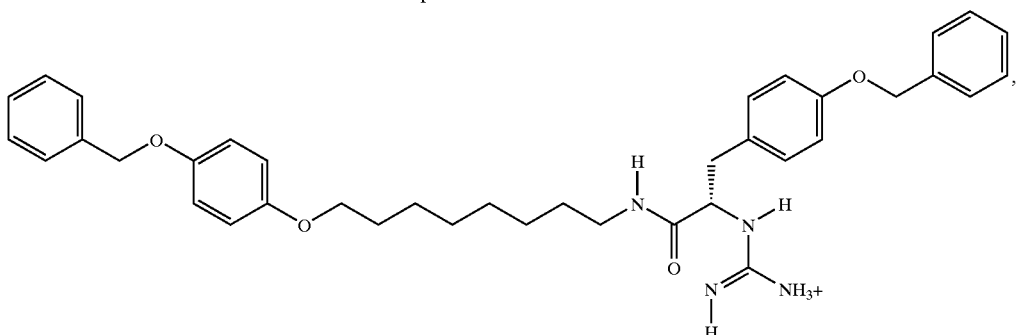
1727'
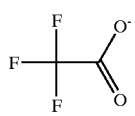
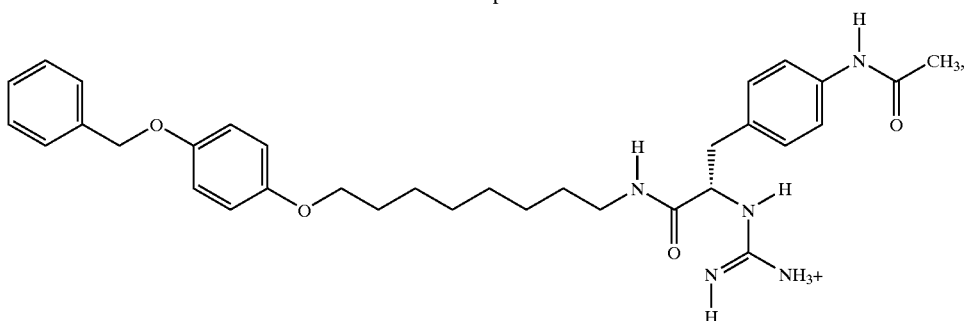
1728'
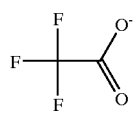
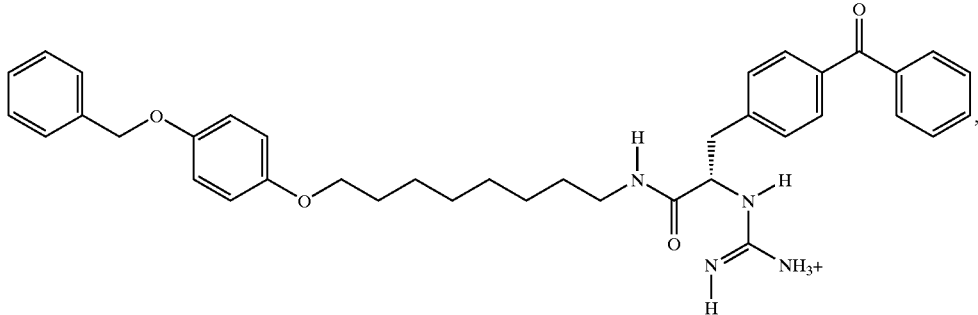
1729'
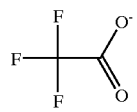

-continued
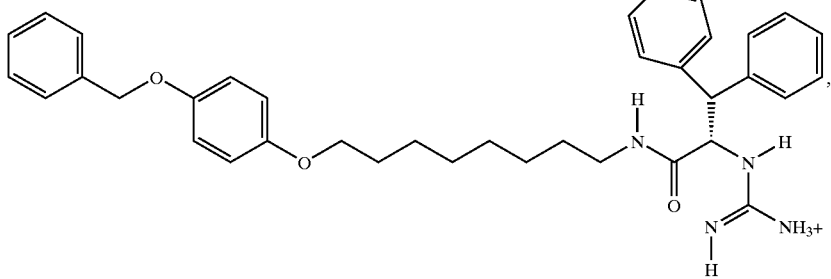
1738'
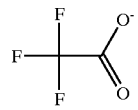
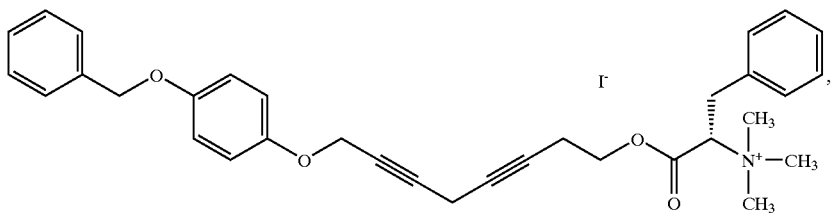
1752'
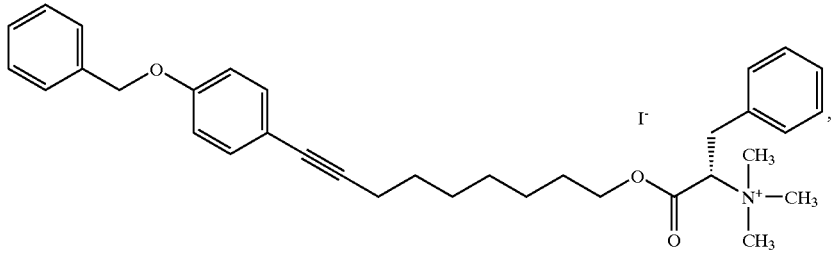
1755'
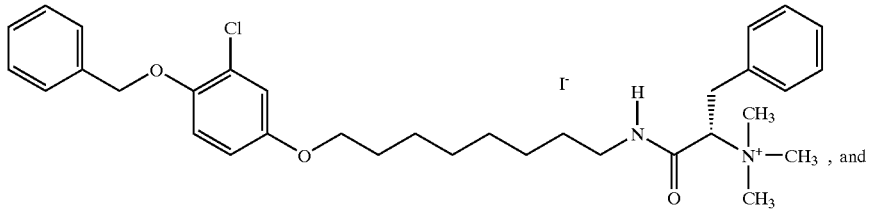
1758'
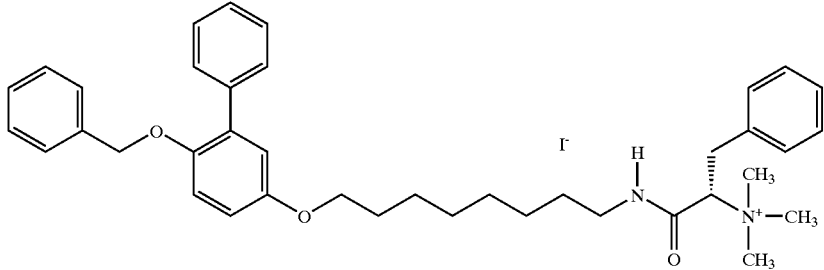
1760'
wherein I⁻ is a pharmaceutically acceptable anion.
* * * * *